United States Patent [19]

Outcalt et al.

[11] Patent Number: 5,187,185
[45] Date of Patent: Feb. 16, 1993

[54] PESTICIDAL 1-ARYLPYRROLES

[75] Inventors: Russell J. Outcalt, Cary; Philip R. Timmons, Durham, both of N.C.; Susan M. Cramp, Dagenham, England; Patricia L. Kwiatkowski; Anibal Lopes, both of Raleigh, N.C.; Paul A. Cain; David N. Sinodis, both of Cary, N.C.; Lee S. Hall, Raleigh, N.C.; Jean-Pierre A. Vors, Lyons, France

[73] Assignee: Rhone-Poulenc AG Company, Research Triangle Park, N.C.

[21] Appl. No.: 533,470

[22] Filed: Jun. 5, 1990

Related U.S. Application Data

[63] Continuation-in-part of Ser. No. 435,362, Nov. 16, 1989, which is a continuation-in-part of Ser. No. 282,439, Dec. 9, 1988, abandoned.

[51] Int. Cl.$^5$ .............................................. A01N 43/36
[52] U.S. Cl. ...................... 514/408; 514/424; 514/425; 514/426; 514/427; 514/428; 514/429
[58] Field of Search ............... 514/408, 424, 425, 426, 514/427, 428, 429

[56] References Cited

U.S. PATENT DOCUMENTS

| | | | |
|---|---|---|---|
| 2,779,766 | 1/1957 | Middleton | 548/550 |
| 2,940,977 | 6/1960 | Middleton | 548/550 |
| 3,772,330 | 11/1973 | Enders et al. | 514/407 |
| 3,950,530 | 4/1976 | Horne, Jr. | 514/407 |
| 4,013,445 | 3/1977 | Bellus et al. | 514/407 |
| 4,339,457 | 7/1982 | Plummer et al. | 514/427 |
| 4,560,769 | 12/1985 | Menig et al. | 548/560 |
| 4,689,342 | 8/1987 | Tessier et al. | 514/427 |
| 4,803,215 | 2/1989 | Jensen-Korte et al. | 514/407 |
| 5,019,130 | 5/1991 | Flood | 8/423 |

FOREIGN PATENT DOCUMENTS

| | | |
|---|---|---|
| 242322 | 10/1987 | European Pat. Off. |
| 293711 | 12/1988 | European Pat. Off. |
| 295117 | 12/1988 | European Pat. Off. |
| 300312 | 1/1989 | European Pat. Off. |
| 312723 | 4/1989 | European Pat. Off. |
| 347488 | 12/1989 | European Pat. Off. |
| 54-03866 | 8/1979 | Japan |
| 8703781 | 7/1987 | PCT Int'l Appl. |
| 1166110 | 10/1969 | United Kingdom ............... 514/425 |

OTHER PUBLICATIONS

CA 92: 128711z Insecticidal pyrrol-1-ylphenyl phosphorothiolates, Okabe et al. (Sumitomo Chem.) 1980 p. 681.
H. Holtschmidt, High Temperature Chlorination of Amines and Acylamines, Angew. Chem. internat. Edit. 12, 632-69 (1962).
A. Broderick and D. Wibberley, 1 H-Pyrrole [2,3-6]-pyridines. Part III, J. Chem. Soc., Perkin Trans. I, 1910-13 (1975).

*Primary Examiner*—Mary C. Lee
*Assistant Examiner*—Joseph K. McKane
*Attorney, Agent, or Firm*—Morgan & Finnegan

[57] ABSTRACT

Substituted-1-arylpyrrole compounds of general formula (I) below, are useful as pesticides, in particular for the control of insects, arachnids, and nematodes. Processes to make the compounds and intermediates used for their preparation are described. Additionally, compositions containing the compounds and methods of use therefore are provided. Preferred compounds are the compounds of general formula (I)

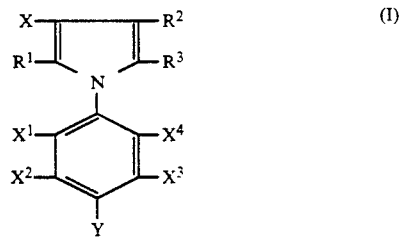

wherein typically preferred substituents are:
X is halogen or a group $R^5S(O)_n$, in which n is 0, 1, or 2 and $R^5$ is $CH_3$, $CF_3$, $CCl_3$, $CF_2Cl$, $CFCl_2$, $CF_2Br$, $CHF_2$, $CHCl_2$ or $CHClF$;
$R^1$ is H, F, Cl, Br, $OCH_3$, $SCH_3$, or $CH_3$ optionally substituted;
$R^2$ is CN;
$R^3$ is H, F, Cl, Br, $OCH_3$, or $CH_3$ optionally substituted;
Y is $CF_3$, $CF_3O$, H, F, Cl or Br;
$X^1$ and $X^4$ are individually H, F, Cl, Br, $CH_3$, $OCH_3$ or $SCH_3$; and
$X^2$ and $X^3$ are each H.

64 Claims, No Drawings

PESTICIDAL 1-ARYLPYRROLES

This is a continuation in part application of copending application Ser. No. 07/435,362, filed Nov. 16, 1989, pending incorporated herein by reference, which is a continuation in part application of copending application Ser. No. 07/282,439, now abandoned Apr. 11, 1990 filed Dec. 9, 1988, incorporated herein by reference.

BACKGROUND OF THE INVENTION

1. Field of the Invention

The invention relates to pesticidal compounds of the chemical family of 1-arylpyrroles, as well as intermediate products: 1-(N,N-dialkylamino)-2,3-dicyanoprop-1-enes; 1-(substituted phenylamino)-2,3-dicyanoprop-1-enes; and 1-(substituted phenyl)-2-amino-4-cyanopyrroles for the preparation of these compounds. The invention further relates to processes for preparing these pyrrole compounds via the above compound intermediates. The invention also relates to the application of said compounds in agriculture, especially as pesticides for controlling arthropods, preferably as insecticides and acaricides and to agrochemical compositions useful to control arthropods, especially insects and arachnids.

2. Description of the Related Art

Many pyrazoles (two nitrogen atom-containing heterocyclic formula) are well known as insecticides. Also some compounds containing the pyrrole group (one nitrogen atom containing formula) are known as insecticides. However, they usually contain also another chemical group in their formula which is well known to have insecticidal properties per se, such as a pyrethroid group, or a carbamate group, or some organophosphoric group. Simple substituted pyrrole derivatives have been described as agrochemical compounds, for example in British patent 2,189,242, but for fungicidal use.

Certain 1-(N-substituted alkylamino)- and 1-(N-substituted phenylamino)-2,3-dicyanoprop-1-enes and cyclized pyrrole compounds obtained therefrom, namely 1-(substituted alkyl)- and 1-(substituted phenyl)-2-amino-4-cyanopyrroles are described by A. Brodrick and D. G. Wibberley, J. Chem. Soc., Perkin Trans. I, 1975, 1910.

SUMMARY OF THE INVENTION

A first aspect of the invention relates to pesticidal 1-arylpyrroles in pesticidal compositions and for pesticidal methods of use, particularly insecticidal and acaricidal, of compounds of formula (Ia)

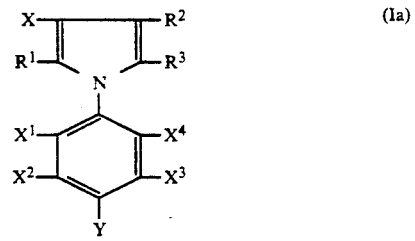

(Ia)

wherein:

X is selected from the group consisting of: halogen, cyano, cyanato, thiocyanato, haloalkyl, alkoxy, haloalkoxy, alkylthio, alkylsulfinyl, alkylsulfonyl, haloalkylthio, haloalkylsulfinyl, haloalkylsulfonyl, haloalkylcarbonyl, alkenylthio, alkenylsulfinyl, alkenylsulfonyl, haloalkenylthio, haloalkenylsulfinyl, haloalkenylsulfonyl, haloalkylthiocarbonyl, phenylthio, phenylsulfinyl, phenylsulfonyl, heteroarylthio, heteroarylsulfinyl, and heteroarylsulfonyl; and wherein the phenyl groups are optionally substituted with halogen, cyano or haloalkyl groups and the heteroaryl groups are five or six membered monocyclic rings, containing one or two of the same or different oxygen, sulfur or nitrogen heteroatoms, and which heteroaryl groups are optionally substituted with halogen, nitro, cyano or haloalkyl groups; and wherein the alkyl, haloalkyl, alkenyl, haloalkenyl, alkoxy and haloalkoxy groups herein are linear or branched chains, having less than 10 carbon atoms, preferably less than 5 carbon atoms, and the halo substitution in all these groups consists of one or more halogen atoms, which are the same or different, from mono substitution up to complete poly substitution;

$R^1$, $R^2$, and $R^3$ are individually selected from the group consisting of: one of the same set of substituents as described for X; a hydrogen atom; an alkyl group; and a substituent of which no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, bis(alkylthio)methyl, bis(arylthio)methyl, alkylthioalkylideneimino, alkoxycarbonylamino, haloalkoxycarbonylamino, a phenyl optionally substituted with halogen, cyano, or haloalkyl, and a heteroaryl group having a five or six membered monocyclic ring, containing one or two of the same or different oxygen, sulfur or nitrogen heteroatoms and which heteroaryl group is optionally substituted with halogen, nitro, cyano or haloalkyl groups; and wherein the alkyl, haloalkyl, alkenyl, haloalkenyl, haloalkoxy, and alkoxy groups herein are linear or branched chains, having less than 10 carbon atoms, preferably less than 5 carbon atoms, and the halo substitution in all these groups herein consists of one or more halogen atoms, which are the same or different, from mono substitution up to complete poly substitution;

or $R^1$, $R^2$, and $R^3$ are as defined above and $R^1$ is furthermore selected from the group consisting of alkenyl, alkynyl, haloalkenyl, haloalkynyl, alkenylamino, alkynylamino, cyanoalkyl, aralkylthio, aralkylsulfinyl, aralkylsulfonyl, alkenyloxy, alkynyloxy, alkoxyalkyl, and alkylthioalkyl, and $R^3$ is furthermore selected from the group consisting of alkenyloxy, alkynyloxy, and alkoxyalkyl; and no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, alkenylamino, alkynylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, bis(alkylthio)methyl, bis(arylthio)methyl, alkylthioalkylideneimino, alkoxycarbonylamino, haloalkoxycarbonylamino, a phenyl optionally substituted with halogen, cyano, or haloalkyl, and a heteroaryl group having a five or six membered monocyclic ring, containing one or two of the same or different oxygen, sulfur or nitrogen heteroatoms and which heteroaryl group is optionally substituted with halogen, nitro, cyano or haloalkyl groups; and wherein the alkyl, haloalkyl, alkenyl, haloalkenyl, alkynyl, haloalkynyl, haloalkoxy, alkoxy, alkenyloxy, and alkynyloxy groups herein are linear or branched chains, having less than 10 carbon atoms, preferably less than 5 carbon atoms, and the halo substitution in all these groups herein consists of one or more halogen atoms, which are the same or different, from mono substitution up to complete poly substitution; and wherein the aralkyl portion in the above mentioned groups is preferably benzyl or heteroarylmethyl, in which the phenyl and heteroaryl portions are optionally substituted as defined above.

Y is selected from the group consisting of: halogen, cyano, alkyl, haloalkyl, alkoxy, haloalkoxy, alkylsulfinyl, alkylsulfonyl, alkylthio, haloalkylthio, haloalkylsulfinyl, haloalkylsulfonyl, alkylcarbonyl, haloalkylcarbonyl, alkenyl, haloalkenyl, haloalkynyl, and alkynyl; and wherein the alkyl, alkoxy, haloalkyl, haloalkoxy, alkenyl, haloalkenyl, alkynyl and haloalkynyl groups herein are linear or branched chains, having less than 10 carbon atoms, preferably less than 5 carbon atoms, and the halo substitution in all these groups herein consists of one or more halogen atoms, which are the same or different, from mono substitution up to as much as complete poly substitution;

or Y is optionally a hydrogen atom when:

X is a halogen atom or a group $R^5S(O)_n$, in which n is 0, 1, or 2 and $R^5$ is alkyl, haloalkyl, alkenyl or haloalkenyl; and the alkyl and alkenyl carbon chains and the halo substitution are as defined above;

$R^1$ and $R^3$ are each a hydrogen atom; and $R^2$ is cyano;

$X^1$, $X^2$, $X^3$ and $X^4$ are individually selected from the same set of substituents as described for Y or a hydrogen atom; and provided:

that at least one of $R^1$, $R^2$, and $R^3$ is selected from the same set of substituents as described for X;

that if $X^4$ and $X^1$ are H, and X is halogen or cyano, then $R^2$ is different from X; and that if $X^4$ and $X^1$ are H, and Y is methyl, then X is different from bromo.

Preferred pesticidal 1-arylpyrroles in pesticidal compositions and for pesticidal methods of use of compounds of formula (Ia), are compounds of formula (Ib), having the structure of formula (Ia), wherein:

X, Y, $X^1$, $X^2$, $X^3$, $X^4$, and the provisos are as defined in formula (Ia); and $R^1$, $R^2$, and $R^3$ are individually selected from the group consisting of: one of the same set of substituents as described for X; a hydrogen atom; an alkyl group; and a substituent of which no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, bis(alkylthio)methyl, bis(arylthio)methyl, alkylthioalkylideneimino, alkoxycarbonylamino, haloalkoxycarbonylamino, a phenyl optionally substituted with halogen, cyano, or haloalkyl, and a heteroaryl group having a five or six membered monocyclic ring, containing one or two of the same or different oxygen, sulfur or nitrogen heteroatoms and which heteroaryl group is optionally substituted with halogen, nitro, cyano or haloalkyl groups; and wherein the alkyl, haloalkyl, alkenyl, haloalkenyl, haloalkoxy, and alkoxy groups herein are linear or branched chains, having less than 10 carbon atoms, preferably less than 5 carbon atoms, and the halo substitution in all these groups herein consists of one or more halogen atoms, which are the same or different, from mono substitution up to complete poly substitution.

Further preferred pesticidal 1-arylpyrroles in pesticidal compositions and for pesticidal methods of use of compounds of formula (Ib) are compounds of formula (Ic), having the structure of formula (Ib), wherein:

X is selected from the group consisting of halogen, cyano, cyanato, thiocyanato, haloalkyl, alkoxy, haloalkoxy, alkylthio, alkylsulfinyl, alkylsulfonyl, haloalkylthio, haloalkylsulfinyl, haloalkylsulfonyl, haloalkylcarbonyl, haloalkylthiocarbonyl, phenylthio, phenylsulfinyl, phenylsulfonyl, heteroarylthio, heteroarylsulfinyl, and heteroarylsulfonyl; and wherein the phenyl groups are optionally substituted with halogen, cyano or haloalkyl groups and the heteroaryl groups are five or six membered monocyclic rings, containing one or two of the same or different oxygen, sulfur or nitrogen heteroatoms, and which heteroaryl groups are optionally substituted with halogen, nitro, cyano or haloalkyl groups; and wherein the alkyl, haloalkyl, alkoxy and haloalkoxy groups herein are linear or branched chains, having less than 10 carbon atoms, preferably less than 5 carbon atoms, and the halo substitution in all these groups is mono substitution or up to as much as complete poly substitution;

$R^1$, $R^2$, and $R^3$ are individually selected from the group consisting of: the same substituents as described for X; a hydrogen atom; an alkyl group; and a substituent of which no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, a phenyl optionally substituted with halogen, cyano, or haloalkyl, and a heteroaryl group having a five or six membered monocyclic ring, containing one or two of the same or different oxygen, sulfur or nitrogen heteroatoms and which heteroaryl group is optionally substituted with halogen, nitro, cyano or haloalkyl groups; and wherein the alkyl, haloalkyl, haloalkoxy, and alkoxy groups herein are linear or branched chains, having less than 10 carbon atoms, preferably less than 5 carbon atoms, and the halo substitution in all these groups herein is mono substitution or up to as much as complete poly substitution;

Y is selected from the group consisting of halogen, cyano, alkyl, haloalkyl, alkoxy, haloalkoxy, alkylsulfinyl, alkylsulfonyl, alkylthio, haloalkylthio, haloalkylsulfinyl, haloalkylsulfonyl, alkylcarbonyl, haloalkylcarbonyl, alkenyl, haloalkenyl, haloalkynyl, and alkynyl; and wherein the alkyl, alkoxy, haloalkyl and haloalkoxy groups herein are linear or branched chains, having less than 10 carbon atoms, and the halo substitution in all these groups herein is mono substitution or up to as much as complete poly substitution; and $X^1$, $X^2$, $X^3$, $X^4$ and the provisos are as described in formula (Ib).

Specific preferred pesticidal 1-arylpyrrole compounds of formula (Ib), which are of interest as insecticides and acaricides, are compounds of formula (II-1), having the structure of formula (Ib), wherein:

X is a halogen atom or a group $R^5S(O)_n$ in which n is 0, 1, or 2 and $R^5$ is alkyl, haloalkyl, alkenyl, or haloalkenyl;

$R^1$ is a hydrogen atom, a halogen atom or alkylthio having less than 5 carbon atoms;

$R^2$ is cyano;

$R^3$ is a hydrogen atom or a halogen atom;

Y is a hydrogen atom, a halogen atom, haloalkyl or haloalkoxy, in which the alkyl and alkoxy portions have less than 5 carbon atoms, with the proviso of Y is hydrogen as defined above in formula (Ib); and $X^1$, $X^2$, $X^3$ and $X^4$ are individually selected from the group consisting of a hydrogen atom, a halogen atom, $C_{1-3}$ alkyl, $C_{1-3}$ alkoxy, and $C_{1-3}$ alkylthio.

Even more specific pesticidal 1-arylpyrroles of formula (Ib) or (Ic), which are preferred and are of particular interest, especially as insecticides and acaricides, are the compounds:

A) General insecticidal compounds are compounds of formula (II-2), having the structure of formula (Ic), wherein:

X is a haloalkylthio, a haloalkylsulfinyl or haloalkylsulfonyl group, preferably $CF_3S(O)_n$, wherein n is 0, 1, or 2;

$R^1$ is a hydrogen atom or a halogen atom such as chlorine or bromine;

$R^2$ is cyano;

$R^3$ is selected from the group consisting of: the same substituents as described for X in compounds of (Ic); a hydrogen atom; an alkyl group; and a substituent which is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, a phenyl optionally substituted with halogen, cyano, or haloalkyl, and a heteroaryl group having a five or six membered monocyclic ring, containing one or two of the same or different oxygen, sulfur or nitrogen heteroatoms and which heteroaryl group is optionally substituted with halogen, nitro, cyano or haloalkyl groups; and wherein the alkyl, haloalkyl, haloalkoxy, and alkoxy groups herein are linear or branched chains, having less than 10 carbon atoms, preferably less than 5 carbon atoms, and the halo substitution in all these groups herein is mono substitution or up to as much as complete poly substitution;

Y is haloalkyl or haloalkoxy;

$X^1$ and $X^4$ are other than a hydrogen atom; and $X^2$ and $X^3$ are each a hydrogen atom.

B) Compounds with high insecticidal activity are those of a formula (II-3), having the structure of formula (Ic), wherein:

X is $R^5S(O)_n$, in which n is 0, 1 or 2 and $R^5$ is $CH_3$, $CF_3$, $CF_2Cl$ or $CFCl_2$;

$R^1$ is H, F, Cl, Br or $NH_2$;

$R^2$ is cyano;

$R^3$ is H, F, Cl, Br, $CF_3$ or CN;

Y is $CF_3$ or $CF_3O$;

$X^1$ is H or Cl;

$X^2$ and $X^3$ are H; and $X^4$ is Cl.

Among these compounds, more preferred compounds are:

B-1  1-(2,6-dichloro-4-trifluoromethylphenyl)-2-chloro-3-cyano-4-(trifluoromethylsufonyl)pyrrole;

B-2  1-(2,6-dichloro-4-trifluoromethylphenyl)-2-chloro-3-cyano-4-(trifluoromethylsulfinyl)pyrrole;

B-3  1-(2,6-dichloro-4-trifluoromethylphenyl)-2-chloro-3-cyano-4-trifluoromethylsulfinyl-5-bromopyrrole;

B-4  1-(2,6-dichloro-4-trifluoromethylphenyl)-2-chloro-3-cyano-4-trifluoromethylsulfonyl-5-bromopyrrole;

B-5  1-(2,6-dichloro-4-trifluoromethylphenyl)-2-chloro-3-cyano-4-(trifluoromethylthio)pyrrole;

B-6  1-(2,6-dichloro-4-trifluoromethylphenyl)-2-bromo-3-trifluoromethylthio-4-cyano-5-chloropyrrole;

B-7  1-(2,6-dichloro-4-trifluoromethylphenyl)-2-[(trifluoromethyl)carbonylamino]-3-trifluoromethylthio-4-cyano-5-chloropyrrole;

B-8  1-(2,6-dichloro-4-trifluoromethylphenyl)-2-(methylcarbonylamino)-3-trifluoromethylthio-4-cyano-5-chloropyrrole;

B-9  1-(2,6-dichloro-4-trifluoromethylphenyl)-2-amino-3-trifluoromethylthio-4-cyano-5-chloropyrrole;

B-10  1-(2-chloro-4-trifluoromethylphenyl)-2-amino-3-trifluoromethylthio-4-cyano-5-chloropyrrole;

B-11  1-(2,6-dichloro-4-trifluoromethylphenyl)-2-amino-3-dichlorofluoromethylthio-4-cyano-5-chloropyrrole;

B-12  1-(2,6-dichloro-4-trifluoromethylphenyl)-2,4-bis(-trifluoromethylthio)-3-cyano-5-aminopyrrole;

B-13  1-(2,6-dichloro-4-trifluoromethylphenyl)-2-amino-3-trifluoromethylthio-4-cyano-5-bromopyrrole;

B-14  1-(2,6-dichloro-4-trifluoromethylphenyl)-2-amino-3-trifluoromethylthio-4-cyanopyrrole;

B-15  1-(4-trifluoromethylphenyl)-2-amino-3-trifluoromethylthio-4-cyano-5-bromopyrrole;

B-16  1-(2-chloro-4-trifluoromethylphenyl)-2-amino-3-trifluoromethylthio-4-cyano-5-bromopyrrole;

B-17  1-(2,6-dichloro-4-trifluoromethylphenyl)-2-chloro-3-cyano-4-(dichlorofluoromethylthio)pyrrole;

B-18  1-(2,6-dichloro-4-trifluoromethylphenyl)-2-chloro-3-cyano-4-(dichlorofluoromethylsulfinyl)pyrrole;

B-19  1-(2,6-dichloro-4-trifluoromethylphenyl)-2-chloro-3-cyano-4-(dichlorofluoromethylsulfonyl)-pyrrole;

B-20  1-(2,6-dichloro-4-trifluoromethylphenyl)-3-cyano-4-(dichlorofluoromethylthio)pyrrole;

B-21  1-(2,6-dichloro-4-trifluoromethylphenyl)-3-cyano-4-(dichlorofluoromethylsulfinyl)pyrrole; and B-22  1-(2,6-dichloro-4-trifluoromethoxyphenyl)-2-chloro-3-cyano-4-(trifluoromethylsulfonyl)pyrrole.

Of these compounds, more particularly preferred compounds are: B-1, -2, -17, -18, -19, and -21.

C) Compounds with surprisingly high levels of acaricidal activity are those of a formula (II-1a), having the structure of formula (II-1), wherein:

X is a halogen atom, or a group $R^5S(O)_n$, in which n is 0, 1, or 2 and $R^5$ is: alkyl, preferably $C_{1-4}$ alkyl; haloalkyl, preferably trihalomethyl in which halo is F, Cl or Br or combinations thereof, more preferably $CF_3$, $CCl_3$, $CF_2Cl$, $CFCl_2$ or $CF_2Br$; alkenyl; or haloalkenyl;

$R^1$ and $R^3$ are each a hydrogen atom;

$R^2$ is cyano;

Y is a hydrogen atom or a halogen atom, preferably F, Cl or Br; or more preferably Cl or Br; and $X^1$, $X^2$, $X^3$ and $X^4$ are individually selected from the group consisting of: hydrogen; halogen; $C_{1-3}$ alkyl; $C_{1-3}$ alkoxy; and $C_{1-3}$ alkylthio; and preferably, $X^1$ and $X^4$ are individually H, F, Cl, Br or $CH_3$ and $X^2$ and $X^3$ are each hydrogen.

Among these compounds, the more preferred compounds are:

C-1  1-(4-bromo-2,6-dichlorophenyl)-3-cyano-4-(chlorodifluoromethylthio)pyrrole;

C-2  1-(4-bromo-2,6-dichlorophenyl)-3-cyano-4-(trifluoromethylthio)pyrrole;

C-3  1-(2,4,6-trichlorophenyl)-3-cyano-4-(chlorodifluoromethylthio)pyrrole;

C-4  1-(2,4,6-trichlorophenyl)-3-cyano-4-(chlorodifluoromethylsulfinyl)pyrrole;

C-5  1-(2,4,6-trichlorophenyl)-3-cyano-4-(dichlorofluoromethylthio)pyrrole;

C-6  1-(2,4,6-trichlorophenyl)-3-cyano-4-(dichlorofluoromethylsulfinyl)pyrrole;

C-7  1-(2,4,6-trichlorophenyl)-3-cyano-4-(dichlorofluoromethylsulfonyl)pyrrole;

C-8  1-(4-bromo-2,6-dichlorophenyl)-3-cyano-4-(dichlorofluoromethylthio)pyrrole;

C-9  1-(4-bromo-2,6-dichlorophenyl)-3-cyano-4-(dichlorofluoromethylsulfinyl)pyrrole;

C-10  1-(4-bromo-2,6-dichlorophenyl)-3-cyano-4-(dichlorofluoromethylsulfonyl)pyrrole;

C-11  1-(2,4,6-trichlorophenyl)-3-cyano-4-(trifluoromethylthio)pyrrole;

C-12  1-(2,4,6-trichlorophenyl)-3-cyano-4-(trifluoromethylsulfinyl)pyrrole;

C-13  1-(2,4,6-trichlorophenyl)-3-cyano-4-(trifluoromethylsulfonyl)pyrrole;

C-14  1-(2,4,6-trichlorophenyl)-3-cyano-4-(trichloromethylthio)pyrrole;

C-15  1-(2,4-dichlorophenyl)-3-cyano-4-(dichlorofluoromethylthio)pyrrole;

C-16  1-(2,4,6-trichlorophenyl)-3-cyano-4-chloropyrrole;

C-17  1-(2,4,6-trichlorophenyl)-3-cyano-4-(chlorodifluoromethylsulfonyl)pyrrole;

C-18  1-(2,6-dichlorophenyl)-3-cyano-4-(dichlorofluoromethylthio)pyrrole;

C-19  1-(4-bromo-2,6-dichlorophenyl)-3-cyano-4-(trifluoromethylsulfinyl)pyrrole;

C-20  1-(4-bromo-2,6-dichlorophenyl)-3-cyano-4-(trifluoromethylsulfonyl)pyrrole;

C-21  1-(4-bromo-2,6-dichlorophenyl)-3-cyano-4-(chlorodifluoromethylsulfinyl)pyrrole;

C-22  1-(4-bromo-2,6-dichlorophenyl)-3-cyano-4-(chlorodifluoromethylsulfonyl)pyrrole;

C-23  1-(4-bromo-2,6-dimethylphenyl)-3-cyano-4-(trifluoromethylsulfinyl)pyrrole;

C-24  1-(4-bromo-2,6-dimethylphenyl)-3-cyano-4-(trifluoromethylsulfonyl)pyrrole;

C-25  1-(4-bromo-2,6-difluorophenyl)-3-cyano-4-(dichlorofluoromethylthio)pyrrole;

C-26  1-(2,4,6-trichlorophenyl)-3-cyano-4-(1,1-dichloro-2,2,2-trifluoroethylthio)pyrrole;

C-27  1-(2,6-dichloro-4-fluorophenyl)-3-cyano-4-(trifluoromethylthio)pyrrole;

C-28  1-(2,6-dichloro-4-fluorophenyl)-3-cyano-4-(trifluoromethylsulfinyl)pyrrole;

C-29  1-(2,6-dichloro-4-fluorophenyl)-3-cyano-4-(trifluoromethylsulfonyl)pyrrole;

C-30  1-(2,4-dichlorophenyl)-3-cyano-4-(chlorodifluoromethylthio)pyrrole; and

C-31  1-(2,6-dichloro-4-fluorophenyl)-3-cyano-4-(dichlorofluoromethylthio)pyrrole.

Of these compounds, more particularly preferred compounds are: C-1, -2, -3, -5, -11, -28, -29, -30, and 31.

D) Compounds with high levels of insecticidal activity are those of a formula (II-1b), having the structure of formula (II-1), wherein:

X is $R^5S(O)_n$, in which n is 0, 1 or 2 and $R^5$ is $CH_3$, $CF_3$, $CF_2Cl$, $CFCl_2$, $CF_2Br$, $CHF_2$, $CHCl_2$ or $CHClF$;

$R^1$ is H, F, Cl or Br;

$R^2$ is cyano;

$R^3$ is H, F, Cl or Br;

Y is $CF_3$ or $CF_3O$;

$X^1$ is H or Cl;

$X^2$ and $X^3$ are H; and $X^4$ is Cl.

Among these compounds, preferred compounds are:

D-1  1-(2,6-dichloro-4-trifluoromethylphenyl)-2-chloro-3-cyano-4-(trifluoromethylthio)pyrrole;

D-2  1-(2,6-dichloro-4-trifluoromethoxyphenyl)-2-chloro-3-cyano-4-(trifluoromethylsulfonyl)pyrrole;

D-3  1-(2,6-dichloro-4-trifluoromethylphenyl)-2-chloro-3-cyano-4-(dichlorofluoromethylthio)pyrrole;

D-4  1-(2,6-dichloro-4-trifluoromethylphenyl)-2-chloro-3-cyano-4-(dichlorofluoromethylsulfinyl)pyrrole;

D-5  1-(2,6-dichloro-4-trifluoromethylphenyl)-2-chloro-3-cyano-4-(dichlorofluoromethylsulfonyl)pyrrole;

D-6  1-(2,6-dichloro-4-trifluoromethylphenyl)-2-chloro-3-cyano-4-(chlorodifluoromethylsulfonyl)pyrrole;

D-7  1-(2,6-dichloro-4-trifluoromethylphenyl)-2-chloro-3-cyano-4-chlorodifluoromethylsulfinyl)pyrrole;

D-8  1-(2,6-dichloro-4-trifluoromethylphenyl)-2-chloro-3-cyano-4-(chlorodifluoromethylthio)pyrrole;

D-9  1-(2,6-dichloro-4-trifluoromethylphenyl)-2-bromo-3-cyano-4-(trifluoromethylsulfinyl)pyrrole;

D-10  1-(2,6-dichloro-4-trifluoromethylphenyl)-2-bromo-3-cyano-4-(trifluoromethylsulfonyl)pyrrole;

D-11  1-(2,6-dichloro-4-trifluoromethylphenyl)-2-bromo-3-cyano-4-(dichlorofluoromethylthio)pyrrole;

D-12  1-(2,6-dichloro-4-trifluoromethylphenyl)-2-bromo-3-cyano-4-(dichlorofluoromethylsulfonyl)pyrrole;

D-13  1-(2,6-dichloro-4-trifluoromethylphenyl)-2-bromo-3-cyano-4-(dichlorofluoromethylsulfinyl)pyrrole;

D-14  1-(2,6-dichloro-4-trifluoromethylphenyl)-2-bromo-3-cyano-4-(chlorodifluoromethylthio)pyrrole;

D-15  1-(2,6-dichloro-4-trifluoromethylphenyl)-2-bromo-3-cyano-4-(chlorodifluoromethylsulfinyl)pyrrole;

D-16  1-(2,6-dichloro-4-trifluoromethylphenyl)-2-chloro-3-cyano-4-(dichlorofluoromethylsulfonyl)-5-bromopyrrole;

D-17 1-(2,6-dichloro-4-trifluoromethylphenyl)-2-bromo-3-cyano-4-(chlorodifluoromethylsulfonyl)-pyrrole;

D-18 1-(2,6-dichloro-4-trifluoromethoxyphenyl)-2-chloro-3-cyano-4-(dichlorofluoromethylsulfinyl)pyrrole;

D-19 1-(2,6-dichloro-4-trifluoromethoxyphenyl)-2-chloro-3-cyano-4-(dichlorofluoromethylsulfonyl)-pyrrole;

D-20 1-(2-chloro-4-trifluoromethylphenyl)-2-chloro-3-cyano-4-(dichlorofluoromethylsulfonyl)pyrrole;

D-21 1-(2-chloro-4-trifluoromethylphenyl)-2-chloro-3-cyano-4-(dichlorofluoromethylsulfinyl)pyrrole;

D-22 1-(2-chloro-4-trifluoromethylphenyl)-2-bromo-3-cyano-4-(dichlorofluoromethylsulfonyl)pyrrole;

D-23 1-(2,6-dichloro-4-trifluoromethylphenyl)-2-chloro-3-cyano-4-(dichlorofluoromethylthio)-5-methylthiopyrrole;

D-24 1-(2,6-dichloro-4-trifluoromethylphenyl)-2-chloro-3-cyano-4-(bromodifluoromethylthio)pyrrole;

D-25 1-(2,6-dichloro-4-trifluoromethylphenyl)-2-chloro-3-cyano-4-(bromodifluoromethylsulfinyl)pyrrole;

D-26 1-(2,6-dichloro-4-trifluoromethylphenyl)-2-chloro-3-cyano-4-(bromodifluoromethylsulfonyl)-pyrrole;

D-27 1-(2,6-dichloro-4-trifluoromethylphenyl)-2-chloro-3-cyano-4-(methylsulfinyl)pyrrole;

D-28 1-(2,6-dichloro-4-trifluoromethylphenyl)-2-chloro-3-cyano-4-(methylsulfonyl)pyrrole;

D-29 1-(2,6-dichloro-4-trifluoromethylphenyl)-2-bromo-3-cyano-4-(trifluoromethylthio)pyrrole;

D-30 1-(2,6-dichloro-4-trifluoromethoxyphenyl)-2-bromo-3-cyano-4-(dichlorofluoromethylsulfinyl)pyrrole; and D-31 1-(2,6-dichloro-4-trifluoromethoxyphenyl)-2-bromo-3-cyano-4-(dichlorofluoromethylsulfonyl)-pyrrole.

Of these compounds, more particularly preferred compounds are: D-3, -4, -5, -6, -7, -8, -12, -13, -23, -24, -27, -29, -30, and -31.

As a second aspect of this invention, preferred pesticidal 1-arylpyrrole compounds, pesticidal compositions, and pesticidal methods of use of compounds of formula (Ia) are of compounds of formula (Ia-1), wherein of the substituents X, $R^1$, $R^2$, and $R^3$, at least one of them is different from the others. Still other preferred compounds, compositions and methods of use of compounds of formula (Ia) are of compounds of formula (Ia-2), wherein X is other than halogen and $R^1$, $R^2$, and $R^3$ are as defined and further include being individually selected from halogen.

As regards to compounds, compositions, and methods of use of compounds of formula (Ia-1), more preferred are those of compounds of a formula (Ib-1), having the structure of formula (Ia-1), wherein:

X, Y, $X^1$, $X^2$, $X^3$, $X^4$, and the provisos are as defined in formula (Ia-1); and $R^1$, $R^2$, and $R^3$ are individually selected from the group consisting of: one of the same set of substituents as described for X; a hydrogen atom; an alkyl group; and a substituent of which no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkysulfonylamino, alkylaminocarbonylamino, arylaminocarbonylamino, benzylideneimino, alkylideneimino, alkoxyalkylideneimino, dialkylaminoalkylideneimino, bis(alkylthio)methyl, bis(arylthio)methyl, alkylthioalkylideneimino, alkoxycarbonylamino, haloalkoxycarbonylamino, a phenyl optionally substituted with halogen, cyano, or haloalkyl, and a heteroaryl group having a five or six membered monocyclic ring, containing one or two of the same or different oxygen, sulfur or nitrogen heteroatoms and which heteroaryl group is optionally substituted with halogen, nitro, cyano or haloalkyl groups; and wherein the alkyl, haloalkyl, alkenyl, haloalkenyl, haloalkoxy, and alkoxy groups herein are linear or branched chains, having less than 10 carbon atoms, preferably less than 5 carbon atoms, and the halo substitution in all these groups herein consists of one or more halogen atoms, which are the same or different, from mono substitution up to complete poly substitution.

Even more preferred compounds, compositions, and methods of use of compounds of formula (Ib-1), are those of compounds of a formula (Ic-1), having the structure of formula (Ib-1), wherein:

X is selected from the group consisting of halogen, cyano, cyanato, thiocyanato, haloalkyl, alkoxy, haloalkoxy, alkylthio, alkylsulfinyl, alkylsulfonyl, haloalkylthio, haloalkylsulfinyl, haloalkylsulfonyl, haloalkylcarbonyl, haloalkylthiocarbonyl, phenylthio, phenylsulfinyl, phenylsulfonyl, heteroarylthio, heteroarylsulfinyl, and heteroarylsulfonyl; and wherein the phenyl groups are optionally substituted with halogen, cyano or haloalkyl groups and the heteroaryl groups are five or six membered monocyclic rings, containing one or two of the same or different oxygen, sulfur or nitrogen heteroatoms, and which heteroaryl groups are optionally substituted with halogen, nitro, cyano or haloalkyl groups; and wherein the alkyl, haloalkyl, alkoxy and haloalkoxy groups herein are linear or branched chains, having less than 10 carbon atoms, preferably less than 5 carbon atoms, and the halo substitution in all these groups is mono substitution or up to as much as complete poly substitution;

$R^1$, $R^2$, and $R^3$ are individually selected from the group consisting of: the same substituents as described for X; a hydrogen atom; an alkyl group; and a substituent of which no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, a phenyl optionally substituted with halogen, cyano, or haloalkyl, and a heteroaryl group having a five or six membered monocyclic ring, containing one or two of the same or different oxygen, sulfur or nitrogen heteroatoms and which heteroaryl group is optionally substituted with halogen, nitro, cyano or haloalkyl groups; and wherein the alkyl, haloalkyl, haloalkoxy, and alkoxy groups herein are linear or branched chains, having less than 10 carbon atoms, preferably less than 5 carbon atoms, and the halo substitution in all these groups herein is mono substitution or up to as much as complete poly substitution;

Y is selected from the group consisting of halogen, cyano, alkyl, haloalkyl, alkoxy, haloalkoxy, alkylsulfinyl, alkylsulfonyl, alkylthio, haloalkylthio, haloalkylsulfinyl, haloalkylsulfonyl, alkylcarbonyl, haloalkylcarbonyl, alkenyl, haloalkenyl, haloalkynyl, and alkynyl; and wherein the alkyl, alkoxy, haloalkyl and haloalkoxy groups herein are linear or branched chains, having less than 10 carbon atoms, and the halo substitution in all these groups herein is mono substitution or up to as much as complete poly substitution; and $X^1$, $X^2$, $X^3$, $X^4$ and the provisos are as described in formula (Ib-1).

Specific preferred pesticidal 1-arylpyrrole compounds, compositions, and methods of use of compounds of formula (Ib-1), which are of insecticidal and acaricidal interest, are those wherein the compounds have a formula (II-4), having a structure of formula (Ib-1), wherein:

X, $R^1$, $R^2$, $R^3$, Y, $X^1$, $X^2$, $X^3$, and $X^4$ have the definitions described in formula (II-1).

Even more specific 1-arylpyrrole compounds, compositions, and methods of use of compounds of formula (Ib-1) or (Ic-1), which are preferred and are of particular insecticidal and acaricide interest, are those wherein the compounds are:

AA) General insecticidal compounds are those of formula (II-5), having a structure of formula (Ic-1), wherein:

X, $R^1$, $R^2$, $R^3$, Y, $X^1$, $X^2$, $X^3$, and $X^4$ have the definitions described in formula (II-2).

BB) Compounds with high insecticidal activity are those of formula (II-6), having the structure of formula (Ic-1), wherein:

X, $R^1$, $R^2$, $R^3$, Y, $X^1$, $X^2$, $X^3$, and $X^4$ have the definitions described in formula (II-3); and the preferred named compounds are identified as B-1 to B-22, above for formula (II-3), more preferably B-1, -2, -17, -18, -19 and -21.

CC) Compounds with surprisingly high levels of acaricidal activity are those of formula (II-4a), having the structure of formula (II-4), wherein:

X, $R^1$, $R^2$, $R^3$, Y, $X^1$, $X^2$, $X^3$, and $X^4$ have the definitions described in formula (II-1a); and the preferred named compounds are identified as C-1 to C-31, above for formula (II-1a), more preferably C-1, -2, -3, -5, -11, -28, -29, -30 and -31.

DD) Compounds with high levels of insecticidal activity are those of formula (II-4b), having the structure of formula (II-4), wherein:

X, $R^1$, $R^2$, $R^3$, Y, $X^1$, $X^2$, $X^3$, and $X^4$ have the definitions provided in formula (II-1b); and the preferred named compounds are identified as D-1 to D-31, above for formula (II-1b), more preferably D-3, -4, -5, -6, -7, -8, -12, -13, -23, -24, -27, -29, -30 and -31.

As still a further preferred part of this invention, pesticidal 1-arylpyrrole compounds, pesticidal compositions and pesticidal methods of use of compounds of formula (Ia-1), with particular insecticidal and acaricidal interest are those wherein the compounds are:

EE) Pesticidal compounds of formula (Ia-1), with particularly high levels of insecticidal activity are those of formula (II-7), having the structure of formula (Ia-1), wherein:

X is a group $R^5S(O)_n$, in which n is 0, 1 or 2 and $R^5$ is: alkyl, preferably $C_{1-4}$ alkyl and more preferably methyl; or haloalkyl, preferably trihalomethyl or dihalomethyl in which halo is F, Cl, or Br or combinations thereof, e.g. $CF_3$, $CCl_3$, $CF_2Cl$, $CFCl_2$, $CF_2Br$, $CHF_2$, $CHClF$, or $CHCl_2$;

$R^1$ is selected from the group consisting of: hydrogen; alkyl; cyanoalkyl; haloalkyl; alkylthio; alkylsulfinyl; alkylsulfonyl; aralkylthio, preferably aralkyl- is benzyl; aralkylsulfinyl, preferably aralkyl- is benzyl; aralkylsulfonyl, preferably aralkyl- is benzyl; alkenylthio; alkynylthio; phenylthio; phenylsulfinyl; phenylsulfonyl; heteroarylthio; heteroarylsulfinyl; heteroarylsulfonyl; alkoxy; alkenyloxy, preferably allyloxy; alkynyloxy, preferably propargyloxy; alkoxyalkyl; and alkylthioalkyl; and wherein the phenyl and heteroaryl portions in the aforementioned groups are optionally substituted as defined in formula (Ia-1) above; and the aralkyl portions in the aforementioned groups are optionally substituted phenyl and optionally substituted heteroaryl as also defined in formula (Ia-1) above;

$R^2$ is cyano;

$R^3$ is selected from the group consisting of: halogen; cyano; alkyl; haloalkyl; alkoxy; alkenyloxy, particularly allyloxy; alkynyloxy, particularly propargyloxy; and alkoxyalkyl;

Y is selected from the group consisting of: halogen, trifluoromethyl, and trifluoromethoxy;

$X^1$ is selected from the group consisting of: hydrogen; halogen; alkyl; alkoxy; alkylthio; alkylsulfinyl; and alkylsulfonyl;

$X^2$ and $X^3$ are hydrogen;

$X^4$ is halogen; and provided:

that if $R^3$ is halogen or completely halo substituted haloalkyl, then $R^1$ is other than hydrogen or $X^1$ is alkyl, alkoxy, alkylthio, alkylsulfinyl or alkylsulfonyl.

Among these compounds, preferred compounds are:

EE-1   1-(2,6-dichloro-4-trifluoromethylphenyl)-2-chloro-3-cyano-4-(trifluoromethylthio)-5-(methylthio)pyrrole;

EE-2   1-(2,6-dichloro-4-trifluoromethylphenyl)-2-chloro-3-cyano-4-(trifluoromethylthio)-5-(methylsulfinyl)pyrrole;

EE-3   1-(2,6-dichloro-4-trifluoromethylphenyl)-2-chloro-3-cyano-4-(dichlorofluoromethylthio)-5-(methylthio)pyrrole;

EE-4   1-(2,6-dichloro-4-trifluoromethylphenyl)-2-chloro-3-cyano-4-(dichlorofluoromethylthio)-5-(methylsulfonyl)pyrrole;

EE-5   1-(2,6-dichloro-4-trifluoromethylphenyl)-2-chloro-3-cyano-4-(dichlorofluoromethylthio)-5-(methylsulfinyl)pyrrole;

EE-6   1-(2,6-dichloro-4-trifluoromethylphenyl)-2-chloro-3-cyano-4-(trifluoromethylsulfinyl)-5-(2-cyanoethyl)pyrrole;

EE-7   1-(2,6-dichloro-4-trifluoromethylphenyl)-2-difluoromethyl-3-cyano-4-(trifluoromethylthio)pyrrole;

EE-8  1-(2,6-dichloro-4-trifluoromethylphenyl)-2-methyl-3-cyano-4-(trifluoromethylthio)pyrrole;

EE-9  1-(2,6-dichloro-4-trifluoromethylphenyl)-2-methyl-3-cyano-4-(trifluoromethylsulfinyl)pyrrole;

EE-10   1-(2,6-dichloro-4-trifluoromethylphenyl)-2-methyl-3-cyano-4-(trifluoromethylsulfonyl)pyrrole;

EE-11   1-(2,6-dichloro-4-trifluoromethylphenyl)-2-difluoromethyl-3-cyano-4-(trifluoromethylsulfinyl)pyrrole;

EE-12 1-(2,6-dichloro-4-trifluoromethylphenyl)-2-difluoromethyl-3-cyano-4-(trifluoromethylsulfonyl)pyrrole;

EE-13 1-(2,6-dichloro-4-trifluoromethylphenyl)-2-difluoromethyl-3-cyano-4-(dichlorofluoromethylthio)pyrrole;

EE-14 1-(2,6-dichloro-4-trifluoromethylphenyl)-2-difluoromethyl-3-cyano-4-(dichlorofluoromethylsulfonyl)pyrrole;

EE-15 1-(2,6-dichloro-4-trifluoromethylphenyl)-2-difluoromethyl-3-cyano-4-(dichlorofluoromethylsulfinyl)pyrrole;

EE-16 1-(2,6-dichloro-4-trifluoromethylphenyl)-2-chloro-3-cyano-4-(dichlorofluoromethylsulfinyl)-5-(methylthio)pyrrole;

EE-17 1-(2,6-dichloro-4-trifluoromethylphenyl)-2-fluoromethyl-3-cyano-4-(trifluoromethylthio)pyrrole;

EE-18 1-(2,6-dichloro-4-trifluoromethylphenyl)-2-fluoromethyl-3-cyano-4-(trifluoromethylsulfonyl)pyrrole;

EE-19 1-(2,6-dichloro-4-trifluoromethylphenyl)-2-fluoromethyl-3-cyano-4-(trifluoromethylsulfinyl)pyrrole;

EE-20 1-(2,6-dichloro-4-trifluoromethylphenyl)-2-chloro-3-cyano-4-(chlorodifluoromethylthio)-5-(methylthio)pyrrole;

EE-21 1-(2,6-dichloro-4-trifluoromethylphenyl)-2-methyl-3-cyano-4-(dichlorofluoromethylthio)pyrrole;

EE-22 1-(2,6-dichloro-4-trifluoromethylphenyl)-2-methyl-3-cyano-4-(dichlorofluoromethylsulfinyl)pyrrole; and EE-23 1-(2,6-dichloro-4-trifluoromethylphenyl)-2,5-dimethyl-3-cyano-4-(dichlorofluoromethylthio)pyrrole.

Of the above compounds, even more preferred compounds are EE-2, -3, -5, -7, -8, -9, -13, -14, -15, -16, -19, -20, -21, -22, and -23.

FF) Compounds of formula (Ia-1), particularly with surprisingly high levels of acaricidal activity, are those of formula (II-8), having the structure of formula (Ia-1), wherein:

X is halogen or a group $R^5S(O)_n$, in which n is 0, 1, or 2 and $R^5$ is selected from the groups consisting of: alkyl, preferably $C_{1-4}$ alkyl; haloalkyl, preferably trihalomethyl or dihalomethyl, in which halo is F, Cl or Br or combinations thereof, e.g., $CF_3$, $CCl_3$, $CF_2Cl$, $CFCl_2$, $CF_2Br$, $CHF_2$, $CHClF$, or $CHCl_2$; alkenyl, preferably $C_{2-4}$ alkenyl; and haloalkenyl, preferably $C_{2-4}$ haloalkenyl;

$R^1$ is selected from the group consisting of: halogen; alkylthio; alkylsulfinyl; alkylsulfonyl; alkyl; alkenyl; alkynyl; haloalkyl; haloalkenyl; haloalkynyl; alkylamino; dialkylamino; alkenylamino, preferably allylamino; alkynylamino, preferably propargylamino; alkylcarbonylamino; haloalkylcarbonylamino; alkylideneimino; benzylideneimino; alkoxyalkylideneimino; and dialkylaminoalkylideneimino; and wherein the alkyl, alkenyl, alkynyl and alkoxy portions of these groups herein are linear or branched chains, having less than 10 carbon atoms, preferably less than 5 carbon atoms, and the halo substitution in all the aforementioned groups herein consists of one or more halogen atoms, which are the same or different, from mono substitution up to complete poly substitution;

$R^2$ is cyano;

$R^3$ is hydrogen;

Y is hydrogen or halogen; and $X^1$, $X^2$, $X^3$, and $X^4$ are individually selected from the group consisting of: hydrogen; halogen; $C_{1-3}$ alkyl; $C_{1-3}$ alkoxy; and $C_{1-3}$ alkylthio; and preferably $X^1$ and $X^4$ are individually selected from the group consisting of hydrogen, fluorine, chlorine, bromine, and methyl and preferably $X^2$ and $X^3$ are each hydrogen.

Among these compounds, more preferred compounds are:

FF-1 2-bromo-3-(chlorodifluoromethylthio)-4-cyano-1-(2,4,6-trichlorophenyl)pyrrole;

FF-2 2-bromo-3-(chlorodifluoromethylsulfinyl)-4-cyano-1-(2,4,6-trichlorophenyl)pyrrole;

FF-3 2-bromo-4-cyano-3-(dichlorofluoromethylthio)-1-(2,4,6-trichlorophenyl)pyrrole;

FF-4 2-bromo-4-cyano-3-(dichlorofluoromethylsulfinyl)-1-(2,4,6-trichlorophenyl)pyrrole;

FF-5 4-cyano-3-(dichlorofluoromethylthio)-2-(methylthio)-1-(2,4,6-trichlorophenyl)pyrrole; and FF-6 4-cyano-3-(dichlorofluoromethylthio)-2-ethoxymethylideneimino-1-(2,4,6-trichlorophenyl)pyrrole.

A third aspect of this invention embraces particular intermediate compounds, their preparation, and use of said intermediate compounds in processes to prepare pesticidal 1-arylpyrrole compounds of general formula (I), i.e. (Ia), (Ia-1), (Ib), (Ib-2), (Ic), or (Ic-1).

The first intermediate compounds are 1-(N,N-dialkylamino)-2,3-dicyanoprop-1-enes of formula (IVa), which may exist as tautomers and their geometric isomers or mixtures thereof:

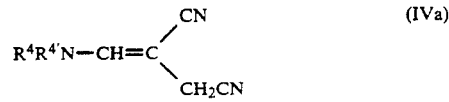

wherein: $R^4$ and $R^{4'}$ are the same or different and are individually selected from the group consisting of: optionally substituted alkyl of less than 10 carbon atoms, preferably less than 5 carbon atoms, which is linear or branched chain; optionally substituted benzyl; optionally substituted cycloalkyl, preferably less than 7 carbon atoms and optionally substituted heterocyclic group which is a five or six membered monocyclic ring containing one or two of the same or different oxygen, sulfur or nitrogen hetero atoms; or $R^4$ and $R^{4'}$ as defined above are joined together to form a heteroarylcyclic group; and wherein the optional substitution for any of the groups herein defined, is as defined for the optional substitution of member groups of $R^1$, $R^2$, and $R^3$ in formula (Ia) above.

Specifically preferred novel compounds of formula (IVa) are:

1-(N,N-dimethylamino)-2,3-dicyanoprop-1-ene;
1-(N,N-diethylamino)-2,3-dicyanoprop-1-ene;
1-(N,N-di-n-butylamino)-2,3-dicyanoprop-1-ene;
1-(N-benzyl-N-methylamino)-2,3-dicyanoprop-1-ene;
1-(piperidin-1-yl)-2,3-dicyanoprop-1-ene;
1-(pyrrolidin-1-yl)-2,3-dicyanoprop-1-ene; and
1-(morpholin-1-yl)-2,3-dicyanoprop-1-ene.

The above first intermediate compounds of formula (IVa) are then reacted with an appropriately substituted aniline of formula (V), as subsequently defined below, to obtain, via transenamination, 1-(substituted phenylamino)-2,3-dicyanoprop-1-enes of formula (IVb), which may likewise exist as tautomers or geometric isomers or mixtures thereof,

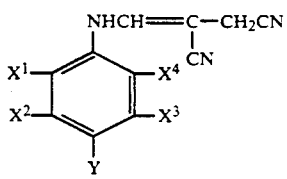
(IVb)

wherein: $X^1$, $X^2$, $X^3$, $X^4$ and Y are as defined above in compounds of formula (Ia).

The above compounds of formula (IVb) are novel provided:
that if one of $X^1$, $X^2$, $X^3$, $X^4$ and Y is Cl, $OCH_3$ or $CH_3$, then at least one of the others is different from H; and
that at least one of $X^1$, $X^2$, $X^3$, $X^4$, and Y is different from H.

More preferred compounds of formula (IVb) are compounds wherein:
Y is H, F, Cl, Br, $CF_3$ or $OCF_3$;
$X^1$ and $X^4$ are individually H, F, Cl, Br, $CH_3$, $OCH_3$, or $SCH_3$;
$X^2$ and $X^3$ are each H; and provided:
that if $X^1$ and $X^4$ are each H, then Y is other than H or Cl; and
that if $X^1$ or $X^4$ is Cl, $OCH_3$ or $CH_3$ and the other is H, then Y is different from H.

The compounds of formula (IVb) are then further reacted to obtain intermediate 1-(substituted phenyl)-2-amino-4-cyanopyrrole compounds of formula (IIIa)

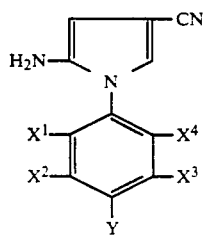
(IIIa)

wherein: $X^1$, $X^2$, $X^3$, $X^4$, and Y are as defined above in compounds of formula (Ia).

The above compounds of formula (IIIa) are novel provided:
that if one of $X^1$, $X^2$, $X^3$, $X^4$, and Y is Cl, $OCH_3$ or $CH_3$, then at least one of the others is different from H; and
that at least one of $X^1$, $X^2$, $X^3$, $X^4$ and Y is different from H.

More preferred novel compounds of formula (IIIa) are compounds of formula (IIIb)

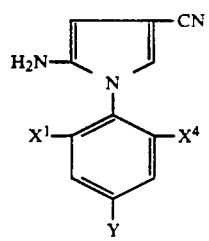
(IIIb)

wherein:

Y is H, F, Cl, Br, $CF_3$ or $OCF_3$;
$X^1$ and $X^4$ are individually H, F, Cl, Br, $CH_3$, $OCH_3$, or $SCH_3$; and provided:
that if $X^1$ and $X^4$ are each H, then Y is other than H or Cl; and
that if $X^1$ or $X^4$ is Cl, $OCH_3$ or $CH_3$ and the other is H, then Y is different from H.

While only those compounds of formulae (IVb) and (IIIa), which are novel are claimed as intermediate compounds as part of this invention, all compounds within the definitions provided above for these formulae are still useful as intermediates in processes to prepare the novel pesticidal 1-arylpyrrole compounds as defined by general formula (I) above.

Still further intermediates and processes to obtain said intermediates comprise an additional part of this invention to ultimately prepare pesticidal 1-arylpyrrole compounds of general formula (I) as defined above. The following more specifically describes two different disulfide processes and intermediates contained therein.

The first disulfide process for the preparation of compounds of general formula (I), most broadly compounds of formula (Ia), wherein $R^1$, $R^2$, $R^3$, Y, $X^1$, $X^2$, $X^3$ and $X^4$ are therein defined and X is a perhaloalkylthio group, comprises the steps of:

a) reacting a compound of formula (XXXVIII)

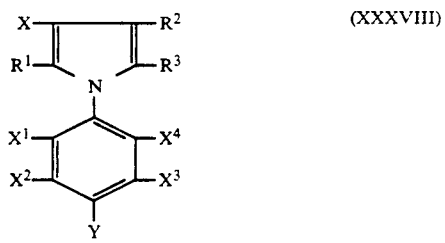
(XXXVIII)

wherein X is hydrogen, with chlorosulfonic acid at a temperature between 0° C. and 150° C. and optionally in a organic solvent, to prepare a compound of formula (XXXIX)

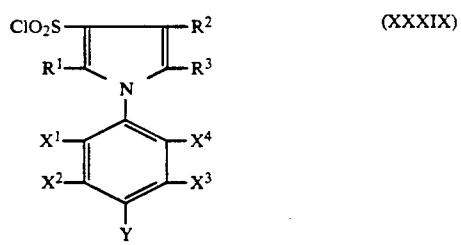
(XXXIX)

wherein X is $-SO_2Cl$ and $R^1$, $R^2$, $R^3$, Y, $X^1$, $X^2$, $X^3$ and $X_4$ are as defined for formula (Ia);

b) reacting the compound of formula (XXXIX), wherein X is $-SO_2Cl$, with a reducing agent at a temperature between 0° C. and 110° C. in an organic solvent to form the disulfide compound of formula (XLI)

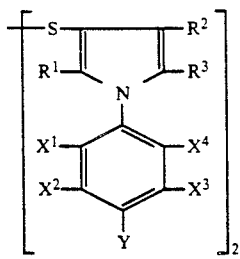

wherein $R^1$, $R^2$, $R^3$, Y, $X^1$, $X^2$, $X^3$ and $X^4$ are as defined for formula (Ia); and c) reacting the disulfide compound of formula (XLI), wherein $R^1$, $R^2$, $R^3$, Y, $X^1$, $X^2$, $X^3$ and $X^4$ are as defined for formula (Ia), with a perhaloalkane of formula $ZCFR^7R^8$, in which Z is Cl, Br or I, $R^7$ is F, Cl or Br, and $R^8$ is F, Cl, Br or a perfluoroalkyl group, in the presence of a free radical promoting reducing agent and optionally in the presence of a base, in an organic solvent at a temperature from about 0° C. to about 85° C. and optionally under pressure, to prepare the pesticidal compound of formula (Ia), wherein X is a perhaloalkylthio group and $R^1$, $R^2$, $R^3$, Y, $X^1$, $X^2$, $X^3$ and $X^4$ are as defined.

The intermediate compounds of formulae (XXXIX) and (XLI) as defined above in the first disulfide process are contemplated by this invention.

A second disulfide process for the preparation of compounds of general formula (I), most broadly compounds of formula (Ia), wherein $R^1$, $R^2$, $R^3$, Y, $X^1$, $X^2$, $X^3$ and $X^4$ are therein defined and X is a perhaloalkylthio group, comprises the steps of:

a) reacting a compound of formula (IIIa)

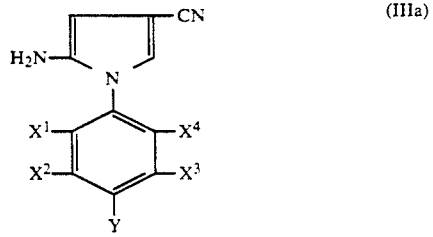

wherein $X^1$, $X^2$, $X^3$, $X^4$ and Y are as defined for formula (Ia), with sulfur monochloride at a temperature between about −100° C. to about 25° C., optionally in an organic solvent, to prepare a disulfide compound of formula (XLI)

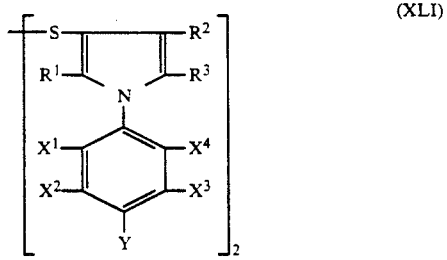

wherein:
$X^1$, $X^2$, $X^3$, $X^4$ and Y are as defined for formula (Ia);
$R^1$ is amino;
$R^2$ is cyano; and
$R^3$ is hydrogen; and b) reacting the disulfide compound of formula (XLI) above, wherein:
$X^1$, $X^2$, $X^3$, $X^4$ and Y are as defined for formula (Ia);
$R^1$ is amino;
$R^2$ is cyano; and
$R^3$ is hydrogen;
with a perhaloalkane of formula $ZCFR^7R^8$, in which Z is Cl, Br or I, $R^7$ is F, Cl or Br, and $R^8$ is F, Cl, Br or a perfluoroalkyl group, in the presence of sodium formate and sulfur dioxide as a free radical promoting reducing agent medium and optionally in the presence of a base, in an organic solvent at a temperature from about 0° C. to about 85° C. and optionally under pressure, to prepare the pesticidal compound of formula (Ia), wherein:
X is a perhaloalkylthio group;
$R^1$ is amino;
$R^2$ is cyano;
$R^3$ is hydrogen; and
$X^1$, $X^2$, $X^3$, $X^4$ and Y are as defined for formula (Ia).

The intermediate disulfide compound of formula (XLI) as defined above in the second disulfide process is also contemplated by this invention.

An object of the present invention is to provide new pesticides, especially insecticides and acaricides, of the pyrrole family.

Another object of the present invention is to provide very active compounds, with broad spectrum pesticidal activity, as well as compounds with selective special activity, e.g., aphicidal, miticidal, foliar insecticidal, soil insecticidal and nematicidal, systemic, antifeeding, or pesticidal activity via seed treatment.

Another object of the present invention is to provide pesticidal compositions and pesticidal methods of use for the pesticidal pyrrole compounds, particularly in agricultural or horticultural crops, forestry, veterinary medicine or livestock husbandry, or in public health.

Another object of the present invention is to provide compounds with a rather simple chemical formula.

Still a further object is to provide intermediate compounds and processes to make the pesticidal pyrrole compounds of the invention.

These and other objects of the invention, in total or in part obtained with the new compounds hereafter defined, shall become readily apparent from the detailed description of the present invention.

DESCRIPTION OF THE PREFERRED EMBODIMENTS

METHODS OR PROCESSES OF SYNTHESIS

The compounds of general formula (I), i.e., (Ia), (Ia-1), (Ib), (Ib-1), (Ic) or (Ic-1), can be prepared by the application or adaptation of known methods (i.e. methods heretofore used or described in the chemical literature): generally pyrrole ring formation followed where necessary by changing substituents. It is to be also understood that, in the description of the following process methods the sequences for the introduction of the various groups on the pyrrole ring may be performed in a different order and that suitable protecting groups may be required as will be apparent to those skilled in the art. Also compounds of general formula (I) may be converted by known methods into other compounds of general formula (I).

In the following description of process methods when symbols appearing in formulae are not specifically defined, it is to be understood that they are "as herein before defined" in accordance with the first definition of each symbol in this specification. The term "protection" shall include conversion to a suitable non-reactive group which may be reconverted when desired, as well as the addition of groups which render the functionality non-reactive. Within the process definitions, unless otherwise stated, amino refers to the unsubstituted amino group.

METHOD 1

According to a feature of the invention, the compounds of general formula (IIIa), in which $X^1$, $X^2$, $X^3$, $X^4$ and Y have the same definitions as that shown in the general definition of the invention,

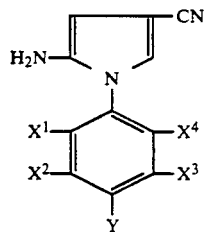

(IIIa)

may be prepared from dicyanoprop-1-ene derivatives of formula (IVb)

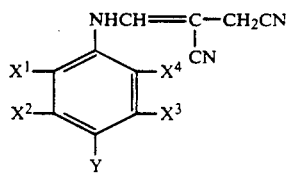

(IVb)

(in which the various symbols are as hereinbefore defined) by reaction with a basic agent, preferably an organic base such as a tertiary amine or amidine, or a hydroxide or carbonate of an alkali metal. The reaction is advantageously carried out between −80° and 150° C., preferably 40° to 100° C. Solvents may be used, such as liquid alcohols, hydrocarbons, halohydrocarbons, ethers, ketones, amides such as N-methyl pyrrolidone, and water.

METHOD 2

According to another feature of the invention, the compounds of formula (IVb) may be prepared from an aniline of formula (V), wherein $X^1$, $X^2$, $X^3$, $X^4$ and Y have the same definitions as shown in general formula (I) of the invention,

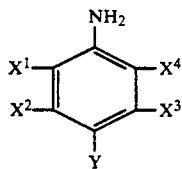

(V)

by reaction with formylsuccinonitrile (i.e. 1-hydroxy-2,3-dicyanoprop-1-ene) or an alkali metal salt of formylsuccinonitrile. This reaction is generally carried out in an organic solvent or in water at a temperature between 10° and 120° C., preferably at reflux temperature.

Formylsuccinonitrile is a known compound, generally made by acidification of its alkaline salt which is obtained by reaction of succinonitrile with a lower alkyl formate in the presence of an alkaline agent according to C. A. Grob and P. Ankli, Helv. Chim. Acta, 1950, 33, 273.

The compounds of formula (IVb) are alternatively prepared from compounds of formula (IVa),

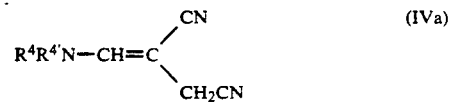

(IVa)

wherein $R^4$ and $R^{4'}$ are as described under Summary of the Invention, by a transenamination reaction with an appropriately substituted aniline of formula (V) as defined above. The reaction is conducted at a temperature in the range from about 0° C. to about 100° C., in the presence of an organic or inorganic acid, and in a suitable solvent, such as the above acid or inert polar organic solvents, e.g. amides, sulfoxides, sulfones, and ethers. The acid can be either a common anhydrous strong mineral acid such as hydrochloric acid or sulfuric acid, or an anhydrous strong organic acid such as trifluoroacetic acid, para-toluenesulfonic acid, methanesulfonic acid or trifluoromethanesulfonic acid. The quantity of acid required for this reaction is within the range of about one molar equivalent to a large excess. In some cases such as with trifluoroacetic acid, methanesulfonic acid or trifluoromethanesulfonic acid, the acid itself can be the solvent of the reaction.

The new compounds of formula (IVa) of this invention can be prepared by reacting the potassium salt of 1-hydroxy-2,3-dicyanoprop-1-ene with an appropriate amount of a salt of the N,N-dialkylamine of a formula $HNR^4R^{4'}$ ($R^4$ and $R^{4'}$ are as described above) in a suitable solvent system. Suitable diluents are organic acids, inert polar organic solvents such as amides, alcohols, sulfoxides, sulfones and ethers alone, or in a mixture with inert apolar halogenated aliphatics (1,2-dichloroethane), and optionally substituted aromatics (toluene and chlorobenzene). Suitable reaction temperatures are between about 20° C. and about 150° C. The potassium salt of 1-hydroxy-2,3-dicyanoprop-1-ene is prepared by formylation of succinonitrile with an alkyl formate in the presence of an appropriate base as described above in METHOD 1 for the preparation of compounds of formula (IVb).

METHOD 3

Compounds of general formula (I) in which X is halogen, $R^1$ is amino, $R^2$ is cyano and $R^3$ is hydrogen and the other substituents have the meaning described in the general description of the invention may be prepared by treating compounds of general formula (IIIa) with halogenating agents such as sulfuryl chloride, N-chlorosuccinimide, N-bromosuccinimide, N-iodosuccinimide, pyridinium bromide perbromide or molecular fluorine, chlorine, bromine or iodine. Suitable organic solvents for these transformations include dichloromethane and acetonitrile. The reactions are carried out between −80° C. and +80° C., preferably between −50° C. and +25° C. It may be advantageous to protect the amino group as the trifluoroacetamide derivative during treatment with elemental fluorine.

METHOD 4

A) Compounds of general formula (I) in which X is a cyano group, $R^1$ is amino, $R^2$ is cyano and $R^3$ is hydrogen and the other substituents have the meanings described in the general description of the invention, may be obtained from the corresponding compounds in which X is a group CH=NOH by dehydration with agents such as acetic anhydride, cyanuric chloride, $P_2O_5$ and the like. With certain of these dehydrating agents it may be necessary to protect the amino group with a suitable protecting group.

B) The intermediate compounds above in which X is a group CH=NOH may be obtained by condensation of hydroxylamine with the corresponding compounds in which X is formyl.

C) The intermediate compounds in which X is a formyl group, that is to say compounds of formula (VI), may be obtained by hydrolysis of the corresponding compounds in which X is a bis(alkylthio)methyl or bis(arylthio)methyl group or treatment with a suitable alkyl nitrite followed by hydrolysis according to E. Fujita, K. Ichikawa and K. Fuji, *Tetrahedron Letters* 1978, 3561. Protection of the amino function with an appropriate protecting group may be necessary during the reaction with alkyl nitrites.

D) The intermediate compounds of general formula (I) in which X is a bis(alkylthio)methyl or bis(arylthio)methyl group, and the other groups are defined as above may be prepared by reaction of a compound of general formula (IIIa) with a tris(alkylthio)methane or tris(arylthio)methane in the presence of a Lewis acid, preferably a sulfonium salt such as dimethyl(methylthio)sulfonium tetrafluoroborate. General conditions for such transformations may be found in *Synthesis* 1984, 166.

METHOD 5

A) Useful intermediate compounds of general formula (I) in which X is hydroxy, $R^1$ is an optionally protected amino group, $R^2$ is a cyano group, $R^3$ is a hydrogen atom and $X^1$, $X^2$, $X^3$, $X^4$ and Y have the definitions shown in the definition of general formula (I) of the invention may be prepared from the corresponding compounds in which X is halogen by conversion to a Grignard reagent or a lithium derivative by standard methods followed by treatment with oxodiperoxymolybdenum(pyridine)(hexamethylphosphoric triamide) (MoOPH) by procedures similar to those described by N. J. Lewis et. al. in *J. Org. Chem.* 1977, 42, 1479. It may be necessary to convert the cyano group in the compound above in which X is halogen to an appropriately protected derivative (for example an oxazoline derivative of the corresponding compound in which the cyano group has been hydrolyzed to a carboxylic acid) prior to formation of the Grignard reagent or lithium derivative. Alternatively, the Grignard reagent or lithium derivative described above may be reacted with a trialkyl borate followed by oxidation with hydrogen peroxide by a procedure analogous to that described by M. F. Hawthorne in *J. Org. Chem.* 1957,22, 1001 or R. W. Hoffmann and K. Ditrich in *Synthesis* 1983, 107.

B) Compounds of general formula (I) in which X is cyanato, $R^1$ is amino, $R^2$ is a cyano group, $R^3$ is a hydrogen atom and $X^1$, $X^2$, $X^3$, $X^4$ and Y have the definitions shown in the general definition of formula (I) of the invention may be prepared from the corresponding compounds in which X is hydroxy, $R^1$ is an optionally protected amino group, $R^3$ is a hydrogen atom and $X^1$, $X^2$, $X^3$, $X^4$ and Y have the definitions shown in the definition of general formula (I) of the invention by treatment with cyanogen halides in the presence of a base by methods similar to those described by D. Martin and M. Bauer in *Org. Synth.* 61, 35, followed by a deprotection step, if necessary.

C) Compounds of general formula (I) in which X is alkoxy, $R^1$ is amino, $R^2$ is a cyano group, $R^3$ is a hydrogen atom and $X^1$, $X^2$, $X^3$, $X^4$ and Y have the definitions shown in general formula (I) of the invention may be prepared from the corresponding compounds in which X is hydroxy, $R^1$ is an optionally protected amino group, $R^3$ is a hydrogen atom and $X^1$, $X^2$, $X^3$, $X^4$ and Y have the definitions shown in general formula (I) of the invention by treatment with an alkyl halide, alkyl sulfonates, dialkyl sulfates and the like, optionally in the presence of a base in a solvent such as acetone or dimethylformamide at a temperature between 25° C. and the reflux temperature of the solvent followed by a deprotection step, if necessary.

D) Compounds of general formula (I) in which X is haloalkoxy, $R^1$ is amino, $R^2$ is a cyano group, $R^3$ is a hydrogen atom and $X^1$, $X^2$, $X^3$, $X^4$ and Y have the definitions shown in general formula (I) of the invention may be prepared from the corresponding compounds in which X is hydroxy, $R^1$ is an optionally protected amino group, $R^3$ is a hydrogen atom and $X^1$, $X^2$, $X^3$, $X^4$ and Y have the definitions shown in general formula (I) of the invention by various haloalkylation methods described in *Syntheses of Fluoroorganic Compounds*; Knunyants, I. L. and Yakobson, G. G., Ed.; Springer-Verlag: Berlin, 1985; pp 263-269, followed by a deprotection step, if necessary.

METHOD 6

Compounds of general formula (I) in which X is a haloalkyl group, $R^1$ is an amino group, $R^2$ is a cyano group, $R^3$ is a hydrogen atom and $X^1$, $X^2$, $X^3$, $X^4$ and Y have the definitions shown in general formula (I) of the invention may be prepared from the corresponding compounds in which X is a formyl group, a carboxylic acid function or a halogen and the amino group is optionally protected. For example, treatment of the formyl compounds with diethylaminosulfur trifluoride in a manner analogous to that described by W. J. Middleton in *J. Org. Chem.* 1975, 40, 574 provides compounds of general formula (I) in which X is a difluoromethyl group and the other substituents are defined as above. Oxidation of the above mentioned intermediate compounds of general formula (I) in which X is formyl with oxidizing agents such as chromium trioxide in sulfuric acid (Jones' reagent) provides intermediate compounds of general formula (I) in which X is a carboxylic acid function, $R^1$ is an amino group, $R^2$ is a cyano group, $R^3$ is a hydrogen atom and $X^1$, $X^2$, $X^3$, $X^4$ and Y have the definitions shown in general formula (I) of the invention. It may be advantageous to protect the amino function as, for example, the trifluoroacetamide derivative during such oxidation reactions. Reaction of the compounds above in which X is a carboxylic acid group with sulfur tetrafluoride as described by G. A. Boswell et. al. *Org. React.* 1974, 21, 1-124 provides compounds in which X is a trifluoromethyl group and the other groups are defined as above.

Alternatively, compounds of general formula (I) in which X is trifluoromethyl, $R^1$ is an amino group, $R^2$ is a cyano group, $R^3$ is a hydrogen atom and $X^1$, $X^2$, $X^3$, $X^4$ and Y have the definitions shown in general formula (I) of the invention may be prepared from compounds of general formula (I) in which X is halogen, preferably iodine, and the other substituents are as defined above by reaction with trifluoromethyl copper under conditions similar to those described by D. J. Burton and D. M. Wiemers in *J. Am. Chem. Soc.* 1986, 108, 832.

METHOD 7

Compounds of general formula (I) in which X is a bromomethyl or chloromethyl group, $R^1$ is an amino group, $R^2$ is a cyano group, $R^3$ is a hydrogen atom and $X^1$, $X^2$, $X^3$, $X^4$ and Y have the definitions shown in general formula (I) of the invention may be obtained by treatment of the corresponding intermediate compounds in which X is a methyl group and the amino group is optionally protected, with N-bromosuccinimide or N-chlorosuccinimide in solvents such as carbon tetrachloride at temperatures between 0° C. and the reflux temperature of the solvent. The compounds above in which X is a methyl group may be obtained from the intermediate compounds of general formula (I) in which X is formyl and the other substituents are as described above by sequential treatment with p-toluenesulfonylhydrazine and sodium cyanoborohydride, according to a method similar to that described in *J. Am. Chem. Soc.* 1971, 93, 1793.

METHOD 8

A) Compounds of general formula (I) in which X is haloalkylcarbonyl, $R^1$ is an amino group, $R^2$ is a cyano group, $R^3$ is a hydrogen atom and $X^1$, $X^2$, $X^3$, $X^4$ and Y have the definitions shown in general formula (I) of the invention, that is to say compounds of formula (VIII), may be obtained by sequential treatment of the corresponding compounds (VI) in which the amino group is optionally protected, with a haloalkylmetal derivative to provide compounds of formula (VII) in which X is a haloalkylcarbinol, followed by oxidation according to the method of R. J. Linderman and D. M. Graves described in *Tetrahedron Lett.* 1987, 28, 4259 and a deprotection step, if necessary. Suitable haloalkylmetal derivatives include perfluoroalkyl lithium derivatives prepared according to P. G. Gassman and N. J. O'Reilly, *J. Org. Chem.*, 1987, 52, 2481-2490 or trimethyltrifluoromethylsilane prepared and used according to G. A. Olah et. al. *J. Am. Chem. Soc.* 1989, 111, 393. References to other haloalkyl metal derivatives may also be found in this reference. With trimethyltrifluoromethylsilane, this process may be illustrated as follows:

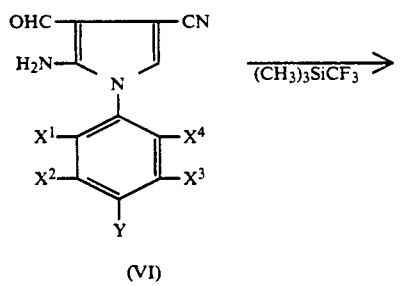

(VI)

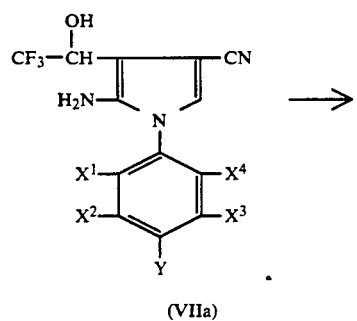

(VIIa)

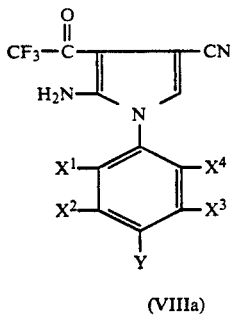

(VIIIa)

B) The compounds of formula (VIII) may be converted to compounds of general formula (I) in which X is a haloalkylthiocarbonyl group, $R^1$ is an amino group, $R^2$ is a cyano group, $R^3$ is a hydrogen atom and $X^1$, $X^2$, $X^3$, $X^4$ and Y have the definitions shown in general formula (I) of the invention by treatment with [2,4-bis(4-methoxyphenyl)-1,3-dithia-2,4-diphosphetane-2,4-disulfide] Lawesson's Reagent).

METHOD 9

The compounds of formula (VII) may be converted to other compounds of general formula (I) in which X represents α-haloalkyl-α-halomethyl groups by treatment with halogenating agents such as thionyl chloride or hydrogen bromide. It may be advantageous to protect the amino function as, for example, a trifluoroacetamide derivative to prevent halogenation of the pyrrole ring during such halogenations.

METHOD 10

A) Compounds of general formula (I) in which X is thiocyanato, $R^1$ is an amino group, $R^2$ is a cyano group, $R^3$ is a hydrogen atom and $X^1$, $X^2$, $X^3$, $X^4$ and Y have the definitions shown in general formula (I) of the invention may be prepared by treatment of compounds of general formula (IIIa) with MSCN wherein M is an alkali metal in the presence of bromine in a solvent such as methanol.

B) Compounds of general formula (I) in which X is an alkylthio, haloalkylthio, alkenylthio, haloalkenylthio, phenylthio or heteroarylthio group, $R^1$ is an amino group, $R^2$ is a cyano group and $R^3$ is a hydrogen atom and $X^1$, $X^2$, $X^3$, $X^4$ and Y have the definitions shown in general formula (I) of the invention and the phenyl and heteroaryl groups being constituted and/or substituted as described therein, that is to say compounds of formula (IX), may be prepared by reaction of a compound of general formula (IIIa) with a sulfenyl halide $R^5$SHal in which $R^5$ is an alkyl, haloalkyl, alkenyl, haloalkenyl, phenyl or heteroaryl group as defined above and Hal is a halogen atom, in a liquid reaction medium. Preferably an organic solvent, e.g. dichloromethane, is used at a temperature of −100° C. to +100° C., preferably −80° C. to +25° C. This reaction may be optionally carried out in the presence of an acid acceptor such as a tertiary amine, e.g. pyridine. The alkylsulfenyl chlorides may be prepared according to S. Thea and G. Cevasco, *Tetrahedron Letters*, 1988, 2865. When a sulfenyl chloride is used, the process may be represented by the following equation:

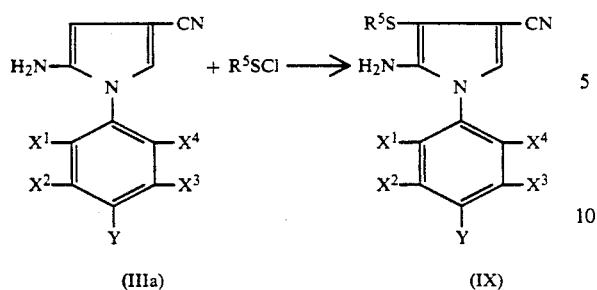

(IIIa)    (IX)

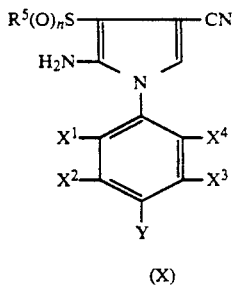

(X)

METHOD 11

Compounds of general formula (I) in which X is thiocyanato, R¹ is an amino group, R² is a cyano group, R³ is a hydrogen atom and X¹, X², X³, X⁴ and Y have the definitions shown in general formula (I) of the invention may be further converted to compounds of general formula (I) in which X is an alkylthio group, R¹ is an amino group, R² is a cyano group, R³ is hydrogen atom and X¹, X², X³, X⁴ and Y have the definitions shown in general formula (I) of the invention by treatment with a base such as sodium or potassium hydroxide in the presence of an alkyl halide, dialkylsulfate or the like in a solvent.

METHOD 12

Compounds of formula (IX) may be oxidized to provide compounds of formula (X) in which X is a group $R^5S(O)_n$, wherein n is 1 or 2 and $R^5$ is as hereinbefore defined. The oxidizing agents which may be used include hydrogen peroxide, peroxyacetic acid, trifluoroperoxyacetic acid and m-chloroperoxybenzoic acid in solvents such as dichloromethane, acetic acid or trifluoroacetic acid at temperatures between −40° C. and +80° C., preferably 0° C. to 25° C. The appropriate reaction conditions, i.e. temperature, length of reaction and amount of oxidant may be changed to provide the sulfinyl (n=1) or sulfonyl (n=2) derivatives as desired. It is also possible to prepare the sulfonyl derivatives from the sulfinyl compounds, as will be apparent to those skilled in the art. With certain haloalkylthio groups, for example trifluoromethylthio, it may be beneficial to protect the amino function as, for example, the trifluoroacetamide derivative. If, for example, trifluoroperoxyacetic acid is chosen as the oxidant, the process may be represented by the following equation:

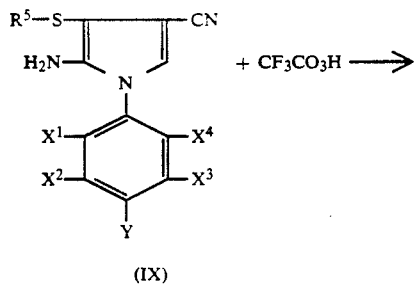

(IX)

METHOD 13

Compounds of general formula (I) in which R³ is halogen, alkenyloxy or alkynyloxy, R¹ is amino, R² is cyano, and X, X¹, X², X³, X⁴ and Y have the meanings given in general formula (I) of the invention may be prepared by treatment of compounds of general formula (I) in which R¹ is amino, R² is cyano, R³ is hydrogen and X, X¹, X², X³, X⁴ and Y have the definitions shown in general formula (I) of the invention, that is to say compounds of formula (XI), by treatment with halogenating agents under similar conditions as described in METHOD 3, except when X is thiocyanato halogenating systems other than sulfuryl chloride in ether should be used. The general transformation is as shown below:

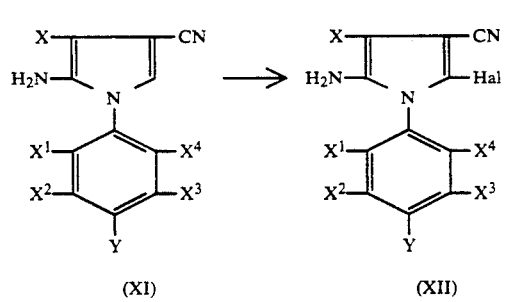

(XI)    (XII)

Hal = Halogen

The compounds of formula (XII), in which R³ is halogen are then optionally converted into the corresponding compounds in which R³ is hydroxy in a similar manner to that of METHOD 5A, these then are reacted with an appropriate haloalkenyl or haloalkynyl reactant such as a halide or optionally via a transetherification reaction with an appropriate alkenyl- or alkynylalkyl ether to give the compounds in which R3 is alkenyloxy or alkynyloxy.

METHOD 14

Compounds of general formula (I) in which R³ is a bis(alkylthio)methyl or bis(arylthio)methyl group, R¹ is amino, R² is cyano and X, X¹, X², X³, X⁴ and Y have the meanings given in general formula (I) of the invention may be prepared by reaction of a compound of formula (XI) with a tris(alkylthio)methane or tris(arylthio)methane, $(R^aS)_3CH$ in the presence of a Lewis acid, preferably a sulfonium salt, in a solvent, at a temperature between 0° C. and the reflux temperature of the solvent, optionally in the presence of an acid acceptor such as pyridine. A more preferred process employs acetonitrile as solvent at 25° C. with tris(methylthio)methane as the tris(alkylthio)methane and dimethyl(methylthio)sulfonium tetrafluoroborate as the Lewis acid without an acid acceptor. The process may be generally represented as shown below:

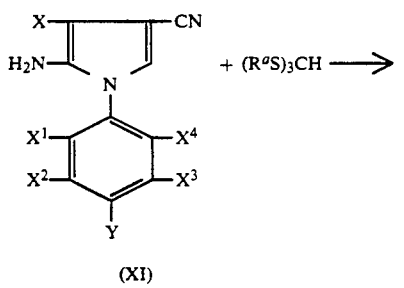

(XI)

METHOD 15

Useful intermediate compounds of general formula (I) in which $R^3$ is formyl, $R^1$ is amino, $R^2$ is cyano and X, $X^1$, $X^2$, $X^3$, $X^4$ and Y have the meanings given in general formula (I) of the invention, that is to say compounds of formula (XIV), may be prepared by hydrolyzing compounds of formula (XIII) or by treating with alkyl nitrites under similar conditions as discussed in METHOD 4C. The process may be generally represented as follows:

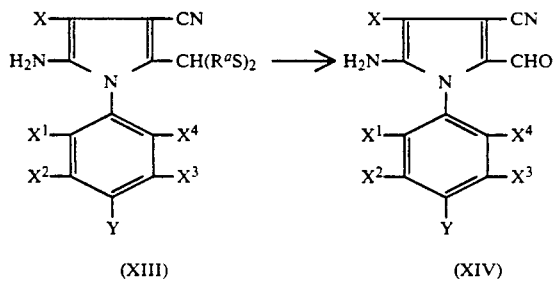

METHOD 16

Intermediate compounds of general formula (I) in which $R^3$ is hydroxyiminoalkylidenyl or alkoxyiminoalkylidenyl, $R^1$ is amino, $R^2$ is cyano and X, $X^1$, $X^2$, $X^3$, $X^4$ and Y have the meanings given in general formula (I) of the invention, useful as intermediates, may be prepared by condensation of a compound of general formula (I) in which $R^3$ is alkylcarbonyl or formyl, $R^1$ is amino, $R^2$ is cyano and X, $X^1$, $X^2$, $X^3$, $X^4$ and Y have the meanings given in general formula (I) of the invention with hydroxylamine or an O-alkylhydroxylamine or their acid addition salts in a solvent such as ethanol. The compounds above in which $R^3$ is alkylcarbonyl are prepared in the same manner as compounds (XIV) using ultimately a 1,1,1-tris(alkylthio or arylthio)alkane as a starting material.

METHOD 17

Useful intermediate compounds of general formula (I), in which $R^3$ is amino, $R^1$ is amino, $R^2$ is cyano and X, $X^1$, $X^2$, $X^3$, $X^4$ and Y have the meanings given in general formula (I) of the invention, may be prepared by reduction of the corresponding compounds in which $R^3$ is nitro with, for example, hydrogen in the presence of a noble metal catalyst such as platinum or palladium or with hydrazine and Raney nickel. With certain combinations of $R^2$ and X substituents, the compounds of formula (I) in which $R^1$ and $R^2$ are simultaneously amino may have limited stability and may require protection of one of the amino groups with a suitable protecting group. The intermediate compounds of general formula (I) in which $R^3$ is nitro, $R^1$ is amino, $R^2$ is cyano and X, $X^1$, $X^2$, $X^3$, $X^4$ and Y have the meanings given in general formula (I) of the invention may be prepared by nitration of compounds of formula (XI) through the action of nitric acid and sulfuric acid or nitric acid in acetic anhydride or other nitrating agents. It may be advantageous during certain nitration reactions to protect the amino function in (XI) with a suitable protecting group such as a acetyl or trifluoroacetyl.

METHOD 18

Various derivatives, useful as intermediates, of a compound of formula (XV) (vide infra) may be prepared by the following methods:

A) Compounds of general formula (I) in which $R^3$ is alkylamino, dialkylamino or aralkylamino, $R^1$ is amino, $R^2$ is cyano and X, $X^1$, $X^2$, $X^3$, $X^4$ and Y have the meanings given in general formula (I) of the invention may be prepared from the corresponding compounds in which $R^3$ is amino and the other substituents are defined as above by alkylation with alkyl or aralkyl halides or sulfonates in organic solvents such as ethanol, acetonitrile, toluene and the like. The production of mono- or dialkylated products may be controlled through manipulation of stoichiometry or reaction conditions. Alternatively, if monoalkylamine products are desired, other methods such as the conversion of the amino group to an alkoxyalkylideneimino group by treatment with an alkylorthoester followed by reduction may be employed. If the desired final products contain $R^1$ as the unsubstituted amino group, it may be necessary to protect the amino group prior to such treatment with a suitable protecting group. In such cases, a compound of general formula (I) in which $R^3$ is amino, $R^1$ is a suitably protected amino group and the other substituents are as defined above, that is to say a compound of formula (XV), is prepared and used as a reactant. The protecting group in (XV) is normally added prior to the nitro reduction step discussed in METHOD 17. Depending on the subsequent transformation intended for the amino group at $R^3$, various protecting groups may be chosen as will be seen in the following examples.

B) Compounds of general formula (I) in which $R^3$ is aminocarbonylamino, $R^1$ is amino, $R^2$ is cyano and X, $X^1$, $X^2$, $X^3$, $X^4$ and Y have the meanings given in general formula (I) of the invention may be prepared from compounds of formula (XV) by treatment with phosgene followed by ammonia followed by a deprotection step.

C) Compounds of general formula (I) in which $R^3$ is alkylcarbonylamino, haloalkylcarbonylamino, or arylcarbonylamino, $R^1$ is amino, $R^2$ is cyano and X, $X^1$, $X^2$, $X^3$, $X^4$ and Y have the meanings given in general formula (I) of the invention, may be prepared by reaction of a compound of formula (XV) with acid chlorides of formula $R^b(C=O)Cl$ or acid anhydrides of formula $[R^b(C=O)]_2O$ in which $R^b$ is an alkyl, haloalkyl or aryl group as defined in the first definition of general for-

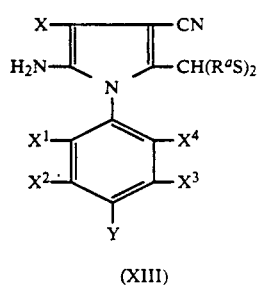

(XIII)

mula (I) followed by a deprotection step. Solvents such as acetonitrile may be used and acid acceptors such as pyridine may be employed under appropriate conditions.

D) Likewise, compounds of general formula (I) in which $R^3$ is alkylsulfonylamino or haloalkylsulfonylamino, $R^1$ is amino, $R^2$ is cyano and X, $X^1$, $X^2$, $X^3$, $X^4$ and Y have the meanings given in general formula (I) of the invention may be prepared from protected amino compounds of formula (XV) by reaction with alkyl or haloalkyl sulfonyl halides or sulfonic acid anhydrides under appropriate conditions followed by a deprotection step. Suitable amino protecting groups in such reactions include the alkoxyalkylideneimino group obtained by treatment of the amino compound with an alkylorthoformate. Deprotection procedures for such groups typically involve aqueous hydrolysis.

E) Compounds of general formula (I) in which $R^3$ is alkylaminocarbonylamino or arylaminocarbonylamino, $R^1$ is amino, $R^2$ is cyano and X, $X^1$, $X^2$, $X^3$, $X^4$ and Y have the meanings given in general formula (I) of the invention may be prepared from a suitably protected amino compound of formula (XV) by reaction with an alkyl or aryl isocyanate in which the alkyl or aryl groups are as defined in the first definition of the invention, followed by deprotection. Proper conditions for formation of ureas are described by J. March in "Advanced Organic Chemistry" McGraw-Hill publ. (1985), p. 802 and references cited therein. Suitable amino protecting groups in such reactions include the alkoxyalkylideneimino group with deprotection as described previously.

F) Compounds of general formula (I) in which $R^3$ is alkoxycarbonylamino or haloalkyloxycarbonylamino, $R^1$ is amino, $R^2$ is cyano and X, $X^1$, $X^2$, $X^3$, $X^4$ and Y have the meanings given in general formula (I) of the invention may be prepared from a suitably protected amino compound of formula (XV) by reaction with an alkyl chloroformate or haloalkyl chloroformate followed by a deprotection step.

G) Compounds of general formula (I) in which $R^3$ is alkylideneimino or benzylideneimino, $R^1$ is amino, $R^2$ is cyano and X, $X^1$, $X^2$, $X^3$, $X^4$ and Y have the meanings given in general formula (I) of the invention may be prepared by condensation of a suitably protected amino compound of formula (XV) with an alkyl or aryl aldehyde in which the alkyl or aryl groups are as defined in the first definition of the invention, followed by a deprotection step. Proper conditions for formation of Schiff's bases will be selected for the condensation step as described by J. March in ibid. p. 1165 and references cited therein. Suitable amino protecting groups include acetyl or trifluoroacetyl and deprotection may be accomplished by alkaline hydrolysis or other methods as described by T. W. Greene in "Protective Groups in Organic Synthesis" J. Wiley publ. (1981) p. 254 and references cited therein.

H) Compounds of general formula (I) in which $R^3$ is alkoxyalkylideneimino, $R^1$ is amino, $R^2$ is cyano and X, $X^1$, $X^2$, $X^3$, $X^4$ and Y have the meanings given in general formula (I) of the invention may be prepared from a protected amino compound of formula (XV) by condensation with an alkylorthoester followed by a deprotection reaction. Suitable protecting groups include amide or carbamate derivatives as discussed by T. W. Greene, ibid, p. 223 and 249.

I) Compounds of general formula (I) in which $R^3$ is dialkylaminoalkylideneimino, $R^1$ is amino, $R^2$ is cyano and X, $X^1$, $X^2$, $X^3$, $X^4$ and Y have the meanings given in general formula (I) of the invention may be prepared by reacting a compound of formula (XV) with a dialkylacetal derivative of an N,N-dialkylalkanamide as described by T. W. Greene, ibid., p. 275., followed by a deprotection step. Alternatively, the compounds can be prepared by reaction of (XV) with an N,N-dialkylalkanamide in the presence of an agent such as phosphorous oxychloride under Vilsmeier conditions. Suitable protecting groups include amide or carbamate derivatives.

J) Compounds of general formula (I) in which $R^3$ is alkylthioalkylideneimino, $R^1$ is amino, $R^2$ is cyano and X, $X^1$, $X^2$, $X^3$, $X^4$ and Y have the meanings given in general formula (I) of the invention may be prepared by reacting a compound of formula (XV) with a tris(alkylthio)alkane in pyridine as solvent, optionally in the presence of a suitable catalyst, for example dimethyl(methylthio)sulfonium tetrafluorborate.

K) Compounds of general formula (I) in which $R^3$ is azido, $R^1$ is amino, $R^2$ is cyano and X, $X^1$, $X^2$, $X^3$, $X^4$ and Y have the meanings given in general formula (I) of the invention may be prepared by reacting a compound of formula (XV) with p-toluenesulfonyl azide under conditions described by J. March ibid., p. 573 and references cited therein, followed by a deprotection step. Alternatively, the compounds described above in which $R^3$ is azido may be prepared from a compound of formula (XV) by conversion of the amino group to a diazonium salt followed by reduction to a hydrazino group followed by treatment with nitrous acid to give the azide followed by a deprotection step.

METHOD 19

A) Useful intermediate compounds of general formula (I) in which $R^3$ is phenyl or heteroaryl substituted as described in general formula (I) of the invention, $R^1$ is amino, $R^2$ is cyano and X, $X^1$, $X^2$, $X^3$, $X^4$ and Y have the meanings given in general formula (I) of the invention may be prepared from a compound of formula (XI) in which the amino group is optionally protected with a suitable protecting group, by treatment with an appropriately substituted phenyl or heteroaryl diazonium salt under the conditions of the Gomberg-Bachmann reaction as described by M. Swainsbury in *Tetrahedron* 1980, 36, 3327–3359 and references cited therein.

B) Alternatively, the intermediate compounds of general formula (I) in which $R^3$ is phenyl or heteroaryl substituted as described in general formula (I) of the invention, $R^1$ is amino, $R^2$ is cyano and X, $X^1$, $X^2$, $X^3$, $X^4$ and Y have the meanings given in general formula (I) of the invention may be prepared from a compound of formula (XII) in which the amino group is optionally protected with a suitable protecting group by treatment with an appropriately substituted phenyl or heteroaryl halide, preferably a bromide or iodide in the presence of copper under the conditions of the Ullmann reaction as described by M. Swainsbury ibid.

C) Alternatively, the intermediate compounds of general formula (I) in which $R^3$ is phenyl or heteroaryl substituted as described in general formula (I) of the invention, $R^1$ is amino, $R^2$ is cyano and X, $X^1$, $X^2$, $X^3$, $X^4$ and Y have the meanings given in general formula (I) of the invention may be prepared from a compound of formula (XII), preferably a bromide or iodide, by treatment with an appropriately substituted phenyl or heteroaryl boronic acid in the presence of palladium (O) under conditions similar to those described by V.

Snieckus et. al. in *Tetrahedron Letters* 1988, 29, 2135 and references cited therein.

METHOD 20

Compounds of general formula (I) in which $R^3$ is a cyano group, $R^1$ is amino, $R^2$ is cyano and X, $X^1$, $X^2$, $X^3$, $X^4$ and Y have the meanings given in general formula (I) of the invention may be prepared from the compounds of general formula (I) in which $R^3$ is hydroxyiminomethylidenyl or alkoxyiminomethylidenyl described in METHOD 16 by dehydration according to procedures described in METHOD 4A.

METHOD 21

Compounds of general formula (I) in which $R^3$ is haloalkylcarbonyl or haloalkylthiocarbonyl, $R^1$ is amino, $R^2$ is cyano and X, $X^1$, $X^2$, $X^3$, $X^4$ and Y have the meanings given in general formula (I) of the invention may be prepared from an optionally amino-protected compound of formula (XIV) by the procedures discussed in METHOD 8 followed by a deprotection step, as necessary.

METHOD 22

A) Compounds of general formula (I) in which $R^3$ is haloalkyl or alkoxyalkyl, $R^1$ is amino, $R^2$ is cyano and X, $X^1$, $X^2$, $X^3$, $X^4$ and Y have the meanings given in general formula (I) of the invention may be prepared compounds of formula (XII) or (XIV) in which the amino group is optionally protected, by the procedures described in METHODS 6, 7 and 9 with deprotection as necessary. The compounds in which $R^3$ is haloalkyl is then optionally reacted with an appropriate alkoxide anion, prepared from the corresponding alkyl alcohol to give the compounds in which $R^3$ is alkoxyalkyl.

B) Compounds of general formula (I) in which $R^3$ is alkyl, $R^1$ is amino, $R^2$ is cyano and X, $X^1$, $X^2$, $X^3$, $X^4$ and Y have the meanings given in general formula (I) of the invention may be prepared from compounds of formula (XIV) in which the amino group is optionally protected, by reaction with a Grignard reagent derived from an alkyl halide or an alkyllithium to produce a carbinol, followed by a dehydration step to produce a compound in which $R^3$ is alkenyl, followed by reduction. Compounds of general formula (I) in which $R^3$ is methyl and the other substituents are as described above may be prepared from compounds of formula (XIV) by the procedure described in METHOD 7.

METHOD 23

Compounds of general formula (I) in which $R^3$ is thiocyanato, alkylthio, haloalkylthio, alkenylthio, haloalkenylthio, phenylthio, or heteroarylthio, $R^1$ is amino, $R^2$ is cyano and X, $X^1$, $X^2$, $X^3$, $X^4$ and Y have the meanings given in general formula (I) of the invention and the phenyl and heteroaryl groups being constituted and/or substituted as described therein, that is to say compounds of formula (XVI), may be prepared from compounds of formula (XI) under similar conditions as described in METHOD 10. The overall process may be represented by the following equation:

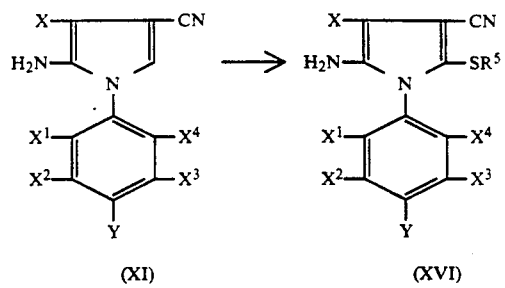

Compounds of formula (XVI) in which $R^5$ represents alkyl may also be prepared from compounds of general formula (I) in which $R^3$ is thiocyanato and the other substituents are defined as in (XVI) by treatment with alkyl halides or the like by procedures similar to those described in METHOD 11.

METHOD 24

Compounds of general formula (I) in which $R^3$ is alkylsulfinyl, alkylsulfonyl, alkenylsulfinyl, alkenylsulfonyl, haloalkylsulfinyl, haloalkylsulfonyl, haloalkenylsufinyl, haloalkenylsulfonyl, phenylsulfinyl, phenylsulfonyl, heteroarylsulfinyl, heteroarylsulfonyl, $R^1$ is amino, $R^2$ is cyano and X, $X^1$, $X^2$, $X^3$, $X^4$ and Y have the meanings given in general formula (I) of the invention and the phenyl and heteroaryl groups being constituted and/or substituted as described therein may be prepared by oxidizing compounds of formula (XVI) according to similar methods as those described in METHOD 12. In those instances when X is an $R^5S$ group which may undergo undesired competitive oxidation, sulfenylation according to the above procedures may be carried out on a compound of general formula (I) in which X is halogen, preferably bromine or iodine, $R^1$ is amino, $R^2$ is cyano, $R^3$ is hydrogen and the other substituents have the meanings given in the general description of the invention, followed by oxidation, followed by treatment with an alkyllithium by a procedure similar to those described by C. Kruse et. al. in Heterocycles 1989, 29, 79, followed by an aqueous quench to give a compound of formula (XVII). Compound (XVII) may then be sulfenylated to give compounds of formula (XVIII). The overall process may be represented as follows:

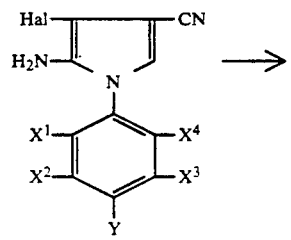

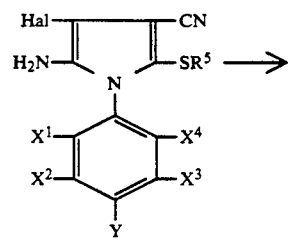

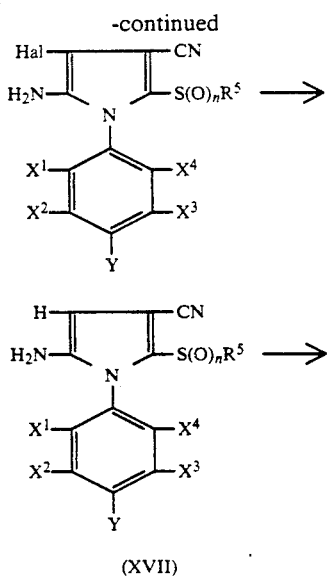

(XVII)

METHOD 25

Compounds of general formula (I) in which $R^3$ is cyanato, alkoxy or haloalkoxy, $R^1$ is amino, $R^2$ is cyano and X, $X^1$, $X^2$, $X^3$, $X^4$ and Y have the meanings given in general formula (I) of the invention may be prepared from compounds of formula (XII) in which the amino group is optionally protected, by procedures similar to those described in METHOD 5, followed by deprotection as required.

METHOD 26

A) Compounds of general formula (I) in which $R^1$ is hydrogen, $R^2$ is cyano and $R^3$, X, $X^1$, $X^2$, $X^3$, $X^4$ and Y have the meanings given in general formula (I) of the invention, that is to say compounds of formula (XX), may be prepared from compounds of general formula (I) in which $R^1$ is amino, $R^2$ is cyano and $R^3$, X, $X^1$, $X^2$, $X^3$, $X^4$ and Y have the meanings given in general formula (I) of the invention, that is to say compounds of formula (XIX), by diazotization, preferably with an alkyl nitrite such as t-butyl nitrite in an inert solvent such as tetrahydrofuran or acetonitrile. This reaction may be conducted between −80° C. and the reflux temperature of the solvent, preferably between 0° C. and 25° C.

B) Compounds of general formula (I) in which $R^1$ is halogen, alkenyloxy or alkynyloxy, $R^2$ is cyano and $R^3$, X, $X^1$, $X^2$, $X^3$, $X^4$ and Y have the meanings given in general formula (I), that is to say compounds of general formula (XXI) of the invention may be prepared from a compound of formula (XIX) by diazotization with an alkyl nitrite, for example t-butyl nitrite, in the presence of a halogen atom donor such as bromoform, carbon tetrachloride, anhydrous cupric chloride or iodine, to give the compounds in which $R^1$ is halogen. The compounds in which $R^1$ is halogen are then optionally reacted to give compounds in which $R^1$ is hydroxy and then finally $R^1$ is alkenyloxy or alkynyloxy in a similar manner to that of METHOD 13.

C) Compounds of general formula (I) in which $R^1$ is thiocyanato, alkylthio, haloalkylthio, alkenylthio, haloalkenylthio, aralkylthio, phenylthio or heteroarylthio, $R^2$ is cyano and $R^3$, X, $X^1$, $X^2$, $X^3$, $X^4$ and Y have the meanings given in general formula (I) and the phenyl and heteroaryl groups being constituted and/or substituted as described therein, that is to say compounds of formula (XXII), may be prepared from a compound of formula (XIX) by treatment with an alkyl nitrite in the presence of $(SCN)_2$ or a disulfide of formula $R^5SSR^5$ in which $R^5$ is an alkyl, haloalkyl, alkenyl, haloalkenyl, aralkyl, phenyl or heteroaryl group as defined above. The reaction is typically performed in a solvent such as chloroform at 0° C. with one to five equivalents of the alkyl nitrite and two to five equivalents of the disulfide.

The overall processes may be illustrated as shown below:

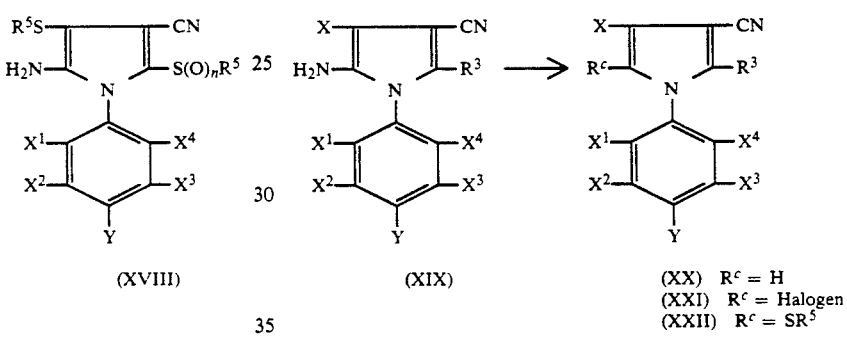

(XVIII)     (XIX)     (XX) $R^c = H$
(XXI) $R^c =$ Halogen
(XXII) $R^c = SR^5$

METHOD 27

Alternatively, many of the compounds of formula (XXII) may be prepared from a compound of general formula (XX) in which $R^3$ is amino by a procedure similar to that described in METHOD 10. Conversion of the amino group to other functional groups of the invention may then be effected by one of the procedures previously described.

METHOD 28

Compounds of general formula (I) in which $R^1$ is alkylsulfinyl, alkylsulfonyl, alkenylsulfinyl, alkenylsulfonyl, haloalkylsulfinyl, haloalkylsulfonyl, haloalkenylsulfinyl, haloalkenylsulfonyl, aralkylsulfinyl, aralkylsulfonyl, phenylsulfinyl, phenylsulfonyl, heteroarylsulfinyl, heteroarylsulfonyl, $R^2$ is cyano and $R^3$, X, $X^1$, $X^2$, $X^3$, $X^4$ and Y have the meanings given in general formula (I) and the phenyl and heteroaryl groups being constituted and/or substituted as described therein may be prepared by oxidation of compounds of formula (XXII) according to methods described in METHOD 24. If the X or $R^3$ groups are also $SR^5$ groups which are to be maintained at the sulfide oxidation level, a similar strategy as that described in METHOD 24 can be adopted to provide the desired compounds.

METHOD 29

Compounds of general formula (I) in which $R^1$ is alkylamino, dialkylamino, alkenylamino, alkynylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, alkoxycarbonylamino, haloalkoxycarbonylamino, alkylideneimino, benzylideneimino, alkoxyalkylideneimino, dialkylaminoalkylideneimino, alkylthioalkylideneimino or azido, $R^2$ is cyano and $R^3$, X, $X^1$, $X^2$, $X^3$, $X^4$ and Y have the meanings given in general formula (I) of the invention may be prepared from a compound of general formula (XIX) by procedures similar to those described in METHOD 18.

METHOD 30

A) Compounds of general formula (I) in which $R^1$ is formyl, $R^2$ is cyano and $R^3$, X, $X^1$, $X^2$, $X^3$, $X^4$ and Y have the meanings given in general formula (I) of the invention may be prepared from a compound of general formula (XIX) by treatment with sodium nitrite, $H_2C=NOH$, copper sulfate and HCl in a manner analogous to that described by W. F. Beech *J. Chem. Soc.* 1954, 1297. If $R^3$ is an amino group in (XIX), suitable protection may be provided. The compound above in which $R^1$ is formyl may be converted to a compound in which $R^1$ is a bis(alkylthio)methyl or bis(arylthio)methyl group by standard methods of thioacetalization as described by T. W. Greene ibid.,, p. 130 and references cited therein. Alternatively, compounds of general formula (I) in which $R^1$ is bis(alkylthio)methyl or bis(arylthio)methyl, $R^2$ is cyano, $R^3$ is amino and X, $X^1$, $X^2$, $X^3$, $X^4$ and Y have the meanings given in general formula (I) of the invention may be prepared from a compound of general formula (XX) in which $R^3$ is amino by a procedure similar to that described in METHOD 14. Conversion of the bis(alkylthio)methyl or bis(arylthio)methyl group to formyl may be effected by procedures analogous to those described in METHOD 15. Conversion of the amino function to other functional groups of the invention may be effected by one the procedures previously described.

B) Compounds of general formula (I) in which $R^1$ is hydroxyiminoalkylidenyl or alkoxyiminoalkylidenyl, $R^2$ is cyano and $R^3$, X, $X^1$, $X^2$, $X^3$, $X^4$ and Y have the meanings given in general formula (I) of the invention may be prepared from compounds of general formula (I) in which $R^1$ is alkylcarbonyl or formyl and the other substituents are as defined above by procedures similar to those described in METHOD 16. The compounds above in which $R^1$ is alkylcarbonyl may be prepared from the corresponding compounds in which $R^1$ is halogen by conversion to a Grignard reagent or lithium derivative, with optional protection of the cyano group as discussed in METHOD 5, followed by reaction with an aliphatic acid chloride or anhydride or alternatively condensation with an aliphatic aldehyde followed by oxidation. Alternatively, the compounds in which $R^1$ is alkylcarbonyl may be prepared from the corresponding compounds in which $R^1$ is formyl by reaction with an alkyl Grignard reagent, followed by oxidation.

C) Compounds of general formula (I) in which $R^1$ is cyano, $R^2$ is cyano and $R^3$, X, $X^1$, $X^2$, $X^3$, $X^4$ and Y have the meanings given in general formula (I) of the invention may be prepared from the corresponding compounds in which $R^1$ is hydroxyiminomethylidenyl or alkoxyiminomethylidenyl by procedures similar to those described in METHOD 4A.

D) Compounds of general formula (I) in which $R^1$ is haloalkylcarbonyl or haloalkylthiocarbonyl, $R^2$ is cyano and $R^3$, X, $X^1$, $X^2$, $X^3$, $X^4$ and Y have the meanings given in general formula (I) of the invention may be prepared from a compound of general formula (I) in which $R^1$ is formyl and the other substituents are defined as above by treatment under conditions similar to those described in METHOD 8.

E) Compounds of general formula (I) in which $R^1$ is haloalkyl, alkyl, alkoxyalkyl, alkylthioalkyl, cyanoalkyl, alkenyl, haloalkenyl, alkynyl or haloalkynyl, $R^2$ is cyano and $R^3$, X, $X^1$, $X^2$, $X^3$, $X^4$ and Y have the meanings given in general formula (I) of the invention may be prepared from a compound of general formula (I) in which $R^1$ is formyl or halogen and the other substituents are defined as above by treatment under conditions similar to those described in METHOD 22, to give compounds in which $R^1$ is haloalkyl or alkyl.

The compounds in which $R^1$ is haloalkyl are then optionally reacted with an appropriate alkoxide, alkylmercaptide or metal cyanide to give the compounds in which $R^1$ is alkoxyalkyl, alkylthioalkyl or cyanoalkyl.

The compounds in which $R^1$ is formyl are optionally converted to compounds in which $R^1$ is alkenyl, haloalkenyl, alkynyl, or haloalkynyl, by employing the Wittig reaction or modifications thereof such as the Wadsworth-Emmons (Horner) Modification. The reaction may be conducted in inert solvents such as tetrahydrofuran, dimethoxyethane or toluene at a reaction temperature from about $-30°$ C. to about 180° C. A representative example of the procedure for the Wittig reaction is given in Org. Synth. Coll. Vol. 5, 751, 1973.

Additionally, the alkynyl analog with alkynyl directly attached to the pyrrole ring, can be introduced from the corresponding $R^1$ is halogen analog, such as an iodo analog, by a reaction with a copper acetylide using a procedure similar to that described by R. E. Atkinson et al., *J. Chem. Soc.* (C), 2173, 1969 or the references cited therein.

METHOD 31

Compounds of general formula (I) in which $R^1$ is phenyl or heteroaryl substituted as described in general formula (I) of the invention, $R^2$ is cyano and $R^3$, X, $X^1$, $X^2$, $X^3$, $X^4$ and Y have the meanings given in general formula (I) of the invention may be prepared from compounds of general formula (I) in which $R^1$ is halogen and the other substituents are as defined above by procedures similar to those described in METHODS 19B) and 19C).

METHOD 32

Compounds of general formula (I) in which $R^1$ is cyanato, alkoxy or haloalkoxy, $R^2$ is cyano and $R^3$, X, $X^1$, $X^2$, $X^3$, $X^4$ and Y have the meanings given in general formula (I) of the invention may be prepared from compounds of formula (XXI) by procedures similar to those described in METHOD 5.

METHOD 33

Compounds of general formula (I) in which $R^2$ is formyl, $R^1$, $R^3$, X, $X^1$, $X^2$, $X^3$, $X^4$ and Y have the meanings given in general formula (I) of the invention, that is to say compounds of formula (XXIV), may be prepared from compounds of formula (I) in which $R^2$ is cyano, $R^1$, $R^3$, X, $X^1$, $X^2$, $X^3$, $X^4$ and Y have the meanings given in general formula (I) of the invention, that is to say compounds of formula (XXIII) by treatment with a reducing agent, preferably diisobutylaluminum hydride in a solvent, preferably a 1:1 mixture of toluene and hexane by a procedure similar to that described by S. Trofimenko in *J. Org. Chem.* 1964, 29, 3046. The overall process is as shown below:

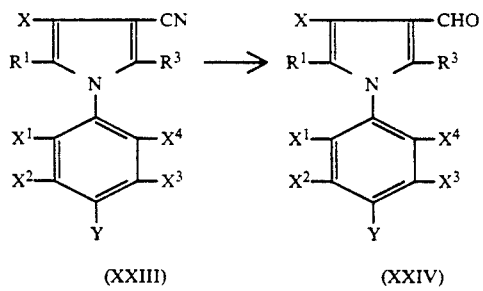
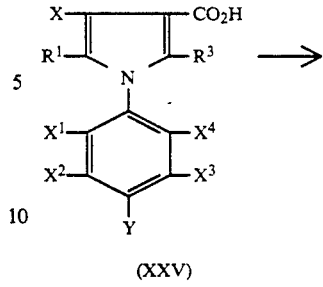

METHOD 34

Useful intermediate compounds of general formula (I) in which $R^2$ is a carboxylic acid function, $R^1$, $R^3$, X, $X^1$, $X^2$, $X^3$, $X^4$ and Y have the meanings given in general formula (I) of the invention, that is to say compounds of formula (XXV), may be prepared by oxidation of the compounds of formula (XXIV) with Jones' reagent. The overall process is as follows:

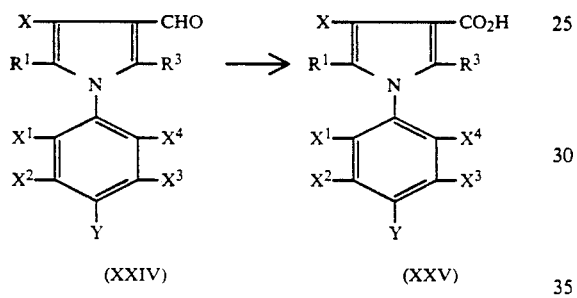

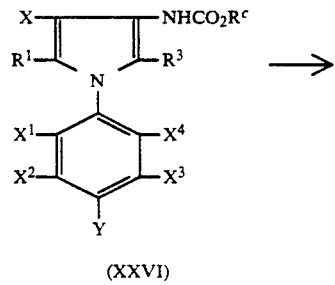

METHOD 35

Compounds of general formula (I) in which $R^2$ is hydroxyiminoalkylidenyl, alkoxyiminoalkylidenyl, haloalkylcarbonyl, haloalkylthiocarbonyl, alkyl, bis(alkylthio)methyl, bis(arylthio)methyl, haloalkyl or cyano and $R^1$, $R^3$, X, $X^1$, $X^2$, $X^3$, $X^4$ and Y have the meanings given in general formula (I) of the invention may be prepared from compounds of formula (XXIV) or compounds of general formula (I) in which $R^2$ is halogen and the other substituents are defined as above, whose preparation is described in METHOD 38, by procedures similar to those described in METHOD 30A) B), D) and E).

METHOD 36

Compounds of general formula (I) in which $R^2$ is amino, $R^1$, $R^3$, X, $X^1$, $X^2$, $X^3$, $X^4$ and Y have the meanings given in general formula (I) of the invention, that is to say compounds of formula (XXVII), may be prepared from the compounds of formula (XXV) by treatment with diphenylphosphoryl azide in the presence of an organic base such as triethylamine in an alcoholic solvent such as tert.-butanol to produce a carbamate (XXVI) followed by hydrolysis. Other methods of producing (XXVII) from (XXV) via a Curtius rearrangement include conversion to the acid chloride followed by reaction with azide ion and treatment with an alcohol as described by J. March in "Advanced Organic Chemistry" McGraw-Hill publ., 1985, 984. The overall transformation is as follows:

METHOD 37

Compounds of general formula (I) in which $R^2$ is alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, alkoxycarbonylamino, haloalkoxycarbonylamino, alkylideneimino, benzylideneimino, alkoxyalkylideneimino, dialkylaminoalkylideneimino, alkylthioalkylideneimino or azido, $R^1$, $R^3$, X, $X^1$, $X^2$, $X^3$, $X^4$ and Y have the meanings given in general formula (I) of the invention may be prepared from the compounds of formula (XXVII) by procedures similar to those described in METHOD 18.

METHOD 38

Compounds of general formula (I), in which $R^2$ is hydrogen, halogen, thiocyanato, alkylthio, haloalkylthio, alkenylthio, haloalkenylthio, phenylthio or heteroarylthio, $R^1$, $R^3$, X, $X^1$, $X^2$, $X^3$, $X^4$ and Y have the meanings given in general formula (I) of the invention and the phenyl and heteroaryl groups being substituted as described therein, may be prepared from the compounds of formula (XXVII) by procedures similar to those described in METHOD 26. Alternatively, the compounds of general formula (I) in which $R^2$ is hydrogen, $R^1$, $R^3$, X, $X^1$, $X^2$, $X^3$, $X^4$ and Y have the meanings given in general formula (I) of the invention may be prepared from compounds of formula (XXV) by heating with 48% HBr in glacial acetic acid at reflux or heating in a high boiling solvent such as decalin or quinoline in the presence of copper.

METHOD 39

Compounds of general formula (I), in which $R^2$ is alkylsulfinyl, alkylsulfonyl, alkenylsulfinyl, alkenylsulfonyl, haloalkylsulfinyl, haloalkylsulfonyl, haloalkenylsulfinyl, haloalkenylsulfonyl, phenylsulfinyl, phenylsulfonyl heteroarylsulfinyl, heteroarylsulfonyl, $R^1$, $R^3$, X, $X^1$, $X^2$, $X^3$, $X^4$ and Y have the meanings given in general formula (I) of the invention and the phenyl and heteroaryl groups being substituted as described therein, may be prepared by oxidizing compounds of general formula (I) in which $R^2$ is alkylthio, haloalkylthio, alkenylthio, haloalkenylthio, phenylthio or heteroarylthio by procedures similar to those described in METHOD 24.

METHOD 40

Compounds of general formula (I) in which $R^2$ is phenyl or heteroaryl substituted as described in general formula (I) of the invention, $R^1$, $R^3$, X, $X^1$, $X^2$, $X^3$, $X^4$ and Y have the meanings given in general formula (I) of the invention may be prepared from compounds of general formula (I) in which $R^2$ is halogen and the other substituents are as defined above by procedures similar to those described in METHODS 19B and 19C.

METHOD 41

Compounds of formula (I) in which $R^2$ is cyanato, alkoxy or haloalkoxy, $R^1$, $R^3$, X, $X^1$, $X^2$, $X^3$, $X^4$ and Y have the meanings given in general formula (I) of the invention may be prepared from compounds of general formula (I) in which $R^2$ is halogen and the other substituents are as defined above by procedures similar to those described in METHOD 5.

In a global manner the process invention may be defined as described below:

$P_1$. A process for the preparation of a compound of formula (Id)

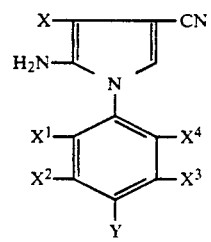

(Id)

wherein $X^1$, $X^2$, $X^3$, $X^4$ and Y have the same meanings as in formula (Ia), X is halogen, trifluoromethyl, cyano, thiocyanato, alkylthio, alkylsulfinyl, alkylsulfonyl, haloalkylthio, haloalkylsulfinyl, haloalkylsulfonyl, alkenylthio, alkenylsulfinyl, alkenylsulfonyl, haloalkenylthio, haloalkenylsulfinyl, haloalkenylsulfonyl, phenylthio, phenylsulfinyl, phenylsulfonyl, heteroarylthio, heteroarylsulfinyl or heteroarylsulfonyl, wherein a compound of formula (IIIa),

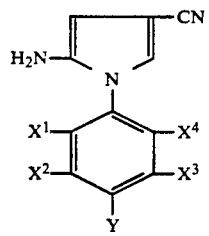

(IIIa)

where amino is optionally protected:

(a) is reacted with a halogenating agent, optionally in the presence of a solvent to obtain a compound of formula (Id) wherein X is halogen, then reacting said compound with trifluoromethyl copper in a known manner to get compounds of formula (Id) where X is trifluoromethyl;

(b) is reacted with a tris(alkylthio)methane or tris(arylthio)methane in the presence of a Lewis acid, then the obtained compound of formula (XXXVI) where X is bis(alkylthio)methyl or bis(arylthio)methyl is reacted with a suitable alkyl nitrite followed by hydrolysis, in order to obtain the compound of formula (XXXVII) where X is formyl, then bringing the said compound into contact with hydroxylamine followed by dehydration with suitable agents such as $P_2O_5$ in a known manner in order to obtain the compound of formula (Id) where X is a cyano group;

(c) is reacted with a compound of formula MSCN, M being an alkali metal, in the presence of bromine, in a solvent such as methanol in order to obtain the compound of formula (Id) where X is a thiocyanato group and then optionally reacting said compound with an alkyl halide or dialkyl sulfate in the presence of a base such as NaOH or KOH in a solvent to get a compound of formula (Id) where X is alkylthio; or (d) is reacted with a sulfenyl halide of formula $R^5SHal$, in which $R^5$ is an alkyl, haloalkyl, phenyl or heteroaryl radical and Hal is a halogen atom, in an organic liquid reaction medium, optionally in the presence of an acid acceptor such as a teritary amine in order to get a compound of formula (Id) where X is alkylthio, haloalkylthio, alkenylthio, haloalkenylthio, phenylthio or heteroarylthio, then optionally oxidizing in a known manner the obtained compound, in order to get a compound of formula (Id) where X is $R^5S(O)_n$, wherein n equals 1 or 2 depending on reaction conditions.

$P_2$. A process for the preparation of a compound of formula (Id) wherein $X^1$, $X^2$, $X^3$, $X^4$ and Y have the same meanings as in formula (Ia), X is cyanato, alkoxy, haloalkoxy, wherein a compound of formula (XXVIII),

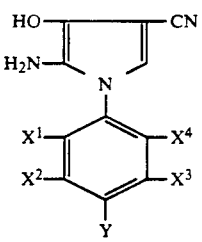

(XXVIII)

where the amino and cyano groups are suitably protected if necessary:

(a) is reacted with cyanogen halide in the presence of an acid acceptor to obtain a compound of formula (Id) where X is cyanato;

(b) is reacted with an alkylating agent, optionally in the presence of a base to obtain a compound of formula (Id) where X is alkoxy; or (c) is reacted in a known haloalkylation manner to obtain a compound of formula (Id) where X is haloalkoxy.

$P_3$. A process for the preparation of a compound of formula (Id) wherein $X^1$, $X^2$, $X^3$, $X^4$ and Y have the same meaning as in formula (Ia) and X is haloalkyl [$CF_2H$, $CF_3$, $BrCH_2$, $ClCH_2$], haloalkylcarbonyl, haloalkylthiocarbonyl or α-haloalkyl-α-halomethyl, wherein a compound of formula (VI),

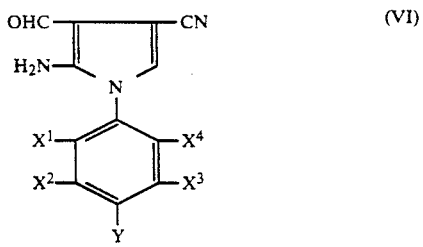

where amino and cyano are suitably protected if needed:

(a) is reacted with a fluorinating agent such as diethylaminosulfur trifluoride in a known manner in order to obtain a compound of formula (Id) wherein X is a difluoromethyl group;

(b) is reacted with a suitable oxidizing agent such as chromium trioxide in sulfuric acid to provide a compound where X is a carboxylic acid group, then submitting said compound to a fluorinating agent such as sulfur tetrafluoride in a known manner to get compound of formula (Id) where X is trifluoromethyl;

(c) is reacted under Wolff-Kishner conditions, or a variant such as treatment with p-toluenesulfonylhydrazide, followed by sodium cyanoborohydride, to obtain a compound where X is a methyl group then submitting said compound to a halogenating agent such as N-bromosuccinimide or N-chlorosuccinimide in a suitable solvent in order to obtain a compound of formula (Id) where X is bromomethyl or chloromethyl; or (d) is reacted sequentially with a haloalkyl metal derivative or trifluoromethyltrimethylsilane to provide a compound of formula (Id) where X is haloalkylcarbinol followed by oxidation in a known manner to provide a compound of formula (Id) where X is haloalkylcarbonyl, then optionally submitting said compound to Lawesson's reagent to get a compound of formula (Id) where X is haloalkyl(thiocarbonyl); or the compound where X is haloalkylcarbinol is reacted with a halogenating agent such as thionyl chloride or hydrogen bromide in order to get a compound of formula (Id) where X is α-haloalkyl-α-halomethyl, all the previous steps having been followed by a deprotection step if needed.

P4. A process for the preparation of a compound of formula (Ie)

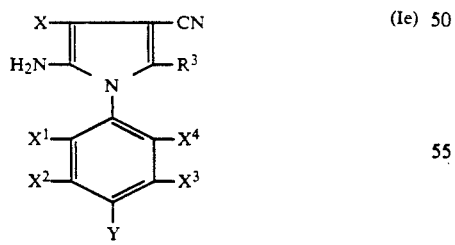

where X, $X^1$, $X^2$, $X^3$, $X^4$ and Y have the same meanings as in formula (Ia) and $R^3$ is halogen, alkenyloxy, alkynyloxy, formyl, bis(alkylthio or arylthio)methyl, haloalkyl, alkoxyalkyl, alkyl, optionally substituted phenyl or heteroaryl, thiocyanato, alkylthio, haloalkylthio, alkenylthio, haloalkenylthio, phenylthio, heteroarylthio, alkylsulfinyl, alkylsulfonyl, alkenylsulfinyl, alkenylsulfonyl, haloalkylsulfinyl, haloalkylsulfonyl, haloalkenylsulfinyl, haloalkenylsulfonyl, phenylsulfinyl, phenylsulfonyl heteroarylsulfinyl or heteroarylsulfonyl, wherein a compound of formula (Id) in which X, cyano and amino are optionally protected in a suitable manner if required:

(a) is reacted according to method $P_1(a)$ to get a compound of formula (Ie) where $R^3$ is halogen, then said compound is optionally reacted with an optionally substituted heteroaryl or phenyl halide, preferably a bromide or iodide in the presence of copper in a known manner, or then said compound in which $R^3$ is preferably bromide or iodide, is optionally reacted with an optionally substituted phenyl or heteroaryl boronic acid in the presence of palladium in a known manner to obtain a compound of formula (Ie) where $R^3$ is an optionally substituted phenyl or heteroaryl group, or then a compound of formula (Ie) where $R^3$ is halogen is reacted according to method $P_1(a)$ to get a compound of formula (Ie) where $R^3$ is trifluoromethyl; or optionally a compound of formula (Ie) where $R^3$ is halogen is converted via a Grignard or lithium reagent into a compound where $R^3$ is hydroxy, said compound then is reacted with a haloalkene or haloalkyne or optionally is reacted with an alkenylalkyl ether or alkynylalkyl ether to obtain a compound of formula (Ie) where $R^3$ is alkenyloxy or alkynyloxy;

(b) is reacted according to method $P_1(b)$ to get first a compound of formula (Ie) where $R^3$ is a bis(alkylthio)methyl group or a bis(arylthio)methyl group and optionally then a compound of formula (Ie) where $R^3$ is formyl;

(c) is reacted with an optionally substituted phenyl or heteroaryl diazonium salt in a known manner to get a compound of formula (Ie) where $R^3$ is optionally substituted phenyl or heteroaryl; or (d) is reacted according to method $P_1(c,d)$ in order to get a compound of formula (Ie) where $R^3$ is thiocyanato, alkylthio, haloalkylthio, alkenylthio, haloalkenylthio, phenylthio or heteroarylthio, then optionally oxidized according to method $P_1(d)$ in order to get the compound of formula (Ie) where $R^3$ is alkylsulfinyl, alkylsulfonyl, alkenylsulfinyl, alkenylsulfonyl, haloalkylsulfinyl, haloalkylsulfonyl, haloalkenylsulfinyl, haloalkenylsulfonyl, phenylsulfinyl, phenylsulfonyl, heteroarylsulfinyl or heteroarylsulfonyl with the proviso that X is not an $R^5S$ group which may undergo undesired oxidation, then when X is a halogen, treatment with an alkyllithium in a known manner followed by an aqueous quench and sulfenylation according to method $P_1(c,d)$ in order to get a compound of formula (Ie) where X is thiocyanato, alkylthio, haloalkylthio, alkenylthio, haloalkenylthio, phenylthio or heteroarylthio.

P5. A process for the preparation of a compound of formula (Ie) wherein X, $X^1$, $X^2$, $X^3$, $X^4$ and Y have the same meanings as in formula (Ia) and $R^3$ is hydroxyiminoalkylidenyl, alkoxyiminoalkylidenyl, cyano, haloalkylcarbonyl, haloalkyl, alkoxyalkyl, haloalkylthiocarbonyl or alkyl wherein a compound of formula (XXIX),

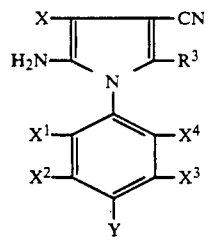 (XXIX)

in which $R^3$ is formyl or alkylcarbonyl and X, cyano and amino are protected in a suitable manner if required:

(a) is condensed with hydroxylamine or O-alkylhydroxylamine or their addition salts in a solvent such as ethanol in order to obtain a compound of formula (Ie) where $R^3$ is hydroxyiminoalkylidenyl or alkoxyiminoalkylidenyl, and when $R^3$ is hydroxyiminomethylidenyl or alkoxyiminomethylidenyl, the elements of water or an alcohol are optionally eliminated according to method $P_1(b)$ to obtain a compound of formula (Ie) where $R^3$ is a cyano group;

(b) is reacted, when $R^3$ is formyl, according to method $P_3(a,b,c,d)$ to obtain a compound of formula (Ie) where $R^3$ is a methyl or haloalkyl or haloalkycarbonyl or haloalkythiocarbonyl group; or optionally, the compound where $R^3$ is haloalkyl is reacted with an alkoxide anion to obtain a compound of formula (Ie) where $R^3$ is alkoxyalkyl; or (c) is reacted, when $R^3$ is formyl, with a Grignard reagent derived from an alkyl halide or an alkyllithium to produce a carbinol, followed by a dehydration step to produce a compound where $R^3$ is alkenyl, followed by reduction in order to get a compound of formula (Ie) where $R^3$ is alkyl, followed optionally by a deprotection step.

$P_6$. A process for the preparation of a compound of formula (XXXIV),

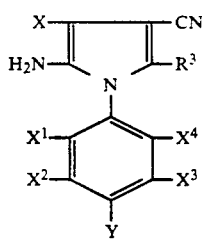 (XXXIV)

useful as an intermediate compounds wherein X, $X^1$, $X^2$, $X^3$, $X^4$ and Y are as defined in formula (Ia) and $R^3$ is amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, alkoxycarbonylamino, haloalkoxycarbonylamino, alkylideneimino, benzylideneimino, alkoxyalkylideneimino, dialkylaminoalkylideneimino, alkylthioalkylideneimino or azido, wherein a compound of formula (XXX),

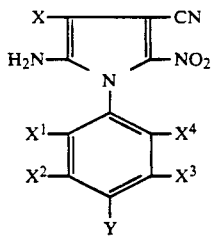 (XXX)

where the amino group is protected in a suitable manner, is reduced in order to get a compound of formula (XXXIV) where $R^3$ is amino, said compound being reacted:

(a) with an appropriate alkylating agent in an organic solvent, the mono or disubstituted amino group being obtained depending on the stoichiometric ratio or reaction conditions or through conversion of the amino group to an alkoxyalkylideneimino followed by reduction in order to obtain a compound of formula (XXXIV) where $R^3$ is alkylamino, dialkylamino or aralkylamino;

(b) with phosgene followed by ammonia to get a compound of formula (XXXIV) where $R^3$ is aminocarbonylamino;

(c) with an alkyl acid chloride or a haloalkyl acid chloride or an aryl acid chloride or an anhydride thereof, optionally in the presence of a solvent and/or an organic acid acceptor to obtain a compound of formula (XXXIV) where $R^3$ is alkylcarbonylamino, haloalkylcarbonylamino or arylcarbonylamino;

(d) with an alkyl or haloalkylsulfonyl halide or an anhydride thereof under appropriate conditions in order to obtain a compound of formula (XXXIV) where $R^3$ is alkylsulfonylamino or haloalkylsulfonylamino;

(e) with an alkyl or aryl isocyanate in a known manner to obtain a compound of formula (XXXIV) where $R^3$ is (alkylamino or arylamino)carbonylamino;

(f) with an alkylchloroformate or haloalkylchloroformate in a known manner to obtain a compound of formula (XXXIV) where $R^3$ is alkoxycarbonylamino or haloalkoxycarbonylamino;

(g) with an alkyl or aryl aldehyde in a known manner to obtain a compound of formula (XXXIV) where $R^3$ is alkylidenimino or benzylidenimino;

(h) with an alkylorthoester to obtain a compound of formula (XXXIV) where $R^3$ is alkoxyalkylideneimino;

(i) with an N,N-dialkylalkanamide or dialkylacetal derivative thereof to obtain a compound of formula (XXXIV) where $R^3$ is dialkylaminoalkylidenimino;

(j) with a tris(alkylthio)alkane in an organic solvent to obtain a compound of formula (XXXIV) where $R^3$ is alkylthioalkylideneimino; or (k) with p-toluenesulfonyl azide in a known manner or by conversion to a diazonium salt followed by reduction to a hydrazino group followed by treatment with nitric acid to give a compound of formula (XXXIV) where $R^3$ is an azido group followed by a deprotection step if required.

$P_7$. A process of preparation of a compound of formula (Ie) wherein X, $X^1$, $X^2$, $X^3$, $X^4$, and Y have the same meanings as in formula (Ia) and $R^3$ is cyanato, alkoxy or haloalkoxy wherein a compound of formula (XXXI)

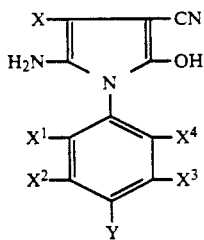

(XXXI)

in which amino, cyano and X, are optionally protected in a suitable manner is reacted according to method $P_2$ (a), (b), (c) to obtain a compound of formula (Ie) wherein $R^3$ is cyanato, alkoxy or haloalkoxy.

$P_8$. A process for the preparation of a compound of formula (If),

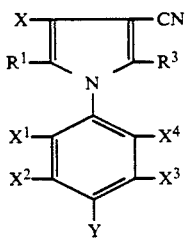

(If)

wherein X, $R^3$, $X^1$, $X^2$, $X^3$, $X^4$, and Y have the same meanings as in formula (Ia) and $R^1$ is hydrogen, halogen, alkenyloxy, alkynyloxy, thiocyanato, alkylthio, haloalkylthio, alkenylthio, haloalkenylthio, aralkylthio, phenylthio, heteroarylthio, alkylsulfinyl, alkylsulfonyl, alkenylsulfinyl, alkenylsulfonyl, haloalkylsulfinyl, haloalkylsulfonyl, haloalkenylsulfinyl, haloalkenylsulfonyl, aralkylsulfinyl, aralkylsulfonyl, phenylsulfinyl, phenylsulfonyl heteroarylsulfinyl, heteroarylsulfonyl, optionally substituted phenyl or heteroaryl, alkylcarbonyl, alkylamino, dialkylamino, alkenylamino, alkynylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, alkoxycarbonylamino, haloalkoxycarbonylamino, alkylideneimino, benzylideneimino, alkoxyalkylideneimino, dialkylaminoalkylideneimino, alkylthioalkylideneimino, azido, bis(alkylthio or arylthio)methyl, formyl, alkenyl, haloalkenyl, alkynyl, haloalkynyl, haloalkylcarbonyl, haloalkylthiocarbonyl, haloalkyl, alkoxyalkyl, alkylthioalkyl, cyanoalkyl, or alkyl, wherein a compound of formula (Ie) or (XXXIV)

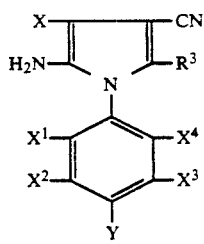

(Ie) or (XXXIV)

prepared according to methods $P_4$ to $P_7$ in which the amino group is deprotected after protecting the X, $R^3$ and cyano group if required:

(a) is reacted with a diazotization agent, preferably with an alkyl nitrite, in an inert solvent to obtain a compound of formula (If) where $R^1$ is H;

(b) is reacted with a diazotization agent, preferably with an alkyl nitrite, in the presence of a halogen donor to obtain a compound of formula (If) where $R^1$ is halogen, then reacting said compound with a Grignard reagent or lithium derivative followed by reaction with an aliphatic acid chloride or anhydride thereof to convert to a compound of formula (If) where $R^1$ is alkylcarbonyl or reacting said compound according to method $P_4$(a) in order to get a compound of formula (If) where $R^1$ is phenyl or heteroaryl; or optionally a compound of formula (If) where $R^1$ is halogen is reacted according to method $P_4$(a) in order to obtain a compound where $R^1$ is hydroxy, which compound is then further reacted to obtain a compound of formula (If) where $R^1$ is alkenyloxy or alkynyloxy;

(c) is reacted with a diazotization agent, preferably with an alkyl nitrite, in the presence of $(SCN)_2$ or a disulfide in a solvent such as chloroform to obtain a compound of formula (If) where $R^1$ is thiocyanato, alkylthio, haloalkylthio, alkenylthio, haloalkenylthio, aralkylthio, phenylthio or heteroarylthio, then optionally oxidized according to method $P_1$(d) to get a compound of formula (If) where $R^1$ is alkylsulfinyl, alkylsulfonyl, alkenylsulfinyl, alkenylsulfonyl, haloalkylsulfinyl, haloalkylsulfonyl, haloalkenylsulfinyl, haloalkenylsulfonyl, aralkylsulfinyl, aralkylsulfonyl, phenylsulfinyl, phenylsulfonyl, heteroarylsulfinyl or heteroarylsulfonyl;

(d) is reacted according to method $P_6$(a-k) to in order to get a compound of formula (If) where $R^1$ is alkylamino, dialkylamino, alkenylamino, alkynylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, alkoxycarbonylamino, haloalkoxycarbonylamino, alkylideneimino, benzylideneimino, alkoxyalkylideneimino, dialkylaminoalkylideneimino, alkylthioalkylideneimino or azido; or (e) is reacted with sodium nitrite and formaldoxime, copper sulfate and HCl in a known manner in order to get a compound of formula (If) where $R^1$ is formyl, then is reacted with an alkyl Grignard reagent and subsequently oxidized to convert to a compound of formual (If) where $R^1$ is alkylcarbonyl, then is reacted according to method $P_5$ so as to obtain a compound of formula (If) where $R^1$ is hydroxyiminoalkylidenyl or alkoxyiminoalkylidenyl and when $R^1$ is formyl is reacted according to method $P_3$(a-d) to obtain a compound of formula (If) where $R^1$ is haloalkylcarbonyl, haloalkylthiocarbonyl, haloalkyl, or alkyl followed if needed by a deprotection step or optionally the compound where $R^1$ is haloalkyl is reacted with an alkoxide, alkylmercaptide or metal cyanide to obtain a compound of formula (If) where $R^1$ is alkoxyalkyl, alkylthioalkyl or cyanoalkyl; or the compound above in which $R^1$ is formyl is converted in a known manner to a compound of formula (If) in which $R^1$ is bis(alkylthio or arylthio)methyl, or the compound where $R^1$ is formyl is converted via a Wittig reagent to a compound of formula (If) where $R^1$ is alkenyl, haloalkenyl, alkynyl, or haloalkynyl.

$P_9$. A process for the preparation of a compound of formula (If) wherein X, $R^3$, $X^1$, $X^2$, $X^3$, $X^4$, and Y have the same meanings as in formula (Ia) and $R^1$ is cyanato, alkoxy or haloalkoxy, wherein a compound of formula (XXXII)

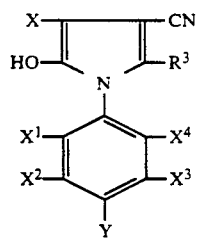

in which X, cyano and $R^3$ are optionally protected in a known manner, is reacted according to method $P_2(a,b,c)$ to obtain a compound of formula (If) where $R^1$ is cyanato, alkoxy or haloalkoxy followed by an optional deprotection step.

$P_{10}$. A process for the preparation of a compound of formula (Ia) wherein X, $R^1$, $R^3$, $X^1$, $X^2$, $X^3$, $X^4$, and Y have the same meanings as in formula (Ia), and $R^2$ is formyl, wherein a compound of formula (If) is treated with a reducing agent, preferably diisobutylaluminum hydride, in a solvent to provide the compound in which $R^2$ is formyl, said compound being optionally oxidized in a known manner to get a corresponding compound of formula (XXXV)

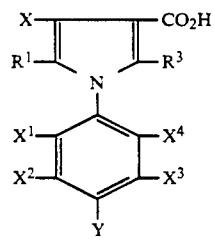

$P_{11}$. A process for the preparation of a compound of formula (Ia) wherein X, $R^1$, $R^3$, $X^1$, $X^2$, $X^3$, $X^4$, and Y have the same meanings as in formula (Ia) and $R^2$ is hydroxyiminoalkylidenyl, alkoxyiminoalkylidenyl, haloalkylcarbonyl, haloalkylthiocarbonyl, alkyl, haloalkyl, bis(alkylthio or arylthio)methyl or cyano, wherein a compound of formula (Ia) in which $R^2$ is formyl, after having optionally protected X, $R^1$, and $R^3$, if required in a known manner, is reacted according to method $P_3(a,b,c,d)$, $P_5(a,b)$ or $P_8(e)$, followed by a deprotection step if required.

$P_{12}$. A process for the preparation of a compound of formula (Ia) wherein X, $R^1$, $R^3$, $X^1$, $X^2$, $X^3$, $X^4$, and Y have the same meanings as in formula (Ia), and $R^2$ is amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, alkoxycarbonylamino, haloalkoxycarbonylamino, alkylideneimino, benzylideneimino, alkoxyalkylideneimino, dialkylaminoalkylideneimino, alkylthioalkylideneimino, azido, hydrogen, halogen, thiocyanato, alkylthio, haloalkylthio, alkenylthio, haloalkenylthio, phenylthio, heteroarylthio, alkylsulfinyl, alkylsulfonyl, alkenylsulfinyl, alkenylsulfonyl, haloalkylsulfinyl, haloalkylsulfonyl, haloalkenylsulfinyl, haloalkenylsulfonyl, phenylsulfinyl, phenylsulfonyl, heteroarylsulfinyl, heteroarylsulfonyl, optionally substituted phenyl or heteroaryl wherein a compound of formula (XXV) after having optionally protected X, $R^1$, and $R^3$, if required in a known manner, is reacted under conditions for the Curtius rearrangement, for example by conversion to an acid chloride followed by reaction with an alkali metal azide, or with diphenyl phosphoryl azide in the presence of an organic base such as triethylamine in an alcoholic solvent to produce a carbamate which may then be hydrolyzed to obtain the corresponding compound in which $R^2$ is amino which is then optionally reacted according to method $P_6(a-k)$ or $P_8(a-c)$, then when $R^2$ is halogen, optionally reacted according to method $P_4(a)$, followed by a deprotection step if necessary.

$P_{13}$. A process for the preparation of a compound of formula (Ia) wherein X, $R^1$, $R^3$, $X^1$, $X^2$, $X^3$, $X^4$, and Y have the same meanings as in formula (Ia) and $R^2$ is cyanato, alkoxy or haloalkoxy, wherein a compound of formula (XXXVI),

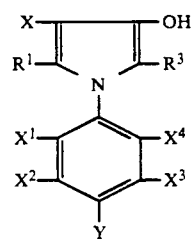

after having optionally protected the X, $R^1$, and $R^3$ groups, if required, is reacted according to method $P_7$ followed by a deprotection step if necessary.

$P_{14}$. A process for the preparation of a compound of formula (XXVIII), (XXXI), (XXXII) or (XXXVI) according to methods $P_2$, $P_7$, $P_9$ or $P_{13}$, wherein the corresponding halogenated compound according to methods $P_1(a)$, $P_4(a)$, $P_8(b)$ or $P_{12}$, after having protected the amino group if present, is converted to a Grignard reagent or lithium derivative, followed by reaction with a trialkyl borate and oxidation in a known manner, followed by a deprotection step if necessary.

$P_{15}$. A process for the preparation of a compound of formula (IIIa)

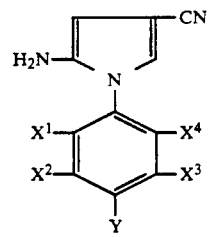

in which $X^1$, $X^2$, $X^3$, $X^4$, and Y have the same meanings as in formula (Ia), provided:
   that if one of $X^1$, $X^2$, $X^3$, $X^4$ and Y is Cl, $OCH_3$ or $CH_3$, then at least one of the others is different from H; and
   that at least one of $X^1$, $X^2$, $X^3$, $X^4$, and Y is different from H.
wherein a dicyanoprop-1-ene derivative of formula (IVb),

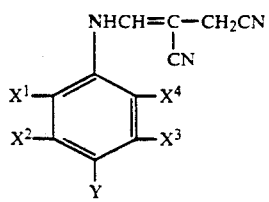

wherein $X^1$, $X^2$, $X^3$, $X^4$ and Y are as defined in formula (IIIa) is reacted with a basic agent.

P16. The invention is also related to compounds of formula (IIIa) and (XXVIII) to (XXXIV) and (XXXVI), wherein the various substituents have the same meaning as previously defined, especially useful as intermediate compounds for preparing compounds of formula (Ia) according to process methods P1 to P15.

OTHER METHODS

Compounds of formula (Ia) wherein X is a perhaloalkylthio group, are additionally prepared by the following process of chlorosulfonation, reduction to a disulfide and finally free radical promoted reduction or alternatively via direct formation of disulfide intermediate followed by the free radical promoted reduction. The processes which are a part of this invention are as follows:

A) Compounds of the general formula (XXXIX) wherein the definitions of $R^1$, $R^2$, $R^3$, Y, $X^1$, $X^2$, $X^3$, and $X^4$ are those herein above defined in formula (Ia), can be prepared from compounds of the general formula (XXXVIII) wherein X is hydrogen, by treatment with chlorosulfonic acid either neat or in the presence of an organic solvent such as chloroform, dichloromethane, carbon tetrachloride, or dimethylformamide at a reaction temperature from 0° C. to 150° C. A more specific example would be the preparation of a compound of the general formula (XXXIX) in which $R^1$ is amino, alkylcarbonylamino, or haloalkylcarbonylamino, $R^2$ is cyano, and $R^3$ is hydrogen, from compounds of the general formula (XXXVIII) in which $R^1$ is amino, alkylcarbonylamino, or haloalkylcarbonylamino, $R^2$ is cyano, $R^3$ is hydrogen, and X is hydrogen, by treatment with chlorosulfonic acid. A representative procedure for chlorosulfonation of an aromatic compound is given in J. March, "Advanced Organic Chemistry," McGraw-Hill publ. (1968), 402.

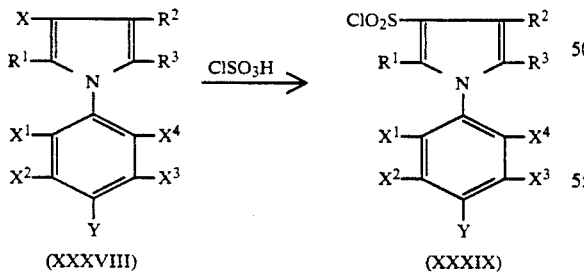

Compounds of the general formula (XL) wherein the definitions of $R^1$, $R^2$, Y, $X^1$, $X^2$, $X^3$, and $X^4$ are those herein above defined in formula (Ia), can be prepared from compounds of the general formula (XXXIX) wherein $R^3$ is hydrogen, by treatment with a chlorinating agent such as chlorine, N-chlorosuccinimide, sulfuryl chloride, etc. in an organic solvent such as diethyl ether, acetonitrile, or dichloromethane at a reaction temperature from −70° C. to 25° C. A more specific example would be the preparation of a compound of the general formula (XL) in which $R^1$ is amino, alkylamido, or haloalkylamido, and $R^2$ is cyano, by treatment of a compound of the general formula (XXXIX) in which $R^1$ is amino, alkylcarbonylamino or haloalkylcarbonylamino and $R^2$ is cyano, and $R^3$ is hydrogen, with sulfuryl chloride in diethyl ether at −40° C.

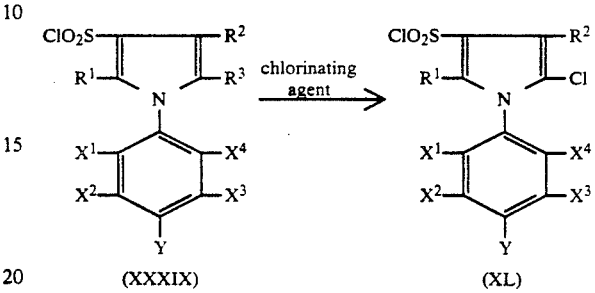

B-1) Compounds of the general formula (XLI) wherein the definitions of $R^1$, $R^2$, Y, $X^1$, $X^2$, $X^3$, and $X^4$ are those herein above defined in formula (Ia), can be prepared from compounds of the general formula (XXXIX) by treatment with a reducing agent, such as triphenylphosphine, in the presence of an organic solvent, such as tetrahydrofuran, toluene, or dichloromethane, at a reaction temperature from 0° C. to 110° C. A more specific example would be the preparation of a compound of the general formula (XLI) in which $R^1$ is hydrogen, amino, alkylcarbonylamino, or haloalkylcarbonylamino, $R^2$ is cyano, and $R^3$ is hydrogen or Cl, from a compound of the general formula (XXXIX) wherein $R^1$ is hydrogen, amino, alkylcarbonylamino, or haloalkylcarbonylamino, $R^2$ is cyano, and $R^3$ is hydrogen or Cl, by treatment with triphenylphosphine in tetrahydrofuran at 25° C. A representative example of a procedure for the reduction of para-toluenesulfonyl chloride to p-tolyldisulfide is provided in G. A. Olah et al, *J. Org. Chem.* 1980, 45, 4792.

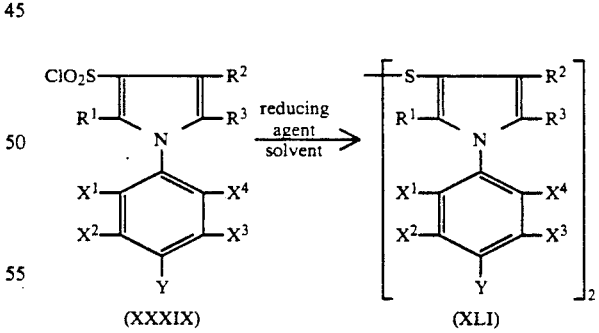

B-2) Compounds of the general formula (XLI) wherein the definitions of $X^1$, $X^2$, $X^3$, and $X^4$ are those herein above defined in formula (Ia), $R^1$ is amino, and $R^3$ is hydrogen, can be prepared from compounds of the general formula (IIIa) by treatment with sulfur monochloride, optionally in an organic solvent such as diethyl ether, ethyl acetate, acetonitrile, or dichloromethane, at a reaction temperature from about −100° C. to about 25° C.

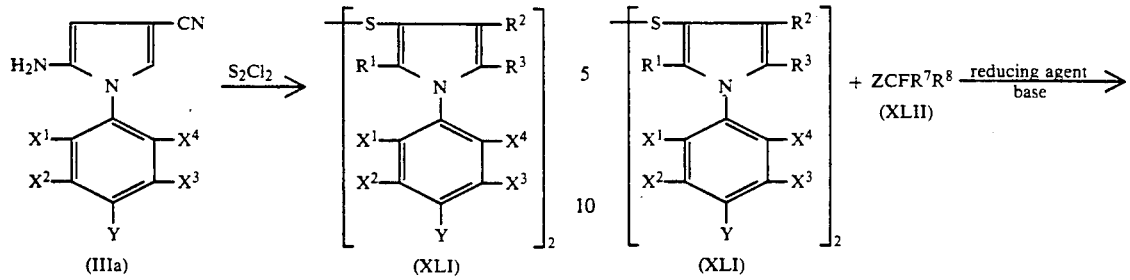

C-1) Compounds of the general formula (Ia) wherein the definitions of $R^1$, $R^2$, Y, $X^1$, $X^2$, $X^3$, and $X^4$ are those herein above defined in formula (Ia), and X is a perhaloalkylthio group, $R^6S$, in which $R^6$ is $CFR^7R^8$ and $R^7$ is F, Cl, or Br, and $R^8$ is F, Cl, Br or a perfluoroalkyl group, can be prepared from the reaction of a compound of the general formula (XLI) and a perhaloalkane compound of the general formula (XLII), $ZCFR^7R^8$, wherein Z is Cl, Br, or I, $R^7$ is F, Cl or Br, and $R^8$ is F, Cl, Br or a perfluoroalkyl group, with a reducing agent which can promote the formation of the free radical $CFR^7R^8$ from $ZCFR^7R^8$, preferably chosen from the metals consisting of zinc, cadmium, aluminum, manganese, or a compound with an oxide of sulfur, e.g., the dithionites or the hydroxymethylsulfinates. The alkaline dithionite, or alkaline earth or metal dithionite corresponds to the general formula (XLIII), $M_n(S_2O_4)$, in which n can be 1 or 2 depending upon the valence of the metal M. When one uses a dithionite of the general formula (XLIII) or a hydroxymethylsulfinate, one needs to add a base chosen from among the alkaline hydroxides, alkaline earth hydroxides, ammonia, triethylbenzylammonium, or the salts of weak acids such as disodium phosphate, sodium metabisulfite, sodium hydrogen sulfite, or sodium borate. The reaction is performed in a solvent (which can solubilize the dithionite or the hydroxymethylsulfinate and the compound (XLII), $ACFR^7R^8$), such as acetonitrile, formamide, dimethylformamide, dimethylacetamide, hexamethylphosphoramide, N-methylpyrrolidone, dimethylsulfoxide, or sulfolane, at a reaction temperature from about 0° C. to about 85° C. The alkaline dithionite can be added to the reaction mixture as a saturated solution in water or formamide. It is also possible to add the dithionite as a solid. When one is working with a gas which is only slightly soluble in the reaction solvent, the reaction pressure can be increased from one atmosphere to 50 atmospheres. A more specific example would be the preparation of a compound of the general formula (Ia) in which $R^1$ is hydrogen, amino, alkylcarbonylamino, or haloalkylcarbonylamino, $R^2$ is cyano, $R^3$ is hydrogen or Cl, and X is a perhaloalkylthio group, $R^6S$, in which $R^6$ is $CFR^7R^8$ and $R^7$ is F, Cl or Br and $R^8$ is F, Cl, Br or a perfluoroalkyl group, from the reaction of a compound of the general formula (XLI) in which $R^1$ is hydrogen, amino, alkylamido, or haloalkylamido, $R^2$ is cyano, and $R^3$ is hydrogen or Cl, and a compound of the general formula (XLII), $ZCFR^7R^8$, wherein Z is Cl, Br or I, $R^7$ is F or Cl, Br, and $R^8$ is F, Cl, Br or a perfluoroalkyl group, with sodium dithionite and disodium phosphate in dimethylformamide at 25° C. The reaction is represented by the following equation:

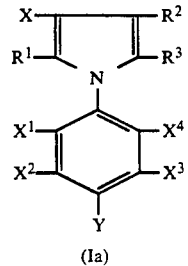

C-2) Alternatively, compounds of the general formula (Ia) wherein the definitions of $R^1$, $R^2$, Y, $X^1$, $X^2$, $X^3$, and $X^4$ are those herein above defined in formula (Ia), and X is a perhaloalkylthio group, $R^6S$, in which $R^6$ is $CFR^7R^8$ and $R^7$ is F, Cl, or Br, and $R^8$ is F, Cl, Br or a perfluoroalkyl group, can be prepared from the reaction of a compound of the general formula (XLI) and a perhaloalkane compound of the general formula (XLII), $ZCFR^7R^8$, wherein Z is Cl, Br, or I, $R^7$ is F, Cl or Br, and $R^8$ is F, Cl, Br or a perfluoroalkyl group, with another reducing agent medium, such as sodium formate along with sulfur dioxide, which also can promote the formation of the free radical $CFR^7R^8$ from $ZCFR^7R^8$. The reaction is conducted optionally in a solvent and in a similar manner to that described in C-1) above.

A more specific example would be the preparation of compounds of formula (Ia) in which $X^1$, $X^2$, $X^3$ and $X^4$ are as defined in formula (Ia), $R^1$ is amino, $R^2$ is cyano, and $R^3$ is hydrogen, from the reaction of a compound of formula (XLI) in which the substituents are as defined above. Said compounds of formula (Ia) can then be further converted into other compounds of formula (Ia) according to Methods 1 to 41 and processes ($P_1$ to $P_{15}$) previously described.

The intermediate chlorosulfonyl compounds of formula (XXXIX) and the intermediate disulfide compounds of formula (XLI) are an additional part of the present invention.

REPRESENTATIVE PYRROLE COMPOUNDS (RPC) OF THE INVENTION

Specific representative pyrrole compounds (RPC) which are contemplated in the invention are compounds of general formula (I), i.e. of formula (Ia), (Ia-1), (Ib), (Ib-1), (Ic), or (Ic-1) as follows:

TABLE 1A: RPC 1–389, wherein $R^2$=CN and the other substituents are as described;

TABLE 1B: RPC 390–491, wherein $X^2$ and $X^3$=H, $X^1$ and $X^4$=Cl, and Y=$CF_3$ and the other substituents are as described;

TABLE 1C: RPC 492–531, wherein $R^2$=CN and the other substituents are as described;

TABLE 1D: RPC 532-538, wherein $R^2 = CN$ and the other substituents are as described; compounds more specifically of formula (II-1a)/(II-4a);

TABLE 1E: RPC 539-905, wherein $R^2 = CN$, $X^2$ and $X^3 = H$, and the other substituents are as described; compounds more specifically of formula (II-7); and TABLE 1F: RPC 906-990, wherein $R^2 = CN$ and the other substituents are as described; compounds more specifically of formula (II-8).

Some of the above RPC pyrroles, specifically RPC 13, 14, 15, 16, 17, 18, 64, 65, 66, 67, 68, 69, 88, 89 and 90 have been synthesized and are identified as Additional Synthesis Examples/ASE) in the following section.

TABLE 1A

REPRESENTATIVE PYRROLE COMPOUNDS (RPC) OF GENERAL FORMULA (I), WHEREIN $R^2 = CN$

SUBSTITUENT GROUPS

| RPC-No. | $R^1$ | X | $R^3$ | $X^1$ | $X^2$ | Y | $X^3$ | $X^4$ |
|---|---|---|---|---|---|---|---|---|
| 1. | H | $SCF_3$ | F | Cl | H | $CF_3$ | H | Cl |
| 2. | H | $SOCF_3$ | F | Cl | H | $CF_3$ | H | Cl |
| 3. | H | $SO_2CF_3$ | F | Cl | H | $CF_3$ | H | Cl |
| 4. | H | $SCF_3$ | Br | Cl | H | $CF_3$ | H | Cl |
| 5. | H | $SOCF_3$ | Br | Cl | H | $CF_3$ | H | Cl |
| 6. | H | $SO_2CF_3$ | Br | Cl | H | $CF_3$ | H | Cl |
| 7. | H | $SCF_3$ | I | Cl | H | $CF_3$ | H | Cl |
| 8. | H | $SOCF_3$ | I | Cl | H | $CF_3$ | H | Cl |
| 9. | H | $SO_2CF_3$ | I | Cl | H | $CF_3$ | H | Cl |
| 10. | H | $SCF_3$ | $CF_3$ | Cl | H | $CF_3$ | H | Cl |
| 11. | H | $SOCF_3$ | $CF_3$ | Cl | H | $CF_3$ | H | Cl |
| 12. | H | $SO_2CF_3$ | $CF_3$ | Cl | H | $CF_3$ | H | Cl |
| 13. | H | $SCF_3$ | $CH_3$ | Cl | H | $CF_3$ | H | Cl |
| 14. | H | $SOCF_3$ | $CH_3$ | Cl | H | $CF_3$ | H | Cl |
| 15. | H | $SO_2CF_3$ | $CH_3$ | Cl | H | $CF_3$ | H | Cl |
| 16. | H | $SCF_3$ | $OCH_3$ | Cl | H | $CF_3$ | H | Cl |
| 17. | H | $SOCF_3$ | $OCH_3$ | Cl | H | $CF_3$ | H | Cl |
| 18. | H | $SO_2CF_3$ | $OCH_3$ | Cl | H | $CF_3$ | H | Cl |
| 19. | H | $SCF_3$ | $OCF_3$ | Cl | H | $CF_3$ | H | Cl |
| 20. | H | $SOCF_3$ | $OCF_3$ | Cl | H | $CF_3$ | H | Cl |
| 21. | H | $SO_2CF_3$ | $OCF_3$ | Cl | H | $CF_3$ | H | Cl |
| 22. | H | $SCF_3$ | $OCF_2Cl$ | Cl | H | $CF_3$ | H | Cl |
| 23. | H | $SOCF_3$ | $OCF_2Cl$ | Cl | H | $CF_3$ | H | Cl |
| 24. | H | $SO_2CF_3$ | $OCF_2Cl$ | Cl | H | $CF_3$ | H | Cl |
| 25. | H | $SCF_3$ | $OCF_2H$ | Cl | H | $CF_3$ | H | Cl |
| 26. | H | $SOCF_3$ | $OCF_2H$ | Cl | H | $CF_3$ | H | Cl |
| 27. | H | $SO_2CF_3$ | $OCF_2H$ | Cl | H | $CF_3$ | H | Cl |
| 28. | H | $SCF_3$ | CHO | Cl | H | $CF_3$ | H | Cl |
| 29. | H | $SOCF_3$ | CHO | Cl | H | $CF_3$ | H | Cl |
| 30. | H | $SO_2CF_3$ | CHO | Cl | H | $CF_3$ | H | Cl |
| 31. | H | $SCF_3$ | CN | Cl | H | $CF_3$ | H | Cl |
| 32. | H | $SOCF_3$ | CN | Cl | H | $CF_3$ | H | Cl |
| 33. | H | $SO_2CF_3$ | CN | Cl | H | $CF_3$ | H | Cl |
| 34. | H | $SOCF_3$ | $SCF_3$ | Cl | H | $CF_3$ | H | Cl |
| 35. | H | $SOCF_3$ | $SO_2CH_3$ | Cl | H | $CF_3$ | H | Cl |
| 36. | H | $SCF_3$ | $SO_2CH_3$ | Cl | H | $CF_3$ | H | Cl |
| 37. | H | $SO_2CF_3$ | $SO_2CH_3$ | Cl | H | $CF_3$ | H | Cl |
| 38. | H | $SCF_3$ | $COCF_3$ | Cl | H | $CF_3$ | H | Cl |
| 39. | H | $SOCF_3$ | $COCF_3$ | Cl | H | $CF_3$ | H | Cl |
| 40. | H | $SO_2CF_3$ | $COCF_3$ | Cl | H | $CF_3$ | H | Cl |
| 41. | H | $SOCF_3$ | $N(CH_3)_2$ | Cl | H | $CF_3$ | H | Cl |
| 42. | H | $SO_2CF_3$ | $N(CH_3)_2$ | Cl | H | $CF_3$ | H | Cl |
| 43. | H | $SCF_3$ | C≡CH | Cl | H | $CF_3$ | H | Cl |
| 44. | H | $SOCF_3$ | $CH_2C$≡CH | Cl | H | $CF_3$ | H | Cl |
| 45. | $NH_2$ | $SO_2CF_3$ | Cl | Cl | H | $CF_3$ | H | Cl |
| 46. | $NH_2$ | $SOCF_3$ | Cl | Cl | H | $CF_3$ | H | Cl |
| 47. | $NH_2$ | $SOCF_3$ | Br | Cl | H | $CF_3$ | H | Cl |
| 48. | $NH_2$ | $SO_2CF_3$ | Br | Cl | H | $CF_3$ | H | Cl |
| 49. | $CH_3CONH$ | $SCF_3$ | Cl | Cl | H | $CF_3$ | H | Cl |
| 50. | $CH_3CONH$ | $SOCF_3$ | Cl | Cl | H | $CF_3$ | H | Cl |
| 51. | $CH_3CONH$ | $SO_2CF_3$ | Cl | Cl | H | $CF_3$ | H | Cl |
| 52. | Cl | $SCF_3$ | Cl | Cl | H | $CF_3$ | H | Cl |
| 53. | Cl | $SOCF_3$ | Cl | Cl | H | $CF_3$ | H | Cl |
| 54. | Cl | $SO_2CF_3$ | Cl | Cl | H | $CF_3$ | H | Cl |
| 55. | F | $SCF_3$ | Cl | Cl | H | $CF_3$ | H | Cl |
| 56. | F | $SOCF_3$ | Cl | Cl | H | $CF_3$ | H | Cl |
| 57. | F | $SO_2CF_3$ | Cl | Cl | H | $CF_3$ | H | Cl |
| 58. | I | $SCF_3$ | Cl | Cl | H | $CF_3$ | H | Cl |
| 59. | I | $SOCF_3$ | Cl | Cl | H | $CF_3$ | H | Cl |
| 60. | I | $SO_2CF_3$ | Cl | Cl | H | $CF_3$ | H | Cl |
| 61. | $CF_3$ | $SCF_3$ | Cl | Cl | H | $CF_3$ | H | Cl |
| 62. | $CF_3$ | $SOCF_3$ | Cl | Cl | H | $CF_3$ | H | Cl |
| 63. | $CF_3$ | $SO_2CF_3$ | Cl | Cl | H | $CF_3$ | H | Cl |
| 64. | $CH_3$ | $SCF_3$ | Cl | Cl | H | $CF_3$ | H | Cl |
| 65. | $CH_3$ | $SOCF_3$ | Cl | Cl | H | $CF_3$ | H | Cl |
| 66. | $CH_3$ | $SO_2CF_3$ | Cl | Cl | H | $CF_3$ | H | Cl |
| 67. | $OCH_3$ | $SCF_3$ | Cl | Cl | H | $CF_3$ | H | Cl |
| 68. | $OCH_3$ | $SOCF_3$ | Cl | Cl | H | $CF_3$ | H | Cl |
| 69. | $OCH_3$ | $SO_2CF_3$ | Cl | Cl | H | $CF_3$ | H | Cl |

TABLE 1A-continued

REPRESENTATIVE PYRROLE COMPOUNDS (RPC) OF GENERAL FORMULA (I). WHEREIN $R^2 = CN$

SUBSTITUENT GROUPS

| RPC-No. | $R^1$ | X | $R^3$ | $X^1$ | $X^2$ | Y | $X^3$ | $X^4$ |
|---|---|---|---|---|---|---|---|---|
| 70. | $OCF_2Cl$ | $SCF_3$ | Cl | Cl | H | $CF_3$ | H | Cl |
| 71. | $OCF_2Cl$ | $SOCF_3$ | Cl | Cl | H | $CF_3$ | H | Cl |
| 72. | $OCF_2Cl$ | $SO_2CF_3$ | Cl | Cl | H | $CF_3$ | H | Cl |
| 73. | $OCF_2H$ | $SCF_3$ | Cl | Cl | H | $CF_3$ | H | Cl |
| 74. | $OCF_2H$ | $SOCF_3$ | Cl | Cl | H | $CF_3$ | H | Cl |
| 75. | $OCF_2H$ | $SO_2CF_3$ | Cl | Cl | H | $CF_3$ | H | Cl |
| 76. | CN | $SCF_3$ | Cl | Cl | H | $CF_3$ | H | Cl |
| 77. | CN | $SOCF_3$ | Cl | Cl | H | $CF_3$ | H | Cl |
| 78. | CN | $SO_2CF_3$ | Cl | Cl | H | $CF_3$ | H | Cl |
| 79. | $N_3$ | $SCF_3$ | Cl | Cl | H | $CF_3$ | H | Cl |
| 80. | $N_3$ | $SOCF_3$ | Cl | Cl | H | $CF_3$ | H | Cl |
| 81. | $N_3$ | $SO_2CF_3$ | Cl | Cl | H | $CF_3$ | H | Cl |
| 82. | phenyl | $SCF_3$ | Cl | Cl | H | $CF_3$ | H | Cl |
| 83. | phenyl | $SOCF_3$ | Cl | Cl | H | $CF_3$ | H | Cl |
| 84. | phenyl | $SO_2CF_3$ | Cl | Cl | H | $CF_3$ | H | Cl |
| 85. | 1-pyrrolyl | $SCF_3$ | Cl | Cl | H | $CF_3$ | H | Cl |
| 86. | 1-pyrrolyl | $SOCF_3$ | Cl | Cl | H | $CF_3$ | H | Cl |
| 87. | 1-pyrrolyl | $SO_2CF_3$ | Cl | Cl | H | $CF_3$ | H | Cl |
| 88. | $SCH_3$ | $SCF_3$ | Cl | Cl | H | $CF_3$ | H | Cl |
| 89. | $SCH_3$ | $SOCF_3$ | Cl | Cl | H | $CF_3$ | H | Cl |
| 90. | $SCH_3$ | $SO_2CF_3$ | Cl | Cl | H | $CF_3$ | H | Cl |
| 91. | $SO_2CF_3$ | $SOCF_3$ | Cl | Cl | H | $CF_3$ | H | Cl |
| 92. | $SO_2CF_3$ | $SO_2CF_3$ | Cl | Cl | H | $CF_3$ | H | Cl |
| 93. | C≡CH | $SCF_3$ | Cl | Cl | H | $CF_3$ | H | Cl |
| 94. | C≡CH | $SOCF_3$ | Cl | Cl | H | $CF_3$ | H | Cl |
| 95. | C≡CH | $SO_2CF_3$ | Cl | Cl | H | $CF_3$ | H | Cl |
| 96. | $SCF_3$ | $SCF_3$ | Cl | Cl | H | $CF_3$ | H | Cl |
| 97. | $SCF_3$ | $SOCF_3$ | Cl | Cl | H | $CF_3$ | H | Cl |
| 98. | $SCF_3$ | $SO_2CF_3$ | Cl | Cl | H | $CF_3$ | H | Cl |
| 99. | H | $SCF_3$ | H | Cl | H | $CF_3$ | H | Cl |
| 100. | H | $SOCF_3$ | H | Cl | H | $CF_3$ | H | Cl |
| 101. | H | $SO_2CF_3$ | H | Cl | H | $CF_3$ | H | Cl |
| 102. | $NH_2$ | $SCF_3$ | H | Cl | H | $CF_3$ | H | Cl |
| 103. | $NH_2$ | $SOCF_3$ | H | Cl | H | $CF_3$ | H | Cl |
| 104. | $NH_2$ | $SO_2CF_3$ | H | Cl | H | $CF_3$ | H | Cl |
| 105. | Cl | $SCF_3$ | H | Cl | H | $CF_3$ | H | Cl |
| 106. | Cl | $SOCF_3$ | H | Cl | H | $CF_3$ | H | Cl |
| 107. | Cl | $SO_2CF_3$ | H | Cl | H | $CF_3$ | H | Cl |
| 108. | F | $SCF_3$ | H | Cl | H | $CF_3$ | H | Cl |
| 109. | F | $SOCF_3$ | H | Cl | H | $CF_3$ | H | Cl |
| 110. | F | $SO_2CF_3$ | H | Cl | H | $CF_3$ | H | Cl |
| 111. | Br | $SCF_3$ | H | Cl | H | $CF_3$ | H | Cl |
| 112. | Br | $SOCF_3$ | H | Cl | H | $CF_3$ | H | Cl |
| 113. | Br | $SO_2CF_3$ | H | Cl | H | $CF_3$ | H | Cl |
| 114. | $CF_3$ | $SCF_3$ | H | Cl | H | $CF_3$ | H | Cl |
| 115. | $CF_3$ | $SOCF_3$ | H | Cl | H | $CF_3$ | H | Cl |
| 116. | $CF_3$ | $SO_2CF_3$ | H | Cl | H | $CF_3$ | H | Cl |
| 117. | CN | $SCF_3$ | H | Cl | H | $CF_3$ | H | Cl |
| 118. | CN | $SOCF_3$ | H | Cl | H | $CF_3$ | H | Cl |
| 119. | CN | $SO_2CF_3$ | H | Cl | H | $CF_3$ | H | Cl |
| 120. | Br | $SCF_3$ | $SCF_3$ | Cl | H | $CF_3$ | H | Cl |
| 121. | $NH_2$ | $SCF_3$ | $SCF_3$ | Cl | H | $CF_3$ | H | Cl |
| 122. | Cl | $SCF_3$ | F | Cl | H | $CF_3$ | H | Cl |
| 123. | Cl | $SOCF_3$ | F | Cl | H | $CF_3$ | H | Cl |
| 124. | Cl | $SO_2CF_3$ | F | Cl | H | $CF_3$ | H | Cl |
| 125. | Br | $SCF_3$ | F | Cl | H | $CF_3$ | H | Cl |
| 126. | Br | $SOCF_3$ | F | Cl | H | $CF_3$ | H | Cl |
| 127. | Br | $SO_2CF_3$ | F | Cl | H | $CF_3$ | H | Cl |
| 128. | $CF_3$ | $SCF_3$ | F | Cl | H | $CF_3$ | H | Cl |
| 129. | $CF_3$ | $SOCF_3$ | F | Cl | H | $CF_3$ | H | Cl |
| 130. | $CF_3$ | $SO_2CF_3$ | F | Cl | H | $CF_3$ | H | Cl |
| 131. | CN | $SCF_3$ | F | Cl | H | $CF_3$ | H | Cl |
| 132. | CN | $SOCF_3$ | F | Cl | H | $CF_3$ | H | Cl |
| 133. | CN | $SO_2CF_3$ | F | Cl | H | $CF_3$ | H | Cl |
| 134. | $NH_2$ | $SCF_3$ | F | Cl | H | $CF_3$ | H | Cl |
| 135. | $NH_2$ | $SOCF_3$ | F | Cl | H | $CF_3$ | H | Cl |
| 136. | $NH_2$ | $SO_2CF_3$ | F | Cl | H | $CF_3$ | H | Cl |
| 137. | H | $SCF_3$ | Cl | Cl | H | $OCF_3$ | H | Cl |
| 138. | H | $SOCF_3$ | Cl | Cl | H | $OCF_3$ | H | Cl |
| 139. | H | $SO_2CF_3$ | Cl | Cl | H | $OCF_3$ | H | Cl |
| 140. | H | $SCF_3$ | H | Cl | H | $OCF_3$ | H | Cl |
| 141. | H | $SOCF_3$ | H | Cl | H | $OCF_3$ | H | Cl |
| 142. | H | $SO_2CF_3$ | H | Cl | H | $OCF_3$ | H | Cl |
| 143. | $NH_2$ | $SCF_3$ | Cl | Cl | H | $OCF_3$ | H | Cl |
| 144. | $NH_2$ | $SOCF_3$ | Cl | Cl | H | $OCF_3$ | H | Cl |
| 145. | $NH_2$ | $SO_2CF_3$ | Cl | Cl | H | $OCF_3$ | H | Cl |
| 146. | $NH_2$ | $SCF_3$ | H | Cl | H | $OCF_3$ | H | Cl |

TABLE 1A-continued
REPRESENTATIVE PYRROLE COMPOUNDS (RPC) OF GENERAL FORMULA (I), WHEREIN $R^2$ = CN.

| | | | SUBSTITUENT GROUPS | | | | | |
|---|---|---|---|---|---|---|---|---|
| RPC-No. | $R^1$ | X | $R^3$ | $X^1$ | $X^2$ | Y | $X^3$ | $X^4$ |
| 147. | $NH_2$ | $SOCF_3$ | H | Cl | H | $OCF_3$ | H | Cl |
| 148. | $NH_2$ | $SO_2CF_3$ | H | Cl | H | $OCF_3$ | H | Cl |
| 149. | H | $SCF_3$ | F | Cl | H | $OCF_3$ | H | Cl |
| 150. | H | $SOCF_3$ | F | Cl | H | $OCF_3$ | H | Cl |
| 151. | H | $SO_2CF_3$ | F | Cl | H | $OCF_3$ | H | Cl |
| 152. | H | $SCF_3$ | CN | Cl | H | $OCF_3$ | H | Cl |
| 153. | H | $SOCF_3$ | CN | Cl | H | $OCF_3$ | H | Cl |
| 154. | H | $SO_2CF_3$ | CN | Cl | H | $OCF_3$ | H | Cl |
| 155. | Cl | $SCF_3$ | H | Cl | H | $OCF_3$ | H | Cl |
| 156. | Cl | $SOCF_3$ | H | Cl | H | $OCF_3$ | H | Cl |
| 157. | Cl | $SO_2CF_3$ | H | Cl | H | $OCF_3$ | H | Cl |
| 158. | Cl | $SCF_3$ | F | Cl | H | $OCF_3$ | H | Cl |
| 159. | Cl | $SOCF_3$ | F | Cl | H | $OCF_3$ | H | Cl |
| 160. | Cl | $SO_2CF_3$ | F | Cl | H | $OCF_3$ | H | H |
| 161. | $NH_2$ | $SCF_3$ | H | Cl | H | $CF_3$ | H | H |
| 162. | $NH_2$ | $SOCF_3$ | H | Cl | H | $CF_3$ | H | H |
| 163. | $NH_2$ | $SO_2CF_3$ | H | Cl | H | $CF_3$ | H | H |
| 164. | $NH_2$ | $SCF_3$ | Cl | Cl | H | $CF_3$ | H | H |
| 165. | $NH_2$ | $SOCF_3$ | Cl. | Cl | H | $CF_3$ | H | H |
| 166. | $NH_2$ | $SO_2CF_3$ | Cl | Cl | H | $CF_3$ | H | H |
| 167. | $NH_2$ | $SCF_3$ | Br | Cl | H | $CF_3$ | H | H |
| 168. | $NH_2$ | $SOCF_3$ | Br | Cl | H | $CF_3$ | H | H |
| 169. | $NH_2$ | $SO_2CF_3$ | Br | Cl | H | $CF_3$ | H | H |
| 170. | H | $SCF_3$ | H | Cl | H | $CF_3$ | H | H |
| 171. | H | $SOCF_3$ | H | Cl | H | $CF_3$ | H | H |
| 172. | H | $SO_2CF_3$ | H | Cl | H | $CF_3$ | H | H |
| 173. | H | $SCF_3$ | Cl | Cl | H | $CF_3$ | H | H |
| 174. | H | $SOCF_3$ | Cl | Cl | H | $CF_3$ | H | H |
| 175. | H | $SO_2CF_3$ | Cl | Cl | H | $CF_3$ | H | H |
| 176. | H | $SCF_3$ | F | Cl | H | $CF_3$ | H | H |
| 177. | H | $SOCF_3$ | F | Cl | H | $CF_3$ | H | H |
| 178. | H | $SO_2CF_3$ | F | Cl | H | $CF_3$ | H | H |
| 179. | $NH_2$ | $SCF_3$ | H | H | H | $CF_3$ | H | H |
| 180. | $NH_2$ | $SOCF_3$ | H | H | H | $CF_3$ | H | H |
| 181. | $NH_2$ | $SO_2CF_3$ | H | H | H | $CF_3$ | H | H |
| 182. | $NH_2$ | $SCF_3$ | $SCF_3$ | H | H | $CF_3$ | H | H |
| 183. | $NH_2$ | $SCF_3$ | Cl | H | H | $CF_3$ | H | H |
| 184. | $NH_2$ | $SOCF_3$ | Cl | H | H | $CF_3$ | H | H |
| 185. | $NH_2$ | $SO_2CF_3$ | Cl | H | H | $CF_3$ | H | H |
| 186. | $NH_2$ | $SCF_3$ | Br | H | H | $CF_3$ | H | H |
| 187. | $NH_2$ | $SOCF_3$ | Br | H | H | $CF_3$ | H | H |
| 188. | $NH_2$ | $SO_2CF_3$ | Br | H | H | $CF_3$ | H | H |
| 189. | H | $SCF_3$ | Cl | H | H | $CF_3$ | H | H |
| 190. | H | $SOCF_3$ | Cl | H | H | $CF_3$ | H | H |
| 191. | H | $SO_2CF_3$ | Cl | H | H | $CF_3$ | H | H |
| 192. | H | $SCF_3$ | F | H | H | $CF_3$ | H | H |
| 193. | H | $SOCF_3$ | F | H | H | $CF_3$ | H | H |
| 194. | H | $SO_2CF_3$ | F | H | H | $CF_3$ | H | H |
| 195. | H | $SCF_3$ | $CF_3$ | H | H | $CF_3$ | H | H |
| 196. | H | $SOCF_3$ | $CF_3$ | H | H | $CF_3$ | H | H |
| 197. | H | $SO_2CF_3$ | $CF_3$ | H | H | $CF_3$ | H | H |
| 198. | Cl | $SCF_3$ | Cl | H | H | $CF_3$ | H | H |
| 199. | Cl | $SOCF_3$ | Cl | H | H | $CF_3$ | H | H |
| 200. | Cl | $SO_2CF_3$ | Cl | H | H | $CF_3$ | H | H |
| 201. | Br | $SCF_3$ | Cl | H | H | $CF_3$ | H | Cl |
| 202. | Br | $SOCF_3$ | Cl | H | H | $CF_3$ | H | Cl |
| 203. | Br | $SO_2CF_3$ | Cl | H | H | $CF_3$ | H | Cl |
| 204. | $NH_2$ | $SCF_3$ | H | $CH_3$ | H | Br | H | $CH_3$ |
| 205. | $NH_2$ | $SOCF_3$ | H | $CH_3$ | H | Br | H | $CH_3$ |
| 206. | $NH_2$ | $SO_2CF_3$ | H | $CH_3$ | H | Br | H | $CH_3$ |
| 207. | H | $SCF_3$ | H | $CH_3$ | H | Br | H | $CH_3$ |
| 208. | H | $SOCF_3$ | H | $CH_3$ | H | Br | H | $CH_3$ |
| 209. | H | $SO_2CF_3$ | H | $CH_3$ | H | Br | H | $CH_3$ |
| 210. | H | $SCF_3$ | Cl | $CH_3$ | H | Br | H | $CH_3$ |
| 211. | H | $SOCF_3$ | Cl | $CH_3$ | H | Br | H | $CH_3$ |
| 212. | H | $SO_2CF_3$ | Cl | $CH_3$ | H | Br | H | $CH_3$ |
| 213. | $NH_2$ | $SCF_3$ | H | Cl | H | Cl | H | Cl |
| 214. | $NH_2$ | $SOCF_3$ | H | Cl | H | Cl | H | Cl |
| 215. | $NH_2$ | $SO_2CF_3$ | H | Cl | H | Cl | H | Cl |
| 216. | H | $SCF_3$ | Cl | Cl | H | Cl | H | Cl |
| 217. | H | $SOCF_3$ | Cl | Cl | H | Cl | H | Cl |
| 218. | H | $SO_2CF_3$ | Cl | Cl | H | Cl | H | Cl |
| 219. | $NH_2$ | $SCF_3$ | H | Cl | H | Cl | H | H |
| 220. | $NH_2$ | $SOCF_3$ | H | Cl | H | Cl | H | H |
| 221. | $NH_2$ | $SO_2CF_3$ | H | Cl | H | Cl | H | H |
| 222. | $NH_2$ | $SCF_3$ | $SCF_3$ | Cl | H | Cl | H | H |
| 223. | $NH_2$ | $SOCF_3$ | Cl | Cl | H | Cl | H | H |

TABLE 1A-continued

REPRESENTATIVE PYRROLE COMPOUNDS (RPC) OF GENERAL FORMULA (I), WHEREIN $R^2$ = CN

| RPC-No. | $R^1$ | X | $R^3$ | $X^1$ | $X^2$ | Y | $X^3$ | $X^4$ |
|---|---|---|---|---|---|---|---|---|
| 224. | $NH_2$ | $SCF_3$ | Cl | Cl | H | Cl | H | H |
| 225. | $NH_2$ | $SO_2CF_3$ | Cl | Cl | H | Cl | H | H |
| 226. | H | $SCF_3$ | Cl | Cl | H | Cl | H | H |
| 227. | H | $SOCF_3$ | Cl | Cl | H | Cl | H | H |
| 228. | H | $SO_2CF_3$ | Cl | Cl | H | Cl | H | H |
| 229. | $NH_2$ | $SCF_3$ | H | H | H | Cl | H | H |
| 230. | H | $SCF_3$ | Cl | Cl | H | $CF_3$ | H | Br |
| 231. | H | $SOCF_3$ | Cl | Cl | H | $CF_3$ | H | Br |
| 232. | H | $SO_2CF_3$ | Cl | Cl | H | $CF_3$ | H | Br |
| 233. | H | $SCF_3$ | Cl | F | H | $CF_3$ | H | F |
| 234. | H | $SOCF_3$ | Cl | F | H | $CF_3$ | H | F |
| 235. | H | $SO_2CF_3$ | Cl | F | H | $CF_3$ | H | F |
| 236. | H | $SCF_3$ | Cl | F | F | $CF_3$ | F | F |
| 237. | H | $SOCF_3$ | Cl | F | F | $CF_3$ | F | F |
| 238. | H | $SO_2CF_3$ | Cl | F | F | $CF_3$ | F | F |
| 239. | H | $SCF_3$ | Br | F | F | $CF_3$ | F | F |
| 240. | H | $SOCF_3$ | Br | F | F | $CF_3$ | F | F |
| 241. | H | $SO_2CF_3$ | Br | F | F | $CF_3$ | F | F |
| 242. | H | $SCF_3$ | Cl | Cl | H | $SCF_3$ | H | Cl |
| 243. | H | $SOCF_3$ | Cl | Cl | H | $SCF_3$ | H | Cl |
| 244. | H | $SO_2CF_3$ | Cl | Cl | H | $SCF_3$ | H | Cl |
| 245. | H | $SCF_3$ | Cl | Cl | H | $SO_2CF_3$ | H | Cl |
| 246. | H | $SOCF_3$ | Cl | Cl | H | $SO_2CF_3$ | H | Cl |
| 247. | H | $SO_2CF_3$ | Cl | Cl | H | $SO_2CF_3$ | H | Cl |
| 248. | $NH_2$ | $SCCl_2F$ | H | Cl | H | $CF_3$ | H | Cl |
| 249. | $NH_2$ | $SOCCl_2F$ | H | Cl | H | $CF_3$ | H | Cl |
| 250. | $NH_2$ | $SO_2CCl_2F$ | H | Cl | H | $CF_3$ | H | Cl |
| 251. | $NH_2$ | $SCCl_2F$ | Cl | Cl | H | $CF_3$ | H | Cl |
| 252. | $NH_2$ | $SOCCl_2F$ | Cl | Cl | H | $CF_3$ | H | Cl |
| 253. | $NH_2$ | $SO_2CCl_2F$ | Cl | Cl | H | $CF_3$ | H | Cl |
| 254. | $NH_2$ | $SCCl_2F$ | F | Cl | H | $CF_3$ | H | Cl |
| 255. | $NH_2$ | $SOCCl_2F$ | F | Cl | H | $CF_3$ | H | Cl |
| 256. | $NH_2$ | $SO_2CCl_2F$ | F | Cl | H | $CF_3$ | H | Cl |
| 257. | H | $SCCl_2F$ | H | Cl | H | $CF_3$ | H | Cl |
| 258. | H | $SOCCl_2F$ | H | Cl | H | $CF_3$ | H | Cl |
| 259. | H | $SO_2CCl_2F$ | H | Cl | H | $CF_3$ | H | Cl |
| 260. | H | $SCCl_2F$ | $CF_3$ | Cl | H | $CF_3$ | H | Cl |
| 261. | H | $SOCCl_2F$ | $CF_3$ | Cl | H | $CF_3$ | H | Cl |
| 262. | H | $SO_2CCl_2F$ | $CF_3$ | Cl | H | $CF_3$ | H | Cl |
| 263. | H | $SCCl_2F$ | CN | Cl | H | $CF_3$ | H | Cl |
| 264. | H | $SOCCl_2F$ | CN | Cl | H | $CF_3$ | H | Cl |
| 265. | H | $SO_2CCl_2F$ | CN | Cl | H | $CF_3$ | H | Cl |
| 266. | CN | $SCCl_2F$ | H | Cl | H | $CF_3$ | H | Cl |
| 267. | CN | $SOCCl_2F$ | H | Cl | H | $CF_3$ | H | Cl |
| 268. | CN | $SO_2CCl_2F$ | H | Cl | H | $CF_3$ | H | Cl |
| 269. | $NH_2$ | $SCClF_2$ | H | Cl | H | $CF_3$ | H | Cl |
| 270. | $NH_2$ | $SOCClF_2$ | H | Cl | H | $CF_3$ | H | Cl |
| 271. | $NH_2$ | $SO_2CClF_2$ | H | Cl | H | $CF_3$ | H | Cl |
| 272. | $NH_2$ | $SCClF_2$ | Cl | Cl | H | $CF_3$ | H | Cl |
| 273. | $NH_2$ | $SOCClF_2$ | Cl | Cl | H | $CF_3$ | H | Cl |
| 274. | $NH_2$ | $SO_2CClF_2$ | Cl | Cl | H | $CF_3$ | H | Cl |
| 275. | H | $SCClF_2$ | Cl | Cl | H | $CF_3$ | H | Cl |
| 276. | H | $SOCClF_2$ | Cl | Cl | H | $CF_3$ | H | Cl |
| 277. | H | $SO_2CClF_2$ | Cl | Cl | H | $CF_3$ | H | Cl |
| 278. | H | $SCClF_2$ | F | Cl | H | $CF_3$ | H | Cl |
| 279. | H | $SOCClF_2$ | F | Cl | H | $CF_3$ | H | Cl |
| 280. | H | $SO_2CClF_2$ | F | Cl | H | $CF_3$ | H | Cl |
| 281. | F | $SCClF_2$ | F | Cl | H | $CF_3$ | H | Cl |
| 282. | F | $SOCClF_2$ | F | Cl | H | $CF_3$ | H | Cl |
| 283. | F | $SO_2CClF_2$ | F | Cl | H | $CF_3$ | H | Cl |
| 284. | Br | $SCClF_2$ | $SO_2CH_3$ | Cl | H | $CF_3$ | H | Cl |
| 285. | Br | $SOCClF_2$ | $SO_2CH_3$ | Cl | H | $CF_3$ | H | Cl |
| 286. | Br | $SO_2CClF_2$ | $SO_2CH_3$ | Cl | H | $CF_3$ | H | Cl |
| 287. | $NH_2$ | SCN | H | Cl | H | $CF_3$ | H | Cl |
| 288. | $NH_2$ | $SCH_3$ | H | Cl | H | $CF_3$ | H | Cl |
| 289. | $NH_2$ | $SOCH_3$ | H | Cl | H | $CF_3$ | H | Cl |
| 290. | $NH_2$ | $SO_2CH_3$ | H | Cl | H | $CF_3$ | H | Cl |
| 291. | $NH_2$ | $SCH_3$ | Cl | Cl | H | $CF_3$ | H | Cl |
| 292. | $NH_2$ | $SOCH_3$ | Cl | Cl | H | $CF_3$ | H | Cl |
| 293. | $NH_2$ | $SO_2CH_3$ | Cl | Cl | H | $CF_3$ | H | Cl |
| 294. | $NH_2$ | $SCH_3$ | F | Cl | H | $CF_3$ | H | Cl |
| 295. | $NH_2$ | $SOCH_3$ | F | Cl | H | $CF_3$ | H | Cl |
| 296. | $NH_2$ | $SO_2CH_3$ | F | Cl | H | $CF_3$ | H | Cl |
| 297. | $NH_2$ | $SCH_3$ | $CF_3$ | Cl | H | $CF_3$ | H | Cl |
| 298. | $NH_2$ | $SOCH_3$ | $CF_3$ | Cl | H | $CF_3$ | H | Cl |
| 299. | $NH_2$ | $SO_2CH_3$ | $CF_3$ | Cl | H | $CF_3$ | H | Cl |
| 300. | H | $SCH_3$ | H | Cl | H | $CF_3$ | H | Cl |

TABLE 1A-continued

REPRESENTATIVE PYRROLE COMPOUNDS (RPC) OF GENERAL FORMULA (I), WHEREIN $R^2$ = CN

| RPC-No. | $R^1$ | X | $R^3$ | $X^1$ | $X^2$ | Y | $X^3$ | $X^4$ |
|---|---|---|---|---|---|---|---|---|
| 301. | H | $SOCH_3$ | H | Cl | H | $CF_3$ | H | Cl |
| 302. | H | $SO_2CH_3$ | H | Cl | H | $CF_3$ | H | Cl |
| 303. | H | $SCH_3$ | Cl | Cl | H | $CF_3$ | H | Cl |
| 304. | H | $SOCH_3$ | Cl | Cl | H | $CF_3$ | H | Cl |
| 305. | H | $SO_2CH_3$ | Cl | Cl | H | $CF_3$ | H | Cl |
| 306. | H | $SCH_3$ | F | Cl | H | $CF_3$ | H | Cl |
| 307. | H | $SOCH_3$ | F | Cl | H | $CF_3$ | H | Cl |
| 308. | H | $SO_2CH_3$ | F | Cl | H | $CF_3$ | H | Cl |
| 309. | Cl | $SCH_3$ | H | Cl | H | $CF_3$ | H | Cl |
| 310. | Cl | $SOCH_3$ | H | Cl | H | $CF_3$ | H | Cl |
| 311. | Cl | $SO_2CH_3$ | H | Cl | H | $CF_3$ | H | Cl |
| 312. | Cl | $SCH_3$ | Cl | Cl | H | $CF_3$ | H | Cl |
| 313. | Cl | $SOCH_3$ | Cl | Cl | H | $CF_3$ | H | Cl |
| 314. | Cl | $SO_2CH_3$ | Cl | Cl | H | $CF_3$ | H | Cl |
| 315. | Cl | $SCH_3$ | F | Cl | H | $CF_3$ | H | Cl |
| 316. | Cl | $SOCH_3$ | F | Cl | H | $CF_3$ | H | Cl |
| 317. | Cl | $SO_2CH_3$ | F | Cl | H | $CF_3$ | H | Cl |
| 318. | Cl | $SCH_3$ | $CF_3$ | Cl | H | $CF_3$ | H | Cl |
| 319. | Cl | $SOCH_3$ | $CF_3$ | Cl | H | $CF_3$ | H | Cl |
| 320. | Cl | $SO_2CH_3$ | $CF_3$ | Cl | H | $CF_3$ | H | Cl |
| 321. | F | $SCH_3$ | H | Cl | H | $CF_3$ | H | Cl |
| 322. | F | $SOCH_3$ | H | Cl | H | $CF_3$ | H | Cl |
| 323. | F | $SO_2CH_3$ | H | Cl | H | $CF_3$ | H | Cl |
| 324. | F | $SCH_3$ | F | Cl | H | $CF_3$ | H | Cl |
| 325. | F | $SOCH_3$ | F | Cl | H | $CF_3$ | H | Cl |
| 326. | F | $SO_2CH_3$ | F | Cl | H | $CF_3$ | H | Cl |
| 327. | F | $SCH_3$ | Cl | Cl | H | $CF_3$ | H | Cl |
| 328. | F | $SOCH_3$ | Cl | Cl | H | $CF_3$ | H | Cl |
| 329. | F | $SO_2CH_3$ | Cl | Cl | H | $CF_3$ | H | Cl |
| 330. | $NH_2$ | $SCF_2CCl_2F$ | H | Cl | H | $CF_3$ | H | Cl |
| 331. | $NH_2$ | $SOCF_2CCl_2F$ | H | Cl | H | $CF_3$ | H | Cl |
| 332. | $NH_2$ | $SO_2CF_2CCl_2F$ | H | Cl | H | $CF_3$ | H | Cl |
| 333. | $NH_2$ | $SCF_2CCl_2F$ | Cl | Cl | H | $CF_3$ | H | Cl |
| 334. | $NH_2$ | $SOCF_2CCl_2F$ | Cl | Cl | H | $CF_3$ | H | Cl |
| 335. | $NH_2$ | $SO_2CF_2CCl_2F$ | Cl | Cl | H | $CF_3$ | H | Cl |
| 336. | $NH_2$ | $SCF_2CCl_2F$ | F | Cl | H | $CF_3$ | H | Cl |
| 337. | $NH_2$ | $SOCF_2CCl_2F$ | F | Cl | H | $CF_3$ | H | Cl |
| 338. | $NH_2$ | $SO_2CF_2CCl_2F$ | F | Cl | H | $CF_3$ | H | Cl |
| 339. | H | $SCF_2CCl_2F$ | H | Cl | H | $CF_3$ | H | Cl |
| 340. | H | $SOCF_2CCl_2F$ | H | Cl | H | $CF_3$ | H | Cl |
| 341. | H | $SO_2CF_2CCl_2F$ | H | Cl | H | $CF_3$ | H | Cl |
| 342. | H | $SCF_2CCl_2F$ | Cl | Cl | H | $CF_3$ | H | Cl |
| 343. | H | $SOCF_2CCl_2F$ | Cl | Cl | H | $CF_3$ | H | Cl |
| 344. | H | $SO_2CF_2CCl_2F$ | Cl | Cl | H | $CF_3$ | H | Cl |
| 345. | F | $SCF_2CCl_2F$ | H | Cl | H | $CF_3$ | H | Cl |
| 346. | F | $SOCF_2CCl_2F$ | H | Cl | H | $CF_3$ | H | Cl |
| 347. | F | $SO_2CF_2CCl_2F$ | H | Cl | H | $CF_3$ | H | Cl |
| 348. | F | $SCF_2CCl_2F$ | Cl | Cl | H | $CF_3$ | H | Cl |
| 349. | F | $SOCF_2CCl_2F$ | Cl | Cl | H | $CF_3$ | H | Cl |
| 350. | F | $SO_2CF_2CCl_2F$ | Cl | Cl | H | $CF_3$ | H | Cl |
| 351. | H | $SCF_2CHF_2$ | Cl | Cl | H | $CF_3$ | H | Cl |
| 352. | H | $SOCF_2CHF_2$ | Cl | Cl | H | $CF_3$ | H | Cl |
| 353. | H | $SO_2CF_2CHF_2$ | Cl | Cl | H | $CF_3$ | H | Cl |
| 354. | H | $SC_6F_5$ | Cl | Cl | H | $CF_3$ | H | Cl |
| 355. | H | $SOC_6F_5$ | Cl | Cl | H | $CF_3$ | H | Cl |
| 356. | H | $SO_2C_6F_5$ | Cl | Cl | H | $CF_3$ | H | Cl |
| 357. | H | $OCF_3$ | Cl | Cl | H | $CF_3$ | H | Cl |
| 358. | H | $OCF_3$ | F | Cl | H | $CF_3$ | H | Cl |
| 359. | F | $OCF_3$ | H | Cl | H | $CF_3$ | H | Cl |
| 360. | F | $OCF_3$ | Cl | Cl | H | $CF_3$ | H | Cl |
| 361. | F | $OCF_3$ | F | Cl | H | $CF_3$ | H | Cl |
| 362. | Cl | $OCF_3$ | H | Cl | H | $CF_3$ | H | Cl |
| 363. | Cl | $OCF_3$ | Cl | Cl | H | $CF_3$ | H | Cl |
| 364. | Cl | $OCF_3$ | $CF_3$ | Cl | H | $CF_3$ | H | Cl |
| 365. | H | $OCF_2H$ | Cl | Cl | H | $CF_3$ | H | Cl |
| 366. | H | $OCF_2H$ | F | Cl | H | $CF_3$ | H | Cl |
| 367. | $NH_2$ | $C(=O)CF_3$ | Cl | Cl | H | $CF_3$ | H | Cl |
| 368. | $NH_2$ | $C(=S)CF_3$ | Cl | Cl | H | $CF_3$ | H | Cl |
| 369. | $NH_2$ | $C(=O)CF_3$ | F | Cl | H | $CF_3$ | H | Cl |
| 370. | $NH_2$ | $C(=S)CF_3$ | F | Cl | H | $CF_3$ | H | Cl |
| 371. | $NH_2$ | $C(=O)CF_3$ | Br | Cl | H | $CF_3$ | H | Cl |
| 372. | $NH_2$ | $C(=S)CF_3$ | Br | Cl | H | $CF_3$ | H | Cl |
| 373. | H | $C(=O)CF_3$ | Cl | Cl | H | $CF_3$ | H | Cl |
| 374. | H | $C(=S)CF_3$ | Cl | Cl | H | $CF_3$ | H | Cl |
| 375. | H | $C(=O)CF_3$ | F | Cl | H | $CF_3$ | H | Cl |
| 376. | H | $C(=S)CF_3$ | F | Cl | H | $CF_3$ | H | Cl |
| 377. | H | $C(=O)CF_3$ | $CF_3$ | Cl | H | $CF_3$ | H | Cl |

TABLE 1A-continued

REPRESENTATIVE PYRROLE COMPOUNDS (RPC) OF GENERAL FORMULA (I), WHEREIN $R^2 = CN$

| RPC-No. | $R^1$ | X | $R^3$ | $X^1$ | $X^2$ | Y | $X^3$ | $X^4$ |
|---|---|---|---|---|---|---|---|---|
| 378. | H | C(=S)CF$_3$ | CF$_3$ | Cl | H | CF$_3$ | H | Cl |
| 379. | H | CF$_3$ | Cl | Cl | H | CF$_3$ | H | Cl |
| 380. | H | CF$_3$ | CN | Cl | H | CF$_3$ | H | Cl |
| 381. | H | SCCl$_2$F | H | Cl | H | Cl | H | OCH$_3$ |
| 382. | H | SOCCl$_2$F | H | Cl | H | Cl | H | OCH$_3$ |
| 383. | H | SCF$_3$ | H | H | H | Cl | H | OCH$_2$CH$_3$ |
| 384. | H | SCF$_2$Cl | H | Cl | H | Cl | H | Br |
| 385. | H | SOCF$_2$Cl | H | Cl | H | Cl | H | Br |
| 386. | H | SCF$_3$ | H | H | H | Cl | H | Br |
| 387. | H | SCF$_2$Cl | H | Cl | H | Cl | H | SCH$_3$ |
| 388. | H | SCCl$_2$F | H | Cl | H | Cl | H | SCH$_3$ |
| 389. | H | SCF$_3$ | H | Cl | H | Cl | H | SCH$_2$CH$_3$ |

TABLE 1B

OTHER REPRESENTATIVE PYRROLE COMPOUNDS (RPC) OF GENERAL FORMULA (I): WHEREIN, $X^2$ & $X^3$ = H; $X^1$ & $X^4$ = Cl; AND Y = CF$_3$

| RPC-No. | $R^1$ | X | $R^3$ | $R^2$ |
|---|---|---|---|---|
| 390. | H | SCF$_3$ | Cl | H |
| 391. | H | SOCF$_3$ | Cl | H |
| 392. | H | SO$_2$CF$_3$ | Cl | H |
| 393. | H | SCF$_3$ | F | H |
| 394. | H | SOCF$_3$ | F | H |
| 395. | H | SO$_2$CF$_3$ | F | H |
| 396. | H | SCF$_3$ | CN | H |
| 397. | H | SOCF$_3$ | CN | H |
| 398. | H | SO$_2$CF$_3$ | CN | H |
| 399. | H | SCF$_3$ | CF$_3$ | H |
| 400. | H | SOCF$_3$ | CF$_3$ | H |
| 401. | H | SO$_2$CF$_3$ | CF$_3$ | H |
| 402. | H | SCF$_3$ | SO$_2$CF$_3$ | H |
| 403. | H | SOCF$_3$ | SO$_2$CF$_3$ | H |
| 404. | H | SO$_2$CF$_3$ | SO$_2$CF$_3$ | H |
| 405. | Cl | SCF$_3$ | Cl | H |
| 406. | Cl | SOCF$_3$ | Cl | H |
| 407. | Cl | SO$_2$CF$_3$ | Cl | H |
| 408. | Cl | SCF$_3$ | F | H |
| 409. | Cl | SOCF$_3$ | F | H |
| 410. | Cl | SCF$_3$ | CN | H |
| 411. | Cl | SOCF$_3$ | CN | H |
| 412. | Cl | SO$_2$CF$_3$ | CN | H |
| 413. | CN | SCF$_3$ | Cl | H |
| 414. | CN | SOCF$_3$ | Cl | H |
| 415. | CN | SO$_2$CF$_3$ | Cl | H |
| 416. | CN | SCF$_3$ | F | H |
| 417. | CN | SOCF$_3$ | F | H |
| 418. | CN | SO$_2$CF$_3$ | F | H |
| 419. | CN | SCF$_3$ | CF$_3$ | H |
| 420. | CN | SOCF$_3$ | CF$_3$ | H |
| 421. | CN | SO$_2$CF$_3$ | CF$_3$ | H |
| 422. | F | SCF$_3$ | Cl | H |
| 423. | F | SOCF$_3$ | Cl | H |
| 424. | F | SO$_2$CF$_3$ | Cl | H |
| 425. | H | SCF$_3$ | Cl | Cl |
| 426. | H | SOCF$_3$ | Cl | Cl |
| 427. | H | SO$_2$CF$_3$ | Cl | Cl |
| 428. | H | SCF$_3$ | F | Cl |
| 429. | H | SOCF$_3$ | F | Cl |
| 430. | H | SO$_2$CF$_3$ | F | Cl |
| 431. | H | SCF$_3$ | CN | Cl |
| 432. | H | SOCF$_3$ | CN | Cl |
| 433. | H | SO$_2$CF$_3$ | CN | Cl |
| 434. | H | SCF$_3$ | CF$_3$ | Cl |
| 435. | H | SOCF$_3$ | CF$_3$ | Cl |
| 436. | H | SO$_2$CF$_3$ | CF$_3$ | Cl |
| 437. | Cl | SCF$_3$ | Cl | Cl |
| 438. | Cl | SOCF$_3$ | Cl | Cl |
| 439. | Cl | SO$_2$CF$_3$ | Cl | Cl |
| 440. | Cl | SCF$_3$ | F | Cl |
| 441. | Cl | SOCF$_3$ | F | Cl |
| 442. | Cl | SO$_2$CF$_3$ | F | Cl |
| 443. | Cl | SCF$_3$ | CN | Cl |
| 444. | Cl | SOCF$_3$ | CN | Cl |
| 445. | Cl | SO$_2$CF$_3$ | CN | Cl |
| 446. | Cl | SCF$_3$ | CF$_3$ | Cl |
| 447. | Cl | SOCF$_3$ | CF$_3$ | Cl |
| 448. | Cl | SO$_2$CF$_3$ | CF$_3$ | Cl |
| 449. | CN | SCF$_3$ | Cl | Cl |
| 450. | CN | SOCF$_3$ | Cl | Cl |
| 451. | CN | SO$_2$CF$_3$ | Cl | Cl |
| 452. | CN | SCF$_3$ | F | Cl |
| 453. | CN | SOCF$_3$ | F | Cl |
| 454. | CN | SO$_2$CF$_3$ | F | Cl |
| 455. | CN | SCF$_3$ | CN | Cl |
| 456. | CN | SOCF$_3$ | CN | Cl |
| 457. | CN | SO$_2$CF$_3$ | CN | Cl |
| 458. | CN | SCF$_3$ | CF$_3$ | Cl |
| 459. | Cl | SO$_2$CF$_3$ | F | H |
| 460. | CN | SOCF$_3$ | CF$_3$ | Cl |
| 461. | CN | SO$_2$CF$_3$ | CF$_3$ | Cl |
| 462. | H | SCF$_3$ | Cl | CF$_3$ |
| 463. | H | SCF$_3$ | F | CF$_3$ |
| 464. | H | SOCF$_3$ | F | CF$_3$ |
| 465. | H | SO$_2$CF$_3$ | F | CF$_3$ |
| 466. | H | SCF$_3$ | CN | CF$_3$ |
| 467. | H | SOCF$_3$ | CN | CF$_3$ |
| 468. | H | SO$_2$CF$_3$ | CN | CF$_3$ |
| 469. | H | SCF$_3$ | Cl | CF$_3$ |
| 470. | H | SOCF$_3$ | Cl | CF$_3$ |
| 471. | H | SO$_2$CF$_3$ | Cl | CF$_3$ |
| 472. | H | SCF$_3$ | Cl | CH$_3$ |
| 473. | H | SOCF$_3$ | Cl | CH$_3$ |
| 474. | H | SO$_2$CF$_3$ | Cl | CH$_3$ |
| 475. | H | SCF$_3$ | F | CH$_3$ |
| 476. | H | SOCF$_3$ | F | CH$_3$ |
| 477. | H | SO$_2$CF$_3$ | F | CH$_3$ |
| 478. | H | SCHF$_2$ | Cl | CN |
| 479. | H | SOCHF$_2$ | Cl | CN |
| 480. | H | SO$_2$CHF$_2$ | Cl | CN |
| 481. | H | SCHF$_2$ | H | CN |
| 482. | H | SOCHF$_2$ | H | CN |
| 483. | H | SO$_2$CHF$_2$ | H | CN |
| 484. | H | SO$_2$CHCl$_2$ | Cl | CN |
| 485. | H | SOCHCl$_2$ | Cl | CN |
| 486. | H | SOCHClF | Cl | CN |
| 487. | H | SO$_2$CHClF | Cl | CN |
| 488. | H | SCHF$_2$ | Cl | Cl |
| 489. | H | SO$_2$CHF$_2$ | Cl | Cl |
| 490. | H | SOCHF$_2$ | Br | CH$_3$ |
| 491. | Cl | SO$_2$CHF$_2$ | Cl | CF$_3$ |

TABLE 1C

REPRESENTATIVE PYRROLE COMPOUNDS (RPC) OF GENERAL FORMULA (I), WHEREIN $R^2 = CN$

| NO. | $R^1$ | X | $R^3$ | $X^1$ | $X^2$ | Y | $X^3$ | $X^4$ |
|---|---|---|---|---|---|---|---|---|
| 492. | Br | CFCl$_2$S | Cl | Cl | H | Cl | H | Cl |
| 493. | Br | CFCl$_2$SO | Cl | Cl | H | Cl | H | Cl |
| 494. | Br | CFCl$_2$SO$_2$ | Cl | Cl | H | Cl | H | Cl |
| 495. | H | CFCl$_2$S | Cl | H | Cl | H | Cl | H |
| 496. | H | CFCl$_2$SO | Cl | H | Cl | H | Cl | H |
| 497. | H | CFCl$_2$SO$_2$ | Cl | H | Cl | H | Cl | H |
| 498. | Br | CFCl$_2$S | Cl | H | Cl | H | Cl | H |
| 499. | Br | CFCl$_2$SO | Cl | H | Cl | H | Cl | H |
| 500. | Br | CFCl$_2$SO$_2$ | Cl | H | Cl | H | Cl | H |
| 501. | H | CF$_2$ClSO | Cl | H | Cl | H | Cl | H |
| 502. | H | CF$_2$ClSO$_2$ | Cl | H | Cl | H | Cl | H |
| 503. | H | CF$_3$S | Cl | H | Cl | H | Cl | H |
| 504. | H | CF$_3$SO | Cl | H | Cl | H | Cl | H |
| 505. | Br | CF$_2$ClS | Cl | H | Cl | H | Cl | H |
| 506. | Cl | CF$_2$ClSO | Cl | H | Cl | H | Cl | H |
| 507. | H | CHF$_2$S | Cl | Cl | H | Cl | H | Cl |
| 508. | H | CHF$_2$SO | Cl | Cl | H | Cl | H | Cl |
| 509. | H | CHF$_2$SO$_2$ | Cl | Cl | H | Cl | H | Cl |
| 510. | H | CFCl$_2$SO | Cl | Cl | Cl | Cl | H | Cl |
| 511. | H | CF$_2$ClSO$_2$ | Br | Cl | Cl | Cl | H | Cl |
| 512. | H | CFCl$_2$S | Cl | H | Cl | Cl | H | Cl |
| 513. | H | CF$_3$SO | Cl | H | Cl | Cl | H | Cl |
| 514. | H | CFCl$_2$SO$_2$ | Cl | H | Cl | Cl | H | Cl |
| 515. | H | CF$_2$ClS | Cl | H | CF$_3$ | H | CF$_3$ | H |
| 516. | H | CF$_2$ClSO | Cl | H | CF$_3$ | H | CF$_3$ | H |
| 517. | H | CFCl$_2$SO | Cl | H | CF$_3$ | H | CF$_3$ | H |
| 518. | H | CF$_2$ClSO$_2$ | Cl | H | CF$_3$ | H | CF$_3$ | H |
| 519. | H | CFCl$_2$SO$_2$ | Cl | H | CF$_3$ | H | CF$_3$ | H |
| 520. | Br | CFCl$_2$S | H | H | CF$_3$ | H | CF$_3$ | H |
| 521. | Br | CFCl$_2$SO | H | H | CF$_3$ | H | CF$_3$ | H |
| 522. | Br | CFCl$_2$SO$_2$ | H | H | CF$_3$ | H | CF$_3$ | H |
| 523. | Br | CF$_2$ClS | Cl | H | CF$_3$ | H | CF$_3$ | H |
| 524. | Br | CF$_2$ClSO | Cl | H | CF$_3$ | H | CF$_3$ | H |
| 525. | Br | CF$_2$ClSO$_2$ | Cl | H | CF$_3$ | H | CF$_3$ | H |
| 526. | H | CFCl$_2$ | H | Cl | H | Cl | H | Cl |
| 527. | H | CF$_3$CF$_2$ | H | Cl | H | Cl | H | Cl |
| 528. | H | CF$_3$ | H | Cl | H | Cl | H | Cl |
| 529. | H | CFCl$_2$ | H | Cl | H | Cl | H | Cl |
| 530. | Br | CF$_3$CF$_2$ | H | Cl | H | Cl | H | Cl |
| 531. | Br | CF$_3$ | H | Cl | H | Cl | H | Cl |

TABLE 1D

REPRESENTATIVE PYRROLE COMPOUNDS (RPC) OF GENERAL FORMULA (I), PARTICULARLY (II-1a/II-4a) WHEREIN $R^2 = CN$)

| NO. | $R^1$ | X | $R^3$ | $X^1$ | $X^2$ | Y | $X^3$ | $X^4$ |
|---|---|---|---|---|---|---|---|---|
| 532. | H | I | H | Cl | H | Cl | H | Cl |
| 533. | H | CHF$_2$S | H | Cl | H | Cl | H | Cl |
| 534. | H | CHF$_2$SO | H | Cl | H | Cl | H | Cl |
| 535. | H | CHF$_2$SO$_2$ | H | Cl | H | Cl | H | Cl |
| 536. | H | CF$_2$ClS | H | Br | H | Cl | H | Cl |
| 537. | H | CF$_3$S | H | Cl | Cl | Cl | H | Cl |
| 538. | H | CF$_3$SO | H | H | Cl | Cl | H | Cl |

TABLE 1E

REPRESENTATIVE PYRROLE COMPOUNDS (RPC) OF GENERAL FORMULA (I), PARTICULARLY (II-7), WHEREIN $R^2 = CN$ AND $X^2$ & $X^3 = H$

| RPC-No. | $R^1$ | X | $R^3$ | $X^1$ | Y | $X^4$ |
|---|---|---|---|---|---|---|
| 539. | CH$_3$SO$_2$ | CF$_3$S | Cl | Cl | CF$_3$ | Cl |
| 540. | CH$_3$SO | CF$_3$SO | Cl | Cl | CF$_3$ | Cl |
| 541. | CH$_3$SO$_2$ | CF$_3$SO | Cl | Cl | CF$_3$ | Cl |
| 542. | CH$_3$SO | CF$_3$SO$_2$ | Cl | Cl | CF$_3$ | Cl |
| 543. | CH$_3$SO$_2$ | CF$_3$SO$_2$ | Cl | Cl | CF$_3$ | Cl |
| 544. | CH$_3$CH$_2$S | CF$_3$S | Cl | Cl | CF$_3$ | Cl |
| 545. | CH$_3$CH$_2$S | CF$_3$SO | Cl | Cl | CF$_3$ | Cl |
| 546. | CH$_3$CH$_2$S | CF$_3$SO$_2$ | Cl | Cl | CF$_3$ | Cl |
| 547. | (CH$_3$)$_3$CS | CF$_3$S | Cl | Cl | CF$_3$ | Cl |
| 548. | (CH$_3$)$_3$CS | CF$_3$SO | Cl | Cl | CF$_3$ | Cl |
| 549. | (CH$_3$)$_3$CS | CF$_3$SO$_2$ | Cl | Cl | CF$_3$ | Cl |
| 550. | CH$_2$=CHCH$_2$S | CF$_3$S | Cl | Cl | CF$_3$ | Cl |
| 551. | CH$_2$=CHCH$_2$S | CF$_3$SO | Cl | Cl | CF$_3$ | Cl |
| 552. | CH$_2$=CHCH$_2$S | CF$_3$SO$_2$ | Cl | Cl | CF$_3$ | Cl |
| 553. | CH≡CCH$_2$S | CF$_3$S | Cl | Cl | CF$_3$ | Cl |
| 554. | CH≡CCH$_2$S | CF$_3$SO | Cl | Cl | CF$_3$ | Cl |
| 555. | CH≡CCH$_2$S | CF$_3$SO$_2$ | Cl | Cl | CF$_3$ | Cl |
| 556. | PhCH$_2$S | CF$_3$S | Cl | Cl | CF$_3$ | Cl |
| 557. | PhCH$_2$S | CF$_3$SO | Cl | Cl | CF$_3$ | Cl |
| 558. | PhCH$_2$S | CF$_3$SO$_2$ | Cl | Cl | CF$_3$ | Cl |
| 559. | 2-FurylS | CF$_3$S | Cl | Cl | CF$_3$ | Cl |
| 560. | 2-FurylS | CF$_3$SO | Cl | Cl | CF$_3$ | Cl |
| 561. | 2-FurylS | CF$_3$SO$_2$ | Cl | Cl | CF$_3$ | Cl |
| 562. | CH$_3$S | CF$_2$ClSO | Cl | Cl | CF$_3$ | Cl |
| 563. | CH$_3$S | CF$_2$ClSO$_2$ | Cl | Cl | CF$_3$ | Cl |
| 564. | CH$_3$SO | CF$_2$ClS | Cl | Cl | CF$_3$ | Cl |
| 565. | CH$_3$SO$_2$ | CF$_2$ClS | Cl | Cl | CF$_3$ | Cl |
| 566. | CH$_3$SO | CF$_2$ClSO | Cl | Cl | CF$_3$ | Cl |
| 567. | CH$_3$SO$_2$ | CF$_2$ClSO | Cl | Cl | CF$_3$ | Cl |
| 568. | CH$_3$SO | CF$_2$ClSO$_2$ | Cl | Cl | CF$_3$ | Cl |
| 569. | CH$_3$SO$_2$ | CF$_2$ClSO$_2$ | Cl | Cl | CF$_3$ | Cl |
| 570. | CH$_3$CH$_2$S | CF$_2$ClS | Cl | Cl | CF$_3$ | Cl |
| 571. | CH$_3$CH$_2$S | CF$_2$ClSO | Cl | Cl | CF$_3$ | Cl |
| 572. | CH$_3$CH$_2$S | CF$_2$ClSO$_2$ | Cl | Cl | CF$_3$ | Cl |
| 573. | (CH$_3$)$_3$CS | CF$_2$ClS | Cl | Cl | CF$_3$ | Cl |
| 574. | (CH$_3$)$_3$CS | CF$_2$ClSO | Cl | Cl | CF$_3$ | Cl |
| 575. | (CH$_3$)$_3$CS | CF$_2$ClSO$_2$ | Cl | Cl | CF$_3$ | Cl |
| 576. | CH$_2$=CHCH$_2$S | CF$_2$ClS | Cl | Cl | CF$_3$ | Cl |
| 577. | CH$_2$=CHCH$_2$S | CF$_2$ClSO | Cl | Cl | CF$_3$ | Cl |
| 578. | CH$_2$=CHCH$_2$S | CF$_2$ClSO$_2$ | Cl | Cl | CF$_3$ | Cl |
| 579. | CH≡CCH$_2$S | CF$_2$ClS | Cl | Cl | CF$_3$ | Cl |
| 580. | CH≡CCH$_2$S | CF$_2$ClSO | Cl | Cl | CF$_3$ | Cl |

TABLE 1E-continued
REPRESENTATIVE PYRROLE COMPOUNDS (RPC) OF GENERAL FORMULA (I), PARTICULARLY (II-7), WHEREIN $R^2 = CN$ AND $X^2$ & $X^3 = H$

| RPC-No. | $R^1$ | X | $R^3$ | $X^1$ | Y | $X^4$ |
|---|---|---|---|---|---|---|
| 581. | CH≡CCH$_2$S | CF$_2$ClSO$_2$ | Cl | Cl | CF$_3$ | Cl |
| 582. | PhCH$_2$S | CF$_2$ClS | Cl | Cl | CF$_3$ | Cl |
| 583. | PhCH$_2$S | CF$_2$ClSO | Cl | Cl | CF$_3$ | Cl |
| 584. | PhCH$_2$S | CF$_2$ClSO$_2$ | Cl | Cl | CF$_3$ | Cl |
| 585. | 2-FurylS | CF$_2$ClS | Cl | Cl | CF$_3$ | Cl |
| 586. | 2-FurylS | CF$_2$ClSO | Cl | Cl | CF$_3$ | Cl |
| 587. | 2-FurylS | CF$_2$ClSO$_2$ | Cl | Cl | CF$_3$ | Cl |
| 588. | CH$_3$S | CFCl$_2$SO$_2$ | Cl | Cl | CF$_3$ | Cl |
| 589. | CH$_3$SO | CFCl$_2$S | Cl | Cl | CF$_3$ | Cl |
| 590. | CH$_3$SO | CFCl$_2$SO | Cl | Cl | CF$_3$ | Cl |
| 591. | CH$_3$SO$_2$ | CFCl$_2$SO | Cl | Cl | CF$_3$ | Cl |
| 592. | CH$_3$SO | CFCl$_2$SO$_2$ | Cl | Cl | CF$_3$ | Cl |
| 593. | CH$_3$SO$_2$ | CFCl$_2$SO$_2$ | Cl | Cl | CF$_3$ | Cl |
| 594. | CH$_3$CH$_2$S | CFCl$_2$S | Cl | Cl | CF$_3$ | Cl |
| 595. | CH$_3$CH$_2$S | CFCl$_2$SO | Cl | Cl | CF$_3$ | Cl |
| 596. | CH$_3$CH$_2$S | CFCl$_2$SO$_2$ | Cl | Cl | CF$_3$ | Cl |
| 597. | (CH$_3$)$_3$CS | CFCl$_2$S | Cl | Cl | CF$_3$ | Cl |
| 598. | (CH$_3$)$_3$CS | CFCl$_2$SO | Cl | Cl | CF$_3$ | Cl |
| 599. | (CH$_3$)$_3$CS | CFCl$_2$SO$_2$ | Cl | Cl | CF$_3$ | Cl |
| 600. | CH$_2$=CHCH$_2$S | CFCl$_2$S | Cl | Cl | CF$_3$ | Cl |
| 601. | CH$_2$=CHCH$_2$S | CFCl$_2$SO | Cl | Cl | CF$_3$ | Cl |
| 602. | CH$_2$=CHCH$_2$S | CFCl$_2$SO$_2$ | Cl | Cl | CF$_3$ | Cl |
| 603. | CH≡CCH$_2$S | CFCl$_2$S | Cl | Cl | CF$_3$ | Cl |
| 604. | CH≡CCH$_2$S | CFCl$_2$SO | Cl | Cl | CF$_3$ | Cl |
| 605. | CH≡CCH$_2$S | CFCl$_2$SO$_2$ | Cl | Cl | CF$_3$ | Cl |
| 606. | PhCH$_2$S | CFCl$_2$S | Cl | Cl | CF$_3$ | Cl |
| 607. | PhCH$_2$S | CFCl$_2$SO | Cl | Cl | CF$_3$ | Cl |
| 608. | PhCH$_2$S | CFCl$_2$SO$_2$ | Cl | Cl | CF$_3$ | Cl |
| 609. | 2-FurylS | CFCl$_2$S | Cl | Cl | CF$_3$ | Cl |
| 610. | 2-FurylS | CFCl$_2$SO | Cl | Cl | CF$_3$ | Cl |
| 611. | 2-FurylS | CFCl$_2$SO$_2$ | Cl | Cl | CF$_3$ | Cl |
| 612. | CH$_3$S | CFCl$_2$S | Br | Cl | CF$_3$ | Cl |
| 613. | CH$_3$S | CFCl$_2$SO | Br | Cl | CF$_3$ | Cl |
| 614. | CH$_3$S | CFCl$_2$SO$_2$ | Br | Cl | CF$_3$ | Cl |
| 615. | CH$_3$SO | CFCl$_2$S | Br | Cl | CF$_3$ | Cl |
| 616. | CH$_3$SO$_2$ | CFCl$_2$S | Br | Cl | CF$_3$ | Cl |
| 617. | CH$_3$SO | CFCl$_2$SO | Br | Cl | CF$_3$ | Cl |
| 618. | CH$_3$SO$_2$ | CFCl$_2$SO | Br | Cl | CF$_3$ | Cl |
| 619. | CH$_3$SO | CFCl$_2$SO$_2$ | Br | Cl | CF$_3$ | Cl |
| 620. | CH$_3$SO$_2$ | CFCl$_2$SO$_2$ | Br | Cl | CF$_3$ | Cl |
| 621. | CH$_3$CH$_2$S | CFCl$_2$S | Br | Cl | CF$_3$ | Cl |
| 622. | CH$_3$CH$_2$S | CFCl$_2$SO | Br | Cl | CF$_3$ | Cl |
| 623. | CH$_3$CH$_2$S | CFCl$_2$SO$_2$ | Br | Cl | CF$_3$ | Cl |
| 624. | (CH$_3$)$_3$CS | CFCl$_2$S | Br | Cl | CF$_3$ | Cl |
| 625. | (CH$_3$)$_3$CS | CFCl$_2$SO | Br | Cl | CF$_3$ | Cl |
| 626. | (CH$_3$)$_3$CS | CFCl$_2$SO$_2$ | Br | Cl | CF$_3$ | Cl |
| 627. | CH$_2$=CHCH$_2$S | CFCl$_2$S | Br | Cl | CF$_3$ | Cl |
| 628. | CH$_2$=CHCH$_2$S | CFCl$_2$SO | Br | Cl | CF$_3$ | Cl |
| 629. | CH$_2$=CHCH$_2$S | CFCl$_2$SO$_2$ | Br | Cl | CF$_3$ | Cl |
| 630. | CH≡CCH$_2$S | CFCl$_2$S | Br | Cl | CF$_3$ | Cl |
| 631. | CH≡CCH$_2$S | CFCl$_2$SO | Br | Cl | CF$_3$ | Cl |
| 632. | CH≡CCH$_2$S | CFCl$_2$SO$_2$ | Br | Cl | CF$_3$ | Cl |
| 633. | CH$_3$S | CFCl$_2$S | CN | Cl | CF$_3$ | Cl |
| 634. | CH$_3$S | CFCl$_2$SO | CN | Cl | CF$_3$ | Cl |
| 635. | CH$_3$S | CFCl$_2$SO$_2$ | CN | Cl | CF$_3$ | Cl |
| 636. | CH$_3$SO | CFCl$_2$S | CN | Cl | CF$_3$ | Cl |
| 637. | CH$_3$SO$_2$ | CFCl$_2$S | CN | Cl | CF$_3$ | Cl |
| 638. | CH$_3$SO | CFCl$_2$SO | CN | Cl | CF$_3$ | Cl |
| 639. | CH$_3$SO$_2$ | CFCl$_2$SO | CN | Cl | CF$_3$ | Cl |
| 640. | CH$_3$SO | CFCl$_2$SO$_2$ | CN | Cl | CF$_3$ | Cl |
| 641. | CH$_3$SO$_2$ | CFCl$_2$SO$_2$ | CN | Cl | CF$_3$ | Cl |
| 642. | CH$_3$CH$_2$S | CFCl$_2$S | CN | Cl | CF$_3$ | Cl |
| 643. | CH$_3$CH$_2$S | CFCl$_2$SO | CN | Cl | CF$_3$ | Cl |
| 644. | CH$_3$CH$_2$S | CFCl$_2$SO$_2$ | CN | Cl | CF$_3$ | Cl |
| 645. | (CH$_3$)$_3$CS | CFCl$_2$S | CN | Cl | CF$_3$ | Cl |
| 646. | (CH$_3$)$_3$CS | CFCl$_2$SO | CN | Cl | CF$_3$ | Cl |
| 647. | (CH$_3$)$_3$CS | CFCl$_2$SO$_2$ | CN | Cl | CF$_3$ | Cl |
| 648. | CH$_2$=CHCH$_2$S | CFCl$_2$S | CN | Cl | CF$_3$ | Cl |
| 649. | CH$_2$=CHCH$_2$S | CFCl$_2$SO | CN | Cl | CF$_3$ | Cl |
| 650. | CH$_2$=CHCH$_2$S | CFCl$_2$SO$_2$ | CN | Cl | CF$_3$ | Cl |
| 651. | CH≡CCH$_2$S | CFCl$_2$S | CN | Cl | CF$_3$ | Cl |
| 652. | CH≡CCH$_2$S | CFCl$_2$SO | CN | Cl | CF$_3$ | Cl |
| 653. | CH≡CCH$_2$S | CFCl$_2$SO$_2$ | CN | Cl | CF$_3$ | Cl |
| 654. | CH$_3$S | CFCl$_2$S | CF$_3$ | Cl | CF$_3$ | Cl |
| 655. | CH$_3$S | CFCl$_2$SO | CF$_3$ | Cl | CF$_3$ | Cl |
| 656. | CH$_3$S | CFCl$_2$SO$_2$ | CF$_3$ | Cl | CF$_3$ | Cl |
| 657. | CH$_3$SO | CFCl$_2$S | CF$_3$ | Cl | CF$_3$ | Cl |
| 658. | CH$_3$SO$_2$ | CFCl$_2$S | CF$_3$ | Cl | CF$_3$ | Cl |

TABLE 1E-continued

REPRESENTATIVE PYRROLE COMPOUNDS (RPC) OF GENERAL FORMULA (I), PARTICULARLY (II-7), WHEREIN $R^2$ = CN AND $X^2$ & $X^3$ = H

| RPC-No. | $R^1$ | X | $R^3$ | $X^1$ | Y | $X^4$ |
|---|---|---|---|---|---|---|
| 659. | CH$_3$SO | CFCl$_2$SO | CF$_3$ | Cl | CF$_3$ | Cl |
| 660. | CH$_3$SO$_2$ | CFCl$_2$SO | CF$_3$ | Cl | CF$_3$ | Cl |
| 661. | CH$_3$SO | CFCl$_2$SO$_2$ | CF$_3$ | Cl | CF$_3$ | Cl |
| 662. | CH$_3$SO$_2$ | CFCl$_2$SO$_2$ | CF$_3$ | Cl | CF$_3$ | Cl |
| 663. | CH$_3$S | CFCl$_2$S | OCH$_3$ | Cl | CF$_3$ | Cl |
| 664. | CH$_3$S | CFCl$_2$SO | OCH$_3$ | Cl | CF$_3$ | Cl |
| 665. | CH$_3$S | CFCl$_2$SO$_2$ | OCH$_3$ | Cl | CF$_3$ | Cl |
| 666. | CH$_3$SO | CFCl$_2$S | OCH$_3$ | Cl | CF$_3$ | Cl |
| 667. | CH$_3$SO$_2$ | CFCl$_2$S | OCH$_3$ | Cl | CF$_3$ | Cl |
| 668. | CH$_3$SO | CFCl$_2$SO | OCH$_3$ | Cl | CF$_3$ | Cl |
| 669. | CH$_3$SO$_2$ | CFCl$_2$SO | OCH$_3$ | Cl | CF$_3$ | Cl |
| 670. | CH$_3$SO | CFCl$_2$SO$_2$ | OCH$_3$ | Cl | CF$_3$ | Cl |
| 671. | CH$_3$SO$_2$ | CFCl$_2$SO$_2$ | OCH$_3$ | Cl | CF$_3$ | Cl |
| 672. | CH$_3$S | CFCl$_2$S | CF$_2$H | Cl | CF$_3$ | Cl |
| 673. | CH$_3$S | CFCl$_2$SO | CF$_2$H | Cl | CF$_3$ | Cl |
| 674. | CH$_3$S | CFCl$_2$SO$_2$ | CF$_2$H | Cl | CF$_3$ | Cl |
| 675. | CH$_3$SO | CFCl$_2$S | CF$_2$H | Cl | CF$_3$ | Cl |
| 676. | CH$_3$SO$_2$ | CFCl$_2$S | CF$_2$H | Cl | CF$_3$ | Cl |
| 677. | CH$_3$SO | CFCl$_2$SO | CF$_2$H | Cl | CF$_3$ | Cl |
| 678. | CH$_3$SO$_2$ | CFCl$_2$SO | CF$_2$H | Cl | CF$_3$ | Cl |
| 679. | CH$_3$SO | CFCl$_2$SO$_2$ | CF$_2$H | Cl | CF$_3$ | Cl |
| 680. | CH$_3$SO$_2$ | CFCl$_2$SO$_2$ | CF$_2$H | Cl | CF$_3$ | Cl |
| 681. | CH$_3$ | CF$_2$ClS | Cl | Cl | CF$_3$ | Cl |
| 682. | CH$_3$ | CF$_2$ClSO | Cl | Cl | CF$_3$ | Cl |
| 683. | CH$_3$ | CF$_2$ClSO$_2$ | Cl | Cl | CF$_3$ | Cl |
| 684. | CH$_3$ | CFCl$_2$S | Cl | Cl | CF$_3$ | Cl |
| 685. | CH$_3$ | CFCl$_2$SO | Cl | Cl | CF$_3$ | Cl |
| 686. | CH$_3$ | CFCl$_2$SO$_2$ | Cl | Cl | CF$_3$ | Cl |
| 687. | CH$_2$CH$_3$ | CF$_3$S | Cl | Cl | CF$_3$ | Cl |
| 688. | CH$_2$CH$_3$ | CF$_3$SO | Cl | Cl | CF$_3$ | Cl |
| 689. | CH$_2$CH$_3$ | CF$_3$SO$_2$ | Cl | Cl | CF$_3$ | Cl |
| 690. | CH$_2$CH$_3$ | CF$_2$ClS | Cl | Cl | CF$_3$ | Cl |
| 691. | CH$_2$CH$_3$ | CF$_2$ClSO | Cl | Cl | CF$_3$ | Cl |
| 692. | CH$_2$CH$_3$ | CF$_2$ClSO$_2$ | Cl | Cl | CF$_3$ | Cl |
| 693. | CH$_2$CH$_3$ | CFCl$_2$S | Cl | Cl | CF$_3$ | Cl |
| 694. | CH$_2$CH$_3$ | CFCl$_2$SO | Cl | Cl | CF$_3$ | Cl |
| 695. | CH$_2$CH$_3$ | CFCl$_2$SO$_2$ | Cl | Cl | CF$_3$ | Cl |
| 696. | CH$_3$CH$_2$(CH$_3$)CH | CF$_3$S | Cl | Cl | CF$_3$ | Cl |
| 697. | CH$_3$CH$_2$(CH$_3$)CH | CF$_3$SO | Cl | Cl | CF$_3$ | Cl |
| 698. | CH$_3$CH$_2$(CH$_3$)CH | CF$_3$SO$_2$ | Cl | Cl | CF$_3$ | Cl |
| 699. | CH$_3$CH$_2$(CH$_3$)CH | CF$_2$ClS | Cl | Cl | CF$_3$ | Cl |
| 700. | CH$_3$CH$_2$(CH$_3$)CH | CF$_2$ClSO | Cl | Cl | CF$_3$ | Cl |
| 701. | CH$_3$CH$_2$(CH$_3$)CH | CF$_2$ClSO$_2$ | Cl | Cl | CF$_3$ | Cl |
| 702. | CH$_3$CH$_2$(CH$_3$)CH | CFCl$_2$S | Cl | Cl | CF$_3$ | Cl |
| 703. | CH$_3$CH$_2$(CH$_3$)CH | CFCl$_2$SO | Cl | Cl | CF$_3$ | Cl |
| 704. | CH$_3$CH$_2$(CH$_3$)CH | CFCl$_2$SO$_2$ | Cl | Cl | CF$_3$ | Cl |
| 705. | CH$_3$O | CFCl$_2$S | Cl | Cl | CF$_3$ | Cl |
| 706. | CH$_3$O | CFCl$_2$SO | Cl | Cl | CF$_3$ | Cl |
| 707. | CH$_3$O | CFCl$_2$SO$_2$ | Cl | Cl | CF$_3$ | Cl |
| 708. | CH$_3$CH$_2$O | CFCl$_2$S | Cl | Cl | CF$_3$ | Cl |
| 709. | CH$_3$CH$_2$O | CFCl$_2$SO | Cl | Cl | CF$_3$ | Cl |
| 710. | CH$_3$CH$_2$O | CFCl$_2$SO$_2$ | Cl | Cl | CF$_3$ | Cl |
| 711. | CH$_2$=CHCH$_2$O | CFCl$_2$S | Cl | Cl | CF$_3$ | Cl |
| 712. | CH$_2$=CHCH$_2$O | CFCl$_2$SO | Cl | Cl | CF$_3$ | Cl |
| 713. | CH$_2$=CHCH$_2$O | CFCl$_2$SO$_2$ | Cl | Cl | CF$_3$ | Cl |
| 714. | CH≡CCH$_2$O | CFCl$_2$S | Cl | Cl | CF$_3$ | Cl |
| 715. | CH≡CCH$_2$O | CFCl$_2$SO | Cl | Cl | CF$_3$ | Cl |
| 716. | CH≡CCH$_2$O | CFCl$_2$SO$_2$ | Cl | Cl | CF$_3$ | Cl |
| 717. | CH$_3$OCH$_2$ | CFCl$_2$S | Cl | Cl | CF$_3$ | Cl |
| 718. | CH$_3$OCH$_2$ | CFCl$_2$SO | Cl | Cl | CF$_3$ | Cl |
| 719. | CH$_3$OCH$_2$ | CFCl$_2$SO$_2$ | Cl | Cl | CF$_3$ | Cl |
| 720. | CH$_3$SCH$_2$ | CFCl$_2$S | Cl | Cl | CF$_3$ | Cl |
| 721. | CH$_3$SCH$_2$ | CFCl$_2$SO | Cl | Cl | CF$_3$ | Cl |
| 722. | CH$_3$SCH$_2$ | CFCl$_2$SO$_2$ | Cl | Cl | CF$_3$ | Cl |
| 723. | FCH$_2$ | CFCl$_2$S | Cl | Cl | CF$_3$ | Cl |
| 724. | FCH$_2$ | CFCl$_2$SO | Cl | Cl | CF$_3$ | Cl |
| 725. | FCH$_2$ | CFCl$_2$SO$_2$ | Cl | Cl | CF$_3$ | Cl |
| 726. | H | CF$_2$ClS | CH$_3$ | Cl | CF$_3$ | Cl |
| 727. | H | CF$_2$ClSO | CH$_3$ | Cl | CF$_3$ | Cl |
| 728. | H | CF$_2$ClSO$_2$ | CH$_3$ | Cl | CF$_3$ | Cl |
| 729. | H | CFCl$_2$SO$_2$ | CH$_3$ | Cl | CF$_3$ | Cl |
| 730. | H | CFCl$_2$S | CH$_3$CH$_2$ | Cl | CF$_3$ | Cl |
| 731. | H | CFCl$_2$SO | CH$_3$CH$_2$ | Cl | CF$_3$ | Cl |
| 732. | H | CFCl$_2$SO$_2$ | CH$_3$CH$_2$ | Cl | CF$_3$ | Cl |
| 733. | H | CF$_2$ClS | CH$_2$F | Cl | CF$_3$ | Cl |
| 734. | H | CF$_2$ClSO | CH$_2$F | Cl | CF$_3$ | Cl |
| 735. | H | CF$_2$ClSO$_2$ | CH$_2$F | Cl | CF$_3$ | Cl |
| 736. | H | CFCl$_2$S | CH$_2$F | Cl | CF$_3$ | Cl |

TABLE 1E-continued

REPRESENTATIVE PYRROLE COMPOUNDS (RPC) OF GENERAL FORMULA (I), PARTICULARLY (II-7), WHEREIN $R^2$ = CN AND $X^2$ & $X^3$ = H

| RPC-No. | $R^1$ | X | $R^3$ | $X^1$ | Y | $X^4$ |
|---|---|---|---|---|---|---|
| 737. | H | $CFCl_2SO$ | $CH_2F$ | Cl | $CF_3$ | Cl |
| 738. | H | $CFCl_2SO_2$ | $CH_2F$ | Cl | $CF_3$ | Cl |
| 739. | H | $CF_2ClS$ | $CF_2H$ | Cl | $CF_3$ | Cl |
| 740. | H | $CF_2ClSO$ | $CF_2H$ | Cl | $CF_3$ | Cl |
| 741. | H | $CF_2ClSO_2$ | $CF_2H$ | Cl | $CF_3$ | Cl |
| 742. | H | $CF_3S$ | $CH_2Cl$ | Cl | $CF_3$ | Cl |
| 743. | H | $CF_3SO$ | $CH_2Cl$ | Cl | $CF_3$ | Cl |
| 744. | H | $CF_3SO_2$ | $CH_2Cl$ | Cl | $CF_3$ | Cl |
| 745. | H | $CF_2ClS$ | $CH_2Cl$ | Cl | $CF_3$ | Cl |
| 746. | H | $CF_2ClSO$ | $CH_2Cl$ | Cl | $CF_3$ | Cl |
| 747. | H | $CF_2ClSO_2$ | $CH_2Cl$ | Cl | $CF_3$ | Cl |
| 748. | H | $CFCl_2S$ | $CH_2Cl$ | Cl | $CF_3$ | Cl |
| 749. | H | $CFCl_2SO$ | $CH_2Cl$ | Cl | $CF_3$ | Cl |
| 750. | H | $CFCl_2SO_2$ | $CH_2Cl$ | Cl | $CF_3$ | Cl |
| 751. | H | $CF_3S$ | $OCH_3$ | Cl | $CF_3$ | Cl |
| 752. | H | $CF_3SO$ | $OCH_3$ | Cl | $CF_3$ | Cl |
| 753. | H | $CF_3SO_2$ | $OCH_3$ | Cl | $CF_3$ | Cl |
| 754. | H | $CF_2ClS$ | $OCH_3$ | Cl | $CF_3$ | Cl |
| 755. | H | $CF_2ClSO$ | $OCH_3$ | Cl | $CF_3$ | Cl |
| 756. | H | $CF_2ClSO_2$ | $OCH_3$ | Cl | $CF_3$ | Cl |
| 757. | H | $CFCl_2S$ | $OCH_3$ | Cl | $CF_3$ | Cl |
| 758. | H | $CFCl_2SO$ | $OCH_3$ | Cl | $CF_3$ | Cl |
| 759. | H | $CFCl_2SO_2$ | $OCH_3$ | Cl | $CF_3$ | Cl |
| 760. | H | $CFCl_2S$ | $OCH_2CH_3$ | Cl | $CF_3$ | Cl |
| 761. | H | $CFCl_2SO$ | $OCH_2CH_3$ | Cl | $CF_3$ | Cl |
| 762. | H | $CFCl_2SO_2$ | $OCH_2CH_3$ | Cl | $CF_3$ | Cl |
| 763. | H | $CFCl_2S$ | $OCH_2CH=CH_2$ | Cl | $CF_3$ | Cl |
| 764. | H | $CFCl_2SO$ | $OCH_2CH=CH_2$ | Cl | $CF_3$ | Cl |
| 765. | H | $CFCl_2SO_2$ | $OCH_2CH=CH_2$ | Cl | $CF_3$ | Cl |
| 766. | H | $CFCl_2S$ | $OCH_2C\equiv CH$ | Cl | $CF_3$ | Cl |
| 767. | H | $CFCl_2SO$ | $OCH_2C\equiv CH$ | Cl | $CF_3$ | Cl |
| 768. | H | $CFCl_2SO_2$ | $OCH_2C\equiv CH$ | Cl | $CF_3$ | Cl |
| 769. | H | $CFCl_2S$ | $CH_2OCH_3$ | Cl | $CF_3$ | Cl |
| 770. | H | $CFCl_2SO$ | $CH_2OCH_3$ | Cl | $CF_3$ | Cl |
| 771. | H | $CFCl_2SO_2$ | $CH_2OCH_3$ | Cl | $CF_3$ | Cl |
| 772. | H | $CF_3S$ | $CH=NOCH_3$ | Cl | $CF_3$ | Cl |
| 773. | H | $CF_3SO$ | $CH=NOCH_3$ | Cl | $CF_3$ | Cl |
| 774. | H | $CF_3SO_2$ | $CH=NOCH_3$ | Cl | $CF_3$ | Cl |
| 775. | H | $CF_2ClS$ | $CH=NOCH_3$ | Cl | $CF_3$ | Cl |
| 776. | H | $CF_2ClSO$ | $CH=NOCH_3$ | Cl | $CF_3$ | Cl |
| 777. | H | $CF_2ClSO_2$ | $CH=NOCH_3$ | Cl | $CF_3$ | Cl |
| 778. | H | $CFCl_2S$ | $CH=NOCH_3$ | Cl | $CF_3$ | Cl |
| 779. | H | $CFCl_2SO$ | $CH=NOCH_3$ | Cl | $CF_3$ | Cl |
| 780. | H | $CFCl_2SO_2$ | $CH=NOCH_3$ | Cl | $CF_3$ | Cl |
| 781. | Br | $CFCl_2S$ | $CH_3$ | Cl | $CF_3$ | Cl |
| 782. | Br | $CFCl_2SO$ | $CH_3$ | Cl | $CF_3$ | Cl |
| 783. | Br | $CFCl_2SO_2$ | $CH_3$ | Cl | $CF_3$ | Cl |
| 784. | Br | $CFCl_2S$ | $CH_2F$ | Cl | $CF_3$ | Cl |
| 785. | Br | $CFCl_2SO$ | $CH_2F$ | Cl | $CF_3$ | Cl |
| 786. | Br | $CFCl_2SO_2$ | $CH_2F$ | Cl | $CF_3$ | Cl |
| 787. | $CH_3$ | $CF_3S$ | $CH_3$ | Cl | $CF_3$ | Cl |
| 788. | $CH_3$ | $CF_3SO$ | $CH_3$ | Cl | $CF_3$ | Cl |
| 789. | $CH_3$ | $CF_3SO_2$ | $CH_3$ | Cl | $CF_3$ | Cl |
| 790. | $CH_3$ | $CF_2ClS$ | $CH_3$ | Cl | $CF_3$ | Cl |
| 791. | $CH_3$ | $CF_2ClSO$ | $CH_3$ | Cl | $CF_3$ | Cl |
| 792. | $CH_3$ | $CF_2ClSO_2$ | $CH_3$ | Cl | $CF_3$ | Cl |
| 793. | $CH_3$ | $CFCl_2SO$ | $CH_3$ | Cl | $CF_3$ | Cl |
| 794. | $CH_3$ | $CFCl_2SO_2$ | $CH_3$ | Cl | $CF_3$ | Cl |
| 795. | $CH_3S$ | $CF_3S$ | Cl | Cl | $OCF_3$ | Cl |
| 796. | $CH_3S$ | $CF_3SO$ | Cl | Cl | $OCF_3$ | Cl |
| 797. | $CH_3S$ | $CF_3SO_2$ | Cl | Cl | $OCF_3$ | Cl |
| 798. | $CH_3S$ | $CF_2ClS$ | Cl | Cl | $OCF_3$ | Cl |
| 799. | $CH_3S$ | $CF_2ClSO$ | Cl | Cl | $OCF_3$ | Cl |
| 800. | $CH_3S$ | $CF_2ClSO_2$ | Cl | Cl | $OCF_3$ | Cl |
| 801. | $CH_3S$ | $CFCl_2S$ | Cl | Cl | $OCF_3$ | Cl |
| 802. | $CH_3S$ | $CFCl_2SO$ | Cl | Cl | $OCF_3$ | Cl |
| 803. | $CH_3S$ | $CFCl_2SO_2$ | Cl | Cl | $OCF_3$ | Cl |
| 804. | $CH_3S$ | $CFCl_2S$ | Br | Cl | $OCF_3$ | Cl |
| 805. | $CH_3S$ | $CFCl_2SO$ | Br | Cl | $OCF_3$ | Cl |
| 806. | $CH_3S$ | $CFCl_2SO_2$ | Br | Cl | $OCF_3$ | Cl |
| 807. | $CH_3S$ | $CFCl_2S$ | CN | Cl | $OCF_3$ | Cl |
| 808. | $CH_3S$ | $CFCl_2SO$ | CN | Cl | $OCF_3$ | Cl |
| 809. | $CH_3S$ | $CFCl_2SO_2$ | CN | Cl | $OCF_3$ | Cl |
| 810. | $CH_3$ | $CFCl_2S$ | Cl | Cl | $OCF_3$ | Cl |
| 811. | $CH_3$ | $CFCl_2SO$ | Cl | Cl | $OCF_3$ | Cl |
| 812. | $CH_3$ | $CFCl_2SO_2$ | Cl | Cl | $OCF_3$ | Cl |
| 813. | H | $CFCl_2S$ | $CH_3$ | Cl | $OCF_3$ | Cl |
| 814. | H | $CFCl_2SO$ | $CH_3$ | Cl | $OCF_3$ | Cl |

TABLE 1E-continued

REPRESENTATIVE PYRROLE COMPOUNDS (RPC) OF GENERAL FORMULA (I), PARTICULARLY (II-7), WHEREIN $R^2$ = CN AND $X^2$ & $X^3$ = H

| RPC-No. | $R^1$ | X | $R^3$ | $X^1$ | Y | $X^4$ |
|---|---|---|---|---|---|---|
| 815. | H | $CFCl_2SO_2$ | $CH_3$ | Cl | $OCF_3$ | Cl |
| 816. | H | $CFCl_2S$ | $CH_2F$ | Cl | $OCF_3$ | Cl |
| 817. | H | $CFCl_2SO$ | $CH_2F$ | Cl | $OCF_3$ | Cl |
| 818. | H | $CFCl_2SO_2$ | $CH_2F$ | Cl | $OCF_3$ | Cl |
| 819. | H | $CFCl_2S$ | $CF_2H$ | Cl | $OCF_3$ | Cl |
| 820. | H | $CFCl_2SO$ | $CF_2H$ | Cl | $OCF_3$ | Cl |
| 821. | H | $CFCl_2SO_2$ | $CF_2H$ | Cl | $OCF_3$ | Cl |
| 822. | H | $CFCl_2S$ | $CH_2Cl$ | Cl | $OCF_3$ | Cl |
| 823. | H | $CFCl_2SO$ | $CH_2Cl$ | Cl | $OCF_3$ | Cl |
| 824. | H | $CFCl_2SO_2$ | $CH_2Cl$ | Cl | $OCF_3$ | Cl |
| 825. | H | $CFCl_2S$ | $OCH_3$ | Cl | $OCF_3$ | Cl |
| 826. | H | $CFCl_2SO$ | $OCH_3$ | Cl | $OCF_3$ | Cl |
| 827. | H | $CFCl_2SO_2$ | $OCH_3$ | Cl | $OCF_3$ | Cl |
| 828. | H | $CFCl_2S$ | $CH_2OCH_3$ | Cl | $OCF_3$ | Cl |
| 829. | H | $CFCl_2SO$ | $CH_2OCH_3$ | Cl | $OCF_3$ | Cl |
| 830. | H | $CFCl_2SO_2$ | $CH_2OCH_3$ | Cl | $OCF_3$ | Cl |
| 831. | $CH_3S$ | $CF_3S$ | Cl | H | $CF_3$ | Cl |
| 832. | $CH_3S$ | $CF_3SO$ | Cl | H | $CF_3$ | Cl |
| 833. | $CH_3S$ | $CF_3SO_2$ | Cl | H | $CF_3$ | Cl |
| 834. | $CH_3S$ | $CF_2ClS$ | Cl | H | $CF_3$ | Cl |
| 835. | $CH_3S$ | $CF_2ClSO$ | Cl | H | $CF_3$ | Cl |
| 836. | $CH_3S$ | $CF_2ClSO_2$ | Cl | H | $CF_3$ | Cl |
| 837. | $CH_3S$ | $CFCl_2S$ | Cl | H | $CF_3$ | Cl |
| 838. | $CH_3S$ | $CFCl_2SO$ | Cl | H | $CF_3$ | Cl |
| 839. | $CH_3S$ | $CFCl_2SO_2$ | Cl | H | $CF_3$ | Cl |
| 840. | $CH_3S$ | $CFCl_2S$ | Br | H | $CF_3$ | Cl |
| 841. | $CH_3S$ | $CFCl_2SO$ | Br | H | $CF_3$ | Cl |
| 842. | $CH_3S$ | $CFCl_2SO_2$ | Br | H | $CF_3$ | Cl |
| 843. | $CH_3S$ | $CFCl_2S$ | CN | H | $CF_3$ | Cl |
| 844. | $CH_3S$ | $CFCl_2SO$ | CN | H | $CF_3$ | Cl |
| 845. | $CH_3S$ | $CFCl_2SO_2$ | CN | H | $CF_3$ | Cl |
| 846. | $CH_3$ | $CFCl_2S$ | Cl | H | $CF_3$ | Cl |
| 847. | $CH_3$ | $CFCl_2SO$ | Cl | H | $CF_3$ | Cl |
| 848. | $CH_3$ | $CFCl_2SO_2$ | Cl | H | $CF_3$ | Cl |
| 849. | H | $CFCl_2S$ | $CH_3$ | H | $CF_3$ | Cl |
| 850. | H | $CFCl_2SO$ | $CH_3$ | H | $CF_3$ | Cl |
| 851. | H | $CFCl_2SO_2$ | $CH_3$ | H | $CF_3$ | Cl |
| 852. | H | $CFCl_2S$ | $CH_2F$ | H | $CF_3$ | Cl |
| 853. | H | $CFCl_2SO$ | $CH_2F$ | H | $CF_3$ | Cl |
| 854. | H | $CFCl_2SO_2$ | $CH_2F$ | H | $CF_3$ | Cl |
| 855. | H | $CFCl_2S$ | $CF_2H$ | H | $CF_3$ | Cl |
| 856. | H | $CFCl_2SO$ | $CF_2H$ | H | $CF_3$ | Cl |
| 857. | H | $CFCl_2SO_2$ | $CF_2H$ | H | $CF_3$ | Cl |
| 858. | H | $CFCl_2S$ | $CH_2Cl$ | H | $CF_3$ | Cl |
| 859. | H | $CFCl_2SO$ | $CH_2Cl$ | H | $CF_3$ | Cl |
| 860. | H | $CFCl_2SO_2$ | $CH_2Cl$ | H | $CF_3$ | Cl |
| 861. | H | $CFCl_2S$ | $OCH_3$ | H | $CF_3$ | Cl |
| 862. | H | $CFCl_2SO$ | $OCH_3$ | H | $CF_3$ | Cl |
| 863. | H | $CFCl_2SO_2$ | $OCH_3$ | H | $CF_3$ | Cl |
| 864. | H | $CFCl_2S$ | $CH_2OCH_3$ | H | $CF_3$ | Cl |
| 865. | H | $CFCl_2SO$ | $CH_2OCH_3$ | H | $CF_3$ | Cl |
| 866. | H | $CFCl_2SO_2$ | $CH_2OCH_3$ | H | $CF_3$ | Cl |
| 867. | $CH_3S$ | $CH_3S$ | Cl | Cl | $CF_3$ | Cl |
| 868. | $CH_3S$ | $CH_3SO$ | Cl | Cl | $CF_3$ | Cl |
| 869. | $CH_3S$ | $CH_3SO_2$ | Cl | Cl | $CF_3$ | Cl |
| 870. | $CH_3SO$ | $CH_3S$ | Cl | Cl | $CF_3$ | Cl |
| 871. | $CH_3SO_2$ | $CH_3S$ | Cl | Cl | $CF_3$ | Cl |
| 872. | $CH_3SO$ | $CH_3SO$ | Cl | Cl | $CF_3$ | Cl |
| 873. | $CH_3SO_2$ | $CH_3SO$ | Cl | Cl | $CF_3$ | Cl |
| 874. | $CH_3SO$ | $CH_3SO_2$ | Cl | Cl | $CF_3$ | Cl |
| 875. | $CH_3SO_2$ | $CH_3SO_2$ | Cl | Cl | $CF_3$ | Cl |
| 876. | $CH_3CH_2S$ | $CH_3S$ | Cl | Cl | $CF_3$ | Cl |
| 877. | $CH_3CH_2S$ | $CH_3SO$ | Cl | Cl | $CF_3$ | Cl |
| 878. | $CH_3CH_2S$ | $CH_3SO_2$ | Cl | Cl | $CF_3$ | Cl |
| 879. | $(CH_3)_3CS$ | $CH_3S$ | Cl | Cl | $CF_3$ | Cl |
| 880. | $(CH_3)_3CS$ | $CH_3SO$ | Cl | Cl | $CF_3$ | Cl |
| 881. | $(CH_3)_3CS$ | $CH_3SO_2$ | Cl | Cl | $CF_3$ | Cl |
| 882. | $CH_2=CHCH_2S$ | $CH_3S$ | Cl | Cl | $CF_3$ | Cl |
| 883. | $CH_2=CHCH_2S$ | $CH_3SO$ | Cl | Cl | $CF_3$ | Cl |
| 884. | $CH_2=CHCH_2S$ | $CH_3SO_2$ | Cl | Cl | $CF_3$ | Cl |
| 885. | $CH\equiv CCH_2S$ | $CH_3S$ | Cl | Cl | $CF_3$ | Cl |
| 886. | $CH\equiv CCH_2S$ | $CH_3SO$ | Cl | Cl | $CF_3$ | Cl |
| 887. | $CH\equiv CCH_2S$ | $CH_3SO_2$ | Cl | Cl | $CF_3$ | Cl |
| 888. | $PhCH_2S$ | $CH_3S$ | Cl | Cl | $CF_3$ | Cl |
| 889. | $PhCH_2S$ | $CH_3SO$ | Cl | Cl | $CF_3$ | Cl |
| 890. | $PhCH_2S$ | $CH_3SO_2$ | Cl | Cl | $CF_3$ | Cl |
| 891. | $CH_3S$ | $CH_3S$ | CN | Cl | $CF_3$ | Cl |
| 892. | $CH_3S$ | $CH_3SO$ | CN | Cl | $CF_3$ | Cl |

TABLE 1E-continued

REPRESENTATIVE PYRROLE COMPOUNDS (RPC) OF GENERAL FORMULA (I), PARTICULARLY (II-7), WHEREIN $R^2$ = CN AND $X^2$ & $X^3$ = H

| RPC-No. | $R^1$ | X | $R^3$ | $X^1$ | Y | $X^4$ |
|---|---|---|---|---|---|---|
| 893. | $CH_3S$ | $CH_3SO_2$ | CN | Cl | $CF_3$ | Cl |
| 894. | $CH_3S$ | $CH_3S$ | $CF_3$ | Cl | $CF_3$ | Cl |
| 895. | $CH_3S$ | $CH_3SO$ | $CF_3$ | Cl | $CF_3$ | Cl |
| 896. | $CH_3S$ | $CH_3SO_2$ | $CF_3$ | Cl | $CF_3$ | Cl |
| 897. | $CH_3S$ | $CH_2FS$ | Cl | Cl | $CF_3$ | Cl |
| 898. | $CH_3S$ | $CH_2FSO$ | Cl | Cl | $CF_3$ | Cl |
| 899. | $CH_3S$ | $CH_2FSO_2$ | Cl | Cl | $CF_3$ | Cl |
| 900. | $CH_3S$ | $CHF_2S$ | Cl | Cl | $CF_3$ | Cl |
| 901. | $CH_3S$ | $CHF_2SO$ | Cl | Cl | $CF_3$ | Cl |
| 902. | $CH_3S$ | $CHF_2SO_2$ | Cl | Cl | $CF_3$ | Cl |
| 903. | $CH_3S$ | $CHFClS$ | Cl | Cl | $CF_3$ | Cl |
| 904. | $CH_3S$ | $CHFClSO$ | Cl | Cl | $CF_3$ | Cl |
| 905. | $CH_3S$ | $CHFClSO_2$ | Cl | Cl | $CF_3$ | Cl |

TABLE 1F

REPRESENTATIVE PYRROLE COMPOUNDS (RPC) OF GENERAL FORMULA (I), PARTICULARLY (II-8), WHEREIN $R^2$ = CN

| NO. | $R^1$ | X | $R^3$ | $X^1$ | $X^2$ | Y | $X^3$ | $X^4$ |
|---|---|---|---|---|---|---|---|---|
| 906. | Br | $CFCl_2SO_2$ | H | Cl | H | Cl | H | Cl |
| 907. | Br | $CF_2ClSO_2$ | H | Cl | H | Cl | H | Cl |
| 908. | Br | $CFCl_2S$ | H | Cl | H | F | H | Cl |
| 909. | Br | $CFCl_2SO$ | H | Cl | H | F | H | Cl |
| 910. | Br | $CFCl_2SO_2$ | H | Cl | H | F | H | Cl |
| 911. | Br | $CF_2ClS$ | H | Cl | H | F | H | Cl |
| 912. | Br | $CF_2ClSO$ | H | Cl | H | F | H | Cl |
| 913. | Br | $CF_3S$ | H | Cl | H | F | H | Cl |
| 914. | Br | $CF_3SO$ | H | Cl | H | Cl | H | Cl |
| 915. | Br | $CF_3S$ | H | Cl | H | Cl | H | Cl |
| 916. | Br | $CF_3SO$ | H | Cl | H | Cl | H | Cl |
| 917. | Br | $CF_3SO_2$ | H | Cl | H | Cl | H | Cl |
| 918. | Br | $CFCl_2S$ | H | Cl | H | Br | H | Cl |
| 919. | Br | $CFCl_2SO$ | H | Cl | H | Br | H | Cl |
| 920. | Br | $CFCl_2SO_2$ | H | Cl | H | Br | H | Cl |
| 921. | Cl | $CFCl_2S$ | H | Cl | H | Cl | H | Cl |
| 922. | Cl | $CFCl_2SO$ | H | Cl | H | Cl | H | Cl |
| 923. | Cl | $CFCl_2SO_2$ | H | Cl | H | Cl | H | Cl |
| 924. | Cl | $CF_2ClS$ | H | Cl | H | Cl | H | Cl |
| 925. | Cl | $CF_3S$ | H | Cl | H | F | H | Cl |
| 926. | Cl | $CF_3SO$ | H | Cl | H | F | H | Cl |
| 927. | Cl | $CF_3SO_2$ | H | Cl | H | F | H | Cl |
| 928. | Br | $CF_3CF_2S$ | H | Cl | H | Cl | H | Cl |
| 929. | Br | $CF_3CF_2SO$ | H | Cl | H | Cl | H | Cl |
| 930. | Br | $CF_3CF_2SO_2$ | H | Cl | H | Cl | H | Cl |
| 931. | Br | $n(C_3F_7)S$ | H | Cl | H | Cl | H | Cl |
| 932. | Br | $n(C_3F_7)SO$ | H | Cl | H | Cl | H | Cl |
| 933. | Br | $n(C_3F_7)SO_2$ | H | Cl | H | Cl | H | Cl |
| 934. | Cl | $t(C_3F_7)S$ | H | Cl | H | Cl | H | Cl |
| 935. | Cl | $t(C_3F_7)SO$ | H | Cl | H | Cl | H | Cl |
| 936. | Cl | $t(C_3F_7)SO_2$ | H | Cl | H | Cl | H | Cl |
| 937. | Cl | $CFBr_2S$ | H | Cl | H | Cl | H | Cl |
| 938. | Cl | $CFBr_2SO$ | H | Cl | H | Cl | H | Cl |
| 939. | Cl | $CFBr_2SO_2$ | H | Cl | H | Cl | H | Cl |
| 940. | Cl | $CFClBrS$ | H | Cl | H | Cl | H | Cl |
| 941. | Cl | $CFClBrSO$ | H | Cl | H | Cl | H | Cl |
| 942. | Cl | $CFClBrSO_2$ | H | Cl | H | Cl | H | Cl |
| 943. | Br | Cl | H | Cl | H | F | H | Cl |
| 944. | Br | I | H | Cl | H | F | H | Cl |
| 945. | Br | I | H | Cl | H | Cl | H | Cl |
| 946. | Br | $CFCl_2S$ | H | H | Cl | H | Cl | H |
| 947. | Br | $CFCl_2SO$ | H | H | Cl | H | Cl | H |
| 948. | Br | $CFCl_2SO_2$ | H | H | Cl | H | Cl | H |
| 949. | $CH_3S$ | $CF_2ClS$ | H | Cl | H | Cl | H | Cl |
| 950. | $CH_3SO$ | $CFCl_2S$ | H | Cl | H | Cl | H | Cl |
| 951. | $CH_3S$ | $CFCl_2SO$ | H | Cl | H | Cl | H | Cl |
| 952. | $CH_3SO$ | $CFCl_2SO$ | H | Cl | H | Cl | H | Cl |
| 953. | $CH_3SO_2$ | $CFCl_2S$ | H | Cl | H | Cl | H | Cl |
| 954. | $CH_3CH_2S$ | $CF_2ClS$ | H | Cl | H | Cl | H | Cl |
| 955. | $t(C_3H_7)S$ | $CF_3S$ | H | Cl | H | Cl | H | Cl |
| 956. | $CH_3$ | $CFCl_2S$ | H | Cl | H | Cl | H | Cl |
| 957. | Br | $CFCl_2S$ | H | Cl | H | Cl | H | H |
| 958. | $CH_3S$ | $CF_2ClS$ | H | Cl | H | Cl | H | H |
| 959. | $CH_3S$ | $CFCl_2S$ | H | Cl | H | F | H | Cl |
| 960. | $CH_3S$ | $CFCl_2SO$ | H | Cl | H | F | H | Cl |
| 961. | $CH_3SO$ | $CFCl_2S$ | H | Cl | H | F | H | Cl |

TABLE 1F-continued

REPRESENTATIVE PYRROLE COMPOUNDS (RPC) OF GENERAL FORMULA (I), PARTICULARLY (II-8), WHEREIN $R^2$ = CN

| NO. | $R^1$ | X | $R^3$ | $X^1$ | $X^2$ | Y | $X^3$ | $X^4$ |
|---|---|---|---|---|---|---|---|---|
| 962. | $CH_3NH$ | $CFCl_2S$ | H | Cl | H | Cl | H | Cl |
| 963. | $(CH_3)_2N$ | $CFCl_2S$ | H | Cl | H | Cl | H | Cl |
| 964. | $C_2H_5OCH=N$ | $CFCl_2SO$ | H | Cl | H | Cl | H | Cl |
| 965. | $C_2H_5OCH=N$ | $CFCl_2SO_2$ | H | Cl | H | Cl | H | Cl |
| 966. | $CH_2=CHCH_2NH$ | $CF_2ClS$ | H | Cl | H | Cl | H | Cl |
| 967. | $CH\equiv CCH_2NH$ | $CF_3S$ | H | Cl | H | Cl | H | Cl |
| 968. | $CH_3CONH$ | $CFCl_2S$ | H | Cl | H | Cl | H | Cl |
| 969. | $CF_3CONH$ | $CFCl_2S$ | H | Cl | H | Cl | H | Cl |
| 970. | $CH_3CH=N$ | $CFCl_2S$ | H | Cl | H | Cl | H | Cl |
| 971. | $PhCH=N$ | $CF_2ClS$ | H | Cl | H | Cl | H | Cl |
| 972. | $C_2H_5OCH=N$ | Cl | H | Cl | H | Cl | H | Cl |
| 973. | $(CH_3)_2NCH=N$ | Br | H | Cl | H | Cl | H | Cl |
| 974. | $CH_3S$ | Cl | H | Cl | H | Cl | H | Cl |
| 975. | $CH_3SO$ | Cl | H | Cl | H | Cl | H | Cl |
| 976. | $t-C_4H_9CONH$ | $CF_2ClSO$ | H | Cl | H | Cl | H | Cl |
| 977. | Br | $CHF_2S$ | H | Cl | H | Cl | H | Cl |
| 978. | Br | Br | H | Cl | H | Cl | H | Cl |
| 979. | Cl | Br | H | Cl | H | Cl | H | Cl |
| 980. | Br | $CH_3S$ | H | Cl | H | Cl | H | Cl |
| 981. | Br | $CH_3SO$ | H | Cl | H | Cl | H | Cl |
| 982. | Br | $CH_3SO_2$ | H | Cl | H | Cl | H | Cl |
| 983. | $CH_3S$ | $CH_3S$ | H | Cl | H | Cl | H | Cl |
| 984. | $CH_3SO$ | $CH_3SO$ | H | Cl | H | Cl | H | Cl |
| 985. | $CH_3S$ | $CH_3SO$ | H | Cl | H | Cl | H | Cl |
| 986. | Br | $CFCl_2S$ | H | Br | H | Cl | H | Cl |
| 987. | Br | $CF_2ClSO$ | H | Cl | Cl | Cl | H | Cl |
| 988. | $CH_3S$ | $CF_2ClS$ | H | H | Cl | Cl | H | Cl |
| 989. | Cl | $CF_2ClSO$ | H | Br | H | Cl | H | Br |
| 990. | $CH_3S$ | $CF_2ClS$ | H | Br | H | Br | H | Cl |

DETAILED EXAMPLES OF COMPOUND SYNTHESIS

The following EXAMPLES 1 to 22 and ADDITIONAL SYNTHESIZED EXAMPLES (ASE 1 to 307) further illustrate the methods of synthesis and the physical properties of the insecticidal compounds of general formula (I) (and their chemical intermediates) according to the invention.

SYNTHESIZED EXAMPLES OF PYRROLES

EXAMPLE 1

A solution of 910 mg (2.07 mmoles) of 1-(2,6-dichloro-4-trifluoromethylphenyl)-2-chloro-3-cyano-4-trifluoromethylthiopyrrole (made according to the process described in EXAMPLE 4) and 492 mg of 80% meta chloroperoxybenzoic acid (394 mg, 2.28 mmoles) in 25 ml of chloroform was stirred at ambient temperature for 1.5 hours and then heated to reflux overnight. An additional 45 mg (0.21 mmoles) of m-chloroperoxybenzoic acid was added and reflux was continued for 1 hour. Heating was then stopped, and the reaction mixture was diluted with dichloromethane and washed with aqueous sodium bicarbonate solution. The organic layer was dried over anhydrous MgSO$_4$ and concentrated under reduced pressure to give a colorless solid residue. This process was repeated so as to get, all together, 950 mg of product which was chromatographed on silica gel, eluting with 2:1 v/v dichloromethanehexane. Early fractions contained 310 mg (24%) of 1-(2,6-dichloro-4-trifluoromethylphenyl)-2-chloro-3-cyano-4-trifluoromethylsulfonylpyrrole (EXAMPLE 1) as a colorless solid. Recrystallization from hexanethyl acetate furnished 240 mg of the sulfone as colorless needles, melting point 198° C.

EXAMPLE 2

Chromatography at the end of EXAMPLE 1 was pursued. Later fractions from the chromatography furnished 600 mg (48%) of 1-(2,6-dichloro-4-trifluoromethylphenyl)-2-chloro-3-cyano-4-trifluoromethylsulfinylpyrrole (EXAMPLE 2) as a colorless solid. Recrystallization from toluene-hexane furnished 390 mg of the sulfoxide as a colorless powder, mp 153.5° C.

EXAMPLES 3A and 3B

EXAMPLES 1 and 2 were repeated with 1-(2,6-dichloro-4-trifluoromethylphenyl)-2-chloro-3-cyano-4-trifluoromethylthio-5-bromopyrrole as starting material made according to the process of EXAMPLE 5. The compound of EXAMPLE 3A is 1-(2,6-dichloro-4-trifluoromethylphenyl)-2-chloro-3-cyano-4-trifluoromethylsulfinyl-5-bromopyrrole. This compound, made using the procedure similar to that of EXAMPLE 2, has a melting point of about 123° C. The compound of EXAMPLE 3B is 1-(2,6-dichloro-4-trifluoromethylphenyl)-2-chloro-3-cyano-4-trifluoromethylsulfonyl-5-bromopyrrole. This compound, made using the procedure similar to that of EXAMPLE 1, has a melting point of about 113° C.

EXAMPLE 4

A solution of 3 g (6.6 mmoles) of 1-(2,6-dichloro-4-trifluoromethylphenyl)-2-amino-3-trifluoromethylthio-4-cyano-5-chloropyrrole (made according to the process described in EXAMPLE 8) in 50 ml of dry tetrahydrofuran was stirred under a nitrogen atmosphere and 3.9 ml (3.4 g, 33 mmoles) of t-butyl nitrite was added. After 30 minutes, the reaction mixture was heated to reflux for about one hour, then concentrated under reduced pressure to give 3.69 g of a solid residue. This process was repeated so as to get all together 4.07 g of solid residue, which was chromatographed on silica gel with a 1:1 v/v dichloromethane-hexane eluent to give 2.9 g (91%) of 1-(2,6-dichloro-4-trifluoromethylphenyl)-2-chloro-3-cyano-4-trifluoromethylthiopyrrole (EXAMPLE 4) as a colorless solid. Recrystallization from hexane-ethyl acetate provided 1.87 g of the product as a colorless powder, melting point at about 137° C.

EXAMPLE 5

To a heterogeneous mixture of 2.4 g (5.28 mmoles) of 1-(2,6-dichloro-4-trifluoromethylphenyl)-2-amino-3-trifluoromethylthio-4-cyano-5-chloropyrrole (made according to the process described in EXAMPLE 8) in 40 ml of bromoform under an inert atmosphere was added 0.94 ml (820 mg, 7.92 mmoles) of t-butyl nitrite. After 15 minutes of stirring at ambient temperature, the reaction mixture was concentrated under reduced pressure to give 3.9 g of residue. This was combined with the product from a previous reaction of 300 mg of the same pyrrole starting material. The crude product was chromatographed on silica gel eluting with 4:1 v/v hexane-dichloromethane. This separated 1.72 g (56%) of 1-(2,6-dichloro-4-trifluoromethylphenyl)-2-bromo-3-trifluoromethylthio-4-cyano-5-chloropyrrole (EXAMPLE 5), which was recrystallized from hexane to give 780 mg of the product as a colorless solid, melting point about 92° C.

EXAMPLE 6

A solution of 1.91 g (4.21 mmoles) of 1-(2,6-dichloro-4-trifluoromethylphenyl)-2-amino-3-trifluoromethylthio-4-cyano-5-chloropyrrole (made according to the process described in EXAMPLE 8), 77 mg (0.63) mmoles) of 4-dimethylaminopyridine and 20 ml of pyridine under an inert atmosphere was cooled at 0° C. and 1.01 ml (1.50 g, 7.14 mmoles) of trifluoroacetic anhydride was added. The reaction mixture was allowed to stir at 0° C. for 1 hour and at 20° C. for 4 hours, when an additional 0.30 ml (2.1 mmoles) of trifluoroacetic anhydride was added. After a total of 24 hours of reaction time, the reaction mixture was diluted with dichloromethane and concentrated. The residue was washed with aqueous HCl followed by water and recrystallized from hexane-ethyl acetate to give 860 mg (37%) of 1-(2,6-dichloro-4-trifluoromethylphenyl)-2-[(trifluoromethyl)carbonylamino]-3-trifluoromethylthio-4-cyano-5-chloropyrrole (EXAMPLE 6) as a slightly green solid, melting point about 190° C.

EXAMPLE 7

A mixture of 1.50 g (3.3 mmoles) of 1-(2,6-dichloro-4-trifluoromethylphenyl)-2-amino-3-trifluoromethylthio-4-cyano-5-chloropyrrole (made according to the process described in EXAMPLE 8), 0.10 g of 4-dimethylaminopyridine, 0.33 ml (0.32 g, 4.1 mmoles) of pyridine, 0.31 ml (0.34 g, 4.3 mmoles) of acetyl chloride and 10 ml of acetonitrile was stirred for four days at 20° C. and 1 day at reflux. An additional 0.03 ml of acetyl chloride was then added and reflux was continued for an additional day when the reaction was cooled, diluted with dichloromethane and partitioned successively with aqueous 1N HCl and a saturated aqueous sodium bicarbonate solution. The organic layer was dried over anhydrous magnesium sulfate and evaporated to give 1.42 g of a beige solid. Chromotography on silica gel eluting with 4:1 v/v hexane-ethyl acetate followed by recrystallization from ethanol-water provided 480 mg (29%) of 1-(2,6-dichloro-4-trifluoromethylphenyl)-2-methylcarbonylamino-3-trifluoromethylthio-4-cyano-5-chloropyrrole (EXAMPLE 7) as colorless needles, melting point about 216° C.

EXAMPLE 8

A stirred solution of 1.50 g (3.57 mmoles) of 1-(2,6-dichloro-4-trifluoromethylphenyl)-2-amino-3-trifluoromethylthio-4-cyanopyrrole (made according to the process described in EXAMPLE 13) in 15 ml of ethyl ether was cooled to −20° C. under an inert atmosphere and a solution of 0.29 ml (0.48 g, 3.6 mmoles) of sulfuryl chloride in 15 ml of anhydrous ethyl ether was added dropwise. The reaction mixture was then allowed to warm to 20° C. and stirred for 2.5 days when an additional 0.03 ml (0.4 mmole) of sulfuryl chloride was added and stirring continued for another day. Another 0.03 ml of sulfuryl chloride was added and after an additional day the reaction was quenched with 28 ml of 10% aqueous potassium carbonate solution. The phases were separated and the aqueous layer was extracted with ether. The ethereal layers were then combined, washed with water, dried over anhydrous magnesium sulfate and concentrated to give 1.56 g of a tan solid. The crude product was chromatographed on silica gel with a 2:1 v/v dichloromethane-hexane eluent to provide 1.30 g (80%) of 1-(2,6-dichloro-4-trifluoromethylphenyl)-2-amino-3-trifluoromethylthio-4-cyano-5-chloropyrrole (EXAMPLE 8) as a slightly rose colored solid. Recrystallization from cyclohexane furnished 810 mg of the product as off-white needles, melting point about 176° C.

EXAMPLE 9

A process similar to that of EXAMPLE 8 was used, except substituting 1-(2-chloro-4-trifluoromethylphenyl)-2-amino-3-trifluoromethylthio-4-cyanopyrrole (mp 169° C.) as the reactant, which was made by a process according to that described in EXAMPLE 13. The final product was 1-(2-chloro-4-trifluoromethylphenyl)-2-amino-3-trifluoromethylthio-4-cyano-5-chloropyrrole (EXAMPLE 9), mp about 148° C.

EXAMPLE 10

A process similar to that of EXAMPLE 8 was used, except substituting 1-(2,6-dichloro-4-trifluoromethylphenyl)-2-amino-3-dichlorofluoromethylthio-4-cyanopyrrole (mp 202° C.) as the reactant, which was made by a process according to that described in EXAMPLE 13. The final product was 1-(2,6-dichloro-4-trifluoromethylphenyl)-2-amino-3-dichlorofluoromethylthio-4-cyano-5-chloropyrrole (EXAMPLE 10), mp about 207° C.

EXAMPLE 11

The compound 1-(2,6-dichloro-4-trifluoromethylphenyl)-2,4-bis(trifluoromethylthio)-3-cyano-5-amino pyrrole (EXAMPLE 11) has a melting point of 161° C. and is made according to the process of EXAMPLE 13 (first compound) using an excess of trifluoromethanesulfenyl chloride.

EXAMPLE 12

To a cold (0° C.) solution of 1.53 g (3.60 mmoles) of 1-(2,6-dichloro-4-trifluoromethylphenyl)-2-amino-3-trifluoromethylthio-4-cyanopyrrole (made according to the process described in EXAMPLE 13, melting point about 182° C.) in 15 ml of pyridine was added, under inert atmosphere, a solution of 1.46 g (3.6 mmoles) of 80% pyridinium bromide perbromide in 15 ml of pyridine. After 30 minutes, the reaction mixture was poured into cold (0° C.) ethyl ether and a precipitate which formed was removed by filtration. The filtrate was washed with aqueous HCl, aqueous NaOH and water. The organic layer was dried over anhydrous magnesium sulfate and evaporated to yield 1.34 g of a brown solid. This was combined with 230 mg of product from an earlier reaction of 300 mg (0.7 mmole) of 1-(2,6-dichloro-4-trifluoromethylphenyl)-2-amino-3-trifluoromethylthio-4-cyanopyrrole and 0.29 g of 80% pyridinium bromide perbromide. The consolidated products were chromatographed on silica gel eluting with 4:1 v/v hexane-ethyl acetate to give 1.31 g (73%) of 1-(2,6-dichloro-4-trifluoromethylphenyl)-2-amino-3-trifluoromethylthio-4-cyano-5-bromopyrrole (EXAMPLE 12) as a white solid. Recrystallization from hexane/ethyl acetate furnished 910 mg of this product as colorless needles, melting point about 160° C.

EXAMPLE 13

A stirred solution of 2.00 g (6.25 mmoles) of 1-(2,6-dichloro-4-trifluoromethylphenyl)-2-amino-4-cyanopyrrole in 60 ml of dichloromethane, made as indicated hereafter, was cooled with an ice bath and 10 ml of a cold (−78° C.) dichloromethane solution containing 0.55 ml (0.85 g, 6.2 mmoles) of trifluoromethanesulfenyl chloride was added in a slow stream. After stirring at 0° C. for two hours, a stream of nitrogen was passed through the reaction mixture for one hour. Partitioning with saturated aqueous sodium bicarbonate and water, drying over anhydrous magnesium sulfate and concentrating in vacuo furnished 3.14 g of a light brown solid. This was chromatographed on silica gel with a 3:2 v/v dichloromethane-hexane eluent to provide two colorless solid samples weighing 900 mg and 950 mg. These were recrystallized from chloroform to provide, respectively, 680 mg and 630 mg of 1-(2,6-dichloro-4-trifluoromethylphenyl)-2-amino-3-trifluoromethylthio-4-cyanopyrrole (EXAMPLE 13), melting point about 182° C.

The reactant used in this process was made according to the following process: A solution of 4.64 g (14.5 mmoles) of 1-[(2,6-dichloro-4-trifluoromethylphenyl)amino]-2,3-dicyanoprop-1-ene and 2.02 ml (1.47 g, 14.5 mmoles) of triethylamine in 30 ml of benzene was heated at reflux overnight and then concentrated in vacuo. The residue was partitioned between ethyl ether and water and the ether layer was dried over anhydrous magnesium sulfate and concentrated to give 3.79 g of a light brown solid. Recrystallization from ethanol-water provided 2.79 g (60%) of 1-(2,6-dichloro-4-trifluoromethylphenyl)-2-amino-4-cyanopyrrole, melting point about 176° C.

The starting 1-arylamino-2,3-dicyanoprop-1-ene was made according to the following process: A 20.5 g (0.140 mole) sample of the potassium salt of formylsuccinonitrile was dissolved in approximately 30 ml of water and made acidic with concentrated hydrochloric acid. This was extracted with ethyl ether, the ethereal extract dried over anhydrous magnesium sulfate and evaporated to give 3.87 g of a brown liquid. This was added to a solution containing 5.04 g (22 mmoles) of 2,6-dichloro-4-trifluoromethylaniline and 40 mg of para-toluene sulfonic acid monohydrate in 50 ml of benzene. The heterogeneous reaction mixture was heated to reflux overnight with separation of water. The reaction mixture was then cooled and concentrated to give 7.66 g of a yellow liquid. Trituration with hexane precipitated 6.68 g (95%) of 1-[(2,6-dichloro-4-trifluoromethylphenyl)amino]-2,3-dicyanoprop-1-ene as a yellow solid. Recrystallization from ethanol/water provided a sample, melting point about 101° C.

EXAMPLES 14A and 14B

To a suspension of 1.17 g (3.30 mmoles) of 1-(4-trifluoromethylphenyl)-2-amino-3-trifluoromethylthio-4-cyanopyrrole and 0.46 ml (0.34 g, 3.3 mmoles) of triethylamine in 20 ml of chloroform cooled to −20° C. was added a solution of 0.19 ml (0.59 g, 3.7 mmoles) of bromine in 5 ml of chloroform. The reaction mixture was stirred at −20° C. for 1 hour and then allowed to warm to 0° C. Another 0.04 ml (0.13 g, 0.8 mmole) of bromine was then added and after 15 minutes of additional stirring, the reaction mixture was diluted with dichloromethane and partitioned with water and a saturated aqueous sodium bicarbonate solution. The organic layer was dried over anhydrous magnesium sulfate and concentrated to give 1.11 g of a brown solid. This material was combined with that from a previous reaction of 1.00 g (2.8 mmoles) of 1-(4-trifluoromethylphenyl)-2-amino-3-trifluoromethylthio-4-cyanopyrrole and 0.15 ml of bromine. Chromatography on silica gel eluting with 3:1 v/v dichloromethane-hexane furnished 1.40 g (52%) of 1-(4-trifluoromethylphenyl)-2-amino-3-trifluoromethylthio-4-cyano-5-bromopyrrole (EXAMPLE 14A) as a yellow solid. Recrystallization from hexane-ethyl acetate provided the product as light yellow platelets, melting point about 175° C.

The 1-(4-trifluoromethylphenyl)-2-amino-3-trifluoromethylthio-4-cyanopyrrole (EXAMPLE 14B), melting point about 152° C., can be made from 1-[(4-trifluoromethylphenyl)amino]-2,3-dicyanoprop-1-ene according to a process similar to the one described in EXAMPLE 13.

EXAMPLES 15A and 15B

1-[(2-Chloro-4-trifluoromethylphenyl)amino-]-2,3-dicyanoprop-1-ene was made according to a process similar to the one described in EXAMPLE 13. This dicyanoprop-1-ene was used to prepare 1-(2-chloro-4-trifluoromethylphenyl)-2-amino-3-trifluoromethylthio-4-cyanopyrrole (EXAMPLE 15A), melting point about 169° C., made according to a process similar to the one described in EXAMPLE 13. This pyrrole was used to prepare 1-(2-chloro-4-trifluoromethylphenyl)-2-amino-3-trifluoromethylthio-4-cyano-5-bromopyrrole (EXAMPLE 15B), melting point about 157° C., according to the process of EXAMPLE 14.

EXAMPLES 16A, 16B and 16C

The 1-(2,6-dichloro-4-trifluoromethylphenyl)-2-amino-4-cyanopyrrole, made according to EXAMPLE 13, was treated with CFCl$_2$-SCl according to the process of EXAMPLE 13 (which used CF$_3$SCl) to provide 1-(2,6-dichloro-4-trifluoromethylphenyl)-2-amino-3-dichlorofluoromethylthio-4-cyanopyrrole, (EXAMPLE 16A), melting point about 202° C.

This compound was treated with sulfuryl chloride by the process of EXAMPLE 8 to provide 1-(2,6-dichloro-4-trifluoromethylphenyl)-2-amino-3-dichlorofluoromethylthio-4-cyano-5-chloropyrrole, (EXAMPLE 16B), of melting point 208° C.

This compound was treated with t-butyl nitrite according to the process of EXAMPLE 4 to provide 1-(2,6-dichloro-4-trifluoromethylphenyl)-2-chloro-3-cyano-4-(dichlorofluoromethylthio)pyrrole (EXAMPLE 16C), melting point about 158° C.

EXAMPLE 17

The last compound of EXAMPLE 16 was reacted according to a process similar to the process of EXAMPLES 1 and 2 using hydrogen peroxide in trifluoroperacetic acid (instead of m-chloro peroxybenzoic acid) to provide 1-(2,6-dichloro-4-trifluoromethylphenyl)-2-chloro-3-cyano-4-(dichlorofluoromethylsulfinyl)pyrrole (EXAMPLE 17), melting point about 119° C.

EXAMPLE 18

According to the process of EXAMPLE 17 using a double amount of hydrogen peroxide, the last compound of EXAMPLE 16 was transformed into 1-(2,6-dichloro-4-trifluoromethylphenyl)-2-chloro-3-cyano-4-(dichlorofluoromethylsulfonyl)pyrrole (EXAMPLE 18), melting point about 179° C.

EXAMPLE 19

The first compound of EXAMPLE 16 was treated with t-butyl nitrite according to the process of EXAMPLE 4 to provide 1-(2,6-dichloro-4-trifluoromethylphenyl)-3-cyano-4-(dichlorofluoromethylthio)pyrrole (EXAMPLE 19), melting point about 120° C.

EXAMPLE 20

The compound of EXAMPLE 19 was oxidized according to the process of EXAMPLE 17 to provide 1-(2,6-dichloro-4-trifluoromethylphenyl)-3-cyano-4-(dichlorofluoromethylsulfinyl)pyrrole (EXAMPLE 20), mp 151° C.

EXAMPLES 21A, 21B and 21C

1-[(2,6-Dichloro-4-trifluoromethoxyphenyl)amino]-2,3-dicyanoprop-1-ene was prepared according to the process of the last compound of EXAMPLE 13, substituting 2,6-dichloro-4-trifluoromethoxyaniline for 2,6-dichloro-4-trifluoromethylaniline.

This compound was converted to 1-(2,6-dichloro-4-trifluoromethoxyphenyl)-2-amino-4-cyanopyrrole according to the process of the second compound of EXAMPLE 13.

This compound was converted to 1-(2,6-dichloro-4-trifluoromethoxyphenyl)-2-amino-3-trifluoromethylthio-4-cyanopyrrole according to the process of the first compound of EXAMPLE 13.

This compound was converted to 1-(2,6-dichloro-4-trifluoromethoxyphenyl)-2-amino-3-(trifluoromethylthio)-4-cyano-5-chloropyrrole (EXAMPLE 21A), mp 196.5° C. according to the process of EXAMPLE 8.

This compound was converted to 1-(2,6-dichloro-4-trifluoromethoxyphenyl)-2-chloro-3-cyano-4-trifluoromethylthiopyrrole (EXAMPLE 21B), melting point 172° C. according to the process of EXAMPLE 4.

This compound was converted to 1-(2,6-dichloro-4-trifluoromethoxyphenyl)-2-chloro-3-cyano-4-trifluoromethylsulfonylpyrrole (EXAMPLE 21C), melting point 187° C., according to the process of EXAMPLE 18.

EXAMPLES 22A, 22B, AND 22C

A mixture of 2-chloro-4-chlorosulfenyl-3-cyano-1-(2,6-dichloro-4-trifluoromethylphenyl)pyrrole and 2-chloro-3-cyano-4-dichlorofluoromethylsulfenyl-1-(2,6-dichloro-4-trifluoromethylphenyl)pyrrole 47.77 g, 0.101 moles, 1.0 eq), obtained as a by-product from over chlorination of the reaction described in EXAMPLE 16B, was dissolved in trifluoroacetic acid (190 mL) at 0° C. 30% H$_2$O$_2$ (10.8 mL, 0.106 moles, 1.05 eq) was added dropwise. The reaction was stirred at 0° C. for 7 hrs. 15 min., then placed in the refrigerator (10° C.) overnight. More 30% H$_2$O$_2$ (10.8 mL, 0.106 moles, 1.05 eq) was added at 0° C. the following morning. The reaction was stirred at 0° C. for 9 hrs, then placed in the refrigerator overnight. More 30% H$_2$O$_2$ (10.8 mL, 0.106 moles, 1.05 eq) was added at 0° C. the following morning. After 3.5 hrs., the reaction was poured into 2 liters of ice-water, vigorously stirred, then filtered.

Similarly, a mixture of 2-chloro-4-chlorosulfenyl-3-cyano-1-(2,6-dichloro-4-trifluoromethylphenyl)-pyrrole and 2-chloro-3-cyano-4-dichlorofluoromethylsulfenyl-1-(2,6-dichloro-4-trifluoromethylphenyl)pyrrole (40.77 g, 0.0848 moles, 1.0 eq) was dissolved in trifluoroacetic acid (188 mL) at 0° C. 30% $H_2O_2$ (17.7 mL, 0.173 moles, 2.05 eq) was added dropwise. The reaction was stirred at 0° C. for 2 hrs. 45 min., then placed in the refrigerator (10° C.) overnight. After stirring for 8 hrs. at 0° C., the reaction mixture was again placed in the refrigerator overnight. The reaction was then allowed to warm to room temperature, and stirred overnight at room temperature. More 30% $H_2O_2$ (9.05 mL, 0.0886 moles, 1.05 eq) was added at 0° C. the following morning and the reaction kept at 0° C. for 6 hrs. 40 min., then allowed to warm to room temperature and stirred over the weekend. The reaction was poured into 2 liters of ice-water, vigorously stirred, then filtered.

The precipitates from both reactions were combined and dissolved in 500 mL of dichloromethane, washed with 500 mL water, 500 mL 10% aqueous $NaHSO_3$, and 500 mL sat. NaCl. The organic phase was dried over $Na_2SO_4$, filtered, and the solvent evaporated to afford 74.96 g (79.9% yield) of a solid. This was recrystallized from 690 mL hexane:dichloromethane (2:1), to which 20 mL dichloromethane was added, to afford 6.98 g of a solid, identified as 2-chloro-4-chlorosulfonyl-3-cyano-1-(2,6-dichloro-4-trifluoromethylphenyl)-pyrrole (EXAMPLE 22A). This was then recrystallized from 103 mL isopropanol to afford 3.97 g, mp 188° C.

A portion of 2-chloro-4-chlorosulfonyl-3-cyano-1-(2,6-dichloro-4-trifluoromethylphenyl)-pyrrole (3.97 g, 9.06 mmoles, 1.0 eq) was dissolved in THF (15.8 mL) at 0° C. Triphenylphosphine (2.41 g, 1.0 eq) was added as a solid. The solution turned yellow. After 2.5 hrs., the ice bath was removed and the reaction allowed to stir at room temperature overnight. More triphenylphosphine was added (2.55 g, 9.72 mmoles. 1.06 eq) and the reaction allowed to stir at room temperature overnight. A precipitate formed, 3 mL THF was added, and the reaction mixture washed twice with sat. NaCl, and back-extracted. The organic phase was dried over $MgSO_4$, filtered, and the solvent evaporated in vacuo to afford a waxy-solid, 9.44 g. This was chromatographed on silica gel to yield 3.39 g of a waxy solid. This was then recrystallized from 140 mL isopropanol to afford 2.54 g (74.9%) bis-[2-chloro-3-cyano-1-(2,6-dichloro-4-trifluoromethylphenyl)-pyrrol-4-yl]-disulfide (EXAMPLE 22B), mp 220° C.

A portion of bis-[2-chloro-3-cyano-1-(2,6-dichloro-4-trifluoromethylphenyl)-pyrrol-4-yl]-disulfide (0.80 g, 1.08 mmoles, 1.0 eq) was dissolved in DMF (10 mL) and cooled to 0° C. $Na_2HPO_4$ (0.46 g, 3.24 mmoles, 3.0 eq) was dissolved in 5 mL water, then added to the DMF solution. A precipitate formed, so 15 mL DMF and 10 mL water were added. Solid $Na_2S_2O_4$ (0.564 g, 3.24 mmoles, 3.0 eq) was added. The reaction turned pale yellow in color. Dibromodifluoromethane (0.65 g, 3.1 mmoles, 2.87 eq) was added to a cold tared vial, then transferred to the reaction. The reaction mixture became colorless with a white precipitate. After 1 hr. 50 min., 10 mL DMF was added, followed by an additional 0.93 g of $CBr_2F_2$, and the reaction vessel sealed and allowed to stir at room temperature overnight. After cooling to 0° C., the reaction mixture was added to 200 mL water and extracted four times with 150 mL ethyl ether. The organic phase was washed twice with 100 mL 5% aqueous HCl, twice with 100 mL sat. $NaHCO_3$, and with 100 mL sat. NaCl. The organic phase was dried over $MgSO_4$, filtered, and the solvent evaporated in vacuo to afford 80.7 mg of a white solid. The initial aqueous phase was then filtered to collect a white solid which had precipitated overnight. It was dissolved in dichloromethane, the solvent evaporated in vacuo, and dried to afford 0.348 g of a white solid (total yield, 0.429 g, 40%). This was combined with the 80.7 mg sample and chromatographed on silica gel to afford 0.362 g white solid, identified as 4-bromodifluoromethylsulfenyl-2-chloro-3-cyano-1-(2,6-dichloro-4-trifluoromethylphenyl)-pyrrole (EXAMPLE 22C) mp 131° C.

ADDITIONAL SYNTHESIZED EXAMPLES (ASE) OF PYRROLES

Following the procedures detailed above for the synthesis of compounds of EXAMPLES 1 to 22 or the other methods or processes of synthesis generally described herein, there were prepared a number of ADDITIONAL SYNTHESIZED EXAMPLES (ASE) of pyrrole compounds of general formula (I). The structures of these compounds and their corresponding melting points are provided in TABLES 2A-2E as described below. It is noted that compounds identified as ASE No's 30, 43, 49, 185, and 192 are not within this invention. Reported melting points in the above EXAMPLES as well as in the ASE examples represent the average value of an observed melting point range determined for a compound or furthermore represent the average value of a number of separate melting point determinations. Additionally, one or more spectroscopic analyses (IR, NMR, GC/MS, etc.) have been performed on each compound for characterization and confirmation of the chemical structure.

TABLE 2A: ASE 1-91, wherein $X^2$ and $X^3$=H and the other substituents are as described;

TABLE 2B: ASE 92-195, wherein $X^2$ and $X^3$=H, $X^1$ and $X^4$=Cl, and Y=$CF_3$ and the other substituents are as described;

TABLE 2C: ASE 196-215, wherein $X^2$ and $X^3$=H and the other substituents are as described; compounds more specifically of formula (II-7);

TABLE 2D: ASE 216-222, wherein $X^2$ and $X^3$=H and the other substituents are as described; compounds more specifically of formula (II-8); and TABLE 2E:
 a) ASE 223-302 and 307, wherein $X^2$ and $X^3$=H and the other substituents are as described;
 b) ASE 303-305, wherein $X^2$ and $X^3$=Cl and the other substituents are as described; and
 c) ASE 306, wherein $X^2$=Cl, $X^3$=H, and the other substituents are as described.

Further specific details of synthetic procedures/methods are provided as follows for ASE No's 47, 176, 197/196, 200, 201, 205, 213, 215, and 302.

ASE 47

To a solution of 5.045 g (10.67 mmoles) of 2-chloro-4-dichlorofluoromethylthio-1-(2,6-dichloro-4-trifluoromethylphenyl)-3-cyanopyrrole in 7 mL of tetrahydrofuran was added a solution of 0.745 g (10.63 mmoles) of sodium methanethiolate in 2.4 mL of water. Some water droplets were seen in the reaction mixture. After stirring at room temperature for 18 hours, 75 mL of tetrahydrofuran was added to solubilize the reaction mixture, but a white precipitate was formed. Ten mL of methanol was added, followed by 0.135 g (1.93 mmoles) of sodium methanethiolate in 10 drops of water. The reaction mixture was decanted, and the decantate stirred at room temperature over the weekend. Sodium methanethiolate (0.4937 g, 7.04 mmoles) in 25 drops of water were added. After 20 minutes, the solvent was evaporated, the residue was dissolved in 50 mL of dichloromethane, which was washed with 50 mL of water, 50 mL of sat. NaCl, 50 mL of water, and 25 mL of sat. NaCl; all aqueous phases were then combined and back-extracted with 50 mL of dichloromethane. The combined organic phase was dried over magnesium sulfate, filtered, and the solvent evaporated to afford 4.61 g (89.1%) of a gold oily solid. This was recrystallized from 3 mL of isopropanol, filtered, and washed with hexane to afford 2.3 g (44.5%) of a white solid of melting point 128° C., identified as 2-chloro-4-dichlorofluoromethylthio-1-(2-chloro-6-methylthio-4-trifluoromethylphenyl)-3-cyanopyrrole (ASE 47).

ASE 166

To a cooled (−3° C.) solution of 8.00 g of 1-(2,6-dichloro-4-trifluoromethylphenyl)-2-amino-3-dichlorofluoromethylthio-4-cyano-5-chloropyrrole prepared as in EXAMPLE 16 in 140 mL of chloroform and 140 mL of dimethyldisulfide was added 2.92 mL (2.53 g, 25.0 mmoles) of t-butyl nitrite. This solution was allowed to warm to room temperature with stirring overnight and then the solvent was removed under reduced pressure. The residue was then chromatographed on silica gel eluting with 9:1 v/v hexane-EtOAc. Early fractions contained 3.73 g of a yellow liquid which partially solidified on standing. This was triturated with hexane to furnish 1.53 g of a pale yellow solid which was combined with 6.18 g of a yellow solid from later fractions of the chromatography. The combined material was recrystallized from ethanol to give 4.84 g (58%) of 1-(2,6-dichloro-4-trifluoromethylphenyl)-2-methylthio-3-dichlorofluoromethylthio-4-cyano-5-chloropyrrole (ASE 166) as a yellow solid of melting point 128° C.

ASE 197/196

To a suspension of 2.90 g (21.6 mmoles) of cupric chloride in a mixture of 20 mL of acetonitrile and 40 mL of acrylonitrile was added 2.73 mL (2.37 g, 23.0 mmoles) of t-butyl nitrite. The resulting black solution was cooled to 0° C. and a solution of 6.66 g (14.7 mmoles) of 1-(2,6-dichloro-4-trifluoromethylphenyl)-2-amino-3-trifluoromethylthio-4-cyano-5-chloropyrrole prepared according to EXAMPLE 8 in 25 mL of acetonitrile was added dropwise and with stirring over a period of 20 minutes. The mixture was allowed to stir for 4 hours at room temperature and was then poured into 400 mL of 1N aqueous HCl and partitioned successively with dichloromethane and water. The organic extracts were dried over anhydrous MgSO4 and concentrated. The residual brown oil was chromatographed on silica gel eluting initially with 2:1 and then 1:1 v/v dichloromethane-hexane to give 5.30 g (69%) of 1-(2,6-dichloro-4-trifluoromethylphenyl)-2-(2-chloro-2-cyanoethyl)-3-trifluoromethylthio-4-cyano-5-chloropyrrole.

The 1-(2,6-dichloro-4-trifluoromethylphenyl)-2-(2-chloro-2-cyanoethyl)-3-trifluoromethylthio-4-cyano-5-chloropyrrole prepared above was dissolved in 125 mL of toluene and treated with 1.65 mL (1.68 g, 11.1 mmoles) of 1,8-diazabicyclo[5.4.0]undec-7-ene (DBU) at room temperature for 1 hour. The reaction mixture was then diluted with ether, washed with water, dried over anhydrous MgSO4 and concentrated to give 4.84 g (98%) of 1-(2,6-dichloro-4-trifluoromethylphenyl)-2-(2-cyanoethenyl)-3-trifluoromethylthio-4-cyano-5-chloropyrrole as a yellow solid.

A 3.03 g (6.18 mmoles) portion of the 1-(2,6-dichloro-4-trifluoromethylphenyl)-2-(2-cyanoethenyl)-3-trifluoromethylthio-4-cyano-5-chloropyrrole prepared above was treated with 467 mg (12.4 mmoles) of sodium borohydride in 250 mL of ethanol at room temperature for 16 hours. An additional 234 mg (6.18 mmoles) of sodium borohydride was then added in two equal portions over a two hour period to complete the reaction. The solvent was then removed under reduced pressure and the residue poured into 25 mL of ice water. The mixture was acidified with aqueous 6N HCl, extracted with dichloromethane (2×50 mL) and the organic extracts were partitioned with saturated aqueous NaHCO3 solution, dried over anhydrous MgSO4 and concentrated. The residue was chromatographed on silica gel eluting with 70/30 v/v dichloromethane-hexane to furnish 1.52 g (50%) of 1-(2,6-dichloro-4-trifluoromethylphenyl)-2-(2-cyanoethyl)-3-trifluoromethylthio-4-cyano-5-chloropyrrole (ASE 196) as a white solid of melting point 150° C.

A 500 mg (1.01 mmole) amount of the 1-(2,6-dichloro-4-trifluoromethylphenyl)-2-(2-cyanoethyl)-3-trifluoromethylthio-4-cyano-5-chloropyrrole prepared above was dissolved in 10 mL of trifluoroacetic acid and stirred at 0° C. overnight with 0.10 mL of 30% hydrogen peroxide. Additional hydrogen peroxide (0.02 mL) was added followed after 7 hours by a further 0.02 mL. The reaction mixture was stored in a refrigerator for two days and then poured into 50 mL of ice water. Partitioning with dichloromethane (2×50 mL), drying over anhydrous MgSO4 and removing the solvent provided 430 mg of a white solid. Chromatography on silica gel with dichloromethane as eluant gave 340 mg (66%) of 1-(2,6-dichloro-4-trifluoromethylphenyl)-2-(2-cyanoethyl)-3-trifluoromethylsulfinyl-4-cyano-5-chloropyrrole (ASE 197) as a white solid which decomposed on melting over a range of 60°–100° C.

ASE 200

To a stirred solution of 5.0 g (11.9 mmoles) of 1-(2,6-dichloro-4-trifluoromethylphenyl)-2-amino-3-trifluoromethylthio-4-cyanopyrrole prepared as described in EXAMPLE 13 and 4.75 mL (5.51 g, 35.7 mmoles) of tris(methylthio)methane in 30 mL of acetonitrile was added 7.00 g (35.7 mmoles) of dimethyl(methylthio)sulfonium tetrafluoroborate in one portion. This mixture was stirred overnight at room temperature and then poured into ice water and partitioned with ether. The ethereal extracts were dried over anhydrous MgSO4 and concentrated to yield a brown oil. Trituration with hexane furnished 5.41 g of a brown solid. This process was repeated with another 5.00 g sample of 1-(2,6-dichloro-4-trifluoromethylphenyl)-2-amino-3-trifluoromethylthio-4-cyanopyrrole to obtain an additional 5.96 g of product. These samples were combined and chromatographed on silica gel eluting with 5:1 v/v hexane-EtOAc to give 8.67 g of a pale yellow solid. Trituration with cyclohexane provided 7.34 g (59%) of 1-(2,6-dichloro-4-trifluoromethylphenyl)-2-amino-3-trifluoromethylthio-4-cyanopyrrole-5-[bis(methylthio)methyl]pyrrole.

A 2.75 g (5.22 mmoles) portion of the product prepared above was treated with 0.59 g (5.75 mmoles) of t-butyl nitrite in a similar manner as that described in EXAMPLE 4 to obtain 1.86 g (70%) of 1-(2,6-dichloro-4-trifluoromethylphenyl)-2-[bis(methylthio)methyl]-3-cyano-4-(trifluoromethylthio)pyrrole as a yellow solid.

A 2.68 g sample of 1-(2,6-dichloro-4-trifluoromethylphenyl)-2-[bis(methylthio)methyl]-3-cyano-4-trifluoromethylthiopyrrole prepared as described above was refluxed with 1.8 g of Raney nickel in 100 mL of methanol solution for 1 hour and 15 minutes. After stirring overnight at room temperature, the reaction was refluxed for an additional hour, then cooled and filtered through celite. The filtrate was concentrated and the residue was dissolved in dichloromethane, dried over anhydrous MgSO$_4$ and the solvent evaporated to give 1.92 g of a brown solid. Chromatography on silica gel eluting with 5:1 v/v hexane-EtOAc furnished 1.64 g (74%) of 1-(2,6-dichloro-4-trifluoromethylphenyl)-2-methyl-3-cyano-4-trifluoromethylthiopyrrole (ASE 200) as a yellow solid. Recrystallization from hexane provided yellow needles of melting point 98.5° C.

ASE 201

A 596 mg (1.42 mmoles) sample of the 1-(2,6-dichloro-4-trifluoromethylphenyl)-2-methyl-3-cyano-4-trifluoromethylthiopyrrole prepared above was treated with 0.15 mL (1.42 mmoles) of 30% hydrogen peroxide in 6 mL of trifluoroacetic acid overnight a 0° C. The reaction mixture was then poured into ice water, extracted with dichloromethane (2×50 mL); the combined organic extracts were dried over anhydrous MgSO$_4$ and the solvent was removed under reduced pressure to leave 490 mg of a yellow residue. This was chromatographed on silica gel with a 5:1 v/v hexane-EtOAc eluant to give 410 mg (66%) of 1-(2,6-dichloro-4-trifluoromethylphenyl)-2-methyl-3-cyano-4-(trifluoromethylsulfinyl)pyrrole (ASE 201) as a yellow solid. Recrystallization from hexane-EtOAc provided 210 mg of the product as colorless crystals of melting point 161° C.

ASE 205

A 10.0 g sample of 1-(2,6-dichloro-4-trifluoromethylphenyl)-2-amino-3-dichlorofluoromethylthio-4-cyanopyrrole was treated with tris(methylthio)methane in the same manner as described in the first part of ASE 200 to provide 9.91 g (80%) of 1-(2,6-dichloro-4-trifluoromethylphenyl)-2-amino-3-dichlorofluoromethylthio-4-cyano-5-[bis(methylthio)methyl]pyrrole. Recrystallization from hexanedichloromethane gave the product as a dark green powder of melting point 177° C.

A portion of 9.24 g (16.5 mmoles) of the product above was deaminated in a similar manner as described in EXAMPLE 4 to furnish 7.40 g (82%) of 1-(2,6-dichloro-4-trifluoromethylphenyl)-2-[bis(methylthio)methyl]-3-cyano-4-(dichlorofluoromethylthio)pyrrole. Recrystallization of the product from cyclohexane gave orange crystals of melting point 167° C.

A portion of 3.50 g of the product prepared above was refluxed in a mixture of 35 mL of trifluoroacetic acid and 35 mL of water for 50 minutes. The reaction mixture was then poured into ice water and partitioned successively with ether, water, aqueous NaHCO$_3$, water and aqueous Na$_2$CO$_3$. The ethereal extracts were dried over anhydrous MgSO$_4$ and the solvent removed under reduced pressure to give 3.03 g of a brown solid. Silica gel chromatography furnished 1.27 g (64%) of 1-(2,6-dichloro-4-trifluoromethylphenyl)-2-formyl-3-cyano-4-(dichlorofluoromethylthio)pyrrole as a yellow solid. Recrystallization from hexane-ether yielded colorless needles of melting point 113.5° C.

A solution of 0.39 mL (0.42 g, 3.0 mmoles) of diethylaminosulfur trifluoride and 0.69 g (1.48 mmole) of the 1-(2,6-dichloro-4-trifluoromethylphenyl)-2-formyl-3-cyano-4-(dichlorofluoromethylthio)pyrrole prepared above in 25 mL of 1-chlorobutane was stirred at room temperature for two days. The reaction mixture was the quenched with 30 mL of saturated aqueous NaHCO$_3$ and partitioned with ether. The ethereal layer was dried over anhydrous MgSO$_4$ and evaporated to give 680 mg of a yellow solid. This crude product was combined with 190 mg of the product of a previous reaction of 200 mg (0.43 mmole) of 1-(2,6-dichloro-4-trifluoromethylphenyl)-2-formyl-3-cyano-4-dichlorofluoromethylthiopyrrole and chromatographed on silica gel with a 1:1 v/v dichloromethane-hexane eluent to obtain 640 mg (69%) of 1-(2,6-dichloro-4-trifluoromethylphenyl)-2-difluoromethyl-3-cyano-4-(dichlorofluoromethylthio)pyrrole (ASE 205). Recrystallization from hexanedichloromethane gave the compound as pale yellow needles of melting point 104.5° C.

ASE 213

To a cold (−66° C.) solution of 1.05 mL (1.22 g, 8.58 mmoles) of boron trifluoride etherate in 20 mL of dichloromethane was added 2.00 g (4.29 mmoles) of 1-(2,6-dichloro-4-trifluoromethylphenyl)-2-formyl-3-cyano-4-(dichlorofluoromethylthio)pyrrole prepared according to the third part of ASE 205 in 8 mL of dichloromethane. This yellow solution was stirred at −67° C. for 5 minutes and then 1.16 mL (0.848 g, 7.30 mmoles) of triethylsilane was added. The reaction stirred at −67° C. for 1.5 hours followed by stirring at −38° C. for 1 hour and was then allowed to warm to room temperature while stirring overnight. 40 mL of water was then added and the aqueous layer was extracted with dichloromethane (1×200, 1×100 mL). The combined organic phases were washed with saturated aqueous NaHCO$_3$, dried over anhydrous MgSO$_4$ and concentrated to afford 1.70 g of a pale yellow solid Chromatography on silica gel eluting with 5:1 v/v hexane-EtOAc furnished 1.49 g (74%) of 1-(2,6-dichloro-4-trifluoromethylphenyl)-2-hydroxymethyl-3-cyano-4-(dichlorofluoromethylthio)pyrrole as an off-white solid.

The product prepared above was treated with 0.68 mL (0.96 g, 4.8 mmoles) of iodotrimethylsilane in 55 mL of chloroform solution initially at 0° C. with gradual warming to room temperature overnight. Another 0.22 mL (310 mg, 1.55 mmoles) of iodotrimethylsilane was then added and stirring was continued for another day. The reaction mixture was then diluted with 50 mL of dichloromethane and washed with a saturated aqueous solution of sodium bisulfite (2×30 mL) and a saturated aqueous solution of sodium bicarbonate (1×50 mL). After drying the organic layer over anhydrous MgSO$_4$ and evaporating, 1.6 g of a mixture of approximately 1 part 1-(2,6-dichloro-4-trifluoromethylphenyl)-2-iodomethyl-3-cyano-4-(dichlorofluoromethylthio)pyrrole and 1.6 parts 1-(2,6-dichloro-4-trifluoromethylphenyl)-2-methyl-3-cyano-4-(dichlorofluoromethylthio)pyrrole was obtained as a yellow oil.

A solution of 300 mg of the mixture of products isolated above, 5 mg (0.03 mmole) of azobisisobutyonitrile and 0.08 mL (93 mg, 0.32 mmole) of tri-n-butyltin hydride in 3 mL of toluene was heated overnight at 80° C. Another 0.04 mL (43 mg, 0.15 mmole) of tri-n-butyltin hydride was added and heating was continued for a total of 20 hours. The reaction mixture was then diluted with 15 mL of ether and partitioned with saturated aqueous NaHCO$_3$ (2×15 mL), dried over anhydrous MgSO$_4$ and concentrated under reduced pressure. The residue was chromatographed on silica gel with a 2:1 v/v dichloromethane-hexane eluent to provide 150 mg of 1-(2,6-dichloro-4-trifluoromethylphenyl)-2-methyl-3-cyano-4-(dichlorofluoromethylthio)pyrrole (ASE 213) as a colorless solid of melting point 109.5° C.

ASE 215

To a refluxing solution of 9.20 g (40.0 mmoles) of 2,6-dichloro-4-trifluoromethylaniline and 0.76 g (4.0 mmoles) of p-toluenesulfonic acid monohydrate in 25 mL of benzene was added dropwise over an 8 hour period with a syringe pump 9.40 mL (9.14 g, 80.1 mmoles) of acetonylacetone. Throughout the addition, water was removed via a Dean-Stark trap. The reaction mixture was then cooled and partitioned with a saturated aqueous solution of NaHCO$_3$ which was back-extracted with ether. The combined organic layers were dried over anhydrous Na$_2$SO$_4$ concentrated. The residual brown oil was chromatographed on silica gel with a 95:5 v/v hexane-EtOAc eluent to afford 10.0 g (81%) of 1-(2,6-dichloro-4-trifluoromethylphenyl)-2,5-dimethylpyrrole as a light brown solid of melting point 63° C.

To a cooled (0° C.) solution of 3.00 g (9.74 mmoles) of the 1-(2,6-dichloro-4-trifluoromethylphenyl)-2,5-dimethylpyrrole prepared above in 60 mL of dichloromethane was added dropwise 1.03 mL (1.67 g, 9.86 mmoles) of dichlorofluoromethanesulfenyl chloride in 5 mL of dichloromethane solution. The mixture was maintained at 0° C. for 3 hours and then washed with a saturated aqueous solution of NaHCO$_3$. Removal of solvent under reduced pressure afforded a black oil which was chromatographed on silica gel with a 1% EtOAc in hexane eluent to give 3.85 g (90%) of 1-(2,6-dichloro-4-trifluoromethylphenyl)-2,5-dimethyl-3-(dichlorofluoromethylthio)pyrrole as a yellow oil: $^1$H NMR (CDCl$_3$): δ2.00 (s, 3H), 2.10 (s, 3H), 6.27 (s, 1H), 7.80 (s, 2H).

To a solution containing 0.90 g (2.04 mmoles) of the 1-(2,6-dichloro-4-trifluoromethylphenyl)-2,5-dimethyl-3-(dichlorofluoromethylthio)pyrrole prepared above in 8 mL of acetonitrile was added a solution of 0.18 mL (0.29 g, 2.07 mmoles) of chlorosulfonyl isocyanate in 1 mL of acetonitrile dropwise over a 5 minute period. After stirring at 0° C. for 2 hours, a solution of 0.18 mL of dimethylformamide in 1 mL of acetonitrile was added and the reaction mixture was maintained at 0° C. for an additional 1.5 hours. The reaction mixture was then diluted with dichloromethane, washed with water and the organic phase was dried over anhydrous Na$_2$SO$_4$. Removal of the solvent under reduced pressure and column chromatography of the residue on silica gel with 4:1 v/v hexane-EtOAc provided 0.80 g (84%) of 4-cyano-1-(2,6-dichloro-4-trifluoromethylphenyl)-2,5-dimethyl-3-(dichlorofluoromethylthio)pyrrole (ASE 215) as a pale yellow solid of melting point 138.5° C.

ASE 302

A solution of 2-amino-1-(2,6-dichloro-4-trifluoromethylphenyl)-4-cyano-pyrrole (20.0 g, 62.5 mmoles) in ethyl acetate (600 mL) was cooled to −78° C. A solution of sulfur monochloride (2.5 mL, 31.3 mmoles, 0.5 eq.) in ethyl acetate (60 mL) was added dropwise over a one hour period, maintaining the reaction temperature below −75° C. After an additional 30 min. stirring, LC indicated that 14% of the starting material still remained, so more sulfur monochloride (0.25 mL, 3.1 mmoles, 0.05 eq.) in ethyl acetate (6 mL) was added. After 30 min., more sulfur monochloride (0.25 mL, 3.1 mmoles, 0.05 eq.) in ethyl acetate (6 mL) was added. After an additional 30 min., more sulfur monochloride (0.5 mL, 6.2 mmoles, 0.1eq.) in ethyl acetate (6 mL) was added. The reaction mixture was quenched with 100 mL of sat. sodium bicarbonate solution, and the reaction mixture allowed to reach room temperature. Water (100 mL) was added, and the phases separated. The organic phase was washed with sat. NaHCO$_3$ (200 mL), sat. NaCl (200 mL), dried over MgSO$_4$, filtered, and the solvent evaporated in vacuo to afford bis-[2-amino-1-(2,6-dichloro-4-trifluoromethylphenyl)-4-cyano-pyrrol-3-yl]-disulfide (25.2 g) as a brown solid. This was triturated in boiling ethanol (300 mL), filtered, washed with hexane, and dried to afford the product as a tan solid, 8.3 g (38%).

A solution of bis-[2-amino-1-(2,6-dichloro-4-trifluoromethylphenyl)-4-cyano-pyrrol-3-yl]-disulfide (13.78 g, 19.62 mmoles) in N,N-dimethylformamide (85 mL) in a 6 oz pressure bottle was purged with nitrogen for 15 min. Sodium formate (5.42 g, 79.62 mmoles, 4.06 eq.) was added. The pressure bottle was then cooled to 0° C. Sulfur dioxide (3.5 mL, 78.35 mmoles, 4.0 eq.) was condensed into a 15 mL graduated conical test tube which was cooled in a Dewar flask with Dry Ice-acetone. The sulfur dioxide was transferred to the pressure bottle via canula. Similarly, perfluoroethyl iodide (8.0 mL, 67.4 mmoles, 3.45 eq.) was condensed and transferred to the pressure bottle. The pressure bottle was sealed and the ice both removed. After two hours, the pressure seemed to stabilize at 31.5 psi. The solution was allowed to stir over the weekend, after which the pressure read 34.5 psi. and the reaction mixture was a brown color. The reaction mixture was added to 400 mL ice-water, and a brown, oily solid precipitated out. This mixture was extracted with 3×200 mL ethyl ether, which was washed with 200 mL sat. NaCl solution, then dried over magnesium sulfate, filtered, and the solvent evaporated in vacuo to afford 23.54 g of 2-amino-1-(2,6-dichloro-4-trifluoromethylphenyl)-4-cyano-3-(pentafluoroethylthio)pyrrole as a green solid. This was triturated with 10 mL of dichloromethane and washed 3×20 mL of hexane to afford the product as a lime-green solid, 11.34 g (61.5%), melting point 183.5° C.

CHEMICAL INTERMEDIATE SYNTHESIS (CIS) EXAMPLES

The following CHEMICAL INTERMEDIATE SYNTHESIS (CIS) EXAMPLES further provide representative methods and procedures to prepare novel intermediate compounds (1-substituted-2,3-dicyanoprop-1-enes) of the invention which in particular are useful to prepare the pesticidal 1-arylpyrrole compounds of the invention.

CIS 1

Preparation of
1-(N,N-dimethylamino)-2,3-dicyanoprop-1-ene:

A 12 liter three-necked round-bottomed flask, fitted with a mechanical stirrer, water condenser, nitrogen inlet and bubbler, was charged with 877 g (6 moles) of the potassium salt of 1-hydroxy-2,3-dicyanoprop-1-ene in 6 l of anhydrous toluene and 300 ml of anhydrous DMF. To this heterogeneous mixture was added 514 g (6.3 moles) of dimethylamine hydrochloride. The mixture was heated to 80° then cooled to room temperature, filtered and the filter cake rinsed with toluene. The filtrate was concentrated under vacuum to yield 933 g containing on 75% weight, 86% yield of an oil which partially crystallized at −5° C. An aliquot of the crystalline portion was collected and recrystallized twice from ether to give white crystals, m.p. 49° C. of 1-(N,N-dimethylamino)-2,3-dicyanoprop-1-ene (CIS 1).

In a manner similar to the procedure described above for CIS 1, the following additional dicyanoprop-1-ene intermediate compounds were prepared.

CIS 2: 1-(N,N-diethylamino)-2,3-dicyanoprop-1-ene, as a pale yellow oil (51% distilled, bp 0.25: 175°–180° C.;

CIS 3: 1-(N,N-di-n-butylamino)-2,3-dicyanoprop-1-ene, as a brown oil (69% distilled, bp 0.15: 175°–177° C.;

CIS 4: 1-(pyrrolidin-1-yl)-2,3-dicyanoprop-1-ene, as a yellow oil (56% distilled, bp 0.075: 174° C.;

CIS 5: 1-(piperidin-1-yl)-2,3-dicyanoprop-1-ene, as a yellow solid (55% distilled, mp 41°–44° C.;

CIS 6: 1-(morpholin-1-yl)-2,3-dicyanoprop-1-ene, as a yellow oil (51% distilled, bp 0.1: 193° C.; and CIS 7: 1-(N-benzyl-N-methylamino)-2,3-dicyanoprop-1-ene, as a yellow oil (64% distilled, bp 0.3: 200° C.

The initial 1-(N,N-dialkylamino)-2,3-dicyanoprop-1-ene intermediate compounds as represented above by CIS 1 to 7 are useful in a transenamination reaction to prepare 1-(substitutedphenyl)-2,3-dicyanoprop-1-ene intermediate compounds for final cyclization to the pesticidal 1-aryl pyrroles. The following is a representative example of a typically preferred intermediate.

CIS 8

Preparation of 1-(2,6-dichloro-4-trifluoromethylphenylamino)-2,3-dicyanoprop-1-ene A 5-liter three-necked round-bottomed flask, fitted with a mechanical stirrer, an addition funnel, a nitrogen inlet and bubbler, was charged with 100 milliliters of acetic acid and 190 ml of acetic anhydride (2 moles). A portion of 380 g of para-toluenesulfonic acid hydrate (2.03 moles) was then added. After cooling to room temperature, 383.4 g (1.667 moles) of 2,6-dichloro-4-trifluoromethylaniline were added. A solution of 386 g of the crude oil of 1-(N,N-dimethylamino)-2,3-dicyanoprop-1-ene (2 moles), obtained as described in CIS 1 in 1 l of acetic acid was added dropwise. The reaction mixture was stirred overnight and poured streamwise into 5 l of efficiently stirred water. The mixture was filtered and the solid was rinsed with distilled water and dried to yield 484 grams (91% yield) of 1-(2,6-dichloro-4-trifluoromethylphenylamino)-2,3-dicyanoprop-1-ene (CIS 8) as a grey-green powder, mp 122.5° C.

TABLE 2A

ADDITIONAL SYNTHESIZED EXAMPLES (ASE) OF PYRROLE COMPOUNDS OF GENERAL FORMULA (I): WHEREIN, $X^2$ & $X^3$ = H

| ASE No. | R1 | X | R2 | R3 | X1 | Y | X4 | M.P. (°C.) |
|---|---|---|---|---|---|---|---|---|
| 1. | $NH_2$ | $CF_3S$ | CN | Cl | $CH_3$ | Br | $CH_3$ | 215.5 |
| 2. | H | $CF_3S$ | CN | Cl | $CH_3$ | Br | $CH_3$ | 121.5 |
| 3. | H | $CF_3SO$ | CN | H | $CH_3$ | Br | $CH_3$ | 103 |
| 4. | H | $CF_3SO_2$ | CN | H | $CH_3$ | Br | $CH_3$ | 145 |
| 5. | H | $CF_3SO$ | CN | Cl | $CH_3$ | Br | $CH_3$ | 152.5 |
| 6. | H | $CF_3SO_2$ | CN | Cl | $CH_3$ | Br | $CH_3$ | 165 |
| 7. | H | $CF_3S$ | CN | H | Cl | Br | Cl | 208 |
| 8. | H | $CF_3S$ | CN | Cl | Cl | Br | Cl | 175 |
| 9. | H | $CF_2ClS$ | CN | H | Cl | Br | Cl | 113 |
| 10. | H | $CF_3SO$ | CN | Cl | Cl | Br | Cl | 141 |
| 11. | $NH_2$ | $CF_2ClS$ | CN | H | Cl | Cl | Cl | 170 |
| 12. | H | $CF_3SO_2$ | CN | Cl | Cl | Br | Cl | 174 |
| 13. | $NH_2$ | $CFCl_2S$ | CN | H | Cl | Br | Cl | 193 |
| 14. | $NH_2$ | $CFCl_2S$ | CN | Cl | Cl | Br | Cl | 240 |
| 15. | H | $CFCl_2S$ | CN | Cl | Cl | Br | Cl | 213.5 |
| 16. | $NH_2$ | $CF_2ClS$ | CN | $CF_2ClS$ | Cl | Cl | Cl | 206.5 |
| 17. | $NH_2$ | $CFCl_2S$ | CN | $CFCl_2S$ | Cl | Br | Cl | 216.5 |
| 18. | H | $CF_2ClSO$ | CN | H | Cl | Br | Cl | 125 |
| 19. | $NH_2$ | $CFCl_2S$ | CN | H | Cl | Cl | Cl | 177.5 |
| 20. | H | $CF_3S$ | CN | H | Cl | Br | Cl | 111.5 |
| 21. | H | $CFCl_2SO$ | CN | Cl | Cl | Br | Cl | 175 |
| 22. | H | $CFCl_2S$ | CN | $CFCl_2S$ | Cl | Br | Cl | 143 |
| 23. | H | $CFCl_2S$ | CN | Cl | Cl | Cl | Cl | 190.5 |
| 24. | H | $CFCl_2SO$ | CN | Cl | Cl | Cl | Cl | 151.5 |
| 25. | H | $CF_3SO_2$ | CN | Cl | $CH_3S$ | $CF_3$ | Cl | 177 |
| 26. | H | $CF_2ClSO$ | CN | Cl | Cl | Cl | Cl | 143 |
| 27. | H | $CF_2ClS$ | CN | Cl | Cl | Cl | Cl | 174 |
| 28. | $NH_2$ | $CFCl_2S$ | CN | H | Cl | $CF_3O$ | Cl | 126.5 |
| 29. | $NH_2$ | $CFCl_2S$ | CN | Cl | Cl | $CF_3O$ | Cl | 188 |
| 30. | H | $CF_3S$ | CH=O | H | Cl | $CF_3$ | Cl | 73.5 |
| 31. | H | $CFCl_2SO_2$ | CN | Cl | Cl | Br | Cl | 195.5 |
| 32. | H | $CF_3S$ | CN | Cl | $CH_3S$ | $CF_3$ | Cl | 117.5 |
| 33. | H | $CFCl_2SO_2$ | CN | Cl | Cl | Cl | Cl | 189.5 |
| 34. | H | $CFCl_2S$ | CN | H | Cl | $CF_3O$ | Cl | 66.5 |
| 35. | H | $CFCl_2S$ | CN | Cl | Cl | $CF_3O$ | Cl | 138 |
| 36. | H | $CF_3S$ | CN | H | Cl | Br | Cl | 128 |
| 37. | H | $CFCl_2S$ | CN | Cl | $CH_3SO$ | $CF_3$ | Cl | 193 |
| 38. | H | $CFCl_2SO_2$ | CN | H | Cl | $CF_3O$ | Cl | 144.5 |
| 39. | H | $CFCl_2SO$ | CN | H | Cl | $CF_3O$ | Cl | 135 |
| 40. | H | $CF_2ClS$ | CN | Cl | Cl | Br | Cl | 190 |
| 41. | H | $CF_2ClS$ | CN | H | Cl | Cl | Cl | 95.5 |
| 42. | H | $CFCl_2SO$ | CN | Cl | Cl | $CF_3O$ | Cl | 119 |
| 43. | $NH_2$ | $CFCl_2S$ | CN | Cl | $CH_3$ | $CO_2CH_3$ | Cl | 220 |
| 44. | H | $CFCl_2SO_2$ | CN | Cl | Cl | $CF_3O$ | Cl | 148.5 |
| 45. | H | $CF_2ClSO$ | CN | Cl | Cl | Br | Cl | 154 |
| 46. | H | $CF_2ClSO$ | CN | H | Cl | Cl | Cl | 133.5 |
| 47. | H | $CFCl_2S$ | CN | Cl | $CH_3S$ | $CF_3$ | Cl | 128 |
| 48. | H | $CFHClSO2$ | CN | Cl | $CH_3S$ | $CF_3$ | Cl | 58.5 |

TABLE 2A-continued

ADDITIONAL SYNTHESIZED EXAMPLES (ASE) OF PYRROLE COMPOUNDS OF GENERAL FORMULA (I): WHEREIN, $X^2$ & $X^3$ = H

SUBSTITUENT GROUPS

| ASE No. | R1 | X | R2 | R3 | X1 | Y | X4 | M.P. (°C.) |
|---|---|---|---|---|---|---|---|---|
| 49. | H | CFCl$_2$S | CN | Cl | CH$_3$ | CO$_2$CH$_3$ | Cl | 133 |
| 50. | NH$_2$ | CFCl$_2$S | CN | H | H | CF$_3$ | Cl | 181.5 |
| 51. | H | CF$_2$ClSO$_2$ | CN | H | Cl | Br | Cl | 199 |
| 52. | H | CFCl$_2$S | CN | H | Cl | Cl | Cl | 123 |
| 53. | H | CFCl$_2$SO | CN | H | Cl | Cl | Cl | 147 |
| 54. | H | CF$_2$ClSO$_2$ | CN | Cl | Cl | Br | Cl | 188.5 |
| 55. | NH$_2$ | CFCl$_2$S | CN | Cl | H | CF$_3$ | Cl | 190.5 |
| 56. | NH$_2$ | CFCl$_2$S | CN | Br | H | CF$_3$ | Cl | 183 |
| 57. | H | CFCl$_2$S | CN | Cl | H | CF$_3$ | Cl | 84.5 |
| 58. | H | CFCl$_2$SO$_2$ | CN | H | Cl | Cl | Cl | 190 |
| 59. | H | CFCl$_2$S | CN | H | Cl | Br | Cl | 141 |
| 60. | H | CFCl$_2$SO$_2$ | CN | Cl | H | CF$_3$ | Cl | 140.5 |
| 61. | H | CFCl$_2$S | CN | Br | H | CF$_3$ | Cl | 104.5 |
| 62. | H | CFCl$_2$SO | CN | Cl | H | CF$_3$ | Cl | 117 |
| 63. | H | CFCl$_2$SO | CN | H | Cl | Br | Cl | 156.5 |
| 64. | H | CFCl$_2$SO$_2$ | CN | Br | H | CF$_3$ | Cl | 150.5 |
| 65. | H | CFCl$_2$SO | CN | Br | H | CF$_3$ | Cl | 154 |
| 66. | H | CF$_3$S | CN | Br | H | CF$_3$ | Cl | 105.5 |
| 67. | H | CF$_2$ClS | CN | Cl | H | CF$_3$ | Cl | 99.5 |
| 68. | H | CF$_3$SO$_2$ | CN | Br | H | CF$_3$ | Cl | 138.5 |
| 69. | H | CF$_3$SO | CN | Br | H | CF$_3$ | Cl | wax |
| 70. | H | CFCl$_2$SO$_2$ | CN | H | Cl | Br | Cl | 212.5 |
| 71. | H | CF$_2$ClSO$_2$ | CN | Cl | H | CF$_3$ | Cl | 130.5 |
| 72. | H | CF$_2$ClSO | CN | Cl | H | CF$_3$ | Cl | 93.5 |
| 73. | H | CF$_3$SO$_2$ | CN | H | Cl | Br | Cl | 184 |
| 74. | H | CF$_3$S | CN | H | Cl | Cl | Cl | 81 |
| 75. | H | CH$_3$S | CN | H | Cl | Br | Cl | 115 |
| 76. | H | CFCl$_2$S | CN | H | F | Br | F | 107 |
| 77. | H | CF$_3$SO | CN | H | Cl | Cl | Cl | 130 |
| 78. | H | CF$_3$SO$_2$ | CN | H | Cl | Cl | Cl | 165 |
| 79. | H | CCl$_3$S | CN | H | Cl | Cl | Cl | 147 |
| 80. | H | CFCl$_2$S | CN | H | H | Cl | Cl | 96 |
| 81. | H | Cl | CN | H | Cl | Cl | Cl | 146.5 |
| 82. | H | CFCl$_2$S | CN | H | H | Cl | H | 121.5 |
| 83. | H | CF$_2$ClSO$_2$ | CN | H | Cl | Cl | Cl | 184 |
| 84. | H | CFCl$_2$SO | CN | Br | H | CF$_3$ | Cl | 116.5 |
| 85. | H | CF$_3$SO$_2$ | CN | CF$_3$S | H | CF$_3$ | Cl | 51 |
| 86. | H | CFCl$_2$S | CN | Br | Cl | CF$_3$O | Cl | 139 |
| 87. | H | CFCl$_2$SO$_2$ | CN | Br | Cl | CF$_3$O | Cl | 129 |
| 88. | NH$_2$ | CF$_2$ClS | CN | Br | H | CF$_3$ | Cl | 151.5 |
| 89. | H | CF$_2$ClS | CN | Br | H | CF$_3$ | Cl | 61.5 |
| 90. | H | CFCl$_2$S | CN | H | Cl | H | Cl | 132 |
| 91. | NH$_2$ | CF$_3$CCl$_2$S | CN | H | Cl | Cl | Cl | 175 |

TABLE 2B

ADDITIONAL SYNTHESIZED EXAMPLES (ASE) OF PYRROLE COMPOUNDS OF GENERAL FORMULA (I): WHEREIN, $X^2$ & $X^3$ = H; $X^1$ & $X^4$ = Cl; AND Y = CF$_3$

SUBSTITUENT GROUPS

| ASE NO. | R$^1$ | X | R$^2$ | R$^3$ | M.P. (°C.) |
|---|---|---|---|---|---|
| 92. | NH$_2$ | CF$_2$ClS | CN | H | 168 |
| 93. | H | CF$_3$SO$_2$ | CN | H | 200.5 |
| 94. | H | CF$_2$ClS | CN | H | 106 |
| 95. | H | CF$_2$ClS | CN | CF$_2$ClS | 116 |
| 96. | NH$_2$ | CF$_2$ClS | CN | Cl | 179.5 |
| 97. | H | CF$_2$ClSO$_2$ | CN | H | 201 |
| 98. | H | CF$_2$ClSO$_2$ | CN | Cl | 194.5 |
| 99. | H | CF$_2$ClSO | CN | Cl | 146.5 |
| 100. | H | CF$_2$ClS | CN | Cl | 141 |
| 101. | H | CF$_3$S | CN | Br | 137.5 |
| 102. | H | CF$_3$SO | CN | Br | 165 |
| 103. | H | CF$_3$SO$_2$ | CN | Br | 197.5 |
| 104. | H | CF$_2$ClSO | CN | H | 128 |
| 105. | H | CF$_3$S | CN | H | 152.5 |
| 106. | NH$_2$ | CFCl$_2$CF$_2$S | CN | H | 186.5 |
| 107. | NH$_2$ | CCl$_3$S | CN | H | 191 |
| 108. | H | CFCl$_2$CF$_2$S | CN | H | 121.5 |
| 109. | H | CFCl$_2$CF$_2$SO$_2$ | CN | H | 160 |
| 110. | H | CFCl$_2$CF$_2$SO | CN | H | 183 |
| 111. | NH$_2$ | CFCl$_2$CF$_2$S | CN | Cl | 187.5 |
| 112. | H | CFCl$_2$CF$_2$SO | CN | Cl | 150.5 |
| 113. | Br | CF$_3$S | CN | H | 163.5 |

TABLE 2B-continued

ADDITIONAL SYNTHESIZED EXAMPLES (ASE) OF PYRROLE
COMPOUNDS OF GENERAL FORMULA (I):
WHEREIN, $X^2$ & $X^3$ = H; $X^1$ & $X^4$ = Cl; AND Y = $CF_3$

SUBSTITUENT GROUPS

| ASE NO. | $R^1$ | X | $R^2$ | $R^3$ | M.P. (°C.) |
|---|---|---|---|---|---|
| 114. | H | $CFCl_2CF_2S$ | CN | Cl | 115 |
| 115. | H | $CCl_3S$ | CN | Cl | 179.5 |
| 116. | H | $CFCl_2CF_2SO_2$ | CN | Cl | 149 |
| 117. | H | $CCl_3SO_2$ | CN | Cl | 201 |
| 118. | H | $CCl_3SO$ | CN | Cl | 153 |
| 119. | Cl | $CF_3SO$ | CN | H | 162 |
| 120. | $NH_2$ | $CH_3S$ | CN | H | 150.5 |
| 121. | H | $CFCl_2S$ | CN | Br | 129.5 |
| 122. | $NH_2$ | $CFCl_2S$ | CN | Br | 196.5 |
| 123. | Br | $CF_3SO$ | CN | H | 171 |
| 124. | H | $CFCl_2SO_2$ | CN | Br | 177.5 |
| 125. | H | $CFCl_2SO$ | CN | Br | 126 |
| 126. | H | SCN | CN | H | 173.5 |
| 127. | Br | $CF_3SO_2$ | CN | H | 180 |
| 128. | H | $CH_3S$ | CN | H | 108 |
| 129. | $NH_2$ | $CF_2ClS$ | CN | Br | 176.5 |
| 130. | Br | $CF_2ClS$ | CN | Cl | 131.5 |
| 131. | H | $CF_2ClS$ | CN | Br | 135.5 |
| 132. | $NH_2$ | Cl | CN | H | 160 |
| 133. | $NH_2$ | $CF_3S$ | CN | SCN | 170 |
| 134. | H | $CF_3S$ | CN | SCN | 106 |
| 135. | Br | $CF_2ClSO$ | CN | Cl | 158.5 |
| 136. | H | Cl | CN | H | 106 |
| 137. | H | $CH_3SO$ | CN | H | 145 |
| 138. | H | $CH_3SO_2$ | CN | H | 173.5 |
| 139. | $NH_2$ | $CF_3S$ | CN | $SCH_3$ | 147 |
| 140. | H | $CF_3S$ | CN | $SOCH_3$ | 144 |
| 141. | H | $CF_2ClSO$ | CN | Br | 145 |
| 142. | Br | $CFCl_2SO_2$ | CN | Cl | 120 |
| 143. | $CF_3CONH$ | $CF_3S$ | CN | H | 188 |
| 144. | H | $CF_2ClSO_2$ | CN | Br | 183.5 |
| 145. | H | $CF_3S$ | CN | $CH_3S$ | 90 |
| 146. | H | $CF_3S$ | CN | $CH_3SO_2$ | 137 |
| 147. | H | $CF_3SO$ | CN | $CH_3SO_2$ | 162 |
| 148. | $NH_2$ | $CF_3CCl_2S$ | CN | H | 210 |
| 149. | $NH_2$ | $CF_3CCl_2S$ | CN | Cl | 228 |
| 150. | H | $CF_3CCl_2S$ | CN | Cl | 171.5 |
| 151. | H | $CF_3CCl_2SO_2$ | CN | Cl | 196.5 |
| 152. | H | $CF_3CCl_2SO$ | CN | Cl | 161.5 |
| 153. | H | $CF_3S$ | CN | $CF_3S$ | 95.5 |
| 154. | $NH_2$ | $CH_3SO$ | CN | H | 131 |
| 155. | $NH_2$ | $CH_3SO_2$ | CN | H | 248.5 |
| 156. | H | $CF_3SO$ | CN | $CF_3S$ | 146.5 |
| 157. | H | $CH_3S$ | CN | Cl | 128.5 |
| 158. | $NH_2$ | $CF_3S$ | CN | $SOCH_3$ | 140 |
| 159. | $CH_3S$ | $CF_3S$ | CN | Cl | 73.5 |
| 160. | $NH_2$ | $CFCl_2SO$ | CN | H | 176 |
| 161. | H | $CF_3SO_2$ | CN | $CF_3S$ | 156.5 |
| 162. | H | $CH_3SO$ | CN | Cl | 130.5 |
| 163. | $NH_2$ | $CF_3S$ | CN | F | 164.5 |
| 164. | H | Cl | CN | Cl | 129.5 |
| 165. | $CH_3SO$ | $CF_3S$ | CN | Cl | 134 |
| 166. | $CH_3S$ | $CFCl_2S$ | CN | Cl | 128 |
| 167. | $NH_2$ | $CFCl_2SO$ | CN | Cl | 166 |
| 168. | $CF_3CONH$ | $CF_3SO$ | CN | H | 196.5 |
| 169. | H | $CF_3S$ | CN | F | 116.5 |
| 170. | $CH_3SO_2$ | $CFCl_2S$ | CN | Cl | 167.5 |
| 171. | $CH_3SO$ | $CFCl_2S$ | CN | Cl | 194.5 |
| 172. | $NH_2$ | $CF_3SO$ | CN | H | dec. above 175 |
| 173. | H | $CF_3S$ | $CF_2H$ | H | 55 |
| 174. | H | $CH_3SO_2$ | CN | Cl | 165.5 |
| 175. | H | Br | CN | Br | 128 |
| 176. | H | Br | CN | H | 120.5 |
| 177. | $NH_2$ | $CFCl_2SO_2$ | CN | Cl | 209 |
| 178. | H | $CF_3SO$ | CN | F | 129.5 |
| 179. | Br | Cl | CN | H | 122 |
| 180. | $NH_2$ | $CF_3SO_2$ | CN | H | 259 |
| 181. | $CH_3SO$ | $CF_3SO$ | CN | Cl | 238.5 |
| 182. | H | $CF_2BrS$ | CN | Cl | 131 |
| 183. | H | $CF_2BrSO$ | CN | Cl | 118 |
| 184. | H | $CF_2BrSO_2$ | CN | Cl | 176.5 |
| 185. | H | $CF_3S$ | $CH_3$ | H | oil |
| 186. | H | $CF_3SO$ | $CH_3$ | Br | 106.5 |
| 187. | H | $CF_3SO_2$ | $CH_3$ | Br | 76.5 |

TABLE 2B-continued

ADDITIONAL SYNTHESIZED EXAMPLES (ASE) OF PYRROLE COMPOUNDS OF GENERAL FORMULA (I): WHEREIN, $X^2$ & $X^3$ = H; $X^1$ & $X^4$ = Cl; AND Y = $CF_3$

| ASE NO. | $R^1$ | X | $R^2$ | $R^3$ | M.P. (°C.) |
|---|---|---|---|---|---|
| 188. | $NH_2$ | $CF_3S$ | CN | $CH(SCH_3)_2$ | 160 |
| 189. | $CH_3SCH=N$ | $CF_3S$ | CN | $CH(SCH_3)_2$ | 125 |
| 190. | H | $CF_3S$ | $(CH_3)_3COCONH$ | Br | 113.5 |
| 191. | H | $CF_3S$ | Br | Br | oil |
| 192. | H | $CF_3SO$ | $CH_3$ | OH* | 150 |
| 193. | Br | $CF_3S$ | $CH_3$ | Br | oil |
| 194. | Br | Br | H | $CF_3S$ | oil |
| 195. | H | $CF_3S$ | CN | I | 108 |

*May exist as the keto tautomer

TABLE 2C

ADDITIONAL SYNTHESIZED EXAMPLES (ASE) OF PYRROLE COMPOUNDS OF GENERAL FORMULA (I), PARTICULARLY (II-7): WHEREIN, $X^2$ & $X^3$ = H

| ASE NO. | $R^1$ | X | $R^2$ | $R^3$ | $X^1$ | Y | $X^4$ | M.P. (°C.) |
|---|---|---|---|---|---|---|---|---|
| 196. | $NCCH_2CH_2$ | $CF_3S$ | CN | Cl | Cl | $CF_3$ | Cl | 150 |
| 197. | $NCCH_2CH_2$ | $CF_3SO$ | CN | Cl | Cl | $CF_3$ | Cl | 80 |
| 198. | $NCCH_2CH_2$ | $CF_3SO_2$ | CN | Cl | Cl | $CF_3$ | Cl | 163 |
| 199. | H | $CF_3S$ | CN | $CF_2H$ | Cl | $CF_3$ | Cl | 107 |
| 200. | H | $CF_3S$ | CN | $CH_3$ | Cl | $CF_3$ | Cl | 99 |
| 201. | H | $CF_3SO$ | CN | $CH_3$ | Cl | $CF_3$ | Cl | 161 |
| 202. | H | $CF_3SO_2$ | CN | $CH_3$ | Cl | $CF_3$ | Cl | 205 |
| 203. | H | $CF_3SO$ | CN | $CF_2H$ | Cl | $CF_3$ | Cl | 123 |
| 204. | H | $CF_3SO_2$ | CN | $CF_2H$ | Cl | $CF_3$ | Cl | 158 |
| 205. | H | $CFCl_2S$ | CN | $CF_2H$ | Cl | $CF_3$ | Cl | 105 |
| 206. | H | $CFCl_2SO_2$ | CN | $CF_2H$ | Cl | $CF_3$ | Cl | 149 |
| 207. | H | $CFCl_2SO$ | CN | $CF_2H$ | Cl | $CF_3$ | Cl | 164 |
| 208. | $CH_3S$ | $CFCl_2SO$ | CN | Cl | Cl | $CF_3$ | Cl | 170 |
| 209. | H | $CF_3S$ | CN | $CH_2F$ | Cl | $CF_3$ | Cl | 104.5 |
| 210. | H | $CF_3SO_2$ | CN | $CH_2F$ | Cl | $CF_3$ | Cl | 161.5 |
| 211. | H | $CF_3SO$ | CN | $CH_2F$ | Cl | $CF_3$ | Cl | 109 |
| 212. | $CH_3S$ | $CF_2ClS$ | CN | Cl | Cl | $CF_3$ | Cl | 90 |
| 213. | H | $CFCl_2S$ | CN | $CH_3$ | Cl | $CF_3$ | Cl | 110 |
| 214. | H | $CFCl_2SO$ | CN | $CH_3$ | Cl | $CF_3$ | Cl | 173 |
| 215. | $CH_3$ | $CFCl_2S$ | CN | $CH_3$ | Cl | $CF_3$ | Cl | 139 |

TABLE 2D

ADDITIONAL SYNTHESIZED EXAMPLES (ASE) OF PYRROLE COMPOUNDS OF GENERAL FORMULA (I), PARTICULARLY (II-8): WHEREIN, $X^2$ & $X^3$ = H

| ASE NO. | $R^1$ | X | $R^2$ | $R^3$ | $X^1$ | Y | $X^4$ | M.P. (°C.) |
|---|---|---|---|---|---|---|---|---|
| 216. | Br | $CF_2ClS$ | CN | H | Cl | Cl | Cl | 117.5 |
| 217. | Br | $CF_2ClSO$ | CN | H | Cl | Cl | Cl | 143.5 |
| 218. | Br | $CFCl_2S$ | CN | H | Cl | Cl | Cl | 134 |
| 219. | Br | $CFCl_2SO$ | CN | H | Cl | Cl | Cl | 167 |
| 220. | $CH_3S$ | $CFCl_2S$ | CN | H | Cl | Cl | Cl | 122 |
| 221. | $C_2H_5OCH=N$ | $CFCl_2S$ | CN | H | Cl | Cl | Cl | 100 |
| 222. | Br | Cl | CN | H | Cl | Cl | Cl | 153.5 |

TABLE 2E

ADDITIONAL SYNTHESIZED EXAMPLES (ASE) OF PYRROLE COMPOUNDS OF GENERAL FORMULA (I)

| ASE NO. | $R^1$ | X | $R^2$ | $R^3$ | $X^1$ | Y | $X^4$ | M.P. (°C.) |
|---|---|---|---|---|---|---|---|---|
| a. WHEREIN $X^2$ & $X^3$ = H | | | | | | | | |
| 223. | H | $CF_3CCl_2S$ | CN | H | Cl | Cl | Cl | 127.5 |
| 224. | H | $CF_3CCl_2S$ | CN | Cl | Cl | Cl | Cl | 214.5 |
| 225. | $NH_2$ | $CF_3CCl_2S$ | CN | Cl | Cl | Cl | Cl | 233.5 |
| 226. | H | $CF_3SO$ | CN | $CF_3S$ | Cl | $CF_3O$ | Cl | 129 |
| 227. | $NH_2$ | $CF_2ClS$ | CN | H | Cl | $CF_3$ | H | 158.5 |
| 228. | Br | Br | H | $CF_3SO_2$ | Cl | $CF_3$ | Cl | Oil |
| 229. | H | $CFCl_2S$ | CN | H | Cl | H | H | 61.5 |
| 230. | H | Br | CN | H | Cl | Cl | Cl | 144.5 |
| 231. | H | $CF_3CCl_2SO_2$ | CN | H | Cl | Cl | Cl | 160.5 |
| 232. | H | $CF_3CCl_2SO$ | CN | Cl | Cl | Cl | Cl | 168.5 |

TABLE 2E-continued

ADDITIONAL SYNTHESIZED EXAMPLES (ASE) OF
PYRROLE COMPOUNDS OF GENERAL FORMULA (I)

SUBSTITUENT GROUPS

| ASE NO. | $R^1$ | X | $R^2$ | $R^3$ | $X^1$ | Y | $X^4$ | M.P. (°C.) |
|---|---|---|---|---|---|---|---|---|
| 233. | H | $CF_3CCl_2SO$ | CN | H | Cl | Cl | Cl | 146 |
| 234. | H | $CF_3CCl_2SO_2$ | CN | Cl | Cl | Cl | Cl | 193.5 |
| 235. | H | CHFClS | CN | Cl | Cl | $CF_3$ | Cl | 96 |
| 236. | H | CHFBrS | CN | Cl | Cl | $CF_3$ | Cl | 87 |
| 237. | $NH_2$ | $CF_2ClS$ | CN | Cl | Cl | $CF_3$ | H | 101.5 |
| 238. | Br | Br | H | $CF_3SO$ | Cl | $CF_3$ | Cl | 82 |
| 239. | H | $CCl_3S$ | CN | H | Cl | Cl | H | 112 |
| 240. | H | $CH_3SO$ | CN | H | Cl | Br | Cl | 160 |
| 241. | H | $CCl_3SO$ | CN | H | Cl | Cl | Cl | 166 |
| 242. | $NH_2$ | CN | H | $CF_3S$ | Cl | $CF_3$ | Cl | 129.5 |
| 243. | H | $CF_2ClS$ | CN | H | Cl | Cl | H | 89.5 |
| 244. | H | $CF_2ClSO$ | CN | H | Cl | Cl | H | 104.5 |
| 245. | H | $CF_3S$ | CN | $(CH_3S)_2CH$ | Cl | $CF_3$ | Cl | 138 |
| 246. | Br | $CF_3SO$ | $CH_3$ | Br | Cl | $CF_3$ | Cl | 120.5 |
| 247. | H | $CFCl_2S$ | CN | H | Cl | F | Cl | 114.5 |
| 248. | H | $CF_3S$ | CN | CHO | Cl | $CF_3$ | Cl | 102 |
| 249. | $NH_2$ | NCS | CN | NCS | Cl | $CF_3$ | Cl | Oil |
| 250. | H | $CF_3SO_2$ | CN | $CF_3S$ | Cl | $CF_3O$ | Cl | 140 |
| 251. | H | $CF_3SO$ | Br | Br | Cl | $CF_3$ | Cl | 101.5 |
| 252. | H | $CF_3SO$ | $CHF_2$ | H | Cl | $CF_3$ | Cl | Oil |
| 253. | $NH_2$ | $CF_3S$ | CN | I | Cl | $CF_3$ | Cl | 140 |
| 254. | H | $CF_2ClSO_2$ | CN | Br | Cl | $CF_3$ | H | 96 |
| 255. | H | $CF_2ClSO$ | CN | Br | Cl | $CF_3$ | H | 75 |
| 256. | H | $CFCl_2SO$ | CN | H | Cl | Cl | H | 126.5 |
| 257. | $NH_2$ | $CF_3CF_2S$ | CN | H | Cl | $CF_3$ | Cl | 185.5 |
| 258. | H | $CF_3SO_2$ | Br | Br | Cl | $CF_3$ | Cl | Oil |
| 259. | $NH_2$ | Cl | CN | NCS | Cl | $CF_3$ | Cl | 195.5 |
| 260. | H | $CF_3S$ | CN | $CF_3$ | Cl | $CF_3$ | Cl | 115.5 |
| 261. | $NH_2$ | $CF_3S$ | CN | Cl | Cl | F | Cl | 196.5 |
| 262. | $NH_2$ | $CF_3S$ | CN | H | Cl | F | Cl | 170.5 |
| 263. | H | $CF_3S$ | CN | H | Cl | F | Cl | 108.5 |
| 264. | H | $CF_3S$ | CN | Cl | Cl | F | Cl | 133.5 |
| 265. | H | Cl | CN | NCS | Cl | $CF_3$ | Cl | 133.5 |
| 266. | H | $CF_3SO$ | CN | H | Cl | F | Cl | 131.5 |
| 267. | H | $CF_3SO_2$ | CN | H | Cl | F | Cl | 128 |
| 268. | H | $CF_3SO_2$ | CN | Cl | Cl | F | Cl | 163.5 |
| 269. | H | $CF_3SO$ | CN | Cl | Cl | F | Cl | 162 |
| 270. | H | $CF_2ClS$ | CN | H | $CH_3$ | Br | H | 82.5 |
| 271. | H | $CF_3S$ | CN | CN | Cl | $CF_3$ | Cl | 130.5 |
| 272. | H | $CF_3SO$ | CN | $CF_3$ | Cl | $CF_3$ | Cl | 110.5 |
| 273. | H | $CF_3SO$ | CN | CN | Cl | $CF_3$ | Cl | 140.5 |
| 274. | $NH_2$ | $CF_2ClS$ | CN | H | Cl | $CF_3O$ | Cl | 126 |
| 275. | $NH_2$ | $CF_2ClS$ | CN | Br | Cl | $CF_3O$ | Cl | 164 |
| 276. | $NH_2$ | $CF_2ClS$ | CN | Cl | Cl | $CF_3O$ | Cl | 143.5 |
| 277. | H | $CFCl_2S$ | CN | $(CH_3S)_2CH$ | Cl | $CF_3$ | Cl | 167 |
| 278. | H | $CFCl_2S$ | CN | CHO | Cl | $CF_3$ | Cl | 113.5 |
| 279. | $NH_2$ | $CF_2ClS$ | CN | H | Cl | $CH_3SO_2$ | Cl | 254.5 |
| 280. | $NH_2$ | $CF_2ClS$ | CN | H | Cl | $CH_3SO_2$ | H | 205 |
| 281. | H | $CF_2ClS$ | CN | Cl | Cl | $CF_3O$ | Cl | 106 |
| 282. | H | $CF_2ClSO$ | CN | Br | Cl | $CF_3O$ | Cl | 95.5 |
| 283. | H | Cl | CN | $CH_3SO$ | Cl | $CF_3$ | Cl | 160.5 |
| 284. | H | $CF_3SO_2$ | CN | CN | Cl | $CF_3$ | Cl | 140.5 |
| 285. | H | Cl | CN | $CFCl_2S$ | Cl | $CF_3$ | Cl | Oil |
| 286. | $NH_2$ | $CF_2ClS$ | CN | Br | Cl | $CH_3SO_2$ | Cl | 234 |
| 287. | H | Cl | CN | $CH_3SO_2$ | Cl | $CF_3$ | Cl | 207 |
| 288. | H | $CF_2ClSO_2$ | CN | Cl | Cl | $CF_3O$ | Cl | 127.5 |
| 289. | H | $CF_2ClSO$ | CN | Cl | Cl | $CF_3O$ | Cl | 112.5 |
| 290. | $NH_2$ | $CHF_2S$ | CN | H | Cl | $CF_3$ | Cl | 152 |
| 291. | H | $CF_3CCl_2S$ | CN | H | Cl | F | Cl | 134.5 |
| 292. | $NH_2$ | $CF_2ClS$ | CN | Br | Cl | $CH_3SO_2$ | H | 135 |
| 293. | H | $CF_3CCl_2SO$ | CN | H | Cl | F | Cl | 161.5 |
| 294. | $NH_2$ | $CF_3CCl_2S$ | CN | Cl | Cl | F | Cl | 223.5 |
| 295. | H | $CF_3CCl_2S$ | CN | Cl | Cl | F | Cl | 196.5 |
| 296. | H | Cl | CN | $CH_3S$ | Cl | $CF_3$ | Cl | 135.5 |
| 297. | $NH_2$ | $CF_3CCl_2S$ | CN | H | Cl | F | Cl | 169.5 |
| 298. | H | $CF_3CCl_2SO_2$ | CN | Cl | Cl | F | Cl | 170.5 |
| 299. | H | $CF_3CCl_2SO$ | CN | Cl | Cl | F | Cl | 156 |
| 300. | H | $CHF_2S$ | CN | H | Cl | $CF_3$ | Cl | 80 |
| 301. | $NH_2$ | $CF_3CF_2S$ | CN | Cl | Cl | $CF_3$ | Cl | 189 |
| 302. | H | $CF_3CF_2S$ | CN | Cl | Cl | $CF_3$ | Cl | 110.5 |
| 307. | H | $CFCl_2SO_2$ | CN | Br | Cl | $CF_3O$ | Cl | 157.5 |
| b. WHEREIN $X^2$ & $X^3$ = Cl | | | | | | | | |
| 303. | H | $CFCl_2S$ | CN | H | H | H | H | 139 |
| 304. | H | $CFCl_2SO_2$ | CN | H | H | H | H | 187.5 |
| 305. | H | $CFCl_2SO$ | CN | H | H | H | H | 180.5 |
| c. WHEREIN $X^2$ = Cl and $X^3$ = H | | | | | | | | |

TABLE 2E-continued

ADDITIONAL SYNTHESIZED EXAMPLES (ASE) OF PYRROLE COMPOUNDS OF GENERAL FORMULA (I)

| ASE NO. | $R^1$ | X | $R^2$ | $R^3$ | $X^1$ | Y | $X^4$ | M.P. (°C.) |
|---|---|---|---|---|---|---|---|---|
| 306. | H | $CFCl_2S$ | CN | H | H | Cl | H | 119.5 |

PESTICIDAL METHODS OF USE AND COMPOSITIONS

According to a feature of the present invention, there is provided a method for the control of arthropods, especially insects and arachnids, plant nematodes, and helminth or protozoan pests at a locus which comprises the treatment of the locus (e.g. by application or administration) with an effective amount of a pesticidal compound of general formula (I), i.e., formula (Ia), (Ia-1), (Ib), (Ib-1), (Ic) or (Ic-1), wherein the various symbols are as hereinbefore defined. The compounds of general formula (I) may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs and cats, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp., (*Ornithodorus moubata*) and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,); Diptera (e.g. Aedes spp., Anopheles spp., Musca spp., Hypoderma spp., Gasterophilus spp., Simulium spp.); Hemiptera (e.g. Triatoma spp.); Phthirapter (e.g. Damalinia spp., Linognathus spp.); Siphonaptera (e.g. Ctenocephalides spp.); Dictyoptera (e.g. Periplaneta spp., Blatella spp.); Hymenoptera (e.g. *Monomorium pharaonis*); for example against infections of the gastrointestinal tract caused by parasitic nematode worms, for example members of the family Trichostrongylidae, *Nippostrongylus brasiliensis*, *Trichinella spiralis*, *Haemonchus contortus*, *Trichostrongylus colubriformis*, *Nematodirus battus*, *Ostertagia circumcincta*, *Trichostrongylus axei*, Cooperia spp. and *Hymenolepis nana*; in the control and treatment of protozoal diseases caused by, for example, Eimeria spp. e.g. *Eimeria tenella*, *Eimeria acervulina*, *Eimeria brunetti*, *Eimeria maxima* and *Eimeria necatrix*, *Trypanosoma cruzi*, Leishamania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal feedstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), in the control of cockroaches, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites and other wood boring pests, for example, Reticulitermes spp., Heterotermes spp., Coptotermes spp. and Camponotos spp.; in agriculture, against adults, larvae and eggs of Lepidoptera (butterflies and moths) e.g. Heliothis spp. such as *Heliothis virescens* (tobacco budworm), *Heliothis armigera* and *Heliothis zea*, Spodoptera spp. such as *S. exempta*, *S. littoralis* (Egyptian cottom worm), *S. eridania* (southern army worm), *Mamestra configurata* (bertha army worm); Earias spp. e.g. *E. insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Pieris spp. (cabbage worms), Laphygma spp. (army worms), Agrotis and Amathes spp. (cutworms), Wiseana spp. (porina moth), Chilo spp. (rice stem borer) Tryporyza spp. and Diatraea spp. (sugar cane borers and rice borers), *Sparganothis pilleriana* (grape berry moth), *Cydia pomonella* (codling moth), Archips spp. (fruit tree tortrix moth), *Plutella xylostella* (diamond back moth); against adult and larvae of Coleoptera (beetles) e.g. *Hypothenemus hampei* (coffe berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryzophilus* (rice water weevil), Meligethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae*, Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp. Hymenoptera e.g. Athalia spp. and Cephus spp. (saw flies), Atta spp. (leaf cutting ants), Solenopsis spp. (fire ants); Diptera e.g. Delia spp. (root flies), Atherigona spp. and Chlorops spp; (shoot flies), Phytomyza spp. (leaf miners), Ceratitis spp. (fruit flies); Thysanoptera such as *Thrips tabaci*; Orthoptera such as Locusta and Schistocerca spp., (locusts) and crickets e.g. Gryllus spp., and Acheta spp.; Collembola e.g. Sminthurus spp. and Onychiurus spp. (springtails), Isoptera e.g. Odontotermes spp. (termites), Dermaptera e.g. Forficula spp. (earwigs) and also other arthropods of agricultural significance such as Acari (mites) e.g. Tetranychus spp.; Panonychus spp. and Bryobia spp. (spider mites), Eriophyes spp. (gall mites), Polyphagotarsonemus spp.; Blaniulus spp. (millipedes), Scutigerella spp. (symphilids), Oniscus spp. (woodlice) and Triops spp; (crustacea); nematodes which attack plants and trees of importance to agriculture, forestry and horticulture either directly or by spreading bacterial, viral, mycoplasma or fungal diseases of the plants, root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. penetrans*); Belonolaimus spp. (e.g. *B gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicyclio- phora spp. (e.g. *H gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

Further pests which can be controlled with the compounds of the invention include: from the order of the Isopoda, for example, *Oniseus asellus, Armadillidium vulgare* and *Porcellio scaber*; from the order of Diplopoda, for example, *Blaniulus guttulatus*; from the order of the Chilopoda, for example *Geophilus carpophagus* and *Scutigera spex*; from the order of the Symphyla for example, *Scutigerella immaculata*; from the order of the Thysanura, for example, *Lepisma saccharian*; from the order the Collembola, for example, *Onychiurus armatus*; from the order of the Orthoptera, for example, *Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregaria*; from the order of Dermaptera, for example, *Forficula auricularia*; from the order of the Isoptera, for example, Reticulitermes spp.; from the order of the Anoplura, for example, *Phylloxera vastatrix*, Pemphigus spp., *Pediculus humanus corporis*, Haematopinus spp. and Linognathus spp.; from the order of the Mallophaga, for example, Trichodectes spp. and Damalinea spp.; from the order of the Thysanoptera, for example, *Hercinothrips femoralis* and *Thrips tabaci*; from the order of the Heteroptera, for example, Eurygaster spp., *Dysdercus intermedius, Piesma quadrata, Cimex lectularius, Rhodnius prolixus* and Triatoma spp.; from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmoplites sordidus, Ceuthorrhynchus assimilis, Hypera postica,* Dermestes spp., Trogoderma spp., Anthrenus spp., Attagenus spp., Lyctus spp., *Maligethes aeneus,* Ptinus spp., *Niptus hololeucrus, Gibbium psylloides,* Tribolium spp., *Tenebrio molitor,* Agriotes spp., Conoderus spp., *Melolontha melolontha, Amphimallon solstitialis* and *Costelytra zealandica*; from the order of the Hymenoptera, for example, Diprion spp., Hoplocampa spp., Lasius spp., *Monomorium pharaonis,* Vespa spp., Solenopsis spp., and Camponotos spp.; from the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyani, Ceratitis capitata, Dacus oleae* and *Tipula paludosa*; from the order of the Siphonaptera, for example, *Xenopsylla cheopis,* Ceratophyllus spp., and Ctenocephalides spp.; from the order of the Arachnida, for example, *Scorpio maurus* and *Latrodectus mactans*; from the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., and Psylla spp.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., Trichoplusiani, *Carpocapsa pomonella,* Pieris spp., Chilo spp., *Pyrausta nubilalis,* Ephestiakuehniella, *Galleria mellonella, Tineola bisselliella, Tinea pellionella, Hofmannophila pseudospretella, Cacoecia podana, Capua reticulana, Choristoneura fumiferana, Clysia ambiguells, Homona magnanime* and *Tortix viridana.*

The invention also provides a method for the control of arthropod or nematode pests of plants which comprises the application to the plants or to the medium in which they grow of an effective amount of a compound of general formula (I).

For the control of arthropods and nematodes, the active compound is generally applied to the locus in which arthropod or nematode infestation is to be controlled at a rate of about 0.005 kg to about 15 kg of active compound per hectare of locus treated, preferably 0.02 kg/ha to 2 kg/ha. Under ideal conditions, depending on the pest to be controlled, the lower rate may offer adequate protection. On the other hand, adverse weather conditions, resistance of the pest and other factors may require that the active ingredient be used in higher proportions. In foliar application, a rate of 0.01 kg to 1 kg/ha may be used. The optimum rate depends usually upon the type of pest being controlled, as well as upon the type and the growth stage of the infested plant, the row spacing and also the method of application.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of general formula (I) may be applied in solid or liquid compositions to the soil principally to control those nematodes dwelling therein but also to the foliage principally to control those nematodes attacking the aerial parts of the plants (e.g.

Aphelenchoides spp. and Ditylenchus spp. listed above).

The compounds of general formula (I) may be of value in controlling pests which feed on parts of the plant remote from the point of application, e.g. leaf feeding insects are killed by the subject compounds applied to roots. In addition the compounds may reduce attacks on the plant by means of antifeeding or repellent effects.

The compounds of general formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffe, cocoa, banana, oil palm, coconut, rubber, spices), orchards and groves (such as of stone and pit fruit, citrus, kiwifruit, avocado, mango, olives and walnuts), vineyards, ornamental plants, flowers and vegetables and shrubs under glass and in gardens and parks, forest trees (both deciduous and evergreen) in forest, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids), or termites, for example, Reticulitermes spp., Heterotermes spp, Coptotermes spp.

They have applications in the protection of stored products such as grains, fruits, nuts, spices and tobacco, whether whole, milled or compounded into products, from moth, beetle, mite and grain weevil (*Sitophilus granarius*) attack. Also protected are stored animal products such as skins, hair, wool and leathers in natural or converted form (e.g. as carpets or textiles) from moth and beetle attack; also stored meat and fish from beetle, mite and fly attack.

The compounds of general formula (I) may be of particular value in the control of arthropods, helminths or protozoa which are injurious to, or spread or act as vectors of diseases in man and domestic animal, for example those hereinbefore mentioned, and more especially in the control of ticks, mites, lice, fleas, midges and biting, nuisance and myiasis flies. The compounds of general formula (I) are particularly useful in controlling arthropods, helminths or protozoa which are present inside domestic host animals or which feed in or on the skin or suck the blood of the animal, for which purpose they may be administered orally, parenterally, percutaneously or topically. Coccidiosis, a disease caused by infections by protozoan parasites of the genus Eimeria, is an important potential cause of economic loss in domestic animals and birds, particularly those raised or kept under intensive conditions. For example, cattle, sheep, pigs and rabbits may be affected, but the disease is especially important in poultry, in particular chickens.

The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal, but the fowl which survive severe infections have had their market value substantially reduced as a result of the infection.

Administration of a small amount of a compound of general formula (I) preferably by combination with poultry feed may be effective in preventing or greatly reducing the incidence of coccidiosis. The compounds are effective against both the cecal form (caused by *E. tenella*) and the intestinal forms (principally caused by *E. acervulina, E. brunetti, E. maxima* and *E. necatrix*.

The compounds of general formula (I) may also exert an inhibitory effect on the oocysts by greatly reducing the number and/or the sporulation of those produced.

The compositions hereinafter described for topical application to man and animals and in the protection of stored products, household goods, property and areas of the general environment may, in general, alternatively be employed for application to growing crops and crop growing loci and as a seed dressing. Suitable means of applying the compounds of general formula (I) include:

to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, geases, shampoos, creams, wax smears and livestock self-treatment systems; to the environment in general or to specific locations where pests may lurk, including stored products, timber, household goods, and domestic and industrial premises, as sprays, fogs, dusts, smokes, waxsmears, lacquers, granules and baits, and in tricklefeeds to waterways, wells, reservoirs and other running or standing water; to domestic animals in feed to control fly larvae feeding in their faeces; to growing crops as foliar sprays, dusts, granules, fogs and foams; also as suspensions of finely divided and encapsulated compounds of general formula (I) as soil and root treatments by liquid drenches, dusts, granules, smokes and foams; and as seed dressings by liquid slurries and dusts.

The compounds of general formula (I) may be applied to control arthropods, helminths or protozoa in compositions of any type known to the art suitable for internal or external administration to vertebrates or application for the control of arthropods in any premises or indoor or outdoor area, containing as active ingredient at least one compound of general formula (I) in association with one or more compatible diluents or adjuvants appropriate for the intended use. All such compositions may be prepared in any manner known to the art.

Compositons suitable for administration to vertebrates or man include preparations suitable for oral, parenteral, percutaneous, e.g. pour-on, or topical administration.

Compositions for oral administration comprise one or more of the compounds of general formula (I) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate active ingredient contained within microcapsules or coated with acid-labile or alkali-labile or other pharmaceutically acceptable enteric coatings. Feed premixes and concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle and solid or semisolid subcutaneous implants or pellets designed to release active ingredient over a protracted period and may be prepared and made sterile in any appropriate manner known to the art.

Compositions for percutaneous and topical administration include sprays, dusts, baths, dips, showers, jets, greases, shampoos, creams, waxsmears, or pour-on preparations and devices (e.g. ear tags attached externally to animals in such a way as to provide local or systemic arthropod control.

Solid or liquid baits suitable for controlling arthropods comprise one or more compounds of general formula (I) and a carrier or diluent which may include a food substance or some other substance to induce consumption by the arthropod. When used in agriculture in practice, the compounds according to the invention are seldom employed alone. Most frequently these compounds form part of compositions. These compositions, which can be employed, e.g., as insecticidal agents, contain a compound according to the invention such as described earlier as the active ingredient in combination with the agriculturally acceptable/compatible solid or liquid carriers and surface-active agents which are equally agriculturally acceptable/compatible. The inert and usual carriers and the usual surface-active agents can, in particular, be employed. These compositions also form part of the invention.

These compositions may also contain all kinds of other ingredients such as, for example, protective colloids, adhesives, thickeners, thixotropic agents, penetrating agents, spray oils (especially for acaridical uses), stabilisers, preservative agents (especially mold preservatives), sequestering agents, or the like, as well as other known active ingredients with pesticidal properties (particularly insecticides, or fungicides) or with properties regulating the growth of plants. More generally, the compounds employed in the invention may be combined with all the solid or liquid additives corresponding to the usual techniques of formulation.

The use doses of the compounds employed in the invention can vary within wide limits, particularly depending on the nature of the pest to be eliminated and the usual degree of infestation of the crops with these pests.

In general, the compositions according to the invention usually contain approximately 0.05 to 95% (by weight) of one or more active ingredients according to the invention, approximately 1 to 95% of one or more solid or liquid carriers and, optionally, approximately 0.1 to 50% of one or more surface-active agents.

In accordance with what has already been stated the compounds employed in the invention are generally combined with carriers and, optionally, surface-active agents.

In the present account, the term "carrier" denotes an organic or inorganic ingredient, natural or synthetic, with which the active ingredient is combined to facilitate its application to the plant, to seeds or to the soil. This carrier is therefore generally inert and it must be agriculturally acceptable/compatible, particularly to the treated plant. The carrier may be solid (clays, natural or synthetic silicates, silica, resins, waxes, solid fertilisers, for example ammonium salts and ground natural minerals, such as kaolins, clays, talc, chalk, quartz, attapulgite, montmorrillonite, bentonite or diatomaceous earth, and ground synthetic minerals, such as silica, alumina, silicates especially aluminium or magnesium silicates. As solid carriers for granules that are suitable are: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; kieselguhr, corn husks, tricalcium phosphate, powdered cork, absorbent carbon black and water soluble polymers, resins, waxes, solid fertilizers, and such solid compositions may, if desired, contain one or more compatible wetting, dispersing, emulsifying or colouring agents which, when solid, may also serve as diluent. The carrier may be also liquid: alcohols, particularly butanol or glycol, as well as their ethers or esters, particularly methylglycol acetate; ketones, particularly acetone, cyclohexanone, methylethyl ketone, methylisobutylketone, and isophorone; petroleum fractions; paraffinic or aromatic hydrocarbons, particularly xylenes or alkyl naphtalenes, petroleum fractions, mineral and vegetable oils; aliphatic chlorinated hydrocarbons, particularly trichloroethane or methylene chloride, or aromatic chlorinated hydrocarbons, particularly chlorobenzenes; water-soluble or strongly polar solvents such as dimethylformamide, dimethyl sulphoxide, or N-methylpyrrolidone as well as water; liquefied gases, and the like, and mixtures thereof.

The surface-active agent may be an emulsifying agent, dispersing agent or wetting agent of the ionic or non-ionic type or a mixture of such surface-active agents. There may be mentioned, e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, and sulphate, sulphonate and phosphate functional derivatives of the above compounds. The presence of at least one surface-active agent is generally essential when the active ingredient and/or the inert carrier are only slightly water soluble or are not water soluble and the carrier agent of the application is water.

Compositions of the invention may contain further different additives such as adhesives and colorants. Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils. It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Compositions containing compounds of general formula (I) which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate e.g. benomyl, iprodione), bactericides, arthropod or vertebrate attractants or repellents or pheromones, reodorants, flavouring agents, dyes and auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with, the compositions of the present invention are: acephate, chlorpyrifos, demeton-S-methyl, disulfoton, ethoprofos, fenitrothion, malathion, monocrotophos, parathion, phosalone, pirimiphos-methyl, triazophos, cyfluthrin, cypermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectin, milbemycins, thiophanate, trichlorfon, dichlorvos, diaveridine and dimetriadazole.

For their agricultural application, the compounds of the general formula (I) are therefore generally in the form of compositions, which are in various solid or liquid forms. Liquid compositions, may be used to treat substrates or sites infested or liable to infestation by arthropods including premises, outdoor or indoor storage or processing areas, containers or equipment and standing or running water.

Solid homogenous or heterogenous compositions containing one or more compounds of general formula (I) for example granules, pellets, briquettes or capsules, may be used to treat standing or running water over a period of time. A similar effect may be achieved using trickle or intermittent feeds of water dispersible concentrates as described herein.

Compositions in the form of aerosols and aqueous or non-aqueous solutions or dispersions suitable for spraying, fogging and low-or ultra-low volume spraying may also be used.

Solid forms of compositions which can be mentioned are dusting powders (with a content of the compound of general formula (I) capable of ranging up to 80%) or wettable powders or granules, particularly those obtained by extrusion, compacting, impregnation of a granular carrier, or granulation starting from a powder (the content of the compound of the formula (I) in these wettable powders or granules being between 0.5 and 80%).

Solutions, in particular emulsifiable concentrates, emulsions, flowables, aerosols, wettable powders (or powder for spraying), dry flowables and pastes, can be mentioned as forms of compositions which are liquid or intended to form liquid compositions when applied.

The emulsifiable or soluble concentrates also comprise most frequently 5 to 80% of active ingredient, while the emulsions or solutions which are ready for application contain, in their case, 0.01 to 20% of active ingredient. Besides the solvent, the emulsifiable concentrates may contain, when required, 2 to 50% of suitable additives, such as stabilisers, surface-active agents, penetrating agents, corrosion inhibitors, colorants or adhesives.

Emulsions of any required concentration, which are particularly suitable for application to plants, may be obtained from these concentrates by dilution with water.

The concentrated suspensions, which can be applied by spraying, are prepared so as to produce a stable fluid product which does not settle (fine grinding) and usually contain from 10 to 75% of active ingredient, from 0.5 to 30% of surface-active agents, from 0.1 to 10% of thixotropic agents, from 0 to 30% of suitable additives such as anti-foaming agents, corrosion inhibitors, stabilisers, penetrating agents, adhesives and, as the carrier, water or an organic liquid in which the active ingredient is poorly soluble or insoluble; some organic solids or inorganic salts may be dissolved in the carrier to help prevent settling or as antifreezes for water.

The wettable powders (or powder for spraying) are usually prepared so that they contain 10 to 80% of active ingredient, and they usually contain, in addition to the solid carrier, from 0 to 5% of a wetting agent, from 3 to 10% of a dispersing agent and, when necessary, from 0 to 80% of one or more stabilisers and/or other additives such as penetrating agents, adhesives, or anti-caking agents, colorants, or the like.

To obtain these wettable powders, the active ingredient or ingredients is, or are, thoroughly mixed in suitable blenders with additional substances which may be impregnated on the porous filler and is, or are, ground using mills or other suitable grinders. This produces wettable powders, the wettability and the suspendability of which are advantageous; they may be suspended in water to give any desired concentration and this suspension can be employed very advantageously in particular for application to plant foliage.

The "water dispersible granules (WG)" (granules which are readily dispersible in water) have a composition which is substantially close to that of the wettable powders. They may be prepared by granulation of formulations described for the wettable powders, either by a wet route (contacting finely divided active ingredient with the inert filler and a little water, e.g. 1 to 20%, or with an aqueous solution of dispersing agent or binder, followed by drying and screening), or by a dry route (compacting followed by grinding and screening).

As already stated, the aqueous dispersions and emulsions, e.g. compositions obtained by diluting with water a wettable powder or an emulsifiable concentrate according to the invention, are included in the general scope of the compositions which may be employed in the present invention. The emulsions may be of the water-in-oil or oil-in-water type and they may have a thick consistency.

All these aqueous dispersions or emulsions or spraying mixtures can be applied to the crops, by any suitable means, chiefly by spraying, at the rates which are generally of the order of 100 to 1,200 liters of spraying mixture per hectare.

The products and compositions according to the invention are conveniently applied to vegetation and in particular to roots or leaves having pests to be eliminated.

Another method of application of the compounds or compositions according to the invention is by chemigation, that is to say the addition of a formulation containing the active ingredient to irrigation water. This irrigation may be sprinkler irrigation for foliar pesticides or it can be ground irrigation or underground irrigation for systemic pesticides. The application dose of active ingredient is generally between 0.1 and 10 kg/ha, preferably between 0.5 and 4 kg/ha. More particularly the rates and concentrations may vary according to the method of application and the nature of the used compositions.

Generally speaking, the compositions for application to control anthropod, plant nematode, helminth or protozoan pests usually contain from 0.00001% to 95%, more particularly from 0.0005% to 50%, by weight of one or more compounds of general formula (I) or of total active ingredients (that is to say the compound(s) of general formula (I) together with other substances toxic to arthropods and plant nematodes, anthelmintics, anticoccidials, synergists, trace elements or stabilisers). The actual compositions employed and their rate of application will be selected to achieve the desired effect(s) by the farmer, livestock producer, medical or veterinary practitioner, pest control operator or other person skilled in the art. Solid and liquid compositions for application topically to animals, timber, stored products or household goods usually contain from 0.00005% to 90%, more particularly from 0.001% to 10%, by weight of one or more compounds of general formula (I). For administration to animals orally or parenterally, including percutaneously solid and liquid compositions normally contain from 0.1% to 90% by weight of one or more compound of general formula (I). Medicated feedstuffs normally contain from 0.001% to 3% by weight of one or more compounds of general formula (I). Concentrates and supplements for mixing with feedstuffs normally contain from 5% to 90% and preferably from 5% to 50%, by weight of one or more compounds of general formula (I). Mineral salt licks normally contain from 0.1% to 10% by weight of one or more compounds of general formula (I).

Dusts and liquid compositions for application to livestock, persons, goods, premises or outdoor areas may contain 0.0001% to 15%, and more especially 0.005% to 2.0%, by weight of one or more compounds of general formula (I). Suitable concentrations in treated waters are between 0.0001 ppm and 20 ppm, and more especially 0.001 ppm to 5.0 ppm. of one or more compounds of general formula (I) and may also be used therapeutically in fish farming with appropriate exposure times. Edible baits may contain from 0.01% to 5% and preferably 0.01% to 1.0% by weight of one or more compounds of general formula (I).

When administered to vertebrates parenterally, orally or by percutaneous or other means, the dosage of compounds of general formula (I) will depend upon the species, age and health of the vertebrate and upon the nature and degree of its actual or potential infestation by arthropod, helminth or protozoan pest. A single dose of 0.1 to 100 mg, preferably 2.0 to 20.0 mg, per kg body weight of the animal or doses of 0.01 to 20.0 mg, preferably 0.1 to 5.0 mg, per kg body weight of the animal per day for sustained medication are generally suitable by oral or parenteral administration. By use of sustained release formulations or devices, the daily doses required over a period of months may be combined and administered to animals on a single occasion.

The following specific examples illustrate the agrochemical compositions containing the compounds of the invention, and thereafter the insecticidal and acaricidal applications and properties of some compounds.

COMPOSITION (FORMULATION) USE EXAMPLES

The following composition EXAMPLES 23 TO 34 illustrate compositions for use against arthropods, especially insects and arachnids, plant nematodes, and helminth or protozoan pests which comprise, as active ingredient, compounds of general formula (I), especially compounds such as those described in the preparative EXAMPLES 1 to 22 and in ASE EXAMPLES 1 to 306. The compositions described in composition EXAMPLES 23 to 34 can each be diluted in water to give a sprayable composition at concentrations suitable for use in the field. Generic chemical descriptions of the ingredients (for which all of the following percentages are in weight percent), used in the composition EXAMPLES 23 TO 34 exemplified below, are as follows:

| | |
|---|---|
| Ethylan BCP: | nonylphenol ethylene oxide condensate |
| Soprophor BSU: | condensate of tristyrylphenol and ethylene oxide |
| Arylan CA: | 70% w/v solution of calcium dodecylbenzenesulphonate |
| Solvesso 150 | light C10-aromatic solvent |
| Arylan S: | sodium dodecylbenzenesulphonate |
| Darvan | sodium lignosulphonate |
| Celite PF | synthetic magnesium silicate carrier |
| Sopropon T36 | sodium salt of polycarboxylic acid |
| Rhodigel 23 | polysaccharide xanthan gum |
| Bentone 38: | organic derivative of magnesium montmorillonite |
| Aerosil | silicon dioxide of microfine particle size |

EXAMPLE 23

A water soluble concentrate is prepared from:

| | |
|---|---|
| Active ingredient | 7% |
| ETHYLAN BCP | 10% |
| N-methylpyrrolidone | 83% | by dissolving the ETHYLAN BCP in a portion of N-methylpyrrolidone, and then adding the active ingredient with heating and stirring until dissolved. The resulting solution is made up to volume by adding the remainder of the solvent.

EXAMPLE 24

An emulsifiable concentrate is prepared from:

| | |
|---|---|
| Active ingredient | 7% |
| Soprophor BSU | 4% |
| Arylan CA | 4% |
| N-methylpyrrolidone | 50% |
| Solvesso 150 | 35% | by dissolving Soprophor BSU, Arylan CA and the active ingredient in N-methylpyrrolidone, and then adding Solvesso 150 to volume.

EXAMPLE 25

A wettable powder is prepared from:

| | |
|---|---|
| Active ingredient | 40% |
| ARYLAN S | 2% |
| Darvan No. 2 | 5% |

| Celite PF | 53% | by mixing the ingredients, and grinding the mixture in a hammer-mill to a particle size less than 50 microns.

EXAMPLE 26

An aqueous flowable formulation is prepared from:

| Active ingredient | 40.00% |
| Ethylan BCP | 1.00% |
| Sopropon T36 | 0.20% |
| Ethylene glycol | 5.00% |
| Rhodigel 23 | 0.15% |
| Water | 53.65% | by intimately mixing the ingredients and grinding in a bead mill until the median particle size is less than 3 microns.

EXAMPLE 27

An emulsifiable suspension concentrate is prepared from:

| Active ingredient | 30.0% |
| Ethylan BCP | 10.0% |
| Bentone 38 | 0.5% |
| Solvesso 150 | 59.5% | by intimately mixing the ingredients and grinding in a bead mill until the median particle size is less than 3 microns.

EXAMPLE 28

Water dispersible granules are prepared from:

| Active ingredient | 30% |
| Darvan No. 2 | 15% |
| Arylan S | 8% |
| Celite PF | 47% | by mixing the ingredients, micronising in a fluid-energy mill, and then granulating in a rotating pelletizer by spraying on sufficient water (up to 10% w/v). The resulting granules are dried in a fluid-bed drier to remove excess water.

EXAMPLE 29

A dusting powder may be prepared by intimately mixing:

| Active ingredient | 1 to 10% |
| Talc superfine | 99 to 90% |

This powder may be applied to a locus of arthropod infestation, for example refuse tips or dumps, stored products or household goods or animals infested by, or at risk of infestation by, arthropods to control the arthropods by oral ingestion. Suitable means for distributing the dusting powder to the locus of arthropod infestation include mechanical blowers, handshakers and livestock self treatment devices.

EXAMPLE 30

An edible bait may be prepared by intimately mixing:

| Active ingredient | 0.1 to 1.0% |
| Wheat flour | 80.0% |
| Molasses | 19.9 to 19.0% |

This edible bait may be distributed at a locus, for example domestic and industrial premises, e.g. kitchens hospitals or stores, or outdoor areas, infested by arthropods, for example ants, locusts, cockroaches and flies, to control arthropods by oral ingestion.

EXAMPLE 31

A solution may be prepared containing:

| Active ingredient | 15% |
| Dimethylsulphoxide | 85% | by dissolving the pyrrole derivative in a portion of the dimethylsulphoxide and then adding more dimethylsulphoxide to the desired volume. This solution may be applied to domestic animals infested by arthropods, percutaneously as a pour-on application or, after sterilisation by filtration through a polytetrafluoroethylene membrane (0.22 micrometer pore size), by parenteral injection, at a rate of application of from 1.2 to 12 ml of solution per 100 kg of animal body weight.

EXAMPLE 32

A wettable powder may be formed from:

| Active ingredient | 50% |
| Ethylan BCP (9 moles of oxide per mole of phenol) | 5% |
| Aerosil | 5% |
| Celite PF | 40% | by adsorbing the Ethylan BCP onto the Aerosil, mixing with the other ingredients and grinding the mixture in a hammer-mill to give a wettable powder, which may be diluted with water to a concentration of from 0.001% to 2% w/v of the active compound and applied to a locus of infestation by arthropods, for example dipterous larvae, or plant nematodes by spraying, or to domestic animals infested by, or at risk of infection by, arthropods, helminths or protozoa, by spraying or dipping, or by oral administration in drinking water, to control the arthropods, helminths or protozoa.

EXAMPLE 33

A slow release bolus may be formed from granules containing a density agent, binder, slow-release agent, and the active ingredient made according to EXAMPLE 27 at varying percentage compositions. By compressing the mixture, a bolus with a specific gravity of 2 or more can be formed and may be administered orally to ruminant domestic animals for retention within the reticulo-rumen to give a continual slow release of pyrrole compound over an extended period of time to control infestation of the ruminant domestic animals by arthropods, helminths or protozoa.

EXAMPLE 34

A slow release composition may be prepared from:

| Active ingredient | 0.5 to 25% |
|---|---|
| Polyvinylchloride base | 75 to 99.5% | by blending the polyvinylchloride base with the active compound and a suitable plasticizer, e.g. dioctyl phthalate, and melt-extruding or moulding the homogeneous composition into suitable shapes, e.g. granules, pellets, brickettes or strips, suitable, for example, for addition to standing water or, in the case of strips, fabrication into collars or ear-tags for attachment to domestic animals, to control insect pests by slow release of the active compound.

Similar compositions may be prepared by replacing the active ingredient in the composition examples by the appropriate quantity of any other compound of general formula (I).

PESTICIDAL METHODS OF USE EXAMPLES

In the following use EXAMPLES 35 TO 50, compounds according to the invention are applied at various concentrations. The use of a 1 ppm (concentration of the compound in parts per million of the test solution applied) foliar solution or suspension or emulsion corresponds approximately to an application of 1 g/ha of active ingredient, based upon an approximate spray volume of 1000 liters/ha (sufficient to run off). Thus in the following applications foliar sprays of from about 6.25 to 500 ppm would correspond to about 6-500 g/ha. For soil applications, a 1 ppm soil concentration, on the basis of about a 7.5 cm soil depth, corresponds to an approximate 1000 g/ha broadcast field application.

EXAMPLE 35

Activity on Aphid:

A mixture was made with:
0.01 g of active ingredient
0.16 g of dimethylformamide
0.838 g of acetone
0.002 g of a surfactant blend comprising both an alkyl arylpolyether alcohol and an alkylaryl polyether alcohol having sulfonic groups on the aryl moiety.
98.99 g of water This diluted aqueous mixture was sprayed on potted dwarf nasturtium plants, whereon adults and nymphal stages of the buckthorn aphid (*Aphis nasturtii*) were reared. The number of aphids per pot was 100-150. The volume of sprayed aqueous mixture was sufficient to wet the plants to runoff. After spraying, the pots were stored at 20° C. for one day, whereafter the alive aphids were rated. The percentage of mortality obtained was 100% for compounds of EXAMPLES 1, 2, 3A, 4, 5, 16C, 17, 18, 19, and 20 and ASE No's 12, 24, 33, 34, 38, 39, 42, 44, 45, 54, 57, 60, 62, 98-100, 102-104, 125, 128, 130, 131, 135, 137, 141, 142, 144, 157, 158, 162, 165, 166, and 174 at a concentration of 100 ppm. Additionally, the percent of mortality obtained was 70-100% for compounds of ASE No's 178, 182, 183, 184, 186, 187, 189, 195, 197, 199, 200, 201, 202, 203, 204, 206, 207, 208, 210, 211, 212, 213, 215, 216, 235, 236, 246, 252, 253, 254, 255, 260, 271, 272, 273, 281, 282, 284, 288, 289, 290, 300, and 302.

EXAMPLE 36

Activity on Mite:

The same formulation procedure as in EXAMPLE 35 was used. However, in this case 150-200 two-spotted mites (*Tetranychus urticae*) were reared on tendergreen beans. After spraying, the plants were kept at 30° C. for 5 days. The percentage of mortality obtained for mites was 100% for the compounds of EXAMPLE 2, 3A, 16C, 17 and 18 and ASE No's 9, 20, 25, 41, 44, 46, 52, 53, 58, 59, 63, 64, 70, 74, 77-81, 83, 90, 98, 99, 102, 124, and 141 at a concentration of 100 ppm. Additionally, the percent mortality obtained was 70-100% for compounds of ASE No's 183, 184, 195, 201, 203, 205, 213, 214, 215, 216, 217, 218, 219, 220, 221, 222, 223, 229, 231, 235, 236, 239, 241, 243, 244, 247, 255, 256, 263, 264, 266, 267, 268, 289, 291, and 293.

EXAMPLES 37-39

Activity on Southern Armyworm

37: The same formulation as in EXAMPLE 35 was used. In this case, second instar larvae of southern armyworm (*Spodoptera eridania*) were reared on Sieva beans of approximately 15 cm in height. Potted bean plants, were placed on a revolving turntable and sprayed with 100 ml of the 100 ppm test compound formulation by use of a DeVibiss spray gun set at 40 psig air pressure. As an untreated control, 100 ml of a water-acetone-DMF-surfactant solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar Southern armyworm larvae were introduced into each dish which was closed and held for five days. Larvae which were unable to move the length of the body, even upon stimulation by prodding, were considered dead. The following percent of mortalities were obtained after 5 days: 100% mortality was provided by compounds of EXAMPLES 3A, 3B, 5, 6, 7, 8, 9, 11, 12, 15B, 16C, 17, 18, 20, 21B, 21C, and ASE No's 42, 44, 60, 62, 64, 98-100, 102, 103, 121, 124, 125, 131, 141, 142, 144, 162, 166, and 174 at a concentration of 100 ppm and 80% mortality was provided by the compound of EXAMPLE 13 at 500 ppm. Additionally, the percent mortality obtained was 70-100% for compounds of ASE No's 177, 178, 182, 183, 184, 195, 197, 199, 200, 201, 203, 204, 205, 206, 208, 209, 210, 212, 213, 214, 215, 235, 236, 244, 254, 255, 260, 271, 272, 273, 281, 282, 284, 288, 289, 300, 302, 303, 304, and 305.

38: The same formulation procedure as in EXAMPLE 35 was used except in this case it contained the following:
2.5 mg of active ingredient
0.05 g of dimethyl formamide
9.9228 g of acetone
0.0247 g of surfactant (as in EXAMPLE 35)
90 g of water The compound of EXAMPLE 4 gave 100% mortality on southern armyworm at 25 ppm.

39: The same formulation procedure as in EXAMPLE 38 was used except in this case it contained the following:
0.625 mg of active ingredient
12.5 mg of dimethylformamide
9.9621 g of acetone
0.0247 g of surfactant (as in EXAMPLE 35)
90 g of water The compounds of EXAMPLES 1 and 2 gave 100% mortality on southern armyworm at 6.25 ppm.

EXAMPLES 40-43

Activity on Mexican Bean Beetle

40: The same formulation procedure as in EXAMPLE 37 was used except in this case it contained the following:
12.5 mg of active ingredient
0.25 g of dimethylformamide
9.726 g of acetone
24.1 mg of surfactant (as in EXAMPLE 35)
89.988 g of water Second instar larvae of the Mexican bean beetle (*Epilachna varivestis*) were reared on Sieva beans of approximately 15 cm in height. Potted bean plants, were placed on a revolving turntable and sprayed with 100 ml of the 100 ppm test compound formulation by use of a DeVilbiss spray gun set at 40 psig air pressure. As an untreated control, 100 ml of a water-acetone-DMF-surfactant solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar Mexican bean beetle larvae were introduced into each dish which was closed and held for five days. Larvae which were unable to move the length of the body, even upon stimulation by prodding, were considered dead. The following percent mortality was obtained after 5 days: 100% mortality was obtained by the compound of EXAMPLE 13 at 125 ppm.

41: Using the formulation procedure as in EXAMPLE 38, but containing the compound of EXAMPLE 8 as active ingredient there was obtained 100% mortality of Mexican bean beetle at 25 ppm.

42: Using the formulation procedure as in EXAMPLE 35, but containing the unbrominated compound of EXAMPLE 15A as active ingredient there was obtained 100% mortality of Mexican bean beetle at 100 ppm.

43: The same formulation procedure as in EXAMPLE 40 was used except in this case it contained:
10 mg of active ingredient
0.2 g of dimethylformamide
9.7657 g of acetone
0.0243 g of surfactant (as in EXAMPLE 35)
90 g of water The following percent mortalities on Mexican bean beetle were obtained: 80% mortality by the compounds of EXAMPLE 15A and 15B at 100 ppm and 100% mortality by the compounds of EXAMPLES 1, 2, 9, 17, 18 and ASE No's 42, 44, 60, 62, 64, 98, 99, 124, 125, 141, 142, and 144 at 100 ppm. Additionally, the percent mortality obtained was 70-100% for compounds of ASE No's 177, 178, 189, 197, 198, 201, 203, 204, 205, 206, 207, 208, 214, 215, 216, 217, 220, 221, 233, 240, 241, 254, 255, 264, 272, 273, 276, 284, 288, 289, 297, and 300.

EXAMPLES 44-46

Activity on Housefly

The toxicant, in the form of a 10 ml aqueous sugar solution containing 10% w/w of sugar and 100 ppm of the chemical toxicant, was formulated in a similar way as in EXAMPLE 35. Further serial dilutions were made as required. The following 3 different formulations were prepared for testing:

|  | EXAMPLE | | |
| --- | --- | --- | --- |
|  | 44 | 45 | 46 |
| Active ingredient, mg | 10 | 10 | 1.25 |
| Dimethylformamide, mg | 160 | 200 | 25 |
| Surfactant (as in EXAMPLE 35), mg. | 2.15 | 24.3 | 14.25 |
| Acetone, g | 8.42 | 9.766 | 5.73 |
| Water, g | 88.99 | 81 | 84.38 |
| Sugar, g | 10 | 9 | 9.84 |

Twenty five adult flies (*Musca domestica*) were anesthetized with carbon dioxide and then transferred over to a bait cup containing the toxicant formulation. After one day at 27° C., the percent mortality of flies was measured and was as follows:

For EXAMPLE 44: 100% mortality by the compounds of EXAMPLES 1, 2, 3B, 4-6, 8, 9, 16C, 17-20, 21B, and 21C and ASE No's 42, 44, 60, 62, 64, 98, 99, 100, 102, 103, 121, 124, 125, 131, 141, 142, 144, 162, 166, and 174 at 100 ppm. Additionally, 70-100% mortality by the compounds of ASE No's 175, 176, 178, 182, 183, 184, 187, 188, 190, 191, 195, 197, 198, 199, 200, 201, 202, 206, 207, 208, 209, 210, 211, 212, 213, 214, 215, 226, 228, 235, 236, 238, 240, 249, 251, 252, 253, 254, 255, 258, 260, 271, 272, 273, 276, 281, 282, 284, 288, 289, 300, and 302.

For EXAMPLE 45: 100% mortality by the compound of EXAMPLE 12 at 100 ppm.

For EXAMPLE 46: 100% mortality by the compounds of EXAMPLES 1,2 and 5 at 12.5 ppm.

EXAMPLE 47

Activity on Southern Corn Rootworm

A formulation was prepared in a similar manner to that used in EXAMPLE 35 except that in this case, only 48.99 g of water was used, providing an initial 200 ppm concentration of the test compound. Aliquots of this formulation were then used directly according to the required test concentration, in ppm (parts per million) by weight, according to the following test procedure.

Into a jar containing 60 g of sandy loam soil was added an aliquot of the 200 ppm test compound formulation (as appropriate for the final soil concentration of the test compound), 3.2 ml of water and five pregerminated corn seedlings. The jar was shaken thoroughly to obtain an even distribution of the test formulation. Following this, twenty southern corn rootworm eggs (*Diabrotica undipunctata howardi*) were placed into a cavity, which was made in the soil. Vermiculite (1 ml) and water (1.7 ml) were then added to this cavity. In a similar manner, an untreated control was prepared by application of the same size aliquot of a water-acetone-DMF emulsifier solution, containing no test compound. Additionally, a treated control with a commercial technical compound, formulated in the same manner, was used as a test standard. After 7 days, the living rootworm larvae were counted using a well known "Berlese" funnel extraction method.

The following compounds all provide 100% control at soil concentrations of 1.45, 0.72 and 0.36 ppm: compounds of EXAMPLES 3B, 4, and 17-19 and ASE No's 98, 99, 101, 105, 113, 119, 121, 124, 125, 130, 173, 195, 199, 203, 204, 205, 207, 209, 252, 260, 271, 272, 282, 300, and 302.

EXAMPLE 48

Activity on Mite Egg (Ovicide Test)

The same formulation as in EXAMPLES 35 was used. Eggs were obtained from adults of the twospotted spider mite from a stock culture. Heavily infested leaves from the stock culture were placed on uninfested bean plants. Females were allowed to oviposit for a period of about 24 hours, after which the leaves of the plant were dipped into a solution of TEPP (tetraethyl diphosphate) in order to kill the motile forms and prevent additional egg laying. This dipping procedure, which was repeated after the plants dried, did not affect the viability of the eggs. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-surfactant solution, containing no test compound, were also sprayed on infested plants. A treated control with a commercial technical compound, typically demeton, formulated in the same manner, was tested as a standard. The sprayed plants were held for seven days, after which a mortality count of egg forms was made along with notations on residual activity on hatched larvae.

The percent mortality obtained was 70–100% for compounds of ASE No's 218, 219, 266, and 267.

EXAMPLE 49

Activity on Southern Root-Knot Nematode

A stock solution or suspension was prepared by adding 15 mg of the test compound to 250 mg of dimethylformamide, 1250 mg of acetone and 3 mg of the surfactant blend referenced above in EXAMPLE 35. Water was then added to bring the total volume to 45 ml and a test compound concentration of 333 ppm. When necessary, sonication was provided to insure complete dispersion.

Infected roots of tomato plants, containing egg masses of southern root-knot nematode, (*Meloidogyne incognita*) were removed from a stock culture and cleaned of soil by shaking and washing with tap water. The nematode eggs were separated from the root tissue and rinsed with water. Samples of the egg suspension were placed on a fine screen over a receiving bowl, in which the water level was adjusted to be in contact with the screen. From the bowl, juveniles were collected on a fine screen. The bottom of a cone-shaped container was plugged with coarse vermiculite and then filled to within 1.5 cm of the top with about a 200 ml volume of pasturized soil. Then into a hole made in the center of the soil in the cone was pipetted an aliquot of the 333 ppm test compound formulation. A treated control with a commercial technical compound, fenamifos, formulated in a similar manner, was tested as a standard. As an untreated control, an aliquot of a water-acetone-DMF-surfactant solution, containing no test compound, was applied in a similar manner. Immediately after treatment of the soil with the test compound there were added to the top of each cone 1000 second stage juvenile southern root-knot nematodes. After 3 days, a single healthy tomato seedling was then transplanted into the cone. The cone, containing the infested soil and tomato seedling, was kept in the greenhouse for 3 weeks. At the termination of the test, roots of the tomato seedling were removed from the cone and evaluated for galling on a rating scale relative to the untreated control as follows:

1- severe galling, equal to untreated control
3- light galling
4- very light galling
5- no galling, i.e., complete control These results were then converted to an ED$_3$ or ED$_5$ value (effective dose to provide a 3 or 5 gall rating).

The compounds of ASE No's 71, 72, 73, 74, and 77 provided ED$_3$ values of between 14.6 to 21 kg/ha.

EXAMPLE 50

Systemic Activity on Southern Armyworm:

The same formulation as in EXAMPLE 49 was used. This test was conducted in conjunction with the southern root-knot nematode evaluation (discussed above). The tomato plants, grown in the soil (at an initial compound test screening rate of 13.2 ppm soil concentration) for nematode evaluation, were then utilized for evaluation of a compounds's uptake via roots and subsequent systemic transport to the tomato foliage. At the termination of the nematode test, the tomato foliage was excised, placed into a plastic container, and infested with second instar larvae of southern armyworm. After about 5 days, the larvae were examined for percent mortality, which in the case of compounds of ASE No's 174 and 200 was 50–100% at soil concentrations of between about 0.4–1.6 ppm.

What is claimed is:

1. A pesticidal composition, which is employed as an insecticidal, acaricidal or nematicidal agent, which comprises one or more compatible components selected from the group consisting of a pesticidally acceptable carrier and a pesticidally acceptable surface-active agent and a pesticidally effective amount of a compound of formula (Ia), as active ingredient,

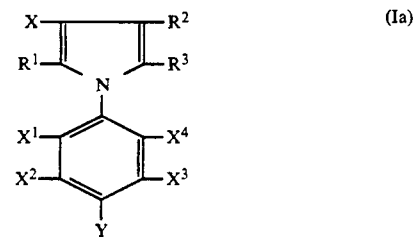

wherein:

X is selected from the group consisting of: halogen, cyano, cyanato, thiocyanato, haloalkyl, alkoxy, haloalkoxy, alkylthio, alkylsulfinyl, alkylsulfonyl, haloalkylthio, haloalkylsulfinyl, haloalkylsulfonyl, haloalkylcarbonyl, alkenylthio, alkenylsulfinyl, alkenylsulfonyl, haloalkenylthio, haloalkenylsulfinyl, haloalkenylsulfonyl, haloalkylthiocarbonyl, phenylthio, phenylsulfinyl, and phenylsulfonyl; and wherein the phenyl groups are optionally substituted with halogen, cyano or haloalkyl groups; and wherein the alkyl, haloalkyl, alkenyl, haloalkenyl, alkoxy and haloalkoxy groups herein are linear or branched chains, having less than 10 carbon atoms, and the halosubstitution in all these groups consists of one or more halogen atoms, which are the same or different, from mono substitution up to complete poly substitution;

$R^1$, $R^2$, and $R^3$ are individually selected from the group consisting of: one of the same set of substituents as described for X; a hydrogen atom; an alkyl group; and a substituent of which no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, bis(alkylthio)methyl, bis(arylthio)methyl, alkylthioalkylideneimino, alkoxycarbonylamino, haloalkoxycarbonylamino, and a phenyl optionally substituted with halogen, cyano or haloalkyl; and wherein the alkyl, haloalkyl, alkenyl, haloalkenyl, haloalkoxy, and alkoxy groups herein are linear or branched chains, having less than 10 carbon atoms, and the halosubstitution in all these groups herein consists of one or more halogen atoms, which are the same of different, from mono substitution up to complete poly substitution; or $R^1$, $R^2$, and $R^3$ are as defined above and $R^1$ is furthermore selected from the group consisting of alkenyl, alkynyl, haloalkenyl, haloalkynyl, alkenylamino, alkynylamino, cyanoalkyl, aralkylthio, aralkylsulfinyl, aralkylsulfonyl, alkenyloxy, alkynyloxy, alkoxyalkyl, and alkylthioalkyl, and $R^3$ is furthermore selected from the group consisting of alkenyloxy, alkynyloxy, and alkoxyalkyl; and no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, alkenylamino, alkynylamino, aminocarbonylamino, alkylcarbonylamino, haloalkylcarbonylamino, arylcarbonylamino, alkylsulfonylamino, haloalkysulfonylamino, alkylaminocarbonylamino, arylaminocarbonylamino, benzylideneimino, alkylideneimino, alkoxyalkylideneimino, dialkylaminoalkylideneimino, bis(alkylthio)-methyl, bis(arylthio)-methyl, alkylthioalkylideneimino, alkoxy-carbonylamino, haloalkoxycarbonylamino, and a phenyl optionally substituted with halogen, cyano or haloalkyl; and wherein the alkyl, haloalkyl, alkenyl, haloalkenyl, alkynyl, haloalkynyl, haloalkoxy, alkoxy, alkenyloxy, and alkynyloxy groups herein are linear or branched chains, having less than 10 carbon atoms, and the halosubstitution in all these groups herein consists of one or more halogen atoms, which are the same or different, from mono substitution up to complete poly substitution; and wherein for the aralkyl portion in the above mentioned groups and the phenyl portion are optionally substituted as defined above;

Y is selected from the group consisting of; halogen, cyano, alkyl, haloalkyl, alkoxy, haloalkoxy, alkylsulfinyl, alkylsulfonyl, alkylthio, haloalkylthio, haloalkylsulfinyl, haloalkylsulfonyl, alkylcarbonyl, haloalkylcarbonyl, alkenyl, haloalkenyl, haloalkynyl, and alkynyl; and wherein the alkyl, alkoxy, haloalkyl, haloalkoxy, alkenyl, haloalkenyl, alkynyl and haloalkynyl groups herein are linear or branched chains, having less than 10 carbon atoms, and the halo substitution in all these groups herein consists of one or more halogen atoms, which are the same or different, from mono substitution up to as much as complete poly substitution; or Y optionally is a hydrogen atom when:

X is a halogen atom or a group $R^5S(O)_n$, in which n is 0, 1, or 2 and $R^5$ is alkyl, haloalkyl, alkenyl or haloalkenyl; and the alkyl and alkenyl carbon chains and the halo-substitution are as defined above;

$R^1$ and $R^3$ are each a hydrogen atom; and $R^2$ is cyano;

$X^1$, $X^2$, $X^3$ and $X^4$ are individually selected from the same set of substituents as described for Y or a hydrogen atom; and provided:

that at least one of $R^1$, $R^2$, and $R^3$ is selected from the same set of substituents as described for X;

that if $X^4$ and $X^1$ are H, and X is halogen or cyano, then $R^2$ is different from X; and that if $X^4$ and $X^1$ are H, and Y is methyl, then X is different from bromo.

2. The pesticidal composition according to claim 1, wherein the pesticidally effective compound of formula (Ia) is a compound (Ib), wherein:

X, Y, $X^1$, $X^2$, $X^3$, $X^4$ and the provisos are as defined in claim 1; and $R^1$, $R^2$, and $R^3$ are individually selected from the group consisting of: one of the same set of substituents as described for X; a hydrogen atom; an alkyl group; and a substituent of which no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, bis(alkylthio)methyl, bis(arylthio)methyl, alkylthioalkylideneimino, alkoxycarbonylamino, haloalkoxycarbonylamino, a phenyl optionally substituted with halogen, cyano or haloalkyl; and wherein the alkyl, haloalkyl, alkenyl, haloalkenyl, haloalkoxy, and alkoxy groups herein are linear or branched chains, having less than 10 carbon atoms, and the halosubstitution in all these groups herein consists of one or more halogen atoms, which are the same or different, from mono substitution up to complete poly substitution.

3. The pesticidal composition according to claim 2, wherein the pesticidally effective compound (Ib) is a compound (Ic), wherein:

X is selected from the group consisting of halogen, cyano, cyanato, thiocyanato, haloalkyl, alkoxy, haloalkoxy, alkylthio, alkylsulfinyl, alkylsulfonyl, haloalkylthio, haloalkylsulfinyl, haloalkylsulfonyl, haloalkylcarbonyl, haloalkylthiocarbonyl, phenylthio, phenylsulfinyl, and phenylsulfonyl; and wherein the phenyl groups are optionally substituted with halogen, cyano or haloalkyl groups; and wherein the alkyl, haloalkyl, alkoxy and haloalkoxy groups herein are linear or branched chains, having less than 10 carbon atoms, and the halosubstitution in all these groups is mono substitution or up to as much as complete poly substitution;

$R^1$, $R^2$, and $R^3$ are individually selected from the group consisting of: the same substituents as described for X; a hydrogen atom; an alkyl group; and a substituent of which no more than one of $R^1$, $R^2$, and $R^3$ is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, and a phenyl optionally substituted with halogen, cyano or haloalkyl; and wherein the alkyl, haloalkyl, haloalkoxy, and alkoxy groups herein are linear or branched chains, having less than 10 carbon atoms, and the halo substitution in all these groups herein is mono substitution or up to as much as complete poly substitution;

Y is selected from the group consisting of halogen, cyano, alkyl, haloalkyl, alkoxy, haloalkoxy, alkylsulfinyl, alkylsulfonyl, alkylthio, haloalkylthio, haloalkylsulfinyl, haloalkylsulfonyl, alkylcarbonyl, haloalkylcarbonyl, alkenyl, haloalkenyl, haloalkynyl, and alkynyl; and wherein the alkyl, alkoxy, haloalkyl and haloalkoxy groups herein are linear or branched chains, having less than 10 carbon atoms, and the halo substitution in all these groups herein is mono substitution or up to as much as complete poly substitution; and $X^1$, $X^2$, $X^3$, $X^4$ and the provisos are as defined in claim 2.

4. The pesticidal composition according to claim 1, wherein the pesticidally effective compound of formula (Ia) is a compound (Ia-1),
wherein:
X, $R^1$, $R^2$, $R^3$, Y, $X^1$, $X^2$, $X^3$, and $X^4$ are as defined in claim 1; and provided:
that of the substituents X, $R^1$, $R^2$, and $R^3$, at least one of them is different from the others.

5. The pesticidal composition of a compound of formula (Ia), according to claim 1, wherein the compatible component is selected from the group consisting of an acceptable carrier and an acceptable surface-active agent.

6. The pesticidal composition of a compound of formula (Ia), according to claim 5, which further comprises one or more ingredients selected from the group consisting of protective colloids, adhesives, thickeners, thixotropic agents, penetrating agents, spray oils, stabilizers, preservative agents, mold preservatives, sequestering agents, and a second pesticidally active ingredient.

7. The pesticidal composition of a compound of formula (Ia), according to claim 5 which comprises: between 0.05% and 95%, by weight, of one or more compounds of formula (Ia) as active ingredient; between 1% and 95%, by weight, of one or more carriers; and between 0.1% and 50%, by weight, of one or more surface-active agents.

8. The pesticidal composition of a compound (Ib), according to claim 2, which further comprises one or more ingredients selected from the group consisting of protective colloids, adhesives, thickeners, thixotropic agents, penetrating agents, spray oils, stabilizers, preservative agents, mold preservatives, sequestering agents, and a second pesticidally active ingredient.

9. The pesticidal composition of a compound (Ib), according to claim 2 which comprises: between 0.05% and 95%, by weight, of one or more compounds (Ib) as active ingredient; between 1% and 95%, by weight, of one or more carriers; and between 0.1% and 50%, by weight, of one or more surface-active agents.

10. The pesticidal composition of a compound (Ic), according to claim 3, which further comprises one or more ingredients selected from the group consisting of protective colloids, adhesives, thickeners, thixotropic agents, penetrating agents, spray oils, stabilizers, preservative agents, mold preservatives, sequestering agents, and a second pesticidally active ingredient.

11. The pesticidal composition of a compound (Ic), according to claim 3, which comprises: between 0.05% and 95%, by weight, of one or more compounds (Ic) as active ingredient; between 1% and 95%, by weight, of one or more carriers; and between 0.1% and 50%, by weight, of one or more surface-active agents.

12. The pesticidal composition of a compound (Iau-1), according to claim 4, wherein the compatible component is selected from the group consisting of an acceptable carrier and an acceptable surface-active agent.

13. The pesticidal composition of a compound (Ia-1), according to claim 12, which further comprises one or more ingredients selected from the group consisting of protective colloids, adhesives, thickeners, thixotropic agents, penetrating agents, spray oils, stabilizers, preservative agents, mold preservatives, sequestering agents, and a second pesticidally active ingredient.

14. The pesticidal composition of a compound (Ia-1), according to claim 12, which comprises: between 0.05% and 95%, by weight, of one or more compounds (Ia-1) as active ingredient; between 1% and 95%, by weight, of one or more carriers; and between 0.1% and 50%, by weight, of one or more surface-active agents.

15. A method for control of arthropod, plant nematode, helminth or protozoan pests at a locus which comprises applying to the locus an effective amount of a pesticidal compound of formula (Ia), wherein the various substituents are as defined in claim 1.

16. A method for control of arthropod, plant nematode, helminth or protozoan pests at a locus which comprises applying to the locus an effective amount of a pesticidal compound of formula (Ia), wherein the pesticidal compound of formula (Ia) is a compound of a formula (Ib), as defined in claim 2.

17. A method for control of arthropod, plant nematode, helminth or protozoan pests at a locus which comprises applying to the locus an effective amount of a pesticidal compound of formula (Ia), wherein the pesticidal compound of formula (Ib) is a compound of a formula (Ic), as defined in claim 3.

18. A method for control of arthropod, plant nematode, helminth or protozoan pests at a locus which comprises applying to the locus an effective amount of a pesticidal compound of formula (Ia), wherein the pesticidal compound of formula (Ia) is a compound of a formula (Ia-1), as defined in claim 4.

19. The method for the control of pests with a compound of formula (Ia), according to claim 15, in veterinary medicine and livestock husbandry or in maintenance of public health for the control of the arthropod, helminth or protozoan pests which are parasitic internally or externally upon warm-blooded vertebrates.

20. The method for the control, according to claim 15, of the arthropod or the nematode pests of plants which comprises applying to the plants or to a medium in which they grow the effective amount of the pesticidal compound of formula (Ia).

21. The method for the control of the arthropod and the nematode pests according to claim 15, wherein the effective amount of the pesticidal compound of formula (Ia), is applied to the locus in which the arthropod or the nematode infestation is to be controlled, said effective amount being between 0.005 kg and 15 kg of the pesticidal compound per hectare of the locus treated.

22. The method for the control of pests, according to claim 21, wherein the effective amount of the pesticidal compound of formula (Ia), per hectare of the locus treated, is between 0.02 kg and 2 kg.

23. The method for the control of pests according to claim 21, wherein the effective amount of the pesticidal compound of formula (Ia) is applied by a foliar application, said effective amount of the pesticidal compound being between 0.01 kg and 1 kg.

24. The method for the control of pests with a compound of formula (Ia), according to claim 22, wherein said arthropod pests are insects or arachnids.

25. The pesticidal composition according to any of claims 1, 2, 3 or 4, wherein the alkyl, alkenyl, alkynyl, and alkoxy portions of the substituents defined by X, $X^1$, $X^2$, $X^3$, $X^4$, $R^1$, $R^2$, $R^3$ and Y have less than 5 carbon atoms.

26. The pesticidal composition according to claim 3, wherein the pesticidally effective compound (Ic) is a compound (II-5), wherein:

X is a haloalkyl-$S(O)_n$ group, wherein n is 0, 1, or 2;

$R^1$ is an hydrogen atom or a halogen atom;

$R^2$ is cyano;

$R^3$ is selected from the group consisting of: the same substituents as described for X in claim 3; a hydrogen atom; an alkyl group; and a substituent which is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, a phenyl optionally substituted with halogen, cyano or haloalkyl; and wherein the alkyl, haloalkyl, haloalkoxy, and alkoxy groups herein are linear or branched chains, having less than 10 carbon atoms, and the halo substitution in all these groups herein is mono substitution or up to as much as complete poly substitution;

Y is a haloalkyl or haloalkoxy;

$X^1$ and $X^4$ are other than a hydrogen atom; and $X^2$ and $X^3$ are each a hydrogen atom.

27. The pesticidal composition according to claim 3, wherein the pesticidally effective compound (Ic) is a compound (II-6), wherein:

X is $R^5S(O)_n$, in which n is 0, 1 or 2 and $R^5$ is $CH_3$, $CF_3$, $CF_2Cl$ or $CFCl_2$;

$R^1$ is H, F, Cl, Br or $NH_2$;

$R^2$ is cyano;

$R^3$ is H, F, Cl, Br, $CF_3$ or CN;

Y is $CF_3$ or $CF_3O$;

$X^1$ is H or Cl;

$X^2$ and $X^3$ are H; and $X^4$ is Cl.

28. The pesticidal composition according to claim 27, wherein the compound (II-6) is:

1-(2,6-dichloro-4-trifluoromethylphenyl)-2-chloro-3-cyano-4-(trifluoromethylsulfonyl)pyrrole;

1-(2,6-dichloro-4-trifluoromethylphenyl)-2-chloro-3-cyano-4-(trifluoromethylsulfinyl)pyrrole;

1-(2,6-dichloro-4-trifluoromethylphenyl)-2-chloro-3-cyano-4-(dichlorofluoromethylthio)pyrrole;

1-(2,6-dichloro-4-trifluoromethylphenyl)-2-chloro-3-cyano-4-(dichlorofluoromethylsulfinyl)pyrrole;

1-(2,6-dichloro-4-trifluoromethylphenyl)-2-chloro-3-cyano-4-(dichlorofluoromethylsulfonyl)pyrrole; or 1-(2,6-dichloro-4-trifluoromethylphenyl)-3-cyano-4-(dichlorofluoromethylsulfinyl)pyrrole.

29. The pesticidal composition according to claim 2, wherein the pesticidally effective compound (Ib) is a compound (II-4), wherein:

X is a halogen atom or a group $R^5S(O)_n$, in which n is 0, 1 or 2 and $R^5$ is alkyl, haloalkyl, alkenyl, or haloalkenyl;

$R^1$ is a hydrogen atom, a halogen atom or alkylthio having less than 5 carbon atoms;

$R^2$ is cyano;

$R^3$ is a hydrogen atom or a halogen atom;

Y is a hydrogen atom, a halogen atom, haloalkyl or haloalkoxy, in which the alkyl and alkoxy portions have less than 5 carbon atoms, with the proviso that Y is a hydrogen atom as defined in claim 2; and $X^1$, $X^2$, $X^3$ and $X^4$ are individually selected from the group consisting of a hydrogen atom, a halogen atom, $C_{1-3}$ alkyl, $C_{1-3}$ alkoxy, and $C_{1-3}$ alkylthio.

30. The pesticidal composition according to claim 29, wherein the pesticidally effective compound (II-4) is a compound (II-4a), wherein:

$R^1$ and $R^3$ are each a hydrogen atom;

Y is a hydrogen atom or halogen atom; and X, $R^2$, $X^1$, $X^2$, $X^3$, and $X^4$ are as defined in claim 29.

31. The pesticidal composition according to claim 30 for the compound (II-4a), wherein:

X is a Cl or Br atom or the group $R^5S(O)_n$, wherein n is 0, 1 or 2 and $R^5$ is $C_{1-4}$ alkyl or trihalomethyl, in which halo is F, Cl, or Br or combinations thereof;

Y is H, F, Cl or Br;

$X^1$ and $X^4$ are individually selected from the group consisting of H, F, Cl, Br and $CH_3$;

$X^2$ and $X^3$ are each a hydrogen atom; and $R^1$, $R^2$ and $R^3$ are as defined in claim 30.

32. The pesticidal composition according to claim 31 for the compound (II-4a), wherein:

X is a Cl or Br atom or the group $R^5S(O)_n$, wherein n is 0, 1 or 2 and $R^5$ is $CF_3$, $CCl_3$, $CF_2Cl$, $CFCl_2$ or $CF_2Br$; and $R^1$, $R^2$, $R^3$, Y, $X^1$, $X^2$, $X^3$ and $X^4$ are as defined in claim 31.

33. The pesticidal composition according to claim 32, wherein the compound (II-4a) is:

1-(4-bromo-2,6-dichlorophenyl)-3-cyano-4-(chlorodifluoromethylthio)pyrrole;

1-(4-bromo-2,6-dichlorophenyl)-3-cyano-4-(trifluoromethylthio)pyrrole;

1-(2,4,6-trichlorophenyl)-3-cyano-4-(chlorodifluoromethylthio)pyrrole;

1-(2,4,6-trichlorophenyl)-3-cyano-4-(dichlorofluoromethylthio)pyrrole;

1-(2,4,6-trichlorophenyl)-3-cyano-4-(trifluoromethylthio)pyrrole;

1-(2,6-dichloro-4-fluorophenyl)-3-cyano-4-(trifluoromethylsulfinyl)pyrrole;

1-(2,6-dichloro-4-fluorophenyl)-3-cyano-4-(trifluoromethylsulfonyl)pyrrole; or 1-(2,6-dichloro-4-fluorophenyl)-3-cyano-4-(dichlorofluoromethylthio)pyrrole.

34. The pesticidal composition according to claim 29, wherein the pesticidally effective compound (II-4) is a compound (II-4b), wherein:
X is $R^5S(O)_n$, in which n is 0, 1 or 2 and $R^5$ is $CH_3$, $CF_3$, $CF_2Cl$, $CFCl_2$, $CF_2Br$, $CHF_2$, $CHCl_2$ or CHClF;
$R^1$ is H, F, Cl or Br;
$R^2$ is cyano;
$R^3$ is H, F, Cl or Br;
Y is $CF_3$ or $CF_3O$;
$X^1$ is H or Cl;
$X^2$ and $X^3$ are H; and
$X^4$ is Cl.

35. The pesticidal composition according to claim 34, wherein the compound (II-4b) is:
1-(2,6-dichloro-4-trifluoromethylphenyl)-2-chloro-3-cyano-4-(dichlorofluoromethylthio)pyrrole;
1-(2,6-dichloro-4-trifluoromethylphenyl)-2-chloro-3-cyano-4-(dichlorofluoromethylsulfinyl)pyrrole;
1-(2,6-dichloro-4-trifluoromethylphenyl)-2-chloro-3-cyano-4-(dichlorofluoromethylsulfonyl)pyrrole;
1-(2,6-dichloro-4-trifluoromethylphenyl)-2-chloro-3-cyano-4-(chlorodifluoromethylsulfonyl)pyrrole;
1-(2,6-dichloro-4-trifluoromethylphenyl)-2-chloro-3-cyano-4-chlorodifluoromethylsulfinyl)pyrrole;
1-(2,6-dichloro-4-trifluoromethylphenyl)-2-chloro-3-cyano-4-(chlorodifluoromethylthio)pyrrole;
1-(2,6-dichloro-4-trifluoromethylphenyl)-2-bromo-3-cyano-4-(dichlorofluoromethylsulfonyl)pyrrole;
1-(2,6-dichloro-4-trifluoromethylphenyl)-2-bromo-3-cyano-4-(dichlorofluoromethylsulfinyl)pyrrole;
1-(2,6-dichloro-4-trifluoromethylphenyl)-2-chloro-3-cyano-4-(bromodifluoromethylthio)pyrrole;
1-(2,6-dichloro-4-trifluoromethylphenyl)-2-chloro-3-cyano-4-(methylsulfinyl)pyrrole;
1-(2,6-dichloro-4-trifluoromethyl-2-bromo-3-cyano-4-(trifluoromethylthio)pyrrole;
1-(2,6-dichloro-4-trifluoromethoxyphenyl)-2-bromo-3-cyano-4-(dichlorofluoromethylsulfinyl)pyrrole; or
1-(2,6-dichloro-4-trifluoromethoxyphenyl)-2-bromo-3-cyano-4-(dichlorofluoromethylsulfonyl)pyrrole.

36. The pesticidal composition according to claim 4, wherein the pesticidally effective compound (Ia-1) is a compound (II-7), wherein:
X is a group $R^5S(O)_n$, in which n is 0, 1 or 2 and $R^5$ is alkyl or haloalkyl;
$R^1$ is selected from the group consisting of: hydrogen; alkyl; cyanoalkyl; haloalkyl; alkylthio; alkylsulfinyl; alkylsulfonyl; aralkylthio; aralkylsulfinyl, aralkylsulfonyl; alkenylthio; alkynylthio; phenylthio; phenylsulfinyl; phenylsulfonyl; alkoxy; alkenyloxy; alkynyloxy; alkoxyalkyl; and alkylthioalkyl; and wherein the phenyl portions in the aforementioned groups are optionally substituted as defined in claim 4; and the aralkyl portions in the aforementioned groups are optionally substituted phenylalkyl as also defined in claim 4;
$R^2$ is cyano;
$R^3$ is selected from the group consisiting of: halogen; cyano; alkyl; haloalkyl; alkoxy; alkenyloxy; alkynyloxy; and alkoxyalkyl;
Y is selected from the group consisting of: halogen, trifluoromethyl, and trifluoromethoxy;
$X^1$ is selected from the group consisting of: hydrogen; halogen; alkyl; alkoxy; alkylthio; alkylsulfinyl; and alkylsulfonyl;
$X^2$ and $X^3$ are hydrogen;
$X^4$ is halogen; and provided:
that if $R^3$ is halogen or completely halo-substituted haloalkyl, then $R^1$ is other than hydrogen or $X^1$ is alkyl, alkoxy, alkylthio, alkylsulfinyl or alkylsulfonyl.

37. The pesticidal composition according to claim 36 for the compound (II-7), wherein:
X is the group $R^5S(O)_n$, in which n is 0, 1, or 2 and $R^5$ is $C_{1-4}$ alkyl, trihalomethyl or dihalomethyl, in which halo is F, Cl, or Br or combinations thereof;
$R^1$ is as defined in claim 36 with aralkyl being benzyl;
$R^3$ is as defined in claim 36 with alkenyloxy being allyloxy and alkynyloxy being propargyloxy; and
$R^2$, Y, $X^1$, $X^2$, $X^3$, $X^4$ and the proviso are as defined in claim 36.

38. The pesticidal composition according to claim 37 for the compound (II-7), wherein:
X is the group $R^5S(O)_n$, in which n is 0, 1, or 2 and $R^5$ is $CH_3$, $CF_3$, $CF_2Cl$, $CFCl_2$, $CF_2Br$, $CHF_2$, CHClF or $CHCl_2$; and
$R^1$, $R^2$, $R^3$, Y, $X^1$, $X^2$, $X^3$, $X^4$ and the proviso are as defined in claim 37.

39. The pesticidal composition according to claim 38, wherein the compound (II-7) is:
1-(2,6-dichloro-4-trifluoromethylphenyl)-2-chloro-3-cyano-4-(trifluoromethylthio)-5-(methylsulfinyl)pyrrole;
1-(2,6-dichloro-4-trifluoromethylphenyl)-2-chloro-3-cyano-4-(dichlorofluoromethylthio)-5-(methylthio)pyrrole;
1-(2,6-dichloro-4-trifluoromethylphenyl)-2-chloro-3-cyano-4-(dichlorofluoromethylthio)-5-(methylsulfinyl)pyrrole;
1-(2,6-dichloro-4-trifluoromethylphenyl)-2-difluoromethyl-3-cyano-4-(trifluoromethylthio)pyrrole;
1-(2,6-dichloro-4-trifluoromethylphenyl)-2-methyl-3-cyano-4-(trifluoromethylthio)pyrrole;
1-(2,6-dichloro-4-trifluoromethylphenyl)-2-methyl-3-cyano-4-(trifluoromethylsulfinyl)pyrrole;
1-(2,6-dichloro-4-trifluoromethylphenyl)-2-difluoromethyl-3-cyano-4-(dichlorofluoromethylthio)pyrrole;
1-(2,6-dichloro-4-trifluoromethylphenyl)-2-difluoromethyl-3-cyano-4-(dichlorofluoromethylsulfonyl)pyrrole;
1-(2,6-dichloro-4-trifluoromethylphenyl)-2-difluoromethyl-3-cyano-4-(dichlorofluoromethylsulfinyl)pyrrole;
1-(2,6-dichloro-4-trifluoromethylphenyl)-2-chloro-3-cyano-4-(dichlorofluoromethylsulfinyl)-5-(methylthio)pyrrole;
1-(2,6-dichloro-4-trifluoromethylphenyl)-2-fluoromethyl-3-cyano-4-(trifluoromethylsulfinyl)pyrrole;
1-(2,6-dichloro-4-trifluoromethylphenyl)-2-chloro-3-cyano-4-(chlorodifluoromethylthio)-5-(methylthio)pyrrole;
1-(2,6-dichloro-4-trifluoromethylphenyl)-2-methyl-3-cyano-4-(dichlorofluoromethylsulfinyl)pyrrole; or
1-(2,6-dichloro-4-trifluoromethylphenyl)-2,5-dimethyl-3-cyano-4-(dichlorofluoromethylthio)pyrrole.

40. The pesticidal composition according to claim 4, wherein the pestidically effective compound (Ia-1) is a compound (II-8), wherein:
X is halogen or a group $R^5S(O)_n$, in which n is 0, 1, or 2 and $R^5$ is selected from the group consisting of: alkyl; haloalkyl, in which halo is F, Cl or Br or combinations thereof; alkenyl; and haloalkenyl; is selected from the group consisting of: halogen, alkylthio; alkylsulfinyl; alkylsulfonyl; alkyl; alkenyl; alkynyl; haloalkyl; haloalkenyl; haloalkynyl; alkylamino; dialkylamino; alkenylamino; alkynylamino; alkylcarbonylamino; haloalkylcarbonylamino; alkylideneimino; benzylideneimino; alkoxyalkylideneimino; and dialkylaminoalkylideneimino; and wherein the alkyl, alkenyl, alkynyl and alkoxy portions of these groups herein are linear or branched chains, having less than 10 carbon atoms, and the halo-substitution in all the aforementioned groups herein consists of one or more halogen atoms, which are the same or different, from mono substitution up to complete poly substitution;

$R^2$ is cyano;

$R^3$ is hydrogen;

Y is hydrogen or halogen; and $X^1$, $X^2$, $X^3$, and $X^4$ are individually selected from the group consisting of: hydrogen; halogen; $C_{1-3}$ alkyl; $C_{1-3}$ alkoxy; and $C_{1-3}$ alkylthio.

41. The pesticidal composition according to claim 40 for the compound (II-8), wherein:

X is halogen or a group $R^5S(O)_n$, in which n is 0, 1 or 2 and $R^5$ is selected from the group consisting of: $C_{1-4}$ alkyl; trihalomethyl; dihalomethyl; $C_{2-4}$ alkenyl; and $C_{2-4}$ alkynyl;

$R^1$ is as defined in claim 40, with alkenylamino being allylamino and alkynylamino being propargylamino; and wherein all carbon chains have less than 5 carbon atoms;

$R^2$, $R^3$ and Y are as defined in claim 40;

$X^1$ and $X^4$ are individually selected from the group consisting of hydrogen, fluorine, chlorine, bromine, and methyl; and $X^2$ and $X^3$ are each hydrogen.

42. The pesticidal composition according to claim 41 for the compound (II-8), wherein:

X is halogen or the group $R^5S(O)_n$, in which n is 0, 1 or 2 and $R^5$ is selected from the group consisting of: $CH_3$, $CF_3$, $CCl_3$, $CF_2Cl$, $CFCl_2$, $CF_2Br$, $CHF_2$, $CHFCl$, or $CHCl_2$; and $R^1$, $R^2$, $R^3$, Y, $X^1$, $X^2$, $X^3$ and $X^4$ are as defined in claim 41.

43. The pesticidal composition according to claim 42, wherein the compound (II-8) is:
2-bromo-3-(chlorodifluoromethylthio)-4-cyano-1-(2,4,6-trichlorophenyl)pyrrole;
2-bromo-3-(chlorodifluoromethylsulfinyl)-4-cyano-1-(2,4,6-trichlorophenyl)pyrrole;
2-bromo-4-cyano-3-(dichlorofluoromethylthio)-1-(2,4,6-trichlorophenyl)pyrrole;
2-bromo-4-cyano-3-(dichlorofluoromethylsulfinyl)-1-(2,4,6-trichlorophenyl)pyrrole;
4-cyano-3-(dichlorofluoromethylthio)-2-(methylthio)-1-(2,4,6-trichlorophenyl)pyrrole; or
4-cyano-3-(dichlorofluoromethylthio)-2-ethoxymethylideneimino-1-(2,4,6-trichlorophenyl)pyrrole.

44. The pesticidal composition according to claim 1, wherein the pesticidally effective compound of formula (Ia) is a compound (Ia-2), wherein:

X, $R^1$, $R^2$, $R^3$, Y, $X^1$, $X^2$, $X^3$, and $X^4$ are as defined in claim 1; and provided:
that X is other than halogen; $R^1$, $R^2$, and $R^3$ are as defined; and further $R^1$, $R^2$, and $R^3$ include being individually selected from halogen.

45. The method for control of pests according to any of claims 15, 16, 17 or 18, wherein the alkyl, alkenyl, alkynyl, and alkoxy portions of the substituents defined by X, $X^1$, $X^2$, $X^3$, $X^4$, $R^1$, $R^2$, $R^3$ and Y have less than 5 carbon atoms.

46. The method for control of pests according to claim 17, wherein the pesticidally effective compound (Ic) is a compound (II-5), wherein:

X is a haloalkyl-S(O)$_n$ group, wherein n is 0, 1, or 2;

$R^1$ is an hydrogen atom or a halogen atom;

$R^2$ is cyano;

$R^3$ is selected from the group consisting of: the same substituents as described for X in claim 17; a hydrogen atom; an alkyl group; and a substituent which is selected from the group consisting of formyl, hydroxyiminoalkylidenyl, alkoxyiminoalkylidenyl, azido, amino, alkylamino, dialkylamino, aralkylamino, aminocarbonylamino, alkylcarbonylamino, haloalkylcarbonylamino, arylcarbonylamino, alkylsulfonylamino, haloalkylsulfonylamino, alkylaminocarbonylamino, arylaminocarbonylamino, benzylideneimino, alkylideneimino, alkoxyalkylideneimino, dialkylaminoalkylideneimino, a phenyl optionally substituted with halogen, cyano or haloalkyl; and wherein the alkyl, haloalkyl, haloalkoxy, and alkoxy groups herein are linear or branched chains, having less than 10 carbon atoms, and the halo substitution in all these groups herein is mono substitution or up to as much as complete poly substitution;

Y is a haloalkyl or haloalkoxy;

$X^1$ and $X^4$ are other than a hydrogen atom; and $X^2$ and $X^3$ are each a hydrogen atom.

47. The method for control of pests according to claim 17, wherein the pesticidally effective compound (Ic) is a compound (II-6), wherein:

X is $R^5S(O)_n$, in which n is 0, 1 or 2 and $R^5$ is $CH_3$, $CF_3$, $CF_2Cl$ or $CFCl_2$;

$R^1$ is H, F, Cl, Br or $NH_2$;

$R^2$ is cyano;

$R^3$ is H, F, Cl, Br, $CF_3$ or CN;

Y is $CF_3$ or $CF_3O$;

$X^1$ is H or Cl;

$X^2$ and $X^3$ are H; and $X^4$ is Cl.

48. The method for control of pests according to claim 47, wherein the compound (II-6) is:
1-(2,6-dichloro-4-trifluoromethylphenyl)-2-chloro-3-cyano-4-(trifluoromethylsulfonyl)pyrrole;
1-(2,6-dichloro-4-trifluoromethylphenyl)-2-chloro-3-cyano-4-(trifluoromethylsulfinyl)pyrrole;
1-(2,6-dichloro-4-trifluoromethylphenyl)-2-chloro-3-cyano-4-(dichlorofluoromethylthio)pyrrole;
1-(2,6-dichloro-4-trifluoromethylphenyl)-2-chloro-3-cyano-4-(dichlorofluoromethylsulfinyl)pyrrole;
1-(2,6-dichloro-4-trifluoromethylphenyl)-2-chloro-3-cyano-4-(dichlorofluoromethylsulfonyl)pyrrole; or
1-(2,6-dichloro-4-trifluoromethylphenyl)-3-cyano-4-(dichlorofluoromethylsulfinyl)pyrrole.

49. The method for control of pests according to claim 16, wherein the pesticidally effective compound (Ib) is a compound (II-4), wherein:

X is a halogen atom or a group $R^5S(O)_n$, in which n is 0, 1 or 2 and $R^5$ is alkyl, haloalkyl, alkenyl, or haloalkenyl;

$R^1$ is a hydrogen atom, a halogen atom or alkylthio having less than 5 carbon atoms;

R$^2$ is cyano;

R$^3$ is a hydrogen atom or a halogen atom;

Y is a hydrogen atom, a halogen atom, haloalkyl or haloalkoxy, in which the alkyl and alkoxy portions have less than 5 carbon atoms, with the proviso that Y is a hydrogen atom as defined in claim 16; and X$^1$, X$^2$, X$^3$ and X$^4$ are individually selected from the group consisting of a hydrogen atom, a halogen atom, C$_{1-3}$ alkyl, C$_{1-3}$ alkoxy, and C$_{1-3}$ alkylthio.

50. The method for control of pests according to claim 49, wherein the pesticidally effective compound (II-4) is a compound (II-4a), wherein:

R$^1$ and R$^3$ are each a hydrogen atom;

Y is a hydrogen atom or halogen atom; and

X, R$^2$, X$^1$, X$^2$, X$^3$, and X$^4$ are as defined in claim 49.

51. The method for control of pests according to claim 50 for the compound (II-4a), wherein:

X is a Cl or Br atom or the group R$^5$S(O)$_n$, wherein n is 0, 1 or 2 and R$^5$ is C$_{1-4}$ alkyl or trihalomethyl, in which halo is F, Cl, or Br or combinations thereof;

Y is H, F, Cl or Br;

X$^1$ and X$^4$ are individually selected from the group consisting of H, F, Cl, Br and CH$_3$;

X$^2$ and X$^3$ are each a hydrogen atom; and

R$^1$, R$^2$ and R$^3$ are as defined in claim 50.

52. The method for the control of pests according to claim 51 for the compound (II-4a), wherein:

X is a Cl or Br atom or the group R$^5$S(O)$_n$, wherein n is 0, 1 or 2 and R$^5$ is CF$_3$, CCl$_3$, CF$_2$Cl, CFCl$_2$ or CF$_2$Br; and R$^1$, R$^2$, R$^3$, Y, X$^1$, X$^2$, X$^3$ and X$^4$ are as defined in claim 51.

53. The method for control of pests according to claim 52, wherein the compound (II-4a) is:

1-(4-bromo-2,6-dichlorophenyl)-3-cyano-4-(chlorodifluoromethylthio)pyrrole;

1-(4-bromo-2,6-dichlorophenyl)-3-cyano-4-(trifluoromethylthio)pyrrole;

1-(2,4,6-trichlorophenyl)-3-cyano-4-(chlorodifluoromethylthio)pyrrole;

1-(2,4,6-trichlorophenyl)-3-cyano-4-(dichlorofluoromethylthio)pyrrole;

1-(2,4,6-trichlorophenyl)-3-cyano-4-(trifluoromethylthio)pyrrole;

1-(2,6-dichloro-4-fluorophenyl)-3-cyano-4-(trifluoromethylsulfinyl)pyrrole;

1-(2,6-dichloro-4-fluorophenyl)-3-cyano-4-(trifluoromethylsulfonyl)pyrrole; or 1-(2,6-dichloro-4-fluorophenyl)-3-cyano-4-(dichlorofluoromethylthio)pyrrole.

54. The method for control of pests according to claim 49, wherein the pesticidally effective compound (II-4) is a compound (II-4b), wherein:

X is R$^5$S(O)$_n$, in which n is 0, 1 or 2 and R$^5$ is CH$_3$, CF$_3$, CF$_2$Cl, CFCl$_2$, CF$_2$Br, CHF$_2$, CHCl$_2$ or CHClF;

R$^1$ is H, F, Cl or Br;

R$^2$ is H, F, Cl or Br;

Y is CF$_3$ or CF$_3$O;

X$^1$ is H or Cl;

X$^2$ and X$^3$ are H; and

X$^4$ is Cl.

55. The method for control of pests according to claim 54, wherein the compound (II-4b) is:

1-(2,6-dichloro-4-trifluoromethylphenyl)-2-chloro-3-cyano-4-(dichlorofluoromethylthio)pyrrole;

1-(2,6-dichloro-4-trifluoromethylphenyl)-2-chloro-3-cyano-4-(dichlorofluoromethylsulfinyl)pyrrole;

1-(2,6-dichloro-4-trifluoromethylphenyl)-2-chloro-3-cyano-4-(dichlorofluoromethylsulfonyl)pyrrole;

1-(2,6-dichloro-4-trifluoromethylphenyl)-2-chloro-3-cyano-4-(chlorodifluoromethylsulfonyl)pyrrole;

1-(2,6-dichloro-4-trifluoromethylphenyl)-2-chloro-3-cyano-4-chlorodifluoromethylsulfinyl)pyrrole;

1-(2,6-dichloro-4-trifluoromethylphenyl)-2-chloro-3-cyano-4-(chlorodifluoromethylthio)pyrrole;

1-(2,6-dichloro-4-trifluoromethylphenyl)-2-bromo-3-cyano-4-(dichlorofluoromethylsulfonyl)pyrrole;

1-(2,6-dichloro-4-trifluoromethylphenyl)-2-bromo-3-cyano-4-(dichlorofluoromethylsulfinyl)pyrrole;

1-(2,6-dichloro-4-trifluoromethylphenyl)-2-chloro-3-cyano-4-(bromodifluoromethylthio)pyrrole;

1-(2,6-dichloro-4-trifluoromethylphenyl)-2-chloro-3-cyano-4-(methylsulfinyl)pyrrole;

1-(2,6-dichloro-4-trifluoromethyl-2-bromo-3-cyano-4-(trifluoromethylthio)pyrrole;

1-(2,6-dichloro-4-trifluoromethoxyphenyl)-2-bromo-3-cyano-4-(dichlorofluoromethylsulfinyl)pyrrole; or 1-(2,6-dichloro-4-trifluoromethoxyphenyl)-2-bromo-3-cyano-4-(dichlorofluoromethylsulfonyl)pyrrole.

56. The method for control of pests according to claim 18, wherein the pesticidally effective compound (Ia-1) is a compound (II-7), wherein:

X is a group R$^5$S(O)$_n$, in which n is 0, 1 or 2 and R$^5$ is alkyl or haloalkyl;

R$^1$ is selected from the group consisting of: hydrogen; alkyl; cyanoalkyl; haloalkyl; alkylthio; alkylsulfinyl; alkylsulfonyl; aralkylthio; aralkylsulfinyl, aralkylsulfonyl; alkenylthio; alkynylthio; phenylthio; phenylsulfinyl; phenylsulfonyl; alkoxy; alkenyloxy; alkynyloxy; alkoxyalkyl; and alkylthioalkyl; and wherein the phenyl portions in the aforementioned groups are optionally substituted as defined in claim 18; and the aralkyl portions in the aforementioned groups are optionally substituted phenylalkyl as also defined in claim 18;

R$^2$ is cyano;

R$^3$ is selected from the group consisting of: halogen; cyano; alkyl; haloalkyl; alkoxy; alkenyloxy; alkynyloxy; and alkoxyalkyl;

Y is selected from the group consisting of: halogen, trifluoromethyl, and trifluoromethoxy;

X$^1$ is selected from the group consisting of: hydrogen; halogen; alkyl; alkoxy; alkylthio; alkylsulfinyl; and alkylsulfonyl;

X$^2$ and X$^3$ are hydrogen;

X$^4$ is halogen; and provided:

that if R$^3$ is halogen or completely halo-substituted haloalkyl, then R$^1$ is other than hydrogen or X$^1$ is alkyl, alkoxy, alkylthio, alkylsulfinyl or alkylsulfonyl.

57. The method for control of pests according to claim 56 for the compound (II-7), wherein:

X is the group R$^5$S(O)$_n$, in which n is 0, 1, or 2 and R$^5$ is C$_{1-4}$ alkyl, trihalomethyl or dihalomethyl, in which halo is F, Cl, or Br or combinations thereof;

R$^1$ is as defined in claim 56 with aralkyl being benzyl;

R$^3$ is as defined in claim 56 with alkenyloxy being allyloxy and alkynyloxy being propargyloxy; and R$^2$, Y, X$^1$, X$^2$, X$^3$, X$^4$ and the proviso are as defined in claim 56.

58. The method for control of pests according to claim 57 for the compound (II-7), wherein:

X is the group $R^5S(O)_n$, in which n is 0, 1, or 2 and $R^5$ is $CH_3$, $CF_3$, $CF_2Cl$, $CFCl_2$, $CF_2Br$, $CHF_2$, CHClF or $CHCl_2$; and $R^1$, $R^2$, $R^3$, Y, $X^1$, $X^2$, $X^3$, $X^4$ and the proviso are as defined in claim 57.

59. The method for control of pests according to claim 58, wherein the compound (II-7) is:

1-(2,6-dichloro-4-trifluoromethylphenyl)-2-chloro-3-cyano-4-(trifluoromethylthio)-5-(methylsulfinyl)pyrrole;

1-(2,6-dichloro-4-trifluoromethylphenyl)-2-chloro-3-cyano-4-(dichlorofluoromethylthio)-5-(methylthio)pyrrole;

1-(2,6-dichloro-4-trifluoromethylphenyl)-2-chloro-3-cyano-4-(dichlorofluoromethylthio)-5-(methylsulfinyl)pyrrole;

1-(2,6-dichloro-4-trifluoromethylphenyl)-2-difluoromethyl-3-cyano-4-(trifluoromethylthio)pyrrole;

1-(2,6-dichloro-4-trifluoromethylphenyl)-2-methyl-3-cyano-4-(trifluoromethylthio)pyrrole;

1-(2,6-dichloro-4-trifluoromethylphenyl)-2-methyl-3-cyano-4-(trifluoromethylsulfinyl)pyrrole;

1-(2,6-dichloro-4-trifluoromethylphenyl)-2-difluoromethyl-3-cyano-4-(dichlorofluoromethylthio)pyrrole;

1-(2,6-dichloro-4-trifluoromethylphenyl)-2-difluoromethyl-3-cyano-4-(dichlorofluoromethylsulfonyl)pyrrole;

1-(2,6-dichloro-4-trifluoromethylphenyl)-2-difluoromethyl-3-cyano-4-(dichlorofluoromethylsulfinyl)pyrrole;

1-(2,6-dichloro-4-trifluoromethylphenyl)-2-chloro-3-cyano-4-(dichlorofluoromethylsulfinyl)-5-(methylthio)pyrrole;

1-(2,6-dichloro-4-trifluoromethylphenyl)-2-fluoromethyl-3-cyano-4-(trifluoromethylsulfinyl)pyrrole;

1-(2,6-dichloro-4-trifluoromethylphenyl)-2-chloro-3-cyano-4-(chlorodifluoromethylthio)-5-(methylthio)pyrrole;

1-(2,6-dichloro-4-trifluoromethylphenyl)-2-methyl-3-cyano-4-(dichlorofluoromethylsulfinyl)pyrrole; or 1-(2,6-dichloro-4-trifluoromethylphenyl)-2,5-dimethyl-3-cyano-4-(dichlorofluoromethylthio)pyrrole.

60. The method for control of pests according to claim 18, wherein the pesticidally effective compound (Ia-1) is a compound (II-8), wherein:

X is halogen or a group $R^5S(O)_n$, in which n is 0, 1, or 2 and $R^5$ is selected from the group consisting of: alkyl; haloalkyl, in which halo is F, Cl or Br or combinations thereof; alkenyl; and haloalkenyl;

$R^1$ is selected from the group consisting of: halogen; alkylthio; alkylsulfinyl; alkylsulfonyl; alkyl; alkenyl; alkynyl; haloalkyl; haloalkenyl; haloalkynyl; alkylamino; dialkylamino; alkenylamino; alkynylamino; alkylcarbonylamino; haloalkylcarbonylamino; alkylideneimino; benzylideneimino; alkoxyalkylideneimino; and dialkylaminoalkylideneimino; and wherein the alkyl, alkenyl, alkynyl and alkoxy portions of these groups herein are linear or branched chains, having less than 10 carbon atoms, and the halosubstitution in all the aforementioned groups herein consists of one or more halogen atoms, which are the same or different, from mono substitution up to complete poly substitution;

$R^2$ is cyano;

$R^3$ is hydrogen;

Y is hydrogen or halogen; and $X^1$, $X^2$, $X^3$, and $X^4$ are individually selected from the group consisting of: hydrogen; halogen; $C_{1-3}$ alkyl; $C_{1-3}$ alkoxy; and $C_{1-3}$ alkylthio.

61. The method for control of pests according to claim 60 for the compound (II-8), wherein:

X is halogen or a group $R^5S(O)_n$, in which n is 0, 1 or 2 and $R^5$ is selected from the group consisting of: $C_{1-4}$ alkyl; trihalomethyl; dihalomethyl; $C_{2-4}$ alkenyl; and $C_{2-4}$ alkynyl;

$R^1$ is as defined in claim 60, with alkenylamino being allylamino and alkynylamino being propargylamino; and wherein all carbon chains have less than 5 carbon atoms;

$R^2$, $R^3$ and Y are as defined in claim 60;

$X^1$ and $X^4$ are individually selected from the group consisting of hydrogen, fluorine, chlorine, bromine, and methyl; and $X^2$ and $X^3$ are each hydrogen.

62. The method for control of pests according to claim 61 for the compound (II-8), wherein:

X is halogen or the group $R^5S(O)_n$, in which n is 0, 1 or 2 and $R^5$ is selected from the group consisting of: $CH_3$, $CF_3$, $CCl_3$, $CF_2Cl$, $CFCl_2$, $CF_2Br$, $CHF_2$, CHFCl, or $CHCl_2$; and $R^1$, $R^2$, $R^3$, Y, $X^1$, $X^2$, $X^3$ and $X^4$ are as defined in claim 61.

63. The method for control of pests according to claim 62, wherein the compound (II-8) is:

2-bromo-3-(chlorodifluoromethylthio)-4-cyano-1-(2,4,6-trichlorophenyl)pyrrole;

2-bromo-3-(chlorodifluoromethylsulfinyl)-4-cyano-1-(2,4,6-trichlorophenyl)pyrrole;

2-bromo-4-cyano-3-(dichlorofluoromethylthio)-1-(2,4,6-trichlorophenyl)pyrrole;

2-bromo-4-cyano-3-(dichlorofluoromethylsulfinyl)-1-(2,4,6-trichlorophenyl)pyrrole;

4-cyano-3-(dichlorofluoromethylthio)-2-(methylthio)-1-(2,4,6-trichlorophenyl)pyrrole; or 4-cyano-3-(dichlorofluoromethylthio)-2-ethoxymethylideneimino-1-(2,4,6-trichlorophenyl)pyrrole.

64. A method for control of pests according to claim 1, wherein the pesticidally effective compound of formula (Ia) is a compound (Ia-2), wherein:

X, $R^1$, $R^2$, $R^3$, Y, $X^1$, $X^2$, $X^3$, and $X^4$ are as defined in claim 1; and provided:

that X is other than halogen; $R^1$, $R^2$, and $R^3$ are as defined; and further $R^1$, $R^2$, and $R^3$ include being individually selected from halogen.

* * * * *